United States Patent
Li et al.

(10) Patent No.: US 11,746,150 B2
(45) Date of Patent: Sep. 5, 2023

(54) ANTI-LRP5/6 ANTIBODIES AND METHODS OF USE

(71) Applicant: Surrozen Operating, Inc., South San Francisco, CA (US)

(72) Inventors: Yang Li, Mountain View, CA (US); Tom Zhiye Yuan, Union City, CA (US); Aaron Ken Sato, Burlingame, CA (US); Wen-Chen Yeh, Belmont, CA (US); Parthasarathy Sampathkumar, South San Francisco, CA (US)

(73) Assignee: Surrozen Operating, Inc., South San Francisco, CA (US)

( * ) Notice: Subject to any disclaimer, the term of this patent is extended or adjusted under 35 U.S.C. 154(b) by 147 days.

(21) Appl. No.: 16/954,483

(22) PCT Filed: Dec. 19, 2018

(86) PCT No.: PCT/US2018/066620
§ 371 (c)(1),
(2) Date: Jun. 16, 2020

(87) PCT Pub. No.: WO2019/126401
PCT Pub. Date: Jun. 27, 2019

(65) Prior Publication Data
US 2021/0079089 A1  Mar. 18, 2021

Related U.S. Application Data

(60) Provisional application No. 62/680,515, filed on Jun. 4, 2018, provisional application No. 62/607,879, filed on Dec. 19, 2017.

(51) Int. Cl.
*C07K 16/28* (2006.01)

(52) U.S. Cl.
CPC .......... *C07K 16/28* (2013.01); *C07K 2317/24* (2013.01); *C07K 2317/55* (2013.01); *C07K 2317/569* (2013.01); *C07K 2317/622* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | |
|---|---|---|
| 4,946,778 A | 8/1990 | Ladner et al. |
| 5,091,513 A | 2/1992 | Huston et al. |
| 5,132,405 A | 7/1992 | Huston et al. |
| 5,151,510 A | 9/1992 | Stec et al. |
| 6,005,079 A | 12/1999 | Casterman et al. |
| 6,528,624 B1 | 3/2003 | Idusogie et al. |
| 6,538,124 B1 | 3/2003 | Idusogie et al. |
| 6,765,087 B1 | 7/2004 | Casterman et al. |
| 6,838,254 B1 | 1/2005 | Hamers et al. |
| 7,297,775 B2 | 11/2007 | Idusogie et al. |
| 7,317,091 B2 | 1/2008 | Lazar et al. |
| 7,364,731 B2 | 4/2008 | Idusogie et al. |
| 7,657,380 B2 | 2/2010 | Lazar et al. |
| 7,662,925 B2 | 2/2010 | Lazar et al. |
| 7,982,013 B2 | 7/2011 | Gurney et al. |
| 8,202,966 B2 | 6/2012 | McCarthy |
| 8,221,751 B2 | 7/2012 | Nakamura et al. |
| 8,343,922 B2 | 1/2013 | Wu et al. |
| 8,461,155 B2 | 6/2013 | Wu et al. |
| 8,507,442 B2 | 8/2013 | Gurney et al. |
| 8,637,506 B2 | 1/2014 | Wu et al. |
| 8,715,941 B2 | 5/2014 | Abo et al. |
| 8,846,041 B2 | 9/2014 | Bourhis et al. |
| 8,859,736 B2 | 10/2014 | Ma et al. |
| 8,883,735 B2 | 11/2014 | Jenkins et al. |
| 8,975,044 B2 | 3/2015 | Gurney et al. |
| 9,359,444 B2 | 6/2016 | Dupont et al. |
| 9,573,998 B2 | 2/2017 | Gurney et al. |
| 11,142,577 B2 | 10/2021 | Garcia et al. |
| 2003/0044409 A1 | 3/2003 | Carson et al. |
| 2003/0099647 A1 | 5/2003 | Deshpande et al. |
| 2003/0157109 A1 | 8/2003 | Corvalan et al. |
| 2003/0165500 A1 | 9/2003 | Rhee et al. |
| 2005/0261181 A1 | 11/2005 | Wu et al. |
| 2006/0127393 A1 | 6/2006 | Li et al. |
| 2006/0263791 A1* | 11/2006 | Moon .................. C12Q 1/6883 435/6.11 |
| 2007/0196872 A1 | 8/2007 | Bex et al. |
| 2007/0207522 A1 | 9/2007 | Laurie et al. |
| 2008/0038272 A1 | 2/2008 | Buehring et al. |
| 2008/0131435 A1 | 6/2008 | Stavenhagen et al. |
| 2008/0138344 A1 | 6/2008 | Stavenhagen et al. |
| 2008/0267955 A1 | 10/2008 | Schluesener et al. |

(Continued)

FOREIGN PATENT DOCUMENTS

| | | |
|---|---|---|
| EP | 1716181 B1 | 12/2009 |
| EP | 2910550 A2 | 8/2015 |
| EP | 3191526 A4 | 3/2018 |
| JP | 2011503025 A | 1/2011 |

(Continued)

OTHER PUBLICATIONS

Koenig "Mutational landscape of antibody variable domains reveals a switch modulating the interdomain conformational dynamics and antigen binding" PNAS E486-E495 (Year: 2017).*

(Continued)

*Primary Examiner* — Adam Weidner
(74) *Attorney, Agent, or Firm* — Cooley LLP

(57) ABSTRACT

The present invention provides anti-LRP5/6 monoclonal antibodies and related compositions, which may be used in any of a variety of therapeutic methods for treating diseases and disorders associated with Wnt pathway signaling.

10 Claims, 3 Drawing Sheets
Specification includes a Sequence Listing.

(56) References Cited

U.S. PATENT DOCUMENTS

| | | |
|---|---|---|
| 2008/0286261 A1 | 11/2008 | Morgan et al. |
| 2009/0028869 A1 | 1/2009 | Dodel et al. |
| 2009/0092599 A1 | 4/2009 | Lazar et al. |
| 2009/0291088 A1 | 11/2009 | Hariharan et al. |
| 2009/0311243 A1 | 12/2009 | Brockbank et al. |
| 2010/0129375 A1 | 5/2010 | Junge et al. |
| 2010/0254979 A1 | 10/2010 | Staunton et al. |
| 2010/0254980 A1 | 10/2010 | Cong et al. |
| 2011/0105606 A1 | 5/2011 | Rabbani et al. |
| 2011/0177073 A1* | 7/2011 | Van Berkel ............ C07K 16/10 435/69.6 |
| 2011/0223140 A1 | 9/2011 | Park et al. |
| 2012/0237523 A1 | 9/2012 | Mascola et al. |
| 2012/0322717 A9 | 12/2012 | Liu et al. |
| 2013/0058934 A1 | 3/2013 | Cong et al. |
| 2013/0064823 A1 | 3/2013 | Cong et al. |
| 2013/0095097 A1 | 4/2013 | Blankenship et al. |
| 2013/0095104 A1 | 4/2013 | Cummings et al. |
| 2013/0183320 A1 | 7/2013 | Wu et al. |
| 2013/0230521 A1 | 9/2013 | Nakamura et al. |
| 2013/0253172 A1 | 9/2013 | Gurney et al. |
| 2013/0274215 A1 | 10/2013 | Thies et al. |
| 2013/0295105 A1 | 11/2013 | Gurney et al. |
| 2014/0044713 A1 | 2/2014 | De Lau et al. |
| 2014/0105917 A1 | 4/2014 | Gurney |
| 2014/0154252 A1 | 6/2014 | Thompson et al. |
| 2014/0200179 A1 | 7/2014 | Garcia et al. |
| 2014/0242078 A1 | 8/2014 | Dupont et al. |
| 2014/0363439 A1 | 12/2014 | Bourhis et al. |
| 2015/0010560 A1 | 1/2015 | Xu et al. |
| 2015/0119555 A1 | 4/2015 | Jung et al. |
| 2015/0196663 A1* | 7/2015 | Shusta ................ A61K 9/0085 435/254.11 |
| 2015/0209407 A1 | 7/2015 | Pignolo |
| 2015/0266947 A1* | 9/2015 | Sierks ................ C07K 16/005 435/6.12 |
| 2015/0376252 A1 | 12/2015 | Xu et al. |
| 2016/0002312 A1 | 1/2016 | Ilan |
| 2016/0024196 A1 | 1/2016 | Majeti et al. |
| 2016/0152947 A1 | 6/2016 | Pioszak |
| 2016/0194394 A1 | 7/2016 | Sidhu et al. |
| 2016/0264960 A1 | 9/2016 | Ishii |
| 2016/0312207 A1 | 10/2016 | Kuo et al. |
| 2017/0071937 A1 | 3/2017 | Karp et al. |
| 2017/0218077 A1 | 8/2017 | Raum et al. |
| 2017/0218078 A1 | 8/2017 | Raum et al. |
| 2017/0240631 A1 | 8/2017 | Monroe et al. |
| 2017/0253670 A1 | 9/2017 | Klein et al. |
| 2017/0306029 A1 | 10/2017 | Garcia et al. |
| 2017/0349659 A1 | 12/2017 | Garcia et al. |
| 2017/0355756 A1* | 12/2017 | Julien ..................... A61P 25/00 |
| 2018/0066067 A1 | 3/2018 | Cong et al. |
| 2019/0093072 A1 | 3/2019 | Koehler et al. |
| 2019/0093079 A1 | 3/2019 | Loose et al. |
| 2020/0024338 A1 | 1/2020 | Luca et al. |
| 2020/0048324 A1 | 2/2020 | Zhang et al. |
| 2020/0199237 A1 | 6/2020 | Garcia et al. |
| 2020/0199238 A1 | 6/2020 | Garcia et al. |
| 2020/0308287 A1 | 10/2020 | Li et al. |
| 2021/0087280 A1 | 3/2021 | Li et al. |
| 2021/0292422 A1 | 9/2021 | Li |
| 2021/0380678 A1 | 12/2021 | Zhang et al. |
| 2021/0403578 A1 | 12/2021 | Garcia et al. |
| 2022/0064337 A1 | 3/2022 | Li et al. |
| 2022/0112278 A1 | 4/2022 | Li et al. |
| 2022/0175884 A1 | 6/2022 | Lee et al. |
| 2022/0195053 A1 | 6/2022 | Li et al. |
| 2022/0275095 A1 | 9/2022 | Li et al. |

FOREIGN PATENT DOCUMENTS

| | | |
|---|---|---|
| JP | 2012503990 A | 2/2012 |
| JP | 2012506568 A | 3/2012 |
| JP | 2012516685 A | 7/2012 |
| JP | 2013527761 A | 7/2013 |
| JP | 2017530099 A | 10/2017 |
| WO | WO-9627011 A1 | 9/1996 |
| WO | WO-9850431 A2 | 11/1998 |
| WO | WO-02092635 A2 | 11/2002 |
| WO | WO2004063351 A2 | 7/2004 |
| WO | WO-2005032574 A1 | 4/2005 |
| WO | WO-2006040163 A1 | 4/2006 |
| WO | WO2006079372 A1 | 8/2006 |
| WO | WO2006088494 A9 | 8/2006 |
| WO | WO2006105338 A2 | 10/2006 |
| WO | WO-2007012449 A1 | 2/2007 |
| WO | WO2007024249 A2 | 3/2007 |
| WO | WO-2007146968 A2 | 12/2007 |
| WO | WO-2007148417 A1 | 12/2007 |
| WO | WO2008068048 * | 6/2008 |
| WO | WO2008084402 A2 | 7/2008 |
| WO | WO-2008134632 A1 | 11/2008 |
| WO | WO2009064944 A2 | 5/2009 |
| WO | WO-2009080251 A1 | 7/2009 |
| WO | WO-2010016766 A2 | 2/2010 |
| WO | WO2010021697 A2 | 2/2010 |
| WO | WO2010037041 A2 | 4/2010 |
| WO | WO-2010054010 A1 | 5/2010 |
| WO | WO2010090513 A2 | 8/2010 |
| WO | WO-2011088226 A2 | 7/2011 |
| WO | WO-2011090762 A1 | 7/2011 |
| WO | WO2011119661 A1 | 9/2011 |
| WO | WO-2011123785 A2 | 10/2011 |
| WO | WO2011138392 A1 | 11/2011 |
| WO | WO2012014076 A2 | 2/2012 |
| WO | WO-2012058768 A1 | 5/2012 |
| WO | WO-2012103360 A2 | 8/2012 |
| WO | WO-2012140274 A9 | 3/2013 |
| WO | WO2013092001 A1 | 6/2013 |
| WO | WO2013109819 A1 | 7/2013 |
| WO | WO-2014029752 A1 | 2/2014 |
| WO | WO-2014124326 A1 | 8/2014 |
| WO | WO-2014159580 A1 | 10/2014 |
| WO | WO-2015036582 A2 | 3/2015 |
| WO | WO-2015063187 A1 | 5/2015 |
| WO | WO2015109212 A1 | 7/2015 |
| WO | WO2016023019 A2 | 2/2016 |
| WO | WO2016040895 A1 | 3/2016 |
| WO | WO-2016168607 A1 | 10/2016 |
| WO | WO-2016205551 A2 | 12/2016 |
| WO | WO-2016205566 A1 | 12/2016 |
| WO | WO-2017127933 A1 | 8/2017 |
| WO | WO2017136820 A2 | 8/2017 |
| WO | WO-2017152102 A2 | 9/2017 |
| WO | WO2018132572 A1 | 7/2018 |
| WO | WO2018140821 A1 | 8/2018 |
| WO | WO-2018220080 A1 | 12/2018 |
| WO | WO2019126398 A1 | 6/2019 |
| WO | WO2019126399 A1 | 6/2019 |
| WO | WO2019126401 A1 | 6/2019 |
| WO | WO-2019159084 A1 | 8/2019 |
| WO | WO2020010308 A1 | 1/2020 |
| WO | WO2020014271 A1 | 1/2020 |
| WO | WO2020132356 A1 | 6/2020 |
| WO | WO2020167848 A1 | 8/2020 |
| WO | WO2020185960 A1 | 9/2020 |
| WO | WO2020206005 A1 | 10/2020 |
| WO | WO2021003054 A1 | 1/2021 |
| WO | WO-2021003416 A1 | 1/2021 |
| WO | WO2021173726 A1 | 9/2021 |
| WO | WO2022104280 A1 | 5/2022 |
| WO | WO-2022192445 A1 | 9/2022 |
| WO | WO-2023044348 A1 | 3/2023 |

OTHER PUBLICATIONS

Kussie "A Single Engineered Amino Acid Substitution Changes Antibody Fine Specificity" J immunol 152(1):146-52 (Year: 1994).*

Chen "Enhancement and destruction of antibody function by somatic mutation: unequal occurrence is controlled by V gene combinatorial associations" EMBO 14(12):2784-2794 (Year: 1995).*

(56) References Cited

OTHER PUBLICATIONS

Whyte "Wnt signaling and injury repair" Cold Spring Harb Perspect Biol 2012;4:a008078 (Year: 2012).*
Chen, S. et al. (Nov. 15, 2011) Structural and functional studies of LRP6 ectodomain reveal a platform for Wnt signaling. Dev Cell., 21(5):848-861. doi: 10.1016/j.devcel.2011.09.007. Epub Oct. 13, 2011.
Ettenberg S.A. et al. (Aug. 31, 2010) "Inhibition of tumorigenesis driven by different Wnt proteins requires blockade of distinct ligand-binding regions by LRP6 antibodies" Proc Natl Acad Sci USA, 107(35):15473-15478.
GenBank Accession No. AF177394.2 "Homo sapiens dickkopf-1 (DKK-1) mRNA, complete cds" Dec. 20, 2016, 2 pages.
GenBank Accession No. AF177395.1 "*Homo sapiens* dickkopf-2 (DKK-2) mRNA, complete cds" Dec. 20, 2016, 2 pages.
GenBank Accession No. NM_014419.4 "*Homo sapiens* dickkopf like acrosomal protein 1 (DKKL1), transcript variant 1, mRNA" Feb. 18, 2021, 4 pages.
GenBank Accession No. NM_014420.3 "*Homo sapiens* dickkopf WNT signaling pathway inhibitor 4 (DKK4), mRNA" Feb. 15, 2021, 4 pages.
GenBank Accession No. NM_014421.3 "*Homo sapiens* dickkopf WNT signaling pathway inhibitor 2 (DKK2), mRNA" Feb. 13, 2021, 4 pages.
GenBank Accession No. NM_015881.6 "*Homo sapiens* dickkopf WNT signaling pathway inhibitor 3 (DKK3), transcript variant 1, mRNA" Feb. 23, 2021, 5 pages.
GenBank Accession No. NP_036374.1 "dickkopf-related protein 1 precursor [*Homo sapiens* ]" Mar. 3, 2021, 3 pages.
GenBank Accession No. NP_055236.1 "dickkopf-related protein 2 precursor [*Homo sapiens* ]" Feb. 13, 2021, 3 pages.
Gong, S. et al. (2017) "Fabs-in-tandem immunoglobulin is a novel and versatile bispecific design for engaging multiple therapeutic targets" mAbs, 9(7):1118-1128, DOI: 10.1080/19420862.2017. 1345401.
Gong, Y. et al. (2010) "Wnt Isoform-Specific Interactions with Coreceptor Specify Inhibition or Potentiation of Signaling by LRP6 Antibodies" PLoS One, 5(9):e12682, doi:10.1371/journal.pone. 0012682; 17 pages.
Gulati, S. et al. (May 18, 2018) "Targeting G protein-coupled receptor signaling at the G protein level with a selective nanobody inhibitor." Nature Communications, 9(1):1996; 15 pages. doi:10. 1038/s41467-018-04432-0.
Gurney, A. et al. (Jul. 2012) "Wnt pathway inhibition via the targeting of Frizzled receptors results in decreased growth and tumorigenicity of human tumors" Proc Natl Acad Sci USA, 109(29): 11717-11722.
International Patent Application No. PCT/US2018/066620, by Surrozen, Inc.: International Search Report and Written Opinion, including Notification of Transmittal; dated May 1, 2019, 13 pages.
Janda, C.Y. et al. (2012) "Structural basis of Wnt recognition by Frizzled" Science, 337(6090):59-64. NIH Public Access Author Manuscript [online]; retrieved from: https://www.ncbi.nlm.nih.gov/pmc/articles/PMC3577348/pdf/nihms443661.pdf; 18 pages.
Joiner, D.M. et al. (Jan. 2013) "LRP5 and LRP6 in development and disease" Trends in Endocronology and Metabolism, 24(1):31-39.
Katoh, M. et al. (Sep. 2017) "Molecular genetics and targeted therapy of WNT-related human diseases (Review)" Intl J Mol Med, 40(3):587-606.
Krupnik, V.E. et al. (1999) "Functional and structural diversity of the human Dickkopf gene family" Gene, 238(2):301-313.
Sato, T. et al. (May 14, 2009) "Single Lgr5 stem cells build crypt-villus structures in vitro without a mesenchymal niche" Nature, 459:262-265, www.nature.com/doifinder/10.1038/nature07935; with "Methods", 1 page.
Sato, T. et al. (2011) "Long-term Expansion of Epithelial Organoids From Human Colon, Adenoma, Adenocarcinoma, and Barrett's Epithelium" Gastroenterology, 141:1762-1772.
Steinhart, Z. et al. (Jan. 2017) "Genome-wide CRISPR screens reveal a Wnt-FZD5 signaling circuit as a druggable vulnerability of RNF43-mutant pancreatic tumors" Nat Med, 23(1):60-68.

Brinkmann, U. et al. (2017) The making of bispecific antibodies. MAbs, 9(2):182-212.
Adams, T.S. et al. (Jul. 2020) Single-cell RNA-seq reveals ectopic and aberrant lung-resident cell populations in idiopathic pulmonary fibrosis. Sci Adv, 6:eaba1983, 16 pages.
Ahn, V. E., et al. (2011) "Structural basis of Wnt signaling inhibition by Dickkopf binding to LRP5/6" Developmental cell, 21(5):862-873.
Aihara, E. et al. (2017) "Trefoil factor peptides and gastrointestinal function" Annual Review of Physiology, 79:357-380.
Akhmetshina, A. et al. (Mar. 2012) Activation of canonical Wnt signalling is required for TGF-β-mediated fibrosis. Nature Communications, 3:735; DOI:10.1038/ncomms1734, 12 pages.
Alsafadi, H. et al. (Mar. 2017) An ex vivo model to induce early fibrosis-like changes in human precision-cut lung slices. Am J Physiol Lung Cell Mol Physiol, 312:L896-L902.
Antoni, L. et al. (2014) "Intestinal barrier in inflammatory bowel disease" World Journal of Gastroenterology: WJG, 20(5):1165-1179.
Aran et al. (2019) "Reference-based analysis of lung single-cell sequencing reveals a transitional profibrotic macrophage". Nature Immunology, 20(2): 163-172.
Arike, L. et al. (2017) "Intestinal Muc2 mucin O-glycosylation is affected by microbiota and regulated by differential expression of glycosyltranferases" Glycobiology, 27(4):318-328.
Atkinson, P.J., et al. (2014) "Hair cell regeneration after ATOH1 gene therapy in the cochlea of profoundly deaf adult guinea pigs." PLoS ONE 9(7):e102077.
Baarsma, H. et al. (2017) Noncanonical WNT-5A signaling impairs endogenous lung repair in COPD. J Exp Med, 214:143-163.
Baarsma, H.A., and M. Königshoff (2017). 'WNT-er is coming' : WNT signalling in chronic lung diseases. Thorax, 72:746-759.
Bafico, A. et al. (Jul. 2001) "Novel mechanism of Wnt signalling inhibition mediated by Dickkopf-1 interaction with LRP6/Arrow" Nature Cell Biology, 3(7):683-686.
Barbas et al., "Human antibody recognition of DNA." Proceedings of the National Academy of Sciences (1995); 92(7): 2529-2533.
Barbas et al., "Recognition of DNA by synthetic antibodies." Journal of the American Chemical Society (1994); 116.5: 2161-2162.
Barkauskas, C.E. et al. (Jul. 2013) Type 2 alveolar cells are stem cells in adult lung. Journal of Clinical Investigation 123(7):3025-3036.
Barkauskas et al. (2017) "Lung organoids: current uses and future promise". Development, 144(6): 986-997.
Barker et al. (2007). "Identification of stem cells in small intestines and colon by marker gene Lgr5." Nature Publishing Group. vol. 449, No. 25 1003-7.
Barker et al. (2009) Crypt stem cells as the cells-of-origin of intestinal cancer. Nature, 457(7229):608-611, Methods, 1 page; doi:10.1038/nature07602.
Barker et al. (2010). "Lgr5-'-ve stem cells drive self-renewal in the stomach and build long-lived gastric units in vitro." Cell Stem Cell. vol. 6, 25-36.
Barnes et al. (2015) "Chronic obstructive pulmonary disease". Nature Reviews, Disease Primer, 1: 1-21.
Basil et al., (2022) "Human distal airways contain a multipotent secretory cell that can regenerate alveoli". Nature, 604(7904): 120-126.
Bergström, J.H. et al. (2014) "AGR2, an endoplasmic reticulum protein, is secreted into the gastrointestinal mucus" PLoS One, 9(8):e104186.
Bergström, J.H. et al. (Nov. 2016) "Gram-positive bacteria are held at a distance in the colon mucus by the lectin-like protein ZG16" Proceedings of the National Academy of Sciences, 113(48):13833-13838.
Beumer, J. et al. (2016) "Regulation and plasticity of intestinal stem cells during homeostasis and regeneration" Development, 143(20):3639-3649.
Bhalla, P. et al. (Apr. 2015) Disseminated, persistent, and fatal infection due to the vaccine strain of varicella-zoster virus in an adult following stem cell transplantation.Clin Infect Dis, 60(7):1068-1074. doi: 10.1093/cid/ciu970.

(56) References Cited

OTHER PUBLICATIONS

Bird, R.E. et al. (Oct. 1988) "Single-chain antigen-binding proteins." Science 242(4877):423-426.
Blagodatski et al. (2014) "Targeting the Wnt pathways for therapies". Molecular Cell Therapy 2(28): 15 pages.
Bohne, B.A. et al. (1976) Irreversible Inner Ear Damage From Rock Music. Trans Sect Otolaryngol Am Acad Ophthalmol Otolaryngol. 82(1):50-59.
Bourhis et al. (2010) "Reconstitution of a Frizzled8.Wnt3a.LRP6 signaling complex reveals multiple Wnt and Dkk1 binding sites on LRP6" The Journal of Biological Chemistry, 285:129172-9179.
Bradley, P. et al. (Sep. 2005) "Toward high-resolution de novo structure prediction for small proteins." Science 309(5742):1868-1871.
Bramhall et al. (2014). "Lgr5-Positive Supporting Cells Generate New Hair Cells in the Postnatal Cochlea." Stem Cell Reports. 2(3): 311-322.
Bramhall, N.F. et al. (2017) Auditory Brainstem Response Altered in Humans With Noise Exposure Despite Normal Outer Hair Cell Function. Ear Hear, 38(1):e1-e12. U.S. Department of Veterans Affairs Public Access Author Manuscript, 27 pages.
Cao et al. (2016) "Targeting of the pulmonary capillary vascular niche promotes lung alveolar repair and ameliorates fibrosis". Nature Medicine, 22(2): 154-162.
Cao, H. et al. (2018) Inhibition of Wnt/β-catenin signaling suppresses myofibroblast differentiation of lung resident mesenchymal stem cells and pulmonary fibrosis. Scientific Reports, 8:13644; DOI.10.1038/s41598-018-28968-9, 14 pages.
Carlier, F.M. et al. (2020). Canonical WNT pathway is activated in the airway epithelium in chronic obstructive pulmonary disease. EBioMedicine, 61:103034; https://doi.org/10.1016/j.ebiom.2020.103034, 17 pages.
Chai et al. (2011). "Dynamic Expression of Lgr5, a Wnt Target Gene, in the Developing and Mature Mouse Cochlea." J. Assoc. Res. Otolaryngology. 12(4): 455-469.
Chang et al (2015) "Structure and functional properties of Norrin mimic Wnt for signaling with Frizzled4, Lrp5/6, and proteoglycane" Life 4 1-27.
Chen et al. (2009). "Aminoglycoside-induced histone deacetylation and hair cell death in the mouse cochlea," J. Neurochem., 108(5): 1226-1236.
Chen, H. et al. (2020) "Development of Potent, Selective Surrogate WNT Molecules and Their Application in Defining Frizzled Requirements." Cell Chem Biol 27:598-609, e594.
Chen, M. et al. (Jul. 2017) Acute inflammation regulates neuroregeneration through the NF-κB pathway in olfactory epithelium. Proceedings of the National Academy of Sciences, 114(30):8089-8094. https://doi.org/10.1073/pnas.1620664114.
Chen, X. et al. (Aug. 2016). Inhibition of Wnt/β-catenin signaling suppresses bleomycin-induced pulmonary fibrosis by attenuating the expression of TGF-β1 and FGF-2. Experimental and Molecular Pathology, 101(1):22-30. HHS Public Access Author Manuscript, 17 pages.
Chen, X. et al. (2018). The hedgehog and Wnt/β-catenin system machinery mediate myofibroblast differentiation of LR-MSCs in pulmonary fibrogenesis. Cell Death & Disease, 9:639; DOI:10.1038/s11419-018-0692-9, 15 pages.
Cheng, H. et al. (1974) Origin, differentiation and renewal of the four main epithelial cell types in the mouse small intestine. V. Unitarian theory of the origin of the four epithelial cell types. American Journal of Anatomy, 141(4):537-561.
Cheng, Z. et al. (Oct. 2011) Crystal structures of the extracellular domain of LRP6 and its complex with DKK1. Nat Struct Mol Biol, 18(11):1204-1210. NIH Public Access Author Manuscript; 20 pages.
Chilosi et al. (2003) "Aberrant Wnt/β-catenin pathway activation in idiopathic pulmonary fibrosis". The American Journal of Pathology, 162(5): 1495-1502.
Clevers et al (2012) "Wnt/b-Catenin signaling and disease" Cell, 149:1192-1205.
Conlon, T.M. et al. (Dec. 2020). Inhibition of LTβR signalling activates WNT-induced regeneration in lung. Nature, 588(7836):151-156. HHS Public Access Author Manuscript, 50 pages.
Conte et al. (2014) "Effect of pirfenidone on proliferation, TGF-β-induced myofibroblast differentiation and fibrogenic activity of primary human lung fibroblasts". European Journal of Pharmaceutical Sciences, 58: 13-19.
Cooper, H.S. et al. (1993) "Clinicopathologic study of dextran sulfate sodium experimental murine colitis" Laboratory Investigation, 69(2):238-249.
Co-pending U.S. Appl. No. 17/429,584, filed Feb. 11, 2020.
Cox et al. (2014). "Spontaneous Hair Cell Regeneration in the Neonatal Mouse Cochlea in Vivo." Development. vol. 141, No. 4, pp. 816-829.
Davidson, G. (2010) "The Cell Cycle and Wnt." Cell Cycle, 9(9):1667-1668.
De Lau, W. et al. (Aug. 2011) "Lgr5 homologues associate with Wnt receptors and mediate R-spondin signalling" Nature, 476(7360):293-297.
De Visser, K., et al. (2012) Developmental stage-specific contribution of LGR5+ cells to basal and luminal epithelial lineages in the postnatal mammary gland. J Pathol, 228:300-309.
Degryse, A. et al. (2010) Repetitive intratracheal bleomycin models several features of idiopathic pulmonary fibrosis. Am J Physiol Lung Cell Mol Physiol, 299:L442-L452.
Deng, S. et al. (2019) "Bitter peptides increase engulf of phagocytes in vitro and inhibit oxidation of myofibrillar protein in peeled shrimp (*Litopenaeus vannamei*) during chilled storage." Aquaculture Reports, 15:100234. 8 pages.
Desai et al. (2014) "Alveolar progenitor and stem cells in lung development, renewal and cancer". Nature, 507(7491): 190-194.
Deshaies, R. J. (Apr. 2020) "Multispecific drugs herald a new era of biopharmaceutical innovation." Nature, 580(7803):329-338.
Dijksterhuis et al. (2015) "Systematic mapping of Wnt-Fzd protein interactions reveals functional selectivity by distinct Wnt-Fzd pairs" The Journal of Biology Chemist 290:11 6789-6798.
Dorofeyev, A.E., et al. (2013) "Mucosal Barrier in Ulcerative Colitis and Crohn's Disease" Gastroenterology Research and Practice, 2013:431231, 9 pages.
Drucker, D. (1999) "Glucagon-like Peptide 2" TEM, 10(4):153-156.
Farin et al. (2012). "Redundant sources of Wnt regulate intestinal stem cells and promote formation ofPaneth cells," Gastroenterology, 143: 1518-1529.
Fedi, P. et al. (Jul. 1999) "Isolation and Biochemical Characterization of the Human Dkk-1 Homologue, a Novel Inhibitor of Mammalian Wnt Signaling." Journal of Biological Chemistry, 274(27):19465-19472.
Fong, Y.W. et al. (Nov. 2014) "The dyskerin ribonucleoprotein complex as an OCT4/SOX2 coactivator in embryonic stem cells" eLife, 3:e03573, 30 pages.
Fowler, T. W et al. (2021) "Development of selective bispecific Wnt mimetics for bone loss and repair." Nature Communications, 12(1):3247, pp. 1-13. https://doi.org/10.1038/s41467-021-23374-8.
Frank et al. (2016) "Emergence of a wave of Wnt signaling that regulates lung alveologenesis by controlling epithelial self-renewal and differentiation". Cell Reports, 17(9): 2312-2325.
Fuerer, C. and R. Nusse (2010) "Lentiviral Vectors to Probe and Manipulate the Wnt Signaling Pathway" PLoS One 5z92):e9370, 7 pages.
Fujii, M. et al. (Dec. 2018) "Human Intestinal Organoids Maintain Self-Renewal Capacity and Cellular Diversity in Niche-Inspired Culture Condition" Cell Stem Cell, 23:787-793.
Fujioka et al. (2015). "Manipulating cell fate in the cochlea: a feasible therapy for hearing loss." Trends Neurosci. 38, 139-44.
Gadkar, K. et al. (2015) "Design and pharmacokinetic characterization of novel antibody formats for ocular therapeutics." Investigative Ophthalmology & Visual Science, 56(9):5390-5400.
GenBank Accession No. NP_004054.3 "cadherin-17 precursor [*Homo sapiens*]" May 25, 2022, 4 pages.
GenBank Accession No. NP_005805.1 "cell surface A33 antigen precursor [*Homo sapiens*]" Jun. 3, 2022, 4 pages.
GenBank Accession No. NP_149038.3 "mucin-13 precursor [*Homo sapiens*]" Oct. 17, 2021, 4 pages.

(56) References Cited

OTHER PUBLICATIONS

"GenVec Provides Investor Update: Highlights ongoing Initiatives Involving the AdenoVerse Gene Delivery Platform" GenVec Press Release, Jan. 20, 2016, 1 page.

"GenVec Provides Update on Hearing Loss Clinical Program: Data Safety Monitoring Board Recommends Trial Continue" GenVec Press Release, May 2, 2016, 1 page.

Getz, J.A., et al., "Protease-resistant Peptide Ligands From a Knottin Scaffold Library," ACS Chemical Biology, Aug. 19, 2011, vol. 6(8), pp. 837-844.

Ghossaini, S. N., et al. (2013) "Round window membrane permeability to golimumab in guinea pigs: a pilot study." The Laryngoscope 123(11):2840-2844.

Gibbs, S. et al. (1993) Molecular Characterization and Evolution of the SPRR Family of Keratinocyte Differentiation Markers Encoding Small Proline-Rich Proteins. Genomics, 16:630-637.

Giotti et al. (2019) "Assembly of a parts list of the human mitotic cell cycle machinery" Journal of Molecular Cell Biology, 11(8):703-718.

Glinka et al. (1998) "Dickkopf-1 is a member of a new family of secreted proteins and functions in head induction." Nature, 391(6665):357-362.

Golde, et al. (2013) "γ-Secretase inhibitors and modulators." Biochimica et Biophysica Acta (BBA)-Biomembranes, 1828(12):2898-2907.

Gougelet, A., et al. (2014) "T-cell factor 4 and β-catenin chromatin occupancies pattern zonal liver metabolism in mice." Hepatology, 59(6):2344-2357. https://doi.org/10.1002/hep.26924.

Gubbels et al. (2008) "Functional auditory hair cells produced in the mammalian cochlea by in utero gene transfer." Nature, 455(7212):537-541.

Guo, L. et al. (2016) WNT/β-catenin signaling regulates cigarette smoke-induced airway inflammation via the PPARd/p38 pathway. Lab Invest, 96:218-229.

Haas, M. et al. (2019) DeltaN-Tp63 Mediates Wnt/β-Catenin-Induced Inhibition of Differentiation in Basal Stem Cells of Mucociliary Epithelia. Cell Reports, 28:3338-3352.

Habermann, A.C. et al. (Jul. 2020) Single-cell RNA sequencing reveals profibrotic roles of distinct epithelial and mesenchymal lineages in pulmonary fibrosis. Sci Adv, 6:eaba1972, 15 pages.

Haegebarth et al. (2009) "Wnt Signaling, Lgr5, and Stem Cells in the Intestine and Skin" American Journal of Pathology, 174(3):715-721.

Hao, H-X. (May 10, 2012) "ZNRF3 promotes Wnt receptor turnover in an R-spondin-sensitive manner" Nature, 485(7397):195-200.

Hawkins et al. (1976) "Hearing Loss and Cochlear Pathology in Monkeys After Noise Exposure" Acta Oto-Laryngologica 81(3-6):337-343.

Head et al. (2013) "Activation of canonical Wnt/β-catenin signaling stimulates proliferation in neuromasts in the zebrafish posterior lateral line." Developmental Dynamics 242(7):832-846.

Henderson et al. (2010) "Inhibition of Wnt/β-catenin/CREB binding protein (CBP) signaling reverses pulmonary fibrosis". Proceedings of the National Academy of Sciences, 107(32): 14309-14314.

Hirata et al. (2013) "Dose-dependent roles for canonical Wnt signalling in de novo crypt formation and cell cycle properties of the colonic epithelium" Development and Stem Cells, 140:66-75.

Ho et al. (2006) "Cysteine-Rich Domains of Muc3 Intestinal Mucin Promote Cell Migration, Inhibit Apoptosis, and Accelerate Wound Healing" Gastroenterology, 131:1501-1517.

Hollnagel, et al. (1999) "Id genes are direct targets of bone morphogenetic protein induction in embryonic stem cells." Journal of Biological Chemistry 274(28):19838-19845.

Holmen et al. (2005) "Wnt-independent activation of β-catenin mediated by a Dkk1-Fz5 fusion protein" Biochemical and Biophysical Research Communications, 328(2):533-539.

Hu et al., (2018) "Long-Term Expansion of Functional Mouse and Human Hepatocytes as 3D Organoids." Cell, 175:1591-1606, e19. doi:10.1016/j.cell.2018.11.013.

Huch et al., (2013) "In vitro expansion of single Lgr5+ liver stem cells induced by Wnt-driven regeneration." Nature 494(7436):247-250.

International Preliminary Report on Patentability for International Patent Application No. PCT/US2018/066620, dated Jun. 23, 2020, 8 pages.

Izumikawa et al. (2005). "Auditory Hair Cell Replacement and Hearing Improvement by Atoh1 Gene Therapy in Deaf Mammals." Nat Med., 11(3): 271-276.

Izumikawa et al. (2008) "Response of the flat cochlear epithelium to forced expression of Atoh1." Hearing Research, 240(1-2):52-56.

Jacques, B.E. et al. (2013) A dual function for canonical Wnt/β-catenin signaling in the developing mammalian cochlea. Development, 139:4395-4404. Erratum, Development 140:247.

Janda, C.Y. et al. (May 11, 2017) "Surrogate Wnt agonists that phenocopy canonical Wnt and β-catenin signaling" Nature, 545(7653):234-237. HHS Public Access Author Manuscript, 35 pages.

Jiang et al. (2016) "A chronic obstructive pulmonary disease susceptibility gene, FAM13A, regulates protein stability of β-catenin". American Journal of Respiratory and Critical Care Medicine, 194(2): 185-197.

Jiang, X. et al., (2015) "Dishevelled promotes Wnt receptor degradation through recruitment of ZNRF3/RNF43 E3 ubiquitin ligases." Molecular Cell, 58(3):522-533.

Jin, Y-R. and J.K. Yoon (Dec. 2012) "The R-spondin family of proteins: Emerging regulators of WNT signaling" Int J Biochem Cell Biol, 44(12):2278-2287, doi: 10.1016/j.biocel.2012.09.006.

Kahn, M. (Jul. 2014) "Can we safely target the WNT pathway?" Nature Reviews, 13(7):513-532.

Kawamoto et al. (2003). "Math1 gene transfer generates new cochlear hair cells in mature guinea pigs in vivo." Journal of Neuroscience. 23(11): 4395-400.

Ke et al. (2013) "Structure and function of Norrin in assembly and activation of a Frizzled 4-Lrp5/6 complex" Genes and Development 27(21):2305-2319; Supplement Material.

Kechai, et al. (2015) "Recent advances in local drug delivery to the inner ear." International journal of pharmaceutics, 494(1):83-101.

Kelley, M.W. (Oct. 2007) Has hair cell loss MET its match? Proc Natl Acad Sci USA, 104(42):16400-16401.

Kelly et al. (2012) "Contractility in type III cochlear fibrocytes is dependent on non-muscle myosin II and intercellular gap junctional coupling." Journal of the Association for Research in Otolaryngology, 13(4):473-484.

Kim, H.-T. et al. (Dec. 2019) WNT/RYK signaling restricts goblet cell differentiation during lung development and repair. Proc Natl Acad Sci USA, 116(51):25697-25706.

Kim, K. A. et al. (2005) "Mitogenic Influence of Human R-Spondin1 on the Intestinal Epithelium." Science, 309(5738):1256-1259. https://doi.org/10.1126/science.1112521.

Kim, T.H. et al. (2011). Blockade of the Wnt/β-Catenin Pathway Attenuates Bleomycin-Induced Pulmonary Fibrosis. Tohoku Journal of Experimental Medicine, 223:45-54.

Kim, Y. S. et al. (2010) "Intestinal Goblet Cells and Mucins in Health and Disease: Recent Insights and Progress" Current Gastroenterology Rep, 12:319-330.

Kinchen et al. (2018) "Structural remodeling of the human colonic mesenchyme in inflammatory bowel disease." Cell, 175(2):372-386.

King et al. (2011) Idiopathic pulmonary fibrosis:. The Lancet, 378(9807): 1949-1961.

Kipp, A., et al. (2007)."Activation of the glutathione peroxidase 2 (GPx2) promoter by β-catenin." Biological Chemistry, 388(10):1027-1033. https://doi.org/10.1515/BC.2007.137.

Kneidinger et al. (2011) "Activation of the WNT/β-catenin pathway attenuates experimental emphysema". American Journal of Respiratory and Critical Care Medicine, 183(6): 723-733.

Knight, M.N. and K. Hankenson (2014) "R-spondins: Novel matricellular regulators of the skeleton" Matrix Biology, 37:157-161.

Königshoff, M. et al. (May 2008) Functional Wnt Signaling Is Increased in Idiopathic Pulmonary Fibrosis. PLoS ONE, 3(5):e2142; doi:10.1371/journal.pone.0002142, 12 pages.

(56) References Cited

OTHER PUBLICATIONS

Kobayashi et al. (2020) "Persistence of a regeneration-associated, transitional alveolar epithelial cell state in pulmonary fibrosis". Nature Cell Biology, 22(8): 934-946.

Koo, B.K. et al. (2012) "Tumour suppressor RNF43 is a stem-cell E3 ligase that induces endocytosis of Wnt receptors." Nature, 488:665-669.

Kraft et al. (2013) "Atoh1 induces auditory hair cell recovery in mice after ototoxic injury." The Laryngoscope, 123(4):992-999.

Krausova et al. (2014) "Wnt signaling in adult intestinal stem cells and cancer." Cellular Signalling, 26(3):570-579. https://doi.org/10.1016/j.cellsig.2013.11.032.

Kruis, W. et al. (2019) Budesonide Suppositories Are Effective and Safe for Treating Acute Ulcerative Proctitis. Clin Gastroenterol Hepatol, 17:98-106.

Kumagai, K. et al. (Dec. 2010) Up-regulation of EGF receptor and its ligands, AREG, EREG, and HB-EGF in oral lichen planus. Oral Surg Oral Med Oral Pathol Oral Radiol Endod, 110(6):748-754.

Kuo et al. (2015). "In Vivo Cochlear Hair Cell Generation and Survival by Coactivation of beta-Catenin and Atohl." Journal of Neuroscience, vol. 35, No. 30, p. 10786-10798.

Kyritsis, N. et al. (2012) "Acute Inflammation Initiates the Regenerative Response in the Adult Zebrafish Brain." Science, 338(6112):1353-1356. https://doi.org/10.1126/science.1228773.

Lam et al. (2014) "Wnt coreceptor Lrp5 is a driver of idiopathic pulmonary fibrosis". American Journal of Respiratory and Critical Care Medicine, 190(2): 185-195.

Lebensohn et al. (2018) "R-spondins can potentiate WNT signaling without LGRs." Elife 7:e33126, 1-18 pages.

Lehrnbecher et al., (1999)"Variant genotypes of the low-affinity Fcγ receptors in two control populations and a review of low-affinity Fcγ receptor polymorphisms in control and disease populations." Blood, The Journal of the American Society of Hematology, 94(12):4220-4232.

Lim, X, et al., (2013) "Interfollicular epidermal stem cells self-renew via autocrine Wnt signaling." Science, 342(6163):1226-1230.

Liu et al. (2012) "Age-dependent in vivo conversion of mouse cochlear pillar and Deiters' cells to immature hair cells by Atoh1 ectopic expression." Journal of Neuroscience. 32(19):6600-6610.

Liu et al. (2014) "In vivo generation of immature inner hair cells in neonatal mouse cochleae by ectopic Atoh1 expression." PloS one, 9(2):e89377, 12 pages.

Liu, J. et al. (2005) "A small-molecule agonist of the Wnt signaling pathway" Angew. Chem. Int. Ed., 44(13):1987-1990.

Mah, A.T. et al. (2016). Wnt pathway regulation of intestinal stem cells. Journal of Physiology, 594(17):4837-4847. https://doi.org/10.1113/JP271754.

Mahtouk, K. et al. (2005). Expression of EGF-family receptors and amphiregulin in multiple myeloma. Amphiregulin is a growth factor for myeloma cells. Oncogene, 24:3512-3524.

Mao, B. et al. (May 2001) LDL-receptor-related protein 6 is a receptor for Dickkopf proteins. Nature 411:321-325.

Mao, B. et al. (Jun. 2002) Kremen proteins are Dickkopf receptors that regulate Wnt/beta-catenin signalling. Nature, 417:664-667.

Markovic, M.A. and P.L. Brubaker (2019). The roles of glucagon-like peptide-2 and the intestinal epithelial insulin-like growth factor-1 receptor in regulating microvillus length. Scientific Reports, 9:13010, 13 pages.

McCann, K.L. et al. (2020). H/ACA snoRNA levels are regulated during stem cell differentiation. Nucleic Acids Research, 48(15):8686-8703. https://doi.org/10.1093/nar/gkaa612.

McLean et al. (2017). "Clonal Expansion of Lgr5-Positive Cells from Mammalian Cochlea and High-Purity Generation of Sensory Hair Cells." Cell Reports, vol. 18, No. 8, p. 1917-1929.

Meteoglu, I. et al. (2008) Id-I: Regulator of EGFR and VEGF and potential target for colorectal cancer therapy. J Exp Clin Cancer Res, 27:69, doi:10.1186/1756-9966-27-69; 7 pages.

Mikels et al. (2006) "Wnts as ligands: processing, secretion and reception" Oncogene, 25:7461-7468.

Milstein, C. et al. (Oct. 6, 1983). "Hybrid Hybridomas and Their Use in Immunohistochemistry," Nature, vol. 305, pp. 537-539.

Minear Steven et al, "Wnt proteins promote bone regeneration.", Science Translational Medicine Apr. 28, 2010, (Apr. 28, 2010), vol. 2, No. 29, ISSN 1946-6242, p. 29ra30, XP055449646.

Mitchell et al (1989) "Alpha-smooth muscle actin in parenchymal cells of bleomycin-injured rat lung". Laboratory Investigation; A Journal of Technical Methods and Pathology, 60(5): 643-650.

Mizutari et al. (2014). "Spontaneous Recovery of Cochlear Fibrocytes After Severe Degeneration Caused by Acute Energy Failure." Frontiers in Phamcacology, vol. 5, No. 198, pp. 1-3.

Molenaar, M. et al. (Aug. 1996) XTcf-3 Transcription Factor Mediates beta-Catenin-Induced Axis Formation in Xenopus Embryos. Cell, 86:391-399.

Murthy et al. (2022) "Human distal lung maps and lineage hierarchies reveal a bipotent progenitor". Nature, 604(7904): 111-119.

Muyldermans, S. (2013) Nanobodies: Natural Single-Domain Antibodies. Annu Rev Biochem, 82:775-797.

Nabhan, A.N. et al. (Mar. 2018). A single cell Wnt signaling niches maintain stemness of alveolar type 2 cells. Science, 359(6380):1118-1123. HHS Public Access Author Manuscript, 28 pages.

Nishino, J. et al. (Oct. 2008) Hmga2 Promotes Neural Stem Cell Self-Renewal in Young but Not Old Mice by Reducing p16lnk4a and p19Arf Expression. Cell, 135(2):227-239. https://doi.org/10.1016/j.cell.2008.09.017.

Nusse, R. (2005) "Wnt signaling in disease and in development" Cell Research, 15(1):28-32.

Oesterle, E.C. et al. (2008) Sox2 and Jagged1 Expression in Normal and Drug-Damaged Adult Mouse Inner Ear. J Assoc Res Otolaryngol (JARO), 9(1):65-89.

Pan, S. et al. (Jun. 2013) Lentivirus carrying the Atoh1 gene infects normal rat cochlea. 8(17):1551-1559.

Parisi, S. et al. (2020). HMGA Proteins in Stemness and Differentiation of Embryonic and Adult Stem Cells. International Journal of Molecular Sciences, 21(1):362, 17 pages. https://doi.org/10.3390/ijms21010362.

Park, J-S. et al. (2014) Human AP Endonuclease 1: A Potential Marker for the Prediction of Environmental Carcinogenesis Risk. Oxidative Medicine and Cellular Longevity, 2014:730301, http://dx.doi.org/10.1155/2014/730301, 15 pages.

Park, S-W. et al. (Apr. 2009) The protein disulfide isomerase AGR2 is essential for production of intestinal mucus. PNAS USA, 106(17):6950-6955.

Pavlovic, Z. et al. (2018) A synthetic anti-Frizzled antibody engineered for broadened specificity exhibits enhanced anti-tumor properties. mAbs,10(8):1157-1167, DOI: 10.1080/19420862.2018.1515565.

Pinto, D. et al. (2003) Canonical Wnt signals are essential for homeostasis of the intestinal epithelium. Genes & Dev, 17:1709-1713.

Powell, A.E. et al. (Mar. 2012). The Pan-ErbB Negative Regulator Lrig1 Is an Intestinal Stem Cell Marker that Functions as a Tumor Suppressor. Cell, 149(1):146-158. https://doi.org/10.1016/j.cell.2012.02.042.

Rey, J-P. et al. (2010) "Wnt modulators in biotech pipeline" Developmental Dynamics, 239(1):102-114.

Reyfman, P.A. et al. (Jun. 2019) Single-Cell Transcriptomic Analysis of Human Lung Provides Insights into the Pathobiology of Pulmonary Fibrosis. American Journal of Respiratory and Critical Care Medicine, 199(12):1517-1536.

Rock et al. (2011) "Multiple stromal populations contribute to pulmonary fibrosis without evidence for epithelial to mesenchymal transition". Proceedings of the National Academy of Sciences, 108(52): E1475-E1483.

Ruzinova, M.B. and R. Benezra (Aug. 2003) Id proteins in development, cell cycle and cancer. Trends Cell Biol, 13(8):410-418.

Safdari Y., et al., "Antibody Humanization Methods—A Review and Update," Biotechnology and Genetic Engineering Reviews, Aug. 2013, vol. 29, No. 2, pp. 175-186.

Santos, A.J.M. et al. (Dec. 2018) The Intestinal Stem Cell Niche: Homeostasis and Adaptations. Trends in Cell Biol, 28(12):1062-1078, https://doi.org/10.1016/j.tcb.2018.08.001.

(56) References Cited

OTHER PUBLICATIONS

Schaefer, W. et al. (Jul. 2011) Immunoglobulin domain crossover as a generic approach for the produciton of bispecific IgG antibodies. Proc Natl Acad Sci USA, 108(27):11187-11192.
Schmid, A. et al. (2017) Modulation of Wnt signaling is essential for the differentiation of ciliated epithelial cells in human airways. FEBS Lett, 591:3493-3506.
Schuijers et al. (2012) Adult mammalian stem cells: the role of Wnt, Lgr5 and R-spondins. EMBO J, 31:2685-2696.
Schutgens, F. et al. (Mar. 2019) Tubuloids derived from human adult kidney and urine for personalized disease modeling. Nat Biotechnol, 37(3):303-313; doi: 10.1038/s41587-019-0048-8. Epub Mar. 4, 2019. PMID: 30833775.
Schwitalla, S. et al. (Jan. 2013) Intestinal Tumorigenesis Initiated by Dedifferentiation and Acquisition of Stem-Cell-like Properties. Cell, 152(1-2):25-38; https://doi.org/10.1016/j.cell.2012.12.012.
ScienceDaily (Aug. 27, 2019) "Researchers engineer antibodies that unlock body's regenerative potential" University of Toronto—Leslie Dan Faculty of Pharmacy [online]. Retrieved Mar. 28, 2021 from: www.sciencedaily.com/releases/2019/08/190827084747.htm, 3 pages.
Sebastian et al. (2017) "Wnt co-receptors Lrp5 and Lrp6 differentially mediate Wnt3a signaling in osteoblasts" PLoS One 12:11 1-19.
Semenov, M.V. et al. (2001) Head inducer Dickkopf-1 is a ligand for Wnt coreceptor LRP6. Curr Biol, 11:951-961.
Shi, F. et al. (Jul. 2012) Wnt-Responsive Lgr5-Expresesing Stem Cells Are Hair Cell Progenitors in the Cochlea. J Neurosci, 32(28):9639-9648.
Shi, J. et al. (2017). Distinct Roles of Wnt/ β-Catenin Signaling in the Pathogenesis of Chronic Obstructive Pulmonary Disease and Idiopathic Pulmonary Fibrosis. Mediators of Inflammation, vol. 2017, Article ID 3520581, 16 pages.
Shi, S.Y., et al., "A biparatopic agonistic antibody that mimics fibroblast growth factor 21 ligand activity" Journal of Biological Chemistry (2018) 293(16):5909-5919.
Simillie, B. et al. (Jul. 2019). Intra- and Inter-cellular Rewiring of the Human Colon during Ulcerative Colitis. Cell, 178(3):714-730; https://doi.org/10.1016/j.cell.2019.06.029.
Skronska-Wasek, W. et al. (Jul. 2017). Reduced Frizzled Receptor 4 Expression Prevents WNT/β-Catenin-driven Alveolar Lung Repair in Chronic Obstructive Pulmonary Disease. American Journal of Respiratory and Critical Care Medicine, 196(2):172-185.
Spanjer et al. (2016) "TGF-β-induced profibrotic signaling is regulated in part by the WNT receptor Frizzled-8". The FASEB Journal, 30(5): 1823-1835.
Spiess, C. et al., "Alternative molecular formats and therapeutic applications for bispecific antibodies," Molecular Immunology, Oct. 2015, 67:95-106.
Staerz, U.D. et al. Apr. 1985) Hybrid antibodies can target sites for attack by T cells. Nature, 314(6012):628-631.
Strunz, M. et al. (2020). Alveolar regeneration through a Krt8+ transitional stem cell state that persists in human lung fibrosis. Nat Commun, 11:3559; https://doi.org/10.1038/s41467-020-17358-3, 20 pages.
Svensson, F. et al. (2018). The central exons of the human MUC2 and MUC6 mucins are highly repetitive and variable inn sequence between individuals. Scientific Reports, 8:17503, DOI:10.1038/s41598-015-35499-w; 10 pages.
Takahashi et al. (2020). Stem Cell Signaling Pathways in the Small Intestine. Int J Mol Sci, 21:2032, doi:10.3390/ijms21062032; 18 pages.
Tao, Y. et al. (2019) "Tailored tetravalent antibodies potently and specifically activate Wnt/Frizzled pathways in cells, organoids and mice" eLife, 8:046134, DOI: https://doi.org/10.7554/eLife.46134, 16 pages.
Tian, H. et al. (Oct. 2011) A reserve stem cell population in small intestine renders Lgr5-positive cells dispensable. Nature, 478:255-259, with Methods, 1 page; Corrigendum, 482:120 (Feb. 2012).
Tomita, H. et al. (2016) Aldehyde dehydrogenase 1A1 in stem cells and cancer. Oncotarget, 7(10):11018-11032.
Tu, S. et al. (2018) The role of Foxq1 in proliferation of human dental pulp stem cell. Biochem Biophys Res Commun, 497:543-549.
Ulsamer, A. et al. (Feb. 2012) Axin Pathway Activity Regulates in Vivo pY654-β-catenin Accumulation and Pulmonary Fibrosis. J Biol Chem, 287(7):5164-5172.
Van Der Post, S. et al. (2019) Structural weakening of the colonic mucus barrier is an early event in ulcerative colitis pathogenesis. 68:2142-2151.
Vincke, C. and S. Muyldermans (2012) "Introduction to heavy chain antibodies and derived Nanobodies" Methods Mol Biol, 911:15-26, doi: 10.1007/978-1-61779-968-6_2.
Vincke, C. et al., "General strategy to humanize a camelid single-domain antibody and identification of a universal humanized nanobody scaffold", J Biol Chem. (2009); 284(5):3273-3284.
Wang, R. et al. (2011) Down-Regulation of the Canonical Wnt β-Catenin Pathway in the Airway Epithelium of Healthy Smokers and Smokers with COPD. PLoS ONE, 6(4):e14793; doi:10.1371/journal.pone.0014793.
Wang, T. et al. (Apr. 2015) Lgr5+ cells regenerate hair cells via proliferation and direct transdifferentiation in damaged neonatal mouse utricle. Nat Commun, 6:6613; DOI: 10.1038/ncomms7613, 15 pages.
Wang, X. et al. (2015) Blocking the Wnt/β-Catenin Pathway by Lentivirus-Mediated Short Hairpin RNA Targeting β-Catenin Gene Suppresses Silica-Induced Lung Fibrosis in Mice. Int J Environ Res Public Health, 12:10739-10754.
Wang, X. et al. (2018) IgG Fc engineering to modulate antibody effector functions. Protein Cell, 9:63-73.
Wang, Z. et al. (2019) Wnt Signaling in vascular eye diseases. Prog Retin Eye Res, 70:110-133.
Wehkamp, J. et al. (2007) "The Paneth cell alpha-defensin deficiency of ileal Crohn's disease is linked to Wnt/Tcf-4" J Immunol, 179:3109-3118.
Wirtz, S. et al. (2017). Chemically induced mouse models of acute and chronic intestinal inflammation. Nature Protocols, 12(7), 1295-1309. https://doi.org/10.1038/nprot.2017.044.
Wong et al. (2015). "Mechanisms of sensorineural cell damage, death and survival in the cochlea." Frontiers in Aging Neuroscience. vol. 7, Article 58, pp. 1-15.
Wu, C. et al. "Simultaneous targeting of multiple disease mediators by a dual-variable-domain immunoglobulin", Nat Biotechnol. Nov. 2007;25(11):1290-7.
Wu et al. (2013). "In vivo delivery of Atoh1 gene to rat cochlea using a dendrimer-based nanocarrier." Journal of biomedical nanotechnology. 9(10): 1736-45.
Xie, Y. et al. (Oct. 2013) "Interaction with both ZNRF3 and LGR4 is required for the signalling activity of R-spondin" EMBO Reports, 14(12):1120-1126.
Xu et al. (2016) "Single-cell RNA sequencing identifies diverse roles of epithelial cells in idiopathic pulmonary fibrosis". JCI Insight, 1(20): 1-19.
Yan, K.S. et al. (May 2017). Non-equivalence of Wnt and R-spondin ligands during Lgr5+ intestinal stem-cell self-renewal. Nature, 545(7653):238-242. doi:10.1038/nature22313; HHS Public Access Author Manuscript, 36 pages.
Zacharias et al. (2018) "Regeneration of the lung alveolus by an evolutionarily conserved epithelial progenitor". Nature, 555(7695): 251-255.
Zapata, G. et al. (1995) Engineering linear F(ab')2 fragments for efficient production in *Escherichia coli* and enhanced antiproferative activity. Protein Eng. 8( 10): 1057-1062.
Zatorski, H. et al. (2019) Role of glucagon-like peptides in inflammatory bowel diseases-current knowledge and future perspectives. Nauryn-Schmiedeberg's Archives of Pharmacology, 392:1321-1330.
Zepp et al. (2017) "Distinct mesenchymal lineages and niches promote epithelial self-renewal and myofibrogenesis in the lung". Cell, 170(6): 1134-1148.

(56) References Cited

OTHER PUBLICATIONS

Zhang et al. (2014) "3D structural fluctuation of IgG1 antibody revealed by individual particle electron tomography" Scientific Reports 5:09803 1-13.

Zhang, M. et al. (Mar. 2020) Targeting the Wnt signaling pathway through R-spondin 3 identifies an anti-fibrosis treatment strategy for multiple organs. PLoS One, 15(3):e0229445.

Zhang, S. et al. (Jul. 2019) Frizzled-9+ Supporting Cells Are Progenitors for the Generation of Hair Cells in the Postnatal Mouse Cochlea. Front Mol Neurosci, 12:184, doi:10.3389/fnmol.2019.00184, 11 pages.

Zhang, T. et al. (2018) Overexpression of FOXQ1 enhances anti-senescence and migration effects of human umbilical cord mesenchymal stem cells in vitro and in vivo. Cell and Tissue Research, 373:379-393.

Zhao, J. et al. (2007). R-spondin1, A Novel Intestinotrophic Mitogen, Ameliorates Experimental Colitis in Mice. Gastroenterology, 132(4):1331-1343. https://doi.org/10.1053/j.gastro.2007.02.001.

Zheng, W. et al. (2006) Evaluation of AGR2 and AGR3 as cadidate genes for inflammatory bowel disease. Genes and Immunity, 7:11-18.

Zhou, B. et al. (Nov. 2020) The angiocrine Rspondin3 instructs interstitial macrophage transition via metabolic-epigenetic reprogramming and resolves inflammatory injury. Nat Immunol, 21:1430-1443, with Methods, 14 pages.

Rong, Chen (2016) "Research progress of Wnt/ ß -Catenin signaling pathway—specific molecular targeted drugs". J. Mod. Med. Health, 32(5):700-702, with Google Translation. doi: 10.3969/j.issn.1009-5519.2016.05.022.

Xiao, Sa , et al., "Establishment of long-term serum-free culture for lacrimal gland stem cells aiming at lacrimal gland repair," Stem Cell Research & Therapy, (Jan. 8, 2020), 11:20, 13 pages.

\* cited by examiner

```
                    SEQUENCE LISTING

<160> NUMBER OF SEQ ID NOS: 621

<210> SEQ ID NO 1
<211> LENGTH: 124
<212> TYPE: PRT
<213> ORGANISM: Artificial Sequence
<220> FEATURE:
<223> OTHER INFORMATION: Made in lab - synthesized variable heavy chain

<400> SEQUENCE: 1

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Ser Trp Phe Arg Gln Ala Pro Gly Lys Glu Arg Glu Phe Val
        35                  40                  45
```

```
Ala Val Ile Gly Arg Ser Gly Gly Ile Lys Tyr Tyr Ala Asp Ser Val
         50                  55                  60

Lys Gly Arg Phe Thr Ile Ser Arg Asp Asn Thr Ile Asn Thr Val Tyr
 65                  70                  75                  80

Leu Gln Met Asn Asn Leu Thr Pro Glu Asp Thr Ala Ile Tyr Tyr Cys
                 85                  90                  95

Ala Thr Arg Arg Pro Phe Asn Ser Tyr Asn Thr Glu Gln Ser Tyr Asp
            100                 105                 110

Ser Trp Gly Arg Gly Thr Leu Val Thr Val Ser Ser
            115                 120

<210> SEQ ID NO 2
<211> LENGTH: 121
<212> TYPE: PRT
<213> ORGANISM: Artificial Sequence
<220> FEATURE:
<223> OTHER INFORMATION: Made in lab - synthesized variable heavy chain

<400> SEQUENCE: 2

Ala Val Gln Leu Val Glu Ser Gly Gly Gly Leu Val Gln Ala Gly Gly
 1               5                  10                  15

Ser Leu Arg Leu Ser Cys Gly Val Ser Gly Ser Ile Phe Ser Ile Tyr
                 20                  25                  30

Ala Met Gly Trp Tyr Arg Gln Ala Pro Gly Lys Glu Arg Glu Leu Val
             35                  40                  45

Ala Val Ile Thr Ser Gly Gly Lys Thr Val Tyr Ala Asp Ser Val Lys
         50                  55                  60

Gly Arg Phe Thr Ile Thr Glu Asp Ala Ala Lys Asn Thr Val Tyr Leu
 65                  70                  75                  80

Gln Met Asn Ser Leu Lys Ala Glu Asp Thr Ala Val Tyr Tyr Cys Tyr
                 85                  90                  95

Ala Asp Ser Arg Ser Ser Trp Tyr Asp Glu Tyr Leu Glu His Trp Gly
            100                 105                 110

Arg Gly Thr Leu Val Thr Val Ser Ser
            115                 120

<210> SEQ ID NO 3
<211> LENGTH: 119
<212> TYPE: PRT
<213> ORGANISM: Artificial Sequence
<220> FEATURE:
<223> OTHER INFORMATION: Made in lab - synthesized variable heavy chain

<400> SEQUENCE: 3

Gln Val Gln Leu Val Glu Ser Gly Gly Gly Leu Val Gln Ala Gly Asp
 1               5                  10                  15

Ser Leu Arg Leu Ser Cys Val Val Ser Gly Arg Thr Phe Ser Val Tyr
                 20                  25                  30

Gly Val Gly Trp Phe Arg Gln Ala Pro Gly Lys Glu Arg Glu Val Val
             35                  40                  45

Ala Ala Val Ser Ala Ser Gly Gly Tyr Thr Trp Tyr Ala Asp Ser Val
         50                  55                  60

Lys Gly Arg Phe Thr Ile Ser Arg Asp Asn Ala Lys Ser Thr Ala Phe
 65                  70                  75                  80

Leu Gln Met Asn Ser Leu Gln Pro Glu Asp Thr Ala Val Tyr Tyr Cys
                 85                  90                  95

Lys Ala Ala Pro Arg Trp Gly Gly Ala Thr Ala Tyr Trp Gly Gln Gly
```

```
                100                 105                 110
Thr Gln Val Thr Val Ser Ser
        115

<210> SEQ ID NO 4
<211> LENGTH: 119
<212> TYPE: PRT
<213> ORGANISM: Artificial Sequence
<220> FEATURE:
<223> OTHER INFORMATION: Made in lab - synthesized variable heavy chain

<400> SEQUENCE: 4

Asp Val Gln Leu Val Glu Ser Gly Gly Gly Leu Val Gln Pro Gly Gly
1               5                   10                  15

Ser Leu Arg Leu Ser Cys Ala Ala Pro Gly Ser Ile Phe Ser Asp Gly
            20                  25                  30

Ala Met Gly Trp Tyr Arg Gln Ala Pro Gly Lys Gln Arg Glu Leu Val
        35                  40                  45

Ala Val Ile Ser Gly Gly Arg Thr Gly Tyr Ala Asp Phe Val Lys Gly
    50                  55                  60

Arg Phe Thr Ile Ser Arg Asp Asn Gly Lys Asn Thr Val Asn Leu Gln
65                  70                  75                  80

Met Asn Arg Leu Glu Pro Glu Asp Thr Ala Val Tyr Phe Cys Asn Thr
                85                  90                  95

Tyr Pro Phe Pro Ile Tyr Lys Lys Gly Tyr Pro Phe Trp Gly Gln Gly
            100                 105                 110

Thr Gln Val Thr Val Ser Ser
        115

<210> SEQ ID NO 5
<211> LENGTH: 124
<212> TYPE: PRT
<213> ORGANISM: Artificial Sequence
<220> FEATURE:
<223> OTHER INFORMATION: Made in lab - synthesized variable heavy chain

<400> SEQUENCE: 5

Asp Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Ser Trp Phe Arg Gln Ala Pro Gly Lys Glu Arg Glu Phe Val
        35                  40                  45

Ala Val Ile Gly Arg Ser Gly Gly Ile Lys Tyr Tyr Ala Asp Ser Val
    50                  55                  60

Lys Gly Arg Phe Thr Ile Ser Arg Asp Asn Thr Ile Asn Thr Val Tyr
65                  70                  75                  80

Leu Gln Met Asn Asn Leu Thr Pro Glu Asp Thr Ala Ile Tyr Tyr Cys
                85                  90                  95

Ala Thr Arg Arg Pro Phe Asn Ser Tyr Asn Thr Glu Gln Ser Tyr Asp
            100                 105                 110

Ser Trp Gly Arg Gly Thr Leu Val Thr Val Ser Ser
        115                 120

<210> SEQ ID NO 6
<211> LENGTH: 121
<212> TYPE: PRT
<213> ORGANISM: Artificial Sequence
<220> FEATURE:
```

<223> OTHER INFORMATION: Made in lab - synthesized variable heavy chain

<400> SEQUENCE: 6

Asp Val Gln Leu Val Glu Ser Gly Gly Gly Leu Val Gln Ala Gly Glu
1               5                   10                  15

Ser Leu Arg Leu Ser Cys Ala Ala Ser Gly Ser Ile Phe Ser Ile Asn
            20                  25                  30

Thr Met Gly Trp Tyr Arg Gln Ala Pro Gly Lys Glu Arg Glu Leu Val
        35                  40                  45

Ala Val Ile Thr Ser Gly Gly Lys Thr Val Tyr Ala Asp Ser Val Lys
    50                  55                  60

Gly Arg Phe Thr Ile Thr Glu Asp Ala Ala Lys Asn Thr Val Tyr Leu
65                  70                  75                  80

Gln Met Asn Ser Leu Lys Ala Glu Asp Thr Ala Val Tyr Tyr Cys Tyr
                85                  90                  95

Ala Asp Ser Arg Ser Ser Trp Tyr Asp Glu Tyr Leu Glu His Trp Gly
            100                 105                 110

Gln Gly Thr Leu Val Thr Val Ser Ser
        115                 120

<210> SEQ ID NO 7
<211> LENGTH: 122
<212> TYPE: PRT
<213> ORGANISM: Artificial Sequence
<220> FEATURE:
<223> OTHER INFORMATION: Made in lab - synthesized variable heavy chain

<400> SEQUENCE: 7

Ala Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser Ala Tyr
            20                  25                  30

Asp Met Gly Trp Phe Arg Gln Ala Pro Gly Lys Glu Arg Glu Leu Val
        35                  40                  45

Gly Gly Ile Arg Trp Ser Gly Gly Thr Thr Leu Tyr Pro Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Ser Ala Val Tyr Tyr Cys
                85                  90                  95

Tyr Ala Arg Thr Val Ile Gly Gly Phe Gly Ala Phe Arg Ala His Trp
            100                 105                 110

Gly Gln Gly Thr Gln Val Thr Val Ser Ser
        115                 120

<210> SEQ ID NO 8
<211> LENGTH: 119
<212> TYPE: PRT
<213> ORGANISM: Artificial Sequence
<220> FEATURE:
<223> OTHER INFORMATION: Made in lab - synthesized variable heavy chain

<400> SEQUENCE: 8

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Met Ile Asn
            20                  25                  30

Thr Met Ala Trp Tyr Arg Gln Ala Pro Gly Asn Gln Arg Glu Leu Val

```
                35                  40                  45

Ala Thr Ile Arg Pro Val Val Ser Glu Thr Thr Tyr Ala Asp Ala Val
             50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Ser Glu Asp Thr Ala Ile Tyr Tyr Cys
                 85                  90                  95

Asn Ala Lys Arg Pro Trp Gly Thr Arg Asp Glu Tyr Trp Gly Gln Gly
            100                 105                 110

Thr Leu Val Thr Val Ser Ser
            115

<210> SEQ ID NO 9
<211> LENGTH: 122
<212> TYPE: PRT
<213> ORGANISM: Artificial Sequence
<220> FEATURE:
<223> OTHER INFORMATION: Made in lab - synthesized variable heavy chain

<400> SEQUENCE: 9

Gln Val Lys Leu Glu Glu Ser Gly Gly Gly Leu Val Gln Pro Gly Gly
 1               5                  10                  15

Ser Leu Arg Leu Ser Cys Glu Thr Ser Ala Thr Ile Val Ser Ile Tyr
             20                  25                  30

Arg Ile Asn Trp Tyr Arg Gln Ala Pro Gly Lys Gln Arg Glu Trp Val
             35                  40                  45

Ala Gly Ile Thr Ser Ser Gly Arg Thr Ile Tyr Ala Asp Ser Val Lys
         50                  55                  60

Gly Arg Phe Thr Ile Ser Arg Asp Asn Ala Lys Asn Thr Val Tyr Leu
 65                  70                  75                  80

Gln Met Asn Asn Leu Lys Pro Glu Asp Thr Ala Val Tyr Tyr Cys Asn
                 85                  90                  95

Ala Ala Ser Thr Val Thr Ala Trp Pro Tyr Tyr Gly Pro Asp Tyr Trp
            100                 105                 110

Gly Lys Gly Thr Leu Val Thr Val Ser Ser
            115                 120

<210> SEQ ID NO 10
<211> LENGTH: 119
<212> TYPE: PRT
<213> ORGANISM: Artificial Sequence
<220> FEATURE:
<223> OTHER INFORMATION: Made in lab - synthesized variable heavy chain

<400> SEQUENCE: 10

Asp Val Gln Leu Val Glu Ser Gly Gly Gly Leu Val Gln Ala Gly Gly
 1               5                  10                  15

Ser Leu Arg Leu Ala Cys Ala Gly Ser Gly Arg Ile Phe Ala Ile Tyr
             20                  25                  30

Asp Ile Ala Trp Tyr Arg His Pro Pro Gly Asn Gln Arg Glu Leu Val
             35                  40                  45

Ala Met Ile Arg Pro Val Val Thr Glu Ile Asp Tyr Ala Asp Ser Val
         50                  55                  60

Lys Gly Arg Phe Thr Ile Ser Arg Asn Asn Ala Met Lys Thr Val Tyr
 65                  70                  75                  80

Leu Gln Met Asn Asn Leu Lys Pro Glu Asp Thr Ala Val Tyr Tyr Cys
                 85                  90                  95
```

Asn Ala Lys Arg Pro Trp Gly Ser Arg Asp Glu Tyr Trp Gly Gln Gly
            100                 105                 110

Thr Gln Val Thr Val Ser Ser
        115

<210> SEQ ID NO 11
<211> LENGTH: 124
<212> TYPE: PRT
<213> ORGANISM: Artificial Sequence
<220> FEATURE:
<223> OTHER INFORMATION: Made in lab - synthesized variable heavy chain

<400> SEQUENCE: 11

Ala Val Gln Leu Val Glu Ser Gly Gly Gly Val Val Gln Ala Gly Asp
1               5                   10                  15

Ser Leu Thr Leu Ser Cys Thr Met Ser Gly Arg Ser Leu Ser Ser Phe
            20                  25                  30

Ala Met Gly Trp Phe Arg Arg Ala Pro Gly Lys Glu Arg Glu Phe Val
        35                  40                  45

Ala Arg Ile Ser Arg Gly Asp Gly Tyr Thr Asp Glu Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Val Gly Pro Glu Asp Thr Ala Val Tyr His Cys
                85                  90                  95

Ala Ala Val Gln Ala Val Ile Gly Gly Thr Leu Thr Thr Ala Tyr Asp
            100                 105                 110

Tyr Trp Gly Gln Gly Thr Leu Val Thr Val Ser Ser
        115                 120

<210> SEQ ID NO 12
<211> LENGTH: 124
<212> TYPE: PRT
<213> ORGANISM: Artificial Sequence
<220> FEATURE:
<223> OTHER INFORMATION: Made in lab - synthesized variable heavy chain

<400> SEQUENCE: 12

Glu Val Gln Leu Val Glu Ser Gly Gly Gly Leu Val Gln Ala Gly Gly
1               5                   10                  15

Ser Leu Arg Val Ser Cys Ala Ala Ser Gly Gly Thr Phe Ser Arg Tyr
            20                  25                  30

His Met Gly Trp Phe Arg Gln Ala Pro Gly Lys Glu Arg Glu Phe Val
        35                  40                  45

Ser Ala Ile Thr Trp Ser Gly Gly Arg Thr Tyr Tyr Ala Asp Phe Val
    50                  55                  60

Lys Gly Arg Phe Thr Ile Ser Arg Asp Asp Ala Arg Asn Thr Val Tyr
65                  70                  75                  80

Leu Gln Met Ser Ser Leu Lys Pro Glu Asp Thr Ala Val Tyr Tyr Cys
                85                  90                  95

Ala Leu Thr Trp Ala Pro Thr Pro Thr Asn Arg Arg Ser Asp Tyr Ala
            100                 105                 110

Tyr Trp Gly Gln Gly Thr Gln Val Thr Val Ser Ser
        115                 120

<210> SEQ ID NO 13
<211> LENGTH: 119
<212> TYPE: PRT
<213> ORGANISM: Artificial Sequence

```
<220> FEATURE:
<223> OTHER INFORMATION: Made in lab - synthesized variable heavy chain

<400> SEQUENCE: 13

Glu Val Gln Leu Val Glu Ser Gly Gly Gly Leu Val Gln Ala Gly Gly
1               5                   10                  15

Ser Leu Arg Leu Ala Cys Ala Gly Ser Gly Arg Ile Phe Ala Ile Tyr
            20                  25                  30

Asp Met Ala Trp Tyr Arg Gln Ala Pro Gly Asn Gln Arg Glu Leu Val
        35                  40                  45

Ala Thr Ile Arg Pro Val Val Ser Glu Thr Thr Tyr Ala Asp Ala Val
    50                  55                  60

Lys Gly Arg Phe Thr Ile Ser Arg Ser Asn Ala Met Lys Thr Val Tyr
65                  70                  75                  80

Leu Gln Met Asn Ser Leu Lys Ser Glu Asp Thr Ala Ile Tyr Tyr Cys
                85                  90                  95

Asn Ala Lys Arg Pro Trp Gly Thr Arg Asp Glu Tyr Trp Gly Gln Gly
            100                 105                 110

Thr Leu Val Thr Val Ser Ser
        115

<210> SEQ ID NO 14
<211> LENGTH: 126
<212> TYPE: PRT
<213> ORGANISM: Artificial Sequence
<220> FEATURE:
<223> OTHER INFORMATION: Made in lab - synthesized variable heavy chain

<400> SEQUENCE: 14

Ala Val Gln Leu Val Asp Ser Gly Gly Gly Leu Val Gln Ala Gly Asp
1               5                   10                  15

Ser Leu Thr Leu Ser Cys Ala Ala Ser Gly Arg Thr Phe Ser Asp Tyr
            20                  25                  30

Ser Met Gly Trp Phe Arg Gln Ala Pro Gly Lys Glu Arg Glu Phe Val
        35                  40                  45

Ala Gly Ile Ser Trp Ile Ala Asp Asn Arg Tyr Tyr Ala Asp Val Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Thr Ala Gly Arg Ser Arg Tyr Leu Tyr Gly Ser Ser Leu Asn Gly Pro
            100                 105                 110

Tyr Asp Tyr Trp Gly Gln Gly Thr Gln Val Thr Val Ser Ser
        115                 120                 125

<210> SEQ ID NO 15
<211> LENGTH: 119
<212> TYPE: PRT
<213> ORGANISM: Artificial Sequence
<220> FEATURE:
<223> OTHER INFORMATION: Made in lab - synthesized variable heavy chain

<400> SEQUENCE: 15

Ala Val Gln Leu Val Glu Ser Gly Gly Gly Leu Val Gln Ala Gly Gly
1               5                   10                  15

Ser Leu Arg Leu Ala Cys Ala Gly Ser Gly Arg Ile Phe Ala Ile Tyr
            20                  25                  30
```

```
Asp Ile Ala Trp Tyr Arg Gln Ala Pro Gly Asn Gln Arg Glu Leu Val
         35                  40                  45

Ala Thr Ile Arg Pro Val Val Ser Glu Thr Thr Tyr Ala Asp Ala Val
 50                      55                  60

Lys Gly Arg Phe Thr Ile Ser Arg Ser Asn Ala Met Lys Thr Val Tyr
 65                  70                  75                  80

Leu Gln Met Asn Ser Leu Lys Ser Glu Asp Thr Ala Ile Tyr Tyr Cys
                 85                  90                  95

Asn Ala Lys Arg Pro Trp Gly Thr Arg Asp Glu Tyr Trp Gly Gln Gly
                100                 105                 110

Thr Leu Val Thr Val Ser Ser
        115
```

```
<210> SEQ ID NO 16
<211> LENGTH: 121
<212> TYPE: PRT
<213> ORGANISM: Artificial Sequence
<220> FEATURE:
<223> OTHER INFORMATION: Made in lab - synthesized variable heavy chain

<400> SEQUENCE: 16

Ala Val Gln Leu Val Asp Ser Gly Gly Gly Leu Val Gln Ala Gly Gly
  1               5                  10                  15

Ser Leu Arg Leu Ser Cys Ala Val Ser Gly Arg Thr Phe Ser Met Tyr
             20                  25                  30

Asp Met Gly Trp Phe Arg Gln Ala Pro Gly Lys Glu Arg Glu Phe Val
         35                  40                  45

Ala Ser Ile Arg Trp Ser Ser Gly Asn Thr Trp Tyr Ala Asp Ser Met
 50                      55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Tyr Ala Asn Ile Tyr Tyr Thr Arg Arg Ala Pro Glu Glu Tyr Trp Gly
                100                 105                 110

Gln Gly Thr Leu Val Thr Val Ser Ser
        115                 120
```

```
<210> SEQ ID NO 17
<211> LENGTH: 119
<212> TYPE: PRT
<213> ORGANISM: Artificial Sequence
<220> FEATURE:
<223> OTHER INFORMATION: Made in lab - synthesized variable heavy chain

<400> SEQUENCE: 17

Glu Val Gln Leu Val Glu Ser Gly Gly Gly Leu Val Gln Pro Gly Gly
  1               5                  10                  15

Ser Leu Arg Leu Ser Cys Ala Val Ser Arg Asn Ile Phe Pro Ile Asp
             20                  25                  30

Asp Met Ser Trp Tyr Arg Gln Ala Pro Gly Lys Gln Arg Glu Leu Val
         35                  40                  45

Ala Thr Val Thr Ser Gly Gly Arg Ile Asn Tyr Ala Asp Ser Val Lys
 50                      55                  60

Gly Arg Phe Thr Ile Ser Arg Asp Gly Ala Arg Thr Ile Asp Leu
 65                  70                  75                  80

Gln Met Asn Asn Leu Lys Pro Glu Asp Thr Ala Val Tyr Tyr Cys Asn
                 85                  90                  95
```

Val Asp Arg Thr Leu Tyr Gly Lys Tyr Lys Glu Tyr Trp Gly Gln Gly
            100                 105                 110

Thr Leu Val Thr Val Ser Ser
        115

<210> SEQ ID NO 18
<211> LENGTH: 111
<212> TYPE: PRT
<213> ORGANISM: Artificial Sequence
<220> FEATURE:
<223> OTHER INFORMATION: Made in lab - synthesized variable heavy chain

<400> SEQUENCE: 18

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Ile Phe Ser Ile Tyr
            20                  25                  30

Asp Met Gly Trp Phe Arg Gln Ala Pro Gly Lys Glu Arg Glu Phe Val
        35                  40                  45

Ser Gly Ile Arg Trp Ser Gly Gly Thr Ser Tyr Ala Asp Ser Val Lys
    50                  55                  60

Gly Arg Phe Thr Ile Ser Lys Asp Asn Ala Lys Asn Thr Ile Tyr Leu
65                  70                  75                  80

Gln Met Asn Asn Leu Lys Ala Glu Asp Thr Ala Val Tyr Tyr Cys Gly
                85                  90                  95

Ser Arg Gly Tyr Trp Gly Gln Gly Thr Leu Val Thr Val Ser Ser
            100                 105                 110

<210> SEQ ID NO 19
<211> LENGTH: 119
<212> TYPE: PRT
<213> ORGANISM: Artificial Sequence
<220> FEATURE:
<223> OTHER INFORMATION: Made in lab - synthesized variable heavy chain

<400> SEQUENCE: 19

Ala Val Gln Leu Val Glu Ser Gly Gly Gly Leu Val Gln Ala Gly Gly
1               5                   10                  15

Ser Leu Arg Leu Ala Cys Ala Gly Ser Gly Arg Ile Phe Ala Ile Tyr
            20                  25                  30

Asp Ile Ala Trp Tyr Arg Gln Ala Pro Gly Asn Gln Arg Glu Leu Val
        35                  40                  45

Ala Thr Ile Arg Pro Val Val Ser Glu Thr Thr Tyr Ala Asp Ala Val
    50                  55                  60

Lys Gly Arg Phe Thr Ile Ser Arg Ser Asn Ala Met Lys Thr Val Tyr
65                  70                  75                  80

Leu Gln Met Asn Ser Leu Lys Ser Glu Asp Thr Ala Ile Tyr Tyr Cys
                85                  90                  95

Asn Ala Lys Arg Pro Trp Gly Thr Arg Asp Glu Tyr Gly Gln Gly
            100                 105                 110

Thr Leu Val Thr Val Ser Ser
        115

<210> SEQ ID NO 20
<211> LENGTH: 121
<212> TYPE: PRT
<213> ORGANISM: Artificial Sequence
<220> FEATURE:
<223> OTHER INFORMATION: Made in lab - synthesized variable heavy chain

<400> SEQUENCE: 20

Ala Val Gln Leu Val Asp Ser Gly Gly Leu Val Gln Ala Gly Gly
1               5                   10                  15

Ser Leu Arg Leu Ser Cys Ala Val Ser Gly Arg Thr Phe Ser Met Tyr
            20                  25                  30

Asp Met Gly Trp Phe Arg Gln Ala Pro Gly Lys Glu Arg Glu Phe Val
        35                  40                  45

Ala Ser Ile Arg Trp Ser Ser Gly Asn Thr Trp Tyr Ala Asp Ser Met
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Tyr Ala Asn Ile Tyr Tyr Thr Arg Arg Ala Pro Glu Glu Tyr Trp Gly
            100                 105                 110

Gln Gly Thr Leu Val Thr Val Ser Ser
        115                 120

<210> SEQ ID NO 21
<211> LENGTH: 126
<212> TYPE: PRT
<213> ORGANISM: Artificial Sequence
<220> FEATURE:
<223> OTHER INFORMATION: Made in lab - synthesized variable heavy chain

<400> SEQUENCE: 21

Glu Val Gln Leu Val Glu Ser Gly Gly Gly Leu Val Gln Ala Gly Gly
1               5                   10                  15

Ser Leu Arg Leu Ser Cys Ala Thr Ser Gly Arg Thr Phe Asn Thr Tyr
            20                  25                  30

Ala Met Gly Trp Phe Arg Gln Ala Pro Gly Lys Glu Arg Glu Phe Val
        35                  40                  45

Ala Ser Val Ser Trp Arg Tyr Asp Arg Thr Tyr Tyr Thr Asp Thr Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Phe Cys
                85                  90                  95

Ala Ala Asp Thr Asn Trp Arg Ala Gly Pro Arg Val Gly Ile Asp Glu
            100                 105                 110

Tyr Ala Tyr Trp Gly Gln Gly Thr Leu Val Thr Val Ser Ser
        115                 120                 125

<210> SEQ ID NO 22
<211> LENGTH: 119
<212> TYPE: PRT
<213> ORGANISM: Artificial Sequence
<220> FEATURE:
<223> OTHER INFORMATION: Made in lab - synthesized variable heavy chain

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Val Ser Arg Asn Ile Phe Pro Ile Asp
            20                  25                  30

Asp Met Ser Trp Tyr Arg Gln Ala Pro Gly Lys Gln Arg Glu Leu Val
        35                  40                  45

```
Ala Thr Val Thr Ser Gly Gly Arg Ile Asn Tyr Ala Asp Ser Val Lys
        50                  55                  60

Gly Arg Phe Thr Ile Ser Arg Asp Gly Ala Arg Thr Ile Asp Leu
65                  70                  75                  80

Gln Met Asn Asn Leu Lys Pro Glu Asp Thr Ala Val Tyr Tyr Cys Asn
                85                  90                  95

Val Asp Arg Thr Leu Tyr Gly Lys Tyr Lys Glu Tyr Trp Gly Gln Gly
            100                 105                 110

Thr Leu Val Thr Val Ser Ser
        115

<210> SEQ ID NO 23
<211> LENGTH: 111
<212> TYPE: PRT
<213> ORGANISM: Artificial Sequence
<220> FEATURE:
<223> OTHER INFORMATION: Made in lab - synthesized variable heavy chain

<400> SEQUENCE: 23

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Ile Phe Ser Ile Tyr
            20                  25                  30

Asp Met Gly Trp Phe Arg Gln Ala Pro Gly Lys Glu Arg Glu Phe Val
        35                  40                  45

Ser Gly Ile Arg Trp Ser Gly Gly Thr Ser Tyr Ala Asp Ser Val Lys
    50                  55                  60

Gly Arg Phe Thr Ile Ser Lys Asp Asn Ala Lys Asn Thr Ile Tyr Leu
65                  70                  75                  80

Gln Met Asn Asn Leu Lys Ala Glu Asp Thr Ala Val Tyr Tyr Cys Gly
                85                  90                  95

Ser Arg Gly Tyr Trp Gly Gln Gly Thr Leu Val Thr Val Ser Ser
            100                 105                 110

<210> SEQ ID NO 24
<211> LENGTH: 117
<212> TYPE: PRT
<213> ORGANISM: Artificial Sequence
<220> FEATURE:
<223> OTHER INFORMATION: Made in lab - synthesized variable heavy chain

<400> SEQUENCE: 24

Asp Val Gln Leu Val Glu Ser Gly Gly Gly Leu Val Gln Pro Gly Gly
1               5                   10                  15

Ser Leu Arg Leu Ser Cys Thr Ser Ser Ala Asn Ile Asn Ser Ile Glu
            20                  25                  30

Thr Leu Gly Trp Tyr Arg Gln Ala Pro Gly Lys Gln Arg Glu Leu Ile
        35                  40                  45

Ala Asn Met Arg Gly Gly Gly Tyr Met Lys Tyr Ala Gly Ser Leu Lys
        50                  55                  60

Gly Arg Phe Thr Met Ser Thr Glu Ser Ala Lys Asn Thr Met Tyr Leu
65                  70                  75                  80

Gln Met Asn Ser Leu Lys Pro Glu Asp Thr Ala Val Tyr Tyr Cys Tyr
                85                  90                  95

Val Lys Leu Arg Asp Asp Asp Tyr Val Tyr Arg Gly Gln Gly Thr Gln
            100                 105                 110

Val Thr Val Ser Ser
```

<210> SEQ ID NO 25
<211> LENGTH: 10
<212> TYPE: PRT
<213> ORGANISM: Artificial
<220> FEATURE:
<223> OTHER INFORMATION: Heavy chain CDR1

<400> SEQUENCE: 25

Gly Phe Thr Phe Ser His Tyr Thr Leu Ser
1               5                   10

<210> SEQ ID NO 26
<211> LENGTH: 17
<212> TYPE: PRT
<213> ORGANISM: Artificial
<220> FEATURE:
<223> OTHER INFORMATION: Heavy chain CDR2

<400> SEQUENCE: 26

Val Ile Ser Gly Asp Gly Ser Tyr Thr Tyr Tyr Ala Asp Ser Val Lys
1               5                   10                  15

Gly

<210> SEQ ID NO 27
<211> LENGTH: 9
<212> TYPE: PRT
<213> ORGANISM: Artificial
<220> FEATURE:
<223> OTHER INFORMATION: Heavy chain CDR3

<400> SEQUENCE: 27

Asn Phe Ile Lys Tyr Val Phe Ala Asn
1               5

<210> SEQ ID NO 28
<211> LENGTH: 11
<212> TYPE: PRT
<213> ORGANISM: Artificial
<220> FEATURE:
<223> OTHER INFORMATION: Light chain CDR1

<400> SEQUENCE: 28

Ser Gly Asp Lys Leu Gly Lys Lys Tyr Ala Ser
1               5                   10

<210> SEQ ID NO 29
<211> LENGTH: 8
<212> TYPE: PRT
<213> ORGANISM: Artificial
<220> FEATURE:
<223> OTHER INFORMATION: Light chain CDR2

<400> SEQUENCE: 29

Glu Lys Asp Asn Arg Pro Ser Gly
1               5

<210> SEQ ID NO 30
<211> LENGTH: 9
<212> TYPE: PRT
<213> ORGANISM: Artificial
<220> FEATURE:
<223> OTHER INFORMATION: Light chain CDR3

<400> SEQUENCE: 30

```
Ser Ser Phe Ala Gly Asn Ser Leu Glu
1               5

<210> SEQ ID NO 31
<211> LENGTH: 11
<212> TYPE: PRT
<213> ORGANISM: Artificial
<220> FEATURE:
<223> OTHER INFORMATION: Light chain CDR1

<400> SEQUENCE: 31

Ser Gly Asp Asn Ile Gly Ser Phe Tyr Val His
1               5                   10

<210> SEQ ID NO 32
<211> LENGTH: 8
<212> TYPE: PRT
<213> ORGANISM: Artificial
<220> FEATURE:
<223> OTHER INFORMATION: Light chain CDR2

<400> SEQUENCE: 32

Asp Lys Ser Asn Arg Pro Ser Gly
1               5

<210> SEQ ID NO 33
<211> LENGTH: 9
<212> TYPE: PRT
<213> ORGANISM: Artificial
<220> FEATURE:
<223> OTHER INFORMATION: Light chain CDR3

<400> SEQUENCE: 33

Gln Ser Tyr Ala Asn Thr Leu Ser Leu
1               5

<210> SEQ ID NO 34
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 34

Asp Thr Phe Ala Asn Tyr Gly Phe Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 35

Phe Ala Phe Lys Asp Tyr Tyr Met Thr
1               5

<210> SEQ ID NO 36
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1
```

```
<400> SEQUENCE: 36

Phe Ala Phe Ser Thr Thr Ala Met Ser
1               5

<210> SEQ ID NO 37
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 37

Phe Ala Leu Ser Gly Tyr Tyr Met Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 38

Phe Pro Phe Arg Tyr Tyr Gly Met Ser
1               5

<210> SEQ ID NO 39
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 39

Phe Pro Phe Glx Tyr Tyr Ser Met Asn
1               5

<210> SEQ ID NO 40
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 40

Phe Arg Phe Ser Ile Ser Thr Met Gly
1               5

<210> SEQ ID NO 41
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 41

Phe Ser Phe Asp Asp Tyr Gly Met Ser
1               5

<210> SEQ ID NO 42
<211> LENGTH: 9
<212> TYPE: PRT
```

```
<213> ORGANISM: Artificial Sequence
<220> FEATURE:
<223> OTHER INFORMATION: Synthesized molecular recognition unit - heavy
      CDR1

<400> SEQUENCE: 42

Phe Ser Phe Glu Thr Tyr Gly Met Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 43

Phe Ser Phe Asn Thr Phe Gly Ile His
1               5

<210> SEQ ID NO 44
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 44

Phe Ser Phe Asn Thr Tyr Ala Met Asn
1               5

<210> SEQ ID NO 45
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 45

Phe Ser Phe Ser Asp Tyr Tyr Met Ser
1               5

<210> SEQ ID NO 46
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 46

Phe Ser Phe Ser Ser Tyr Ser Met Asn
1               5

<210> SEQ ID NO 47
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 47

Phe Thr Phe Asp Ala Tyr Ala Met His
1               5
```

```
<210> SEQ ID NO 48
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 48

Phe Thr Phe Asp Asp Tyr Gly Met Ser
1               5

<210> SEQ ID NO 49
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 49

Phe Thr Phe Asp Glu Tyr Ala Met His
1               5

<210> SEQ ID NO 50
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 50

Phe Thr Phe Asn Ser Tyr Ser Met Asp
1               5

<210> SEQ ID NO 51
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 51

Phe Thr Phe Arg Asn Tyr Ala Ile His
1               5

<210> SEQ ID NO 52
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 52

Phe Thr Phe Ser Ala His Gly Met His
1               5

<210> SEQ ID NO 53
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1
```

```
<400> SEQUENCE: 53

Phe Thr Phe Ser Asp Phe Ala Met Thr
1               5

<210> SEQ ID NO 54
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 54

Phe Thr Phe Ser Asp His Tyr Met Ser
1               5

<210> SEQ ID NO 55
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 55

Phe Thr Phe Ser Asp Tyr Tyr Met Ser
1               5

<210> SEQ ID NO 56
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 56

Phe Thr Phe Ser Lys Thr Asp Met His
1               5

<210> SEQ ID NO 57
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 57

Phe Thr Phe Ser Asn Ser Asp Met Asn
1               5

<210> SEQ ID NO 58
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 58

Phe Thr Phe Ser Asn Tyr Trp Ile His
1               5

<210> SEQ ID NO 59
<211> LENGTH: 9
```

```
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 59

Phe Thr Phe Ser Arg His Ser Met Asn
1               5

<210> SEQ ID NO 60
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 60

Phe Thr Phe Ser Ser His Ser Thr His
1               5

<210> SEQ ID NO 61
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 61

Phe Thr Phe Ser Ser Ser Ala Met His
1               5

<210> SEQ ID NO 62
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 62

Phe Thr Phe Ser Ser Ser Trp Met His
1               5

<210> SEQ ID NO 63
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 63

Phe Thr Phe Ser Ser Tyr Ala Met His
1               5

<210> SEQ ID NO 64
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 64

Phe Thr Phe Ser Ser Tyr Ala Met Ser
```

```
<210> SEQ ID NO 65
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 65

Phe Thr Phe Ser Ser Tyr Asp Met His
1               5

<210> SEQ ID NO 66
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 66

Phe Thr Phe Ser Ser Tyr Ser Met Asn
1               5

<210> SEQ ID NO 67
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 67

Phe Thr Phe Ser Ser Tyr Trp Met His
1               5

<210> SEQ ID NO 68
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 68

Phe Thr Phe Ser Ser Glx Glx Met His
1               5

<210> SEQ ID NO 69
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 69

Phe Thr Phe Ser Thr Phe Gly Met His
1               5

<210> SEQ ID NO 70
<211> LENGTH: 9
<212> TYPE: PRT
<213> ORGANISM: Artificial Sequence
<220> FEATURE:
<223> OTHER INFORMATION: Synthesized molecular recognition unit - heavy
```

CDR1

<400> SEQUENCE: 70

Phe Thr Phe Ser Thr His Ala Phe His
1               5

<210> SEQ ID NO 71
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 71

Phe Thr Phe Ser Thr Tyr Gly Met His
1               5

<210> SEQ ID NO 72
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 72

Phe Thr Phe Ser Thr Tyr Ser Met Asn
1               5

<210> SEQ ID NO 73
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 73

Phe Thr Phe Ser Thr Tyr Tyr Met Ser
1               5

<210> SEQ ID NO 74
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 74

Phe Thr Phe Thr Asp Tyr Gly Leu His
1               5

<210> SEQ ID NO 75
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 75

Phe Thr Phe Thr Ser Ser Ala Met Gln
1               5

<210> SEQ ID NO 76

```
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 76

Phe Thr Phe Thr Ser Ser Ala Val Gln
1               5

<210> SEQ ID NO 77
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 77

Phe Thr Phe Glx Asn Ala Trp Met Ser
1               5

<210> SEQ ID NO 78
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 78

Phe Thr Leu Arg Asn His Trp Leu Ser
1               5

<210> SEQ ID NO 79
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 79

Phe Thr Val Ser Ser Asn Tyr Met Ser
1               5

<210> SEQ ID NO 80
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 80

Gly Asp Leu Ser Ile Tyr Thr Ile Asn
1               5

<210> SEQ ID NO 81
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 81
```

-continued

Gly Ser Phe Ser Asp Tyr Tyr Trp Ser
1               5

<210> SEQ ID NO 82
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 82

Gly Ser Phe Ser Gly Tyr Tyr Trp Thr
1               5

<210> SEQ ID NO 83
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 83

Gly Ser Leu Ser Gly Tyr Tyr Trp Ser
1               5

<210> SEQ ID NO 84
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 84

Gly Thr Phe His Thr Tyr Gly Leu Ser
1               5

<210> SEQ ID NO 85
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 85

Gly Thr Phe Asn Ser Asn Ala Ile Ser
1               5

<210> SEQ ID NO 86
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 86

Gly Thr Phe Asn Thr His Thr Ile Thr
1               5

<210> SEQ ID NO 87
<211> LENGTH: 9
<212> TYPE: PRT
<213> ORGANISM: Artificial Sequence
<220> FEATURE:

<223> OTHER INFORMATION: Synthesized molecular recognition unit - heavy
      CDR1

<400> SEQUENCE: 87

Gly Thr Phe Ser His Tyr Thr Ile Ser
1               5

<210> SEQ ID NO 88
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 88

Gly Thr Phe Ser Arg Tyr His Met Gly
1               5

<210> SEQ ID NO 89
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 89

Gly Thr Phe Ser Ser His Ala Ile Asn
1               5

<210> SEQ ID NO 90
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 90

Gly Thr Phe Ser Ser Tyr Ala Ile Ser
1               5

<210> SEQ ID NO 91
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 91

Gly Thr Phe Ser Ser Tyr Thr Ile Ser
1               5

<210> SEQ ID NO 92
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 92

Gly Thr Phe Ser Glx Tyr Ala Ile Ser
1               5

```
<210> SEQ ID NO 93
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 93

Gly Thr Ile Ser Asp Tyr Thr Val Ser
1               5

<210> SEQ ID NO 94
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 94

His Thr Phe Leu Thr Tyr Asp Ile Asn
1               5

<210> SEQ ID NO 95
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 95

His Thr Phe Ser Ser Tyr Ala Met Gly
1               5

<210> SEQ ID NO 96
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 96

Ile Ala Phe Arg Tyr Tyr Asp Met Gly
1               5

<210> SEQ ID NO 97
<211> LENGTH: 8
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 97

Ile Ser Ser Val Tyr Gly Met Gly
1               5

<210> SEQ ID NO 98
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 98
```

```
Leu Pro Phe Ser Arg Tyr Ala Met Ala
1               5
```

<210> SEQ ID NO 99
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 99

```
Leu Ser Phe Ser Ser Tyr Ala Met Gly
1               5
```

<210> SEQ ID NO 100
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 100

```
Leu Ser Ser Gly Arg Pro Phe Ser Ser Tyr Val Met Gly
1               5                   10
```

<210> SEQ ID NO 101
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 101

```
Leu Thr Phe Asp Asp His Ala Met His
1               5
```

<210> SEQ ID NO 102
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 102

```
Leu Thr Phe Ser Asn Ala Ala Met Ala
1               5
```

<210> SEQ ID NO 103
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 103

```
Leu Thr Phe Thr Ser His Gly Met Ser
1               5
```

<210> SEQ ID NO 104
<211> LENGTH: 9
<212> TYPE: PRT
<213> ORGANISM: Artificial Sequence

```
<220> FEATURE:
<223> OTHER INFORMATION: Synthesized molecular recognition unit - heavy
      CDR1

<400> SEQUENCE: 104

Leu Thr Val Ser Ser Asn Tyr Met Ser
1               5

<210> SEQ ID NO 105
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 105

Asn Ile Phe Pro Ile Asp Asp Met Ser
1               5

<210> SEQ ID NO 106
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 106

Asn Ile Asn Ser Ile Glu Thr Leu Gly
1               5

<210> SEQ ID NO 107
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 107

Arg Ile Phe Ala Ile Tyr Asp Ile Ala
1               5

<210> SEQ ID NO 108
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 108

Arg Ile Phe Ala Ile Tyr Asp Met Ala
1               5

<210> SEQ ID NO 109
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 109

Arg Ile Phe Ser Ile Tyr Asp Ile Ala
1               5
```

<210> SEQ ID NO 110
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 110

Arg Ile Phe Ser Ile Tyr Asp Met Gly
1               5

<210> SEQ ID NO 111
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 111

Arg Leu Leu Ser Tyr Tyr Ala Leu Ala
1               5

<210> SEQ ID NO 112
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 112

Arg Arg Phe Thr Thr Tyr Gly Met Gly
1               5

<210> SEQ ID NO 113
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 113

Arg Ser Phe Asn Ser Tyr Thr Thr Thr
1               5

<210> SEQ ID NO 114
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 114

Arg Ser Phe Asn Ser Tyr Val Ile Gly
1               5

<210> SEQ ID NO 115
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

```
<400> SEQUENCE: 115

Arg Ser Phe Ser Asp Phe Phe Met Gly
1               5

<210> SEQ ID NO 116
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 116

Arg Ser Leu Ser Ser Phe Ala Met Gly
1               5

<210> SEQ ID NO 117
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 117

Arg Ser Val Ser Ile Tyr Pro Met Gly
1               5

<210> SEQ ID NO 118
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 118

Arg Ser Val Ser Ser Tyr Asn Met Gly
1               5

<210> SEQ ID NO 119
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 119

Arg Thr Phe Gly Asn Tyr Asp Met Gly
1               5

<210> SEQ ID NO 120
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 120

Arg Thr Phe Gly Ser Asp Val Met Gly
1               5

<210> SEQ ID NO 121
<211> LENGTH: 9
<212> TYPE: PRT
```

```
<213> ORGANISM: Artificial Sequence
<220> FEATURE:
<223> OTHER INFORMATION: Synthesized molecular recognition unit - heavy
      CDR1

<400> SEQUENCE: 121

Arg Thr Phe Gly Thr Tyr Pro Asn Gly
1               5

<210> SEQ ID NO 122
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 122

Arg Thr Phe Asn Ile Asp Asp Met Gly
1               5

<210> SEQ ID NO 123
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 123

Arg Thr Phe Asn Ser Gly Thr Met Gly
1               5

<210> SEQ ID NO 124
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 124

Arg Thr Phe Asn Thr Tyr Ala Met Gly
1               5

<210> SEQ ID NO 125
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 125

Arg Thr Phe Arg Arg Tyr Ala Met Gly
1               5

<210> SEQ ID NO 126
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 126

Arg Thr Phe Arg Ser Tyr Thr Met Gly
1               5
```

```
<210> SEQ ID NO 127
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 127

Arg Thr Phe Ser Asp Tyr Ser Met Ala
1               5

<210> SEQ ID NO 128
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 128

Arg Thr Phe Ser Asp Tyr Ser Met Gly
1               5

<210> SEQ ID NO 129
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 129

Arg Thr Phe Ser Met Tyr Asp Met Gly
1               5

<210> SEQ ID NO 130
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 130

Arg Thr Phe Ser Asn Tyr Ala Val Gly
1               5

<210> SEQ ID NO 131
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 131

Arg Thr Phe Ser Arg Tyr Ala Met Ala
1               5

<210> SEQ ID NO 132
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1
```

<400> SEQUENCE: 132

Arg Thr Phe Ser Arg Tyr Ala Met Gly
1               5

<210> SEQ ID NO 133
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 133

Arg Thr Phe Ser Arg Tyr Val Met Gly
1               5

<210> SEQ ID NO 134
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 134

Arg Thr Phe Ser Ser Tyr Ala Met Ala
1               5

<210> SEQ ID NO 135
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 135

Arg Thr Phe Ser Ser Tyr Ala Met Ser
1               5

<210> SEQ ID NO 136
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 136

Arg Thr Phe Ser Ser Tyr Ala Val Gly
1               5

<210> SEQ ID NO 137
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 137

Arg Thr Phe Ser Val Tyr Gly Val Gly
1               5

<210> SEQ ID NO 138
<211> LENGTH: 9

```
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 138

Arg Thr Phe Ser Tyr Tyr Ala Met Gly
1               5

<210> SEQ ID NO 139
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 139

Arg Thr Leu Ser Ala Tyr Asp Met Gly
1               5

<210> SEQ ID NO 140
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 140

Arg Thr Leu Ser Arg Tyr Ser Met Gly
1               5

<210> SEQ ID NO 141
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 141

Arg Thr Leu Ser Ser Phe Ala Met Gly
1               5

<210> SEQ ID NO 142
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 142

Arg Val Leu Ser Tyr Tyr Ala Met Ala
1               5

<210> SEQ ID NO 143
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 143

Ser Ile Phe Met Ile Asn Thr Met Ala
```

```
1               5

<210> SEQ ID NO 144
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 144

Ser Ile Phe Arg Leu Gly Thr Met Tyr
1               5

<210> SEQ ID NO 145
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 145

Ser Ile Phe Ser Asp Gly Ala Met Gly
1               5

<210> SEQ ID NO 146
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 146

Ser Ile Phe Ser Ile Asn Thr Met Gly
1               5

<210> SEQ ID NO 147
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 147

Ser Ile Phe Ser Ile Tyr Ala Met Gly
1               5

<210> SEQ ID NO 148
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 148

Ser Ile Ser Ser Phe Asn Thr Met Gly
1               5

<210> SEQ ID NO 149
<211> LENGTH: 9
<212> TYPE: PRT
<213> ORGANISM: Artificial Sequence
<220> FEATURE:
<223> OTHER INFORMATION: Synthesized molecular recognition unit - heavy
```

```
        CDR1

<400> SEQUENCE: 149

Ser Ile Val Arg Ser Leu Pro Met Ala
1               5

<210> SEQ ID NO 150
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 150

Ser Leu Phe Ser Phe Asn Ala Met Gly
1               5

<210> SEQ ID NO 151
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 151

Ser Leu Phe Ser Phe Asn Ala Val Gly
1               5

<210> SEQ ID NO 152
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 152

Ser Val Phe Thr Thr Phe Ala Lys Gly
1               5

<210> SEQ ID NO 153
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 153

Thr Ile Phe Ser Ile Asn Thr Met Gly
1               5

<210> SEQ ID NO 154
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 154

Thr Ile Val Ser Ile Tyr Arg Ile Asn
1               5

<210> SEQ ID NO 155
```

```
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 155

Val Ile Phe Ala Leu Tyr Asp Ile Ala
1               5

<210> SEQ ID NO 156
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 156

Val Thr Phe Ser Arg Tyr Pro Ile Ser
1               5

<210> SEQ ID NO 157
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 157

Tyr Gly Phe Thr Gly Tyr Tyr Ile His
1               5

<210> SEQ ID NO 158
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 158

Tyr Ile Phe Thr Asp Tyr Tyr Met His
1               5

<210> SEQ ID NO 159
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 159

Tyr Ser Phe Thr Arg Thr Asp Met His
1               5

<210> SEQ ID NO 160
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 160
```

Tyr Thr Phe Ala Ser Tyr Asp Ile His
1               5

<210> SEQ ID NO 161
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 161

Tyr Thr Phe Ser Tyr Arg Tyr Leu His
1               5

<210> SEQ ID NO 162
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 162

Tyr Thr Phe Thr Asp Tyr Phe Met Asn
1               5

<210> SEQ ID NO 163
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 163

Tyr Thr Phe Thr Gly Tyr Tyr Ile His
1               5

<210> SEQ ID NO 164
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 164

Tyr Thr Phe Thr Gly Tyr Tyr Met His
1               5

<210> SEQ ID NO 165
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 165

Tyr Thr Phe Thr Asn Asn Phe Met His
1               5

<210> SEQ ID NO 166
<211> LENGTH: 9
<212> TYPE: PRT
<213> ORGANISM: Artificial Sequence
<220> FEATURE:

<223> OTHER INFORMATION: Synthesized molecular recognition unit - heavy
      CDR1

<400> SEQUENCE: 166

Tyr Thr Phe Thr Asn Tyr Cys Met His
1               5

<210> SEQ ID NO 167
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 167

Tyr Thr Phe Thr Ser Tyr Ala Met Asn
1               5

<210> SEQ ID NO 168
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 168

Tyr Thr Phe Thr Ser Tyr Asp Ile Asn
1               5

<210> SEQ ID NO 169
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 169

Tyr Thr Phe Thr Ser Tyr Tyr Met His
1               5

<210> SEQ ID NO 170
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 170

Tyr Thr Phe Thr Tyr Arg Tyr Leu His
1               5

<210> SEQ ID NO 171
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 171

Tyr Thr Ile Ser Asn Tyr Tyr Ile His
1               5

```
<210> SEQ ID NO 172
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR1

<400> SEQUENCE: 172

Tyr Glx Phe Thr Asp Tyr Tyr Met His
1               5

<210> SEQ ID NO 173
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 173

Ala Ala Ile Lys Trp Ser Gly Thr Asn Thr Tyr Tyr Ala
1               5                   10

<210> SEQ ID NO 174
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 174

Ala Ala Ile Asn Trp Ser Gly Asp Ser Thr Lys Tyr Ala
1               5                   10

<210> SEQ ID NO 175
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 175

Ala Ala Ile Gln Trp Ser Ala Asp Asn Thr Phe Tyr Ala
1               5                   10

<210> SEQ ID NO 176
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 176

Ala Ala Ile Arg Trp Ser Gly Asp Asn Thr Tyr Tyr Ala
1               5                   10

<210> SEQ ID NO 177
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 177
```

```
Ala Ala Ile Arg Trp Ser Gly Gly Thr Tyr Tyr Ala
1               5                   10

<210> SEQ ID NO 178
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 178

Ala Ala Ile Ser Gly Ser Gly Gly Ser Thr Thr Tyr Ala
1               5                   10

<210> SEQ ID NO 179
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 179

Ala Ala Ile Ser Gln Ser Gly Tyr Val Arg Tyr Tyr Ala
1               5                   10

<210> SEQ ID NO 180
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 180

Ala Ala Ile Ser Arg Phe Gly Gly Ser Thr Tyr Tyr Ala
1               5                   10

<210> SEQ ID NO 181
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 181

Ala Ala Ile Ser Arg Phe Gly Gly Ser Thr Tyr Tyr Val
1               5                   10

<210> SEQ ID NO 182
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 182

Ala Ala Ile Ser Arg Asn Gly Asp Lys Ser His Tyr Ser
1               5                   10

<210> SEQ ID NO 183
<211> LENGTH: 13
<212> TYPE: PRT
<213> ORGANISM: Artificial Sequence
```

```
<220> FEATURE:
<223> OTHER INFORMATION: Synthesized molecular recognition unit - heavy
      CDR2

<400> SEQUENCE: 183

Ala Ala Ile Ser Arg Arg Gly Gly Ile Ile Glu Tyr Gly
1               5                   10

<210> SEQ ID NO 184
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 184

Ala Ala Ile Ser Arg Ser Gly Ala Asn Thr Ala Tyr Ser
1               5                   10

<210> SEQ ID NO 185
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 185

Ala Ala Ile Ser Arg Ser Gly Asp Arg Ile Tyr Tyr Ser
1               5                   10

<210> SEQ ID NO 186
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 186

Ala Ala Ile Ser Arg Ser Gly Gly Ile Tyr Tyr Ala
1               5                   10

<210> SEQ ID NO 187
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 187

Ala Ala Ile Ser Arg Ser Gly Val Ser Thr Tyr Tyr Ala
1               5                   10

<210> SEQ ID NO 188
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 188

Ala Ala Ile Ser Trp Gly Gly Arg Thr Ala Tyr Ala
1               5                   10
```

<210> SEQ ID NO 189
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 189

Ala Ala Ile Ser Trp Ser Gly Gly Ser Thr Lys Tyr Ala
1               5                   10

<210> SEQ ID NO 190
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 190

Ala Ala Ile Ser Tyr Ser Gly Gly Ser Thr Lys Tyr Ala
1               5                   10

<210> SEQ ID NO 191
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 191

Ala Ala Ile Thr Arg Ser Gly Ser Asn Thr Tyr Tyr Ala
1               5                   10

<210> SEQ ID NO 192
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 192

Ala Ala Ile Thr Trp Asn Gly Arg Ser Ser Asp Tyr Ala
1               5                   10

<210> SEQ ID NO 193
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 193

Ala Ala Ile Thr Trp Arg Gly Gly Ile Thr Tyr Tyr Ala
1               5                   10

<210> SEQ ID NO 194
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

```
<400> SEQUENCE: 194

Ala Ala Ile Thr Trp Arg Gly Gly Ser Thr Tyr Tyr Ala
1               5                   10

<210> SEQ ID NO 195
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 195

Ala Ala Val Ser Ala Ser Gly Gly Tyr Thr Trp Tyr Ala
1               5                   10

<210> SEQ ID NO 196
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 196

Ala Ala Val Thr Trp Arg Ser Gly Ser Thr Tyr Tyr Ala
1               5                   10

<210> SEQ ID NO 197
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 197

Ala Gly Ile Arg Trp Ser Gly Ser Thr Leu Tyr Ala
1               5                   10

<210> SEQ ID NO 198
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 198

Ala Gly Ile Ser Trp Ile Ala Asp Asn Arg Tyr Tyr Ala
1               5                   10

<210> SEQ ID NO 199
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 199

Ala Gly Ile Thr Arg Gly Gly Ala Thr Thr Tyr Tyr Ser
1               5                   10

<210> SEQ ID NO 200
<211> LENGTH: 12
<212> TYPE: PRT
```

```
<213> ORGANISM: Artificial Sequence
<220> FEATURE:
<223> OTHER INFORMATION: Synthesized molecular recognition unit - heavy
      CDR2

<400> SEQUENCE: 200

Ala Gly Ile Thr Ser Ser Gly Arg Thr Ile Tyr Ala
1               5                   10

<210> SEQ ID NO 201
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 201

Ala Gly Met Ser Gly Glu Gly Arg Asn Thr Lys Tyr Arg
1               5                   10

<210> SEQ ID NO 202
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 202

Ala Leu Thr Gly Trp Gly Asp Gly Ser Thr Thr Tyr Tyr Glu
1               5                   10

<210> SEQ ID NO 203
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 203

Ala Met Ile Arg Pro Val Val Thr Glu Ile Asp Tyr Ala
1               5                   10

<210> SEQ ID NO 204
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 204

Ala Asn Met Arg Gly Gly Gly Tyr Met Lys Tyr Ala
1               5                   10

<210> SEQ ID NO 205
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 205

Ala Arg Ile Gly Trp Asn Gly Gly Ser Ile Val Tyr Ala
1               5                   10
```

<210> SEQ ID NO 206
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 206

Ala Arg Ile Ser Arg Gly Asp Gly Tyr Thr Asp Glu Ala
1               5                   10

<210> SEQ ID NO 207
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 207

Ala Ser Ile Gly Lys Ser Gly Ser Thr Asn Tyr Ala
1               5                   10

<210> SEQ ID NO 208
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 208

Ala Ser Ile Arg Trp Ser Gly Gln Ser Pro Tyr Tyr Ala
1               5                   10

<210> SEQ ID NO 209
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 209

Ala Ser Ile Arg Trp Ser Ser Gly Asn Thr Trp Tyr Ala
1               5                   10

<210> SEQ ID NO 210
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 210

Ala Ser Ile Ser Ser Gly Gly Arg Thr Asn Tyr Ala
1               5                   10

<210> SEQ ID NO 211
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 211

Ala Ser Ile Ser Ser Gly Ser Arg Thr Asn Tyr Ala
1               5                   10

<210> SEQ ID NO 212
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 212

Ala Ser Ile Ser Ser Thr Ser Gly Ser Lys Tyr Tyr Ala
1               5                   10

<210> SEQ ID NO 213
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 213

Ala Ser Ile Thr Ala Ser Ser Asp Arg Thr Phe Tyr Ala
1               5                   10

<210> SEQ ID NO 214
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 214

Ala Ser Val Ser Trp Arg Tyr Asp Arg Thr Tyr Tyr Thr
1               5                   10

<210> SEQ ID NO 215
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 215

Ala Thr Ile Asn Asp Ala Gln Arg Tyr Tyr Ala
1               5                   10

<210> SEQ ID NO 216
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 216

Ala Thr Ile Arg Pro Val Val Ser Glu Thr Thr Tyr Ala
1               5                   10

<210> SEQ ID NO 217
<211> LENGTH: 13

```
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 217

Ala Thr Ile Arg Pro Val Val Thr Glu Thr Asp Tyr Ala
1               5                   10

<210> SEQ ID NO 218
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 218

Ala Thr Ile Arg Pro Val Val Thr Gln Ile Asp Tyr Ala
1               5                   10

<210> SEQ ID NO 219
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 219

Ala Thr Ile Ser Ala Ser Gly Gly Asn Thr Ala Tyr Ala
1               5                   10

<210> SEQ ID NO 220
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 220

Ala Thr Ile Ser Arg Ser Gly Gly Asn Thr Tyr Tyr Ala
1               5                   10

<210> SEQ ID NO 221
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 221

Ala Thr Ile Ser Trp Ser Gly Ser Ser Ala Asn Tyr Glu
1               5                   10

<210> SEQ ID NO 222
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 222

Ala Thr Met Thr Ser Gly Gly Asn Thr Asn Tyr Ala
```

```
1               5                   10
```

<210> SEQ ID NO 223
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 223

Ala Thr Val Thr Ser Gly Gly Arg Ile Asn Tyr Ala
1               5                   10

<210> SEQ ID NO 224
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 224

Ala Val Ile Gly Arg Ser Gly Gly Ile Lys Tyr Tyr Ala
1               5                   10

<210> SEQ ID NO 225
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 225

Ala Val Ile Ser Gly Gly Arg Thr Gly Tyr Ala
1               5                   10

<210> SEQ ID NO 226
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 226

Ala Val Ile Ser Tyr Asp Gly Ser Asn Lys Tyr Tyr Ala
1               5                   10

<210> SEQ ID NO 227
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 227

Ala Val Ile Thr Ser Gly Gly Lys Thr Val Tyr Ala
1               5                   10

<210> SEQ ID NO 228
<211> LENGTH: 12
<212> TYPE: PRT
<213> ORGANISM: Artificial Sequence
<220> FEATURE:
<223> OTHER INFORMATION: Synthesized molecular recognition unit - heavy

```
                                CDR2

<400> SEQUENCE: 228

Ala Val Ile Thr Thr Gly Gly Asp Thr Ser Tyr Ser
1               5                   10

<210> SEQ ID NO 229
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 229

Ala Val Thr Ser Tyr Asp Gly Gly Lys Lys Asn Tyr Ala
1               5                   10

<210> SEQ ID NO 230
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 230

Ala Tyr Ile Thr Gly Gly Gly Arg Thr Met Asp Gly
1               5                   10

<210> SEQ ID NO 231
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 231

Gly Ala Ile Ser Arg Ser Gly Asn Asn Thr Tyr Tyr Ala
1               5                   10

<210> SEQ ID NO 232
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 232

Gly Glu Ile Asn His Ser Gly Ala Thr Asn Tyr Asn
1               5                   10

<210> SEQ ID NO 233
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 233

Gly Glu Ile Asn His Ser Gly Ser Thr Asn Tyr Asn
1               5                   10

<210> SEQ ID NO 234
```

```
<210> SEQ ID NO 234
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 234

Gly Gly Phe Asp Pro Glu Asp Gly Glu Thr Ile Tyr Ala
1               5                   10

<210> SEQ ID NO 235
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 235

Gly Gly Ile Ile Pro Ile Phe Gly Thr Ala Asp Tyr Ala
1               5                   10

<210> SEQ ID NO 236
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 236

Gly Gly Ile Ile Pro Ile Phe Gly Thr Ala Asn Tyr Ala
1               5                   10

<210> SEQ ID NO 237
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 237

Gly Gly Ile Ile Pro Leu Phe Gly Thr Ala Asn Tyr Ala
1               5                   10

<210> SEQ ID NO 238
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 238

Gly Gly Ile Ile Pro Val Phe Gly Thr Ala Asp Tyr Ala
1               5                   10

<210> SEQ ID NO 239
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 239
```

-continued

Gly Gly Ile Ile Pro Val Phe Gly Thr Ala Asn Tyr Ala
1               5                   10

<210> SEQ ID NO 240
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 240

Gly Gly Ile Arg Trp Ser Gly Gly Thr Thr Leu Tyr Pro
1               5                   10

<210> SEQ ID NO 241
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 241

Gly Gly Ile Val Pro Ala Tyr Arg Arg Ala Asn Tyr Ala
1               5                   10

<210> SEQ ID NO 242
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 242

Gly Gly Val Ile Pro Ile Phe Gly Thr Ala Asp Tyr Ala
1               5                   10

<210> SEQ ID NO 243
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 243

Gly His Val Asp Pro Gly Asp Gly Glu Thr Ile Tyr Ala
1               5                   10

<210> SEQ ID NO 244
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 244

Gly Ile Ile Asn Pro Ser Asp Gly Ser Thr Ser His Ala
1               5                   10

<210> SEQ ID NO 245
<211> LENGTH: 13
<212> TYPE: PRT
<213> ORGANISM: Artificial Sequence
<220> FEATURE:

```
<223> OTHER INFORMATION: Synthesized molecular recognition unit - heavy
      CDR2

<400> SEQUENCE: 245

Gly Ile Ile Asn Pro Ser Gly Asp Ser Thr Arg Phe Ala
1               5                   10

<210> SEQ ID NO 246
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 246

Gly Ile Ile Asn Pro Ser Gly Gly Ser Thr Ile Tyr Ala
1               5                   10

<210> SEQ ID NO 247
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 247

Gly Ile Ile Asn Pro Ser Gly Gly Ser Thr Asn Tyr Ala
1               5                   10

<210> SEQ ID NO 248
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 248

Gly Ile Ile Asn Pro Ser Gly Gly Ser Thr Ser Tyr Ala
1               5                   10

<210> SEQ ID NO 249
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 249

Gly Met Ile Asn Pro Ser Gly Gly Ser Thr Thr Tyr Ala
1               5                   10

<210> SEQ ID NO 250
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 250

Gly Arg Ile Ile Pro Ile Phe Gly Thr Ala Asn Tyr Ala
1               5                   10
```

```
<210> SEQ ID NO 251
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 251

Gly Arg Ile Ile Pro Ile His Gly Ile Ala Asn Tyr Ala
1               5                   10

<210> SEQ ID NO 252
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 252

Gly Arg Ile Ile Pro Ile Leu Gly Arg Ala Asn Tyr Ala
1               5                   10

<210> SEQ ID NO 253
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 253

Gly Arg Ile Ile Pro Ile Leu Gly Arg Thr Asn Tyr Ala
1               5                   10

<210> SEQ ID NO 254
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 254

Gly Arg Ile Ile Pro Ile Leu Gly Ser Thr Asn Tyr Ala
1               5                   10

<210> SEQ ID NO 255
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 255

Gly Arg Ile Ile Pro Val Leu Lys Ile Thr Asn Tyr Ala
1               5                   10

<210> SEQ ID NO 256
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 256
```

```
Gly Arg Ile Asn Pro Asn Gly Gly Thr Ile Tyr Ala
1               5                   10

<210> SEQ ID NO 257
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 257

Gly Arg Ile Thr Pro Arg Leu Gly Ile Ala Asn Tyr Ala
1               5                   10

<210> SEQ ID NO 258
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 258

Gly Trp Ile Asn Ala Gly Asn Gly Asn Thr Lys Tyr Ser
1               5                   10

<210> SEQ ID NO 259
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 259

Gly Trp Ile Asn Ala Gly Asn Gly Asn Thr Thr Tyr Ala
1               5                   10

<210> SEQ ID NO 260
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 260

Gly Trp Ile Asn Pro Asn Ser Gly Asp Thr Asn Tyr Ala
1               5                   10

<210> SEQ ID NO 261

<400> SEQUENCE: 261

000

<210> SEQ ID NO 262

<400> SEQUENCE: 262

000

<210> SEQ ID NO 263

<400> SEQUENCE: 263
```

```
000

<210> SEQ ID NO 264
<400> SEQUENCE: 264
000

<210> SEQ ID NO 265
<400> SEQUENCE: 265
000

<210> SEQ ID NO 266
<400> SEQUENCE: 266
000

<210> SEQ ID NO 267
<400> SEQUENCE: 267
000

<210> SEQ ID NO 268
<400> SEQUENCE: 268
000

<210> SEQ ID NO 269
<400> SEQUENCE: 269
000

<210> SEQ ID NO 270
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 270

Gly Trp Ile Asn Pro Asn Ser Gly Gly Thr Asn Tyr Ala
1               5                   10

<210> SEQ ID NO 271
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 271

Gly Trp Ile Ser Ala Asn Asn Gly Asn Thr Asp Tyr Ala
1               5                   10

<210> SEQ ID NO 272
<211> LENGTH: 13
<212> TYPE: PRT
<213> ORGANISM: Artificial Sequence
<220> FEATURE:
<223> OTHER INFORMATION: Synthesized molecular recognition unit - heavy
```

```
                CDR2

<400> SEQUENCE: 272

Gly Trp Met Asn Pro Asn Ser Gly Asn Thr Gly Tyr Ala
1               5                   10

<210> SEQ ID NO 273
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2
<220> FEATURE:
<221> NAME/KEY: misc_feature
<222> LOCATION: (2)..(2)
<223> OTHER INFORMATION: Xaa can be any naturally occurring amino acid

<400> SEQUENCE: 273

Gly Xaa Val Asn Ala Gly Asn Gly Asn Thr Thr Tyr Ala
1               5                   10

<210> SEQ ID NO 274
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 274

Gly Tyr Ile Ser Ala Tyr Thr Gly His Thr Ser Tyr Ala
1               5                   10

<210> SEQ ID NO 275
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 275

Ser Ala Ile Gly Ala Gly Gly Gly Thr Tyr Tyr Ala
1               5                   10

<210> SEQ ID NO 276
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 276

Ser Ala Ile Gly Thr Gly Gly Asp Thr Tyr Tyr Ala
1               5                   10

<210> SEQ ID NO 277
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 277

Ser Ala Ile Gly Thr Gly Gly Gly Thr Tyr Tyr Ala
```

```
1               5                   10

<210> SEQ ID NO 278
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 278

Ser Ala Ile Arg Gly Ser Gly Glu Arg Thr Tyr Tyr Ala
1               5                   10

<210> SEQ ID NO 279
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 279

Ser Ala Ile Ser Gly Arg Asp Gly Arg Thr Tyr Tyr Ala
1               5                   10

<210> SEQ ID NO 280
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 280

Ser Ala Ile Ser Gly Ser Gly Gly Ser Thr Tyr Tyr Ala
1               5                   10

<210> SEQ ID NO 281
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 281

Ser Ala Ile Ser Ser Gly Ser Asp Arg Thr Tyr Tyr Ala
1               5                   10

<210> SEQ ID NO 282
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 282

Ser Ala Ile Thr Trp Ser Gly Gly Arg Thr Tyr Tyr Ala
1               5                   10

<210> SEQ ID NO 283
<211> LENGTH: 12
<212> TYPE: PRT
<213> ORGANISM: Artificial Sequence
<220> FEATURE:
<223> OTHER INFORMATION: Synthesized molecular recognition unit - heavy
```

```
                          CDR2

<400> SEQUENCE: 283

Ser Gly Ile Arg Trp Ser Gly Gly Thr Ser Tyr Ala
1               5                   10

<210> SEQ ID NO 284
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 284

Ser Gly Ile Ser Glu Ser Gly Gly Arg Thr Tyr Tyr Ala
1               5                   10

<210> SEQ ID NO 285
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 285

Ser Gly Ile Ser Gly Ser Gly Gly Arg Thr His Tyr Ala
1               5                   10

<210> SEQ ID NO 286
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 286

Ser Gly Ile Ser Gly Ser Gly Gly Ser Thr Tyr Tyr Ala
1               5                   10

<210> SEQ ID NO 287
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 287

Ser Gly Ile Ser Trp Asn Gly Gly Lys Thr His Tyr Val
1               5                   10

<210> SEQ ID NO 288
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 288

Ser Gly Ile Ser Trp Asn Ser Gly Arg Ile Gly Tyr Ala
1               5                   10

<210> SEQ ID NO 289
```

```
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 289

Ser Gly Ile Ser Trp Asn Ser Gly Ser Ile Gly Tyr Ala
1               5                   10

<210> SEQ ID NO 290
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 290

Ser Gly Ile Ser Trp Asn Ser Gly Thr Thr Gly Tyr Ser
1               5                   10

<210> SEQ ID NO 291
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 291

Ser Gly Ile Thr Ser Asn Gly Gly Ala Thr Tyr Tyr Ala
1               5                   10

<210> SEQ ID NO 292
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 292

Ser Gly Val Ser Trp Asn Gly Ser Arg Thr His Tyr Ala
1               5                   10

<210> SEQ ID NO 293
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 293

Ser Met Ile Ser Tyr Asn Gly Gly Arg Ala Phe Tyr Ala
1               5                   10

<210> SEQ ID NO 294
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 294
```

```
Ser Ser Ile Ser Gly Ser Gly Gly Val Thr Tyr Tyr Ala
1               5                   10
```

<210> SEQ ID NO 295
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 295

```
Ser Ser Ile Ser Pro Arg Gly Gly Ser Thr Tyr Tyr Ala
1               5                   10
```

<210> SEQ ID NO 296
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 296

```
Ser Ser Ile Ser Ser Ser Ser Thr Tyr Ile Arg Tyr Ala
1               5                   10
```

<210> SEQ ID NO 297
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 297

```
Ser Ser Ile Ser Val Ser Ser Gly Thr Thr His Tyr Ala
1               5                   10
```

<210> SEQ ID NO 298
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 298

```
Ser Thr Ile Asn Pro Gly Gly Leu Ser Lys Ser Tyr Ala
1               5                   10
```

<210> SEQ ID NO 299
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 299

```
Ser Thr Ile Ser Asp Thr Asn Ser Gly Thr Tyr Tyr Ala
1               5                   10
```

<210> SEQ ID NO 300
<211> LENGTH: 13
<212> TYPE: PRT
<213> ORGANISM: Artificial Sequence
<220> FEATURE:

<223> OTHER INFORMATION: Synthesized molecular recognition unit - heavy
      CDR2

<400> SEQUENCE: 300

Ser Thr Ile Ser Gly Ser Gly Gly Arg Thr Tyr Tyr Ala
1               5                   10

<210> SEQ ID NO 301
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 301

Ser Thr Ile Ser Gly Ser Gly Gly Ser Thr Tyr Tyr Ala
1               5                   10

<210> SEQ ID NO 302
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 302

Ser Thr Ile Thr Ser Ser Gly Gly Ser Thr Tyr Tyr Ala
1               5                   10

<210> SEQ ID NO 303
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 303

Ser Thr Ile Thr Thr Asp Ser Arg Gly Thr Tyr Tyr Ala
1               5                   10

<210> SEQ ID NO 304
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 304

Ser Thr Leu Ser Gly Asp Ala Asn Asn Ala Tyr Tyr Ala
1               5                   10

<210> SEQ ID NO 305
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 305

Ser Val Ile Ser Ser Gly Gly Thr Ile Tyr Tyr Ala
1               5                   10

```
<210> SEQ ID NO 306
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 306

Ser Tyr Ile Ser Gly Asp Ser Gly Tyr Thr Asn Tyr Ala
1               5                   10

<210> SEQ ID NO 307
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 307

Ser Tyr Ile Ser Gly Asn Ser Gly Tyr Thr Asn Tyr Ala
1               5                   10

<210> SEQ ID NO 308
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 308

Ser Tyr Ile Ser Ser Ser Gly Arg Thr Ile Phe Tyr Ala
1               5                   10

<210> SEQ ID NO 309
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 309

Ser Tyr Ile Ser Ser Ser Ser Ser Thr Ile Tyr Tyr Ala
1               5                   10

<210> SEQ ID NO 310
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 310

Ser Tyr Ser Ser Gly Asn Ser Gly Tyr Thr Asn Tyr Ala
1               5                   10

<210> SEQ ID NO 311
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 311
```

Ser Tyr Val Ser Asp Ser Gly Ser Ser Val Tyr Tyr Ala
1               5                   10

<210> SEQ ID NO 312
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR2

<400> SEQUENCE: 312

Glx His Val Asp Pro Glu Asp Gly Glu Thr Ile Tyr Ala
1               5                   10

<210> SEQ ID NO 313
<211> LENGTH: 24
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 313

Cys Ala Ala Ala Arg Arg Ser Gly Thr Tyr Asp Ile Gly Gln Tyr Leu
1               5                   10                  15

Arg Glu Ser Ala Tyr Val Phe Trp
            20

<210> SEQ ID NO 314
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 314

Cys Ala Ala Ala Tyr Ser Tyr Ser Gln Tyr Gly Ser Ser Tyr Ser Tyr
1               5                   10                  15

Trp

<210> SEQ ID NO 315
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 315

Cys Ala Ala Asp Asp Leu Gly Leu Glu Leu His Tyr Trp
1               5                   10

<210> SEQ ID NO 316
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 316

Cys Ala Ala Asp Pro Arg Gly Val Thr Leu Pro Arg Ala Thr Ala Tyr
1               5                   10                  15

Glu Tyr Trp

<210> SEQ ID NO 317
<211> LENGTH: 22
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 317

Cys Ala Ala Asp Arg Ile Glu Asn Tyr Leu Gly Arg Tyr Tyr Asp Pro
1               5                   10                  15

Ser Glu Tyr Glu Tyr Trp
            20

<210> SEQ ID NO 318
<211> LENGTH: 21
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 318

Cys Ala Ala Asp Thr Asn Trp Arg Ala Gly Pro Arg Val Gly Ile Asp
1               5                   10                  15

Glu Tyr Ala Tyr Trp
            20

<210> SEQ ID NO 319
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 319

Cys Ala Ala Gly Pro Asn Trp Ser Thr Arg Asn Arg Glu Tyr Asp Tyr
1               5                   10                  15

Trp

<210> SEQ ID NO 320
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 320

Cys Ala Ala Gly Ser Thr Val Val Ala Glu Phe Asn Tyr Trp
1               5                   10

<210> SEQ ID NO 321
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 321

Cys Ala Ala Lys Phe Gly Val Leu Ala Thr Thr Glu Ser Arg His Asp
1               5                   10                  15

Tyr Trp

<210> SEQ ID NO 322
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 322

Cys Ala Ala Gln Phe Arg Asn Asp Tyr Gly Leu Arg Tyr Gln Ser Thr
1               5                   10                  15

Asn Asn Tyr Trp
            20

<210> SEQ ID NO 323
<211> LENGTH: 21
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 323

Cys Ala Ala Arg Thr Ser Gly Gly Leu Phe His Tyr Arg Arg Ser Asp
1               5                   10                  15

His Trp Asp Thr Trp
            20

<210> SEQ ID NO 324
<211> LENGTH: 22
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 324

Cys Ala Ala Ser Met Glu Ala Met Asn Ser Leu Arg Val Asn Lys Glu
1               5                   10                  15

Arg Tyr Tyr Gln Ser Trp
            20

<210> SEQ ID NO 325
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 325

Cys Ala Ala Ser Val Tyr Ile Ser Arg Arg Asp Ser Asp Tyr Gly Tyr
1               5                   10                  15

Trp

<210> SEQ ID NO 326
<211> LENGTH: 21
<212> TYPE: PRT
<213> ORGANISM: Artificial Sequence
<220> FEATURE:
<223> OTHER INFORMATION: Synthesized molecular recognition unit - heavy
      CDR3

```
<400> SEQUENCE: 326

Cys Ala Ala Val Phe Thr Gly Arg Phe Tyr Gly Arg Pro Pro Arg Glu
1               5                   10                  15

Lys Tyr Asp Tyr Trp
            20

<210> SEQ ID NO 327
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 327

Cys Ala Ala Val Gln Ala Val Ile Gly Gly Thr Leu Thr Thr Ala Tyr
1               5                   10                  15

Asp Tyr Trp

<210> SEQ ID NO 328
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 328

Cys Ala Ala Tyr Ser Thr Phe Asn Thr Asp Val Ala Ser Met Lys Pro
1               5                   10                  15

Asp Tyr Trp

<210> SEQ ID NO 329
<211> LENGTH: 21
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 329

Cys Ala Gly Asp Arg Ser Arg Tyr Leu Tyr Gly Asp Ser Leu Arg Gly
1               5                   10                  15

Pro Tyr Gly Tyr Trp
            20

<210> SEQ ID NO 330
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 330

Cys Ala Ile Val Arg Gly Lys Lys Trp Tyr Phe Asp Leu Trp
1               5                   10

<210> SEQ ID NO 331
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3
```

<400> SEQUENCE: 331

Cys Ala Lys Ala Gln Ala Thr Gly Trp Ser Gly Tyr Tyr Thr Phe Asp
1               5                   10                  15

Tyr Trp

<210> SEQ ID NO 332
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 332

Cys Ala Lys Asp Asp Phe Ser Leu Tyr Gly Met Asp Val Trp
1               5                   10

<210> SEQ ID NO 333
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 333

Cys Ala Lys Asp Gly Thr Asp Gly Arg Phe Asp Pro Trp
1               5                   10

<210> SEQ ID NO 334
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 334

Cys Ala Lys Asp Leu Gly Ile Gln Leu Pro Asp Tyr Tyr Phe Asp Tyr
1               5                   10                  15

Trp

<210> SEQ ID NO 335
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 335

Cys Ala Lys Asp Leu Gly Arg Ala Ala Ala Gly Ser Met Asp Val Trp
1               5                   10                  15

<210> SEQ ID NO 336
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 336

Cys Ala Lys Asp Met Val His Leu Ile Val Ala Leu Ala Ile Asp Tyr
1               5                   10                  15

Trp

<210> SEQ ID NO 337
<211> LENGTH: 8
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 337

Cys Ala Lys Asp Ser Gly Leu Val
1               5

<210> SEQ ID NO 338
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 338

Cys Ala Lys Asp Ser Gly Asn Tyr Gly Tyr Tyr Gly Met Asp Val Trp
1               5                   10                  15

<210> SEQ ID NO 339
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 339

Cys Ala Lys Glu Asp Tyr Asp Ser Ser Gly Tyr Tyr Tyr Tyr Phe
1               5                   10                  15

Gln His Trp

<210> SEQ ID NO 340
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 340

Cys Ala Lys Gly Gly Asp Tyr Phe Tyr Tyr Tyr Gly Met Asp Val
1               5                   10                  15

Trp

<210> SEQ ID NO 341
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 341

Cys Ala Lys Gly Gly Asp Tyr Tyr Tyr Tyr Tyr Gly Met Asp Val
1               5                   10                  15

Trp

<210> SEQ ID NO 342
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 342

Cys Ala Lys Gly Gly Arg Asp Gly Tyr Lys Gly Tyr Phe Asp Tyr Trp
1               5                   10                  15

<210> SEQ ID NO 343
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 343

Cys Ala Lys Gly Gly Ser Leu Asp Met Asp Val Trp
1               5                   10

<210> SEQ ID NO 344
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 344

Cys Ala Lys Gly Gly Tyr Glu Leu Asp Tyr Trp
1               5                   10

<210> SEQ ID NO 345
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 345

Cys Ala Lys Gly Trp Leu Asp Phe Asp Tyr Trp
1               5                   10

<210> SEQ ID NO 346
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 346

Cys Ala Lys Ser Ile Ala Ala Ala Gly Thr Gly Tyr Tyr Gly Met Asp
1               5                   10                  15

Val Trp

<210> SEQ ID NO 347
<211> LENGTH: 18
<212> TYPE: PRT
<213> ORGANISM: Artificial Sequence
<220> FEATURE:
<223> OTHER INFORMATION: Synthesized molecular recognition unit - heavy

```
                CDR3

<400> SEQUENCE: 347

Cys Ala Lys Thr Tyr Tyr Asp Phe Trp Ser Gly Tyr Tyr Thr Phe Asp
1               5                   10                  15

Tyr Trp

<210> SEQ ID NO 348
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 348

Cys Ala Lys Val Ala Ser Gly Trp Ser Trp Pro Phe Asp Ile Trp
1               5                   10                  15

<210> SEQ ID NO 349
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 349

Cys Ala Leu Thr Trp Ala Pro Thr Pro Thr Asn Arg Arg Ser Asp Tyr
1               5                   10                  15

Ala Tyr Trp

<210> SEQ ID NO 350
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 350

Cys Ala Asn Gly Leu Glu Asp Ala Tyr Ala Phe Asp Ile Trp
1               5                   10

<210> SEQ ID NO 351
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 351

Cys Ala Pro Ala Leu Thr Asp Ala Gly Ser Phe Asp Tyr Trp
1               5                   10

<210> SEQ ID NO 352
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 352

Cys Ala Pro Tyr Tyr Tyr Asp Lys Ser Ala Lys Pro Leu Arg Ser Tyr
```

Phe Asp His Trp
            20

<210> SEQ ID NO 353
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 353

Cys Ala Arg Ala Ala Gly Asn Phe Trp Ser Gly Tyr Tyr Thr Phe Asp
1               5                   10                  15

Tyr Trp

<210> SEQ ID NO 354
<211> LENGTH: 21
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 354

Cys Ala Arg Ala Gly Ile Ala Ala Ala Pro Gly Ser Arg Asn Tyr Tyr
1               5                   10                  15

Gly Met Asp Val Trp
            20

<210> SEQ ID NO 355
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 355

Cys Ala Arg Ala Gly Thr Asn Trp Gly Gly Trp Tyr Phe Asp Leu Trp
1               5                   10                  15

<210> SEQ ID NO 356
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 356

Cys Ala Arg Ala Gly Tyr Gly Arg Tyr Tyr Tyr Gly Met Asp Val Trp
1               5                   10                  15

<210> SEQ ID NO 357
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 357

Cys Ala Arg Ala Gly Tyr Trp Ser Gly Tyr Gly Tyr Tyr Gly Met Asp
1               5                   10                  15

Val Trp

<210> SEQ ID NO 358
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 358

Cys Ala Arg Ala Gly Tyr Tyr Asp Ser Ser Gly Tyr Tyr Ala Phe Asp
1               5                   10                  15

Ile Trp

<210> SEQ ID NO 359
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 359

Cys Ala Arg Ala Thr Gly Ser Gly Trp Tyr Thr Asp Leu Gly Tyr Trp
1               5                   10                  15

<210> SEQ ID NO 360
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 360

Cys Ala Arg Asp Ala Gly Gly Asp Tyr Asp Tyr Trp
1               5                   10

<210> SEQ ID NO 361
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 361

Cys Ala Arg Asp Ala Ser Gly Gly Ser Thr Gly Trp Tyr Tyr Phe Asp
1               5                   10                  15

Ser Trp

<210> SEQ ID NO 362
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 362

Cys Ala Arg Asp Asp Gly Leu Gly Gly Met Asp Val Trp
1               5                   10

<210> SEQ ID NO 363

```
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 363

Cys Ala Arg Asp Asp Ser Met Gly Ala Phe Asp Ile Trp
1               5                   10

<210> SEQ ID NO 364
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 364

Cys Ala Arg Asp Glu Val Glu Gly Gly Met Asp Val Trp
1               5                   10

<210> SEQ ID NO 365
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 365

Cys Ala Arg Asp Phe Leu Gly Ser Thr Gly Asp Tyr Trp
1               5                   10

<210> SEQ ID NO 366
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 366

Cys Ala Arg Asp Gly Gly Ile Arg Asp Phe Asp Tyr Trp
1               5                   10

<210> SEQ ID NO 367
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 367

Cys Ala Arg Asp His Ser Ser Gly Trp Arg His Tyr Phe Asp Tyr Trp
1               5                   10                  15

<210> SEQ ID NO 368
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 368
```

```
Cys Ala Arg Asp Lys Gly Tyr Ala Phe Asp Ile Trp
1               5                   10

<210> SEQ ID NO 369
<211> LENGTH: 8
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 369

Cys Ala Arg Asp Leu Asp Tyr Trp
1               5

<210> SEQ ID NO 370
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 370

Cys Ala Arg Asp Leu Gly Gly Thr Ala Asp Tyr Trp
1               5                   10

<210> SEQ ID NO 371
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 371

Cys Ala Arg Asp Leu Arg Asn Trp Gly Ser Pro Tyr Trp Tyr Phe Asp
1               5                   10                  15

Leu Trp

<210> SEQ ID NO 372
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 372

Cys Ala Arg Asp Gln Asp Tyr Gly Asp Tyr Gly Trp Tyr Tyr Tyr Gly
1               5                   10                  15

Met Asp Val Trp
            20

<210> SEQ ID NO 373
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 373

Cys Ala Arg Asp Arg Glu Gln Gln Ile Leu Asp Tyr Trp
1               5                   10
```

```
<210> SEQ ID NO 374
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 374

Cys Ala Arg Asp Ser Asp Trp Gly Val Val Asp Pro Trp
1               5                   10

<210> SEQ ID NO 375
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 375

Cys Ala Arg Asp Val Gly Ala Phe Asp Ile Trp
1               5                   10

<210> SEQ ID NO 376
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 376

Cys Ala Arg Asp Trp Glu Leu Tyr Gly Met Asp Val Trp
1               5                   10

<210> SEQ ID NO 377
<211> LENGTH: 21
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 377

Cys Ala Arg Asp Trp Gly Ile Ala Ala Ala Gly Asp Tyr Tyr Tyr
1               5                   10                  15

Gly Met Asp Val Trp
            20

<210> SEQ ID NO 378
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 378

Cys Ala Arg Asp Tyr Ser Asp Arg Ser Gly Ile Asp Tyr Trp
1               5                   10

<210> SEQ ID NO 379
<211> LENGTH: 18
<212> TYPE: PRT
<213> ORGANISM: Artificial Sequence
<220> FEATURE:
<223> OTHER INFORMATION: Synthesized molecular recognition unit - heavy
```

CDR3

<400> SEQUENCE: 379

Cys Ala Arg Asp Tyr Tyr Gly Ser Gly Ser Tyr Asn Tyr Gly Met Asp
1               5                   10                  15
Val Trp

<210> SEQ ID NO 380
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 380

Cys Ala Arg Glu Ala Ala Glu Ile Pro Val Gly Ala Phe Asp Ile Trp
1               5                   10                  15

<210> SEQ ID NO 381
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 381

Cys Ala Arg Glu Ala Tyr Tyr Tyr Tyr Gly Met Asp Val Trp
1               5                   10                  15

<210> SEQ ID NO 382
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 382

Cys Ala Arg Glu Glu Gly Val Gly Gly Met Asp Val Trp
1               5                   10

<210> SEQ ID NO 383
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 383

Cys Ala Arg Glu Glu Arg Gly Ala Thr Gly Arg Ala Phe Asp Ile Trp
1               5                   10                  15

<210> SEQ ID NO 384
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 384

Cys Ala Arg Glu Gly Gly Tyr Tyr Phe Asp Tyr Trp
1               5                   10

```
<210> SEQ ID NO 385
<211> LENGTH: 22
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 385

Cys Ala Arg Glu Ser Ala Leu Tyr Ser Ser Ser Trp Tyr Tyr Tyr Tyr
1               5                   10                  15

Tyr Gly Met Asp Val Trp
            20

<210> SEQ ID NO 386
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 386

Cys Ala Arg Glu Val Ala Val Lys Asp Tyr Tyr Tyr Tyr Tyr Met Asp
1               5                   10                  15

Val Trp

<210> SEQ ID NO 387
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 387

Cys Ala Arg Glu Tyr Ser Tyr Gly Tyr Phe Arg Tyr Trp
1               5                   10

<210> SEQ ID NO 388
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 388

Cys Ala Arg Gly Asp Leu Glu Phe Asp Tyr Trp
1               5                   10

<210> SEQ ID NO 389
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 389

Cys Ala Arg Gly Glu Gln Trp Leu Val Trp Gly Phe Asp Pro Trp
1               5                   10                  15

<210> SEQ ID NO 390
<211> LENGTH: 10
<212> TYPE: PRT
```

```
<213> ORGANISM: Artificial Sequence
<220> FEATURE:
<223> OTHER INFORMATION: Synthesized molecular recognition unit - heavy
      CDR3

<400> SEQUENCE: 390

Cys Ala Arg Gly Gly Asp Phe Asp Tyr Trp
1               5                   10

<210> SEQ ID NO 391
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 391

Cys Ala Arg Gly Gly Asp Ser Ser Gly Tyr Tyr Tyr Tyr Ala Phe Asp
1               5                   10                  15

Ile Trp

<210> SEQ ID NO 392
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 392

Cys Ala Arg Gly Gly Gly Pro Asn Glu His Asp Tyr Tyr Phe Asp Tyr
1               5                   10                  15

Trp

<210> SEQ ID NO 393
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 393

Cys Ala Arg Gly Gly Asn Thr Tyr Tyr Tyr Tyr Tyr Gly Met Asp Val
1               5                   10                  15

Trp

<210> SEQ ID NO 394
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 394

Cys Ala Arg Gly Gly Ser Gly Ser Tyr Tyr Tyr Ala Phe Asp Ile Trp
1               5                   10                  15

<210> SEQ ID NO 395
<211> LENGTH: 17
<212> TYPE: PRT
<213> ORGANISM: Artificial Sequence
<220> FEATURE:
<223> OTHER INFORMATION: Synthesized molecular recognition unit - heavy
```

CDR3

<400> SEQUENCE: 395

Cys Ala Arg Gly Gly Ser Gly Trp Ser Asn Tyr Tyr Gly Met Asp Val
1               5                   10                  15

Trp

<210> SEQ ID NO 396
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 396

Cys Ala Arg Gly Gly Tyr Ser Thr Leu Asp Tyr Trp
1               5                   10

<210> SEQ ID NO 397
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 397

Cys Ala Arg Gly Leu Tyr Lys Arg Tyr Ser Tyr Gly Tyr Gly Met Asp
1               5                   10                  15

Val Trp

<210> SEQ ID NO 398
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 398

Cys Ala Arg Gly Asn Leu Asp Phe Asp Tyr Trp
1               5                   10

<210> SEQ ID NO 399
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 399

Cys Ala Arg Gly Asn Pro Tyr Tyr Phe Asp Tyr Trp
1               5                   10

<210> SEQ ID NO 400
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 400

Cys Ala Arg Gly Pro Ala Ala Ile Gly Ile Leu Gly Trp Phe Asp Pro

```
1               5                   10                  15

Trp

<210> SEQ ID NO 401
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 401

Cys Ala Arg Gly Pro Tyr Tyr Phe Asp Tyr Trp
1               5                   10

<210> SEQ ID NO 402
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 402

Cys Ala Arg Gly Arg Gly Lys Lys Asn Tyr Tyr Tyr Gly Met Asp Val
1               5                   10                  15

Trp

<210> SEQ ID NO 403
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 403

Cys Ala Arg Gly Arg Gly Tyr Ser Tyr Gly Tyr Tyr Ala Phe Asp Ile
1               5                   10                  15

Trp

<210> SEQ ID NO 404
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 404

Cys Ala Arg Gly Ser Asp Cys Ser Gly Gly Ser Cys Tyr Tyr Ser Phe
1               5                   10                  15

Asp Tyr Trp

<210> SEQ ID NO 405
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 405

Cys Ala Arg Gly Ser Gly Trp Ser Gly Leu Asp Tyr Trp
1               5                   10
```

```
<210> SEQ ID NO 406
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 406

Cys Ala Arg Gly Ser Gly Tyr Tyr Gly Pro Gly Tyr Tyr Gly Met Asp
1               5                   10                  15

Val Trp

<210> SEQ ID NO 407
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 407

Cys Ala Arg Gly Ser Tyr Gly Met Asp Val Trp
1               5                   10

<210> SEQ ID NO 408
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 408

Cys Ala Arg Gly Thr Thr Gly Lys Gly Tyr Tyr Tyr Tyr Gly Met Asp
1               5                   10                  15

Val Trp

<210> SEQ ID NO 409
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 409

Cys Ala Arg Gly Val Ser Ser Gly Tyr Tyr Tyr Tyr Tyr Gly Met Asp
1               5                   10                  15

Val Trp

<210> SEQ ID NO 410
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 410

Cys Ala Arg Gly Tyr Gly Asp Tyr Asp Leu Trp
1               5                   10

<210> SEQ ID NO 411
```

<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 411

Cys Ala Arg Gly Tyr Tyr Asp Phe Asp Tyr Trp
1               5                   10

<210> SEQ ID NO 412
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 412

Cys Ala Arg His Leu Ser Ser Gly Tyr Leu Ser Tyr Tyr Gly Met Asp
1               5                   10                  15

Val Trp

<210> SEQ ID NO 413
<211> LENGTH: 24
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 413

Cys Ala Arg His Pro Gly Ser Phe Gly Gly Tyr Ser Tyr Ala Trp Tyr
1               5                   10                  15

Tyr Tyr Tyr Gly Met Asp Val Trp
            20

<210> SEQ ID NO 414
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 414

Cys Ala Arg Leu Asp Tyr Gly Glu Thr Glu Gly Asn Gly Asp Trp
1               5                   10                  15

<210> SEQ ID NO 415
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 415

Cys Ala Arg Leu Gly Ser Tyr Gly Ser Pro Tyr Tyr Tyr Tyr Gly Met
1               5                   10                  15

Asp Val Trp

<210> SEQ ID NO 416
<211> LENGTH: 18
<212> TYPE: PRT

-continued

```
<213> ORGANISM: Artificial Sequence
<220> FEATURE:
<223> OTHER INFORMATION: Synthesized molecular recognition unit - heavy
      CDR3

<400> SEQUENCE: 416

Cys Ala Arg Leu Gly Ser Tyr Pro Gly Pro Tyr Tyr Tyr Met Asp
1               5                   10                  15

Val Trp

<210> SEQ ID NO 417
<211> LENGTH: 20
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 417

Cys Ala Arg Arg Gly Gly Asp Val Thr Val Pro Ala Ala Tyr Tyr Ala
1               5                   10                  15

Met Asp Val Trp
            20

<210> SEQ ID NO 418
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 418

Cys Ala Arg Thr Leu Ser Gly Tyr Ser Ser Ser Trp Tyr Val Phe Asp
1               5                   10                  15

Tyr Trp

<210> SEQ ID NO 419
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 419

Cys Ala Arg Tyr Ser Gly Tyr Asp Phe Asp Tyr Trp
1               5                   10

<210> SEQ ID NO 420
<211> LENGTH: 10
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 420

Cys Ala Ser Ala Ala Asp Phe Asp Tyr Trp
1               5                   10

<210> SEQ ID NO 421
<211> LENGTH: 18
<212> TYPE: PRT
<213> ORGANISM: Artificial Sequence
<220> FEATURE:
```

```
<223> OTHER INFORMATION: Synthesized molecular recognition unit - heavy
      CDR3

<400> SEQUENCE: 421

Cys Ala Ser Ala Lys Asn Asp Phe Trp Ser Gly Tyr Phe Ala Phe Asp
1               5                   10                  15

Tyr Trp

<210> SEQ ID NO 422
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 422

Cys Ala Ser Asp Ile Val Val Asp Asp Ala Phe Asp Thr Trp
1               5                   10

<210> SEQ ID NO 423
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 423

Cys Ala Ser Gly Asp Thr Tyr Asp Leu Tyr Ser Leu Asp Val Trp
1               5                   10                  15

<210> SEQ ID NO 424
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 424

Cys Ala Ser Gly Ser Tyr Tyr Ser Asp Phe Asp Tyr Trp
1               5                   10

<210> SEQ ID NO 425
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 425

Cys Ala Ser Gly Tyr Ser Tyr Gly Leu Tyr Tyr Tyr Gly Met Asp Val
1               5                   10                  15

Trp

<210> SEQ ID NO 426
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 426
```

```
Cys Ala Ser Ser Val Val Pro Ala Gly Pro Ala Gly Val Tyr Ala Phe
1               5                   10                  15

Asp Ile Trp

<210> SEQ ID NO 427
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 427

Cys Ala Ser Thr Val Thr Thr Asp Ala Phe Asp Ile Trp
1               5                   10

<210> SEQ ID NO 428
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 428

Cys Ala Ser Tyr Phe Gly Val Met Asp Val Trp
1               5                   10

<210> SEQ ID NO 429
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 429

Cys Ala Thr Ala Tyr Gly Ser Ser Ser Leu Asn Ile Asp Tyr Trp
1               5                   10                  15

<210> SEQ ID NO 430
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 430

Cys Ala Thr Asp Glu Tyr Ser Ser Ser Tyr Ala Phe Asp Ile Trp
1               5                   10                  15

<210> SEQ ID NO 431
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 431

Cys Ala Thr Asp Tyr Gly Asp Tyr Tyr Tyr Gly Met Asp Val Trp
1               5                   10                  15

<210> SEQ ID NO 432
<211> LENGTH: 13
<212> TYPE: PRT
```

```
<213> ORGANISM: Artificial Sequence
<220> FEATURE:
<223> OTHER INFORMATION: Synthesized molecular recognition unit - heavy
      CDR3

<400> SEQUENCE: 432

Cys Ala Thr Glu Ala Ala Leu Asp Ala Phe Asp Ile Trp
1               5                   10

<210> SEQ ID NO 433
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 433

Cys Ala Thr Gly Pro Asn Ser Ile Tyr
1               5

<210> SEQ ID NO 434
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 434

Cys Ala Thr Arg Arg Pro Phe Asn Ser Tyr Asn Thr Glu Gln Ser Tyr
1               5                   10                  15

Asp Ser Trp

<210> SEQ ID NO 435
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 435

Cys Ala Thr Arg Thr Gly Tyr Ser Tyr Gly Phe Asn Phe Trp Ala Phe
1               5                   10                  15

Asp Ile Trp

<210> SEQ ID NO 436
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 436

Cys Ala Thr Ser Pro Tyr Gly Val Phe Thr Leu Asp Tyr Trp
1               5                   10

<210> SEQ ID NO 437
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3
```

```
<400> SEQUENCE: 437

Cys Ala Thr Val Thr Gly Tyr Ser Ser Ala Gly Ala Phe Asp Ile Trp
1               5                   10                  15

<210> SEQ ID NO 438
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 438

Cys Ala Val Val Asp Asp Ala Phe Asp Ile Trp
1               5                   10

<210> SEQ ID NO 439
<211> LENGTH: 7
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 439

Cys Gly Ser Arg Gly Tyr Trp
1               5

<210> SEQ ID NO 440
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 440

Cys His Ala Lys Gln Leu Arg Asn Gly Gln Met Tyr Thr Tyr Trp
1               5                   10                  15

<210> SEQ ID NO 441
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 441

Cys His Ala Val Glu Asn Ile Leu Gly Arg Phe Val Asp Tyr Trp
1               5                   10                  15

<210> SEQ ID NO 442
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 442

Cys His Gly Arg Asp Tyr Gly Ser Asn Ala Pro Gln Tyr Trp
1               5                   10

<210> SEQ ID NO 443
<211> LENGTH: 14
<212> TYPE: PRT
```

```
<213> ORGANISM: Artificial Sequence
<220> FEATURE:
<223> OTHER INFORMATION: Synthesized molecular recognition unit - heavy
      CDR3

<400> SEQUENCE: 443

Cys Lys Ala Ala Pro Arg Trp Gly Gly Ala Thr Ala Tyr Trp
1               5                   10

<210> SEQ ID NO 444
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 444

Cys Lys Ile Tyr Gly Leu Asn Gly Gln Pro Leu Gly Ser Trp
1               5                   10

<210> SEQ ID NO 445
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 445

Cys Lys Leu Gln Val Arg Pro Ile Gly Tyr Ser Ser Ala Tyr Ser Arg
1               5                   10                  15

Asn Tyr Trp

<210> SEQ ID NO 446
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 446

Cys Lys Gln His Pro Asn Gly Tyr Arg
1               5

<210> SEQ ID NO 447
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 447

Cys Asn Ala Ala Ser Thr Val Thr Ala Trp Pro Tyr Tyr Gly Pro Asp
1               5                   10                  15

Tyr Trp

<210> SEQ ID NO 448
<211> LENGTH: 19
<212> TYPE: PRT
<213> ORGANISM: Artificial Sequence
<220> FEATURE:
<223> OTHER INFORMATION: Synthesized molecular recognition unit - heavy
      CDR3
```

```
<400> SEQUENCE: 448

Cys Asn Ala Asp Gly Tyr Ser Trp Asp Gly Arg Ser Gly Arg Arg Leu
1               5                   10                  15

Glu Leu Trp

<210> SEQ ID NO 449
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 449

Cys Asn Ala Asp Ile Lys Thr Thr Thr Tyr Ser Pro Leu Arg Asn Tyr
1               5                   10                  15

Trp

<210> SEQ ID NO 450
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 450

Cys Asn Ala Glu Thr Tyr Ser Gly Asn Thr Ile Trp
1               5                   10

<210> SEQ ID NO 451
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 451

Cys Asn Ala Phe Val Arg Ser Asp Phe Asp Arg Tyr Tyr Asp Tyr Trp
1               5                   10                  15

<210> SEQ ID NO 452
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 452

Cys Asn Ala Lys Arg Pro Trp Gly Ser Arg Asp Glu Tyr Trp
1               5                   10

<210> SEQ ID NO 453
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 453

Cys Asn Ala Asn Tyr Arg Gly Asn Arg Tyr Trp
1               5                   10
```

<210> SEQ ID NO 454
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 454

Cys Asn Ala Pro Ala Trp Leu Tyr Asp Asp Asp Tyr Trp
1               5                   10

<210> SEQ ID NO 455
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 455

Cys Asn Ala Val Thr Phe Gly Gly Asn Thr Ile Arg
1               5                   10

<210> SEQ ID NO 456
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 456

Cys Asn Ala Val Thr Tyr Asp Gly Tyr
1               5

<210> SEQ ID NO 457
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 457

Cys Asn Ala Val Thr Tyr Asn Gly Tyr Thr Ile Arg
1               5                   10

<210> SEQ ID NO 458
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 458

Cys Asn Ala Val Val Val Gly Leu Ser Arg Arg Ile Asp Asn Ile Trp
1               5                   10                  15

<210> SEQ ID NO 459
<211> LENGTH: 10
<212> TYPE: PRT
<213> ORGANISM: Artificial Sequence
<220> FEATURE:
<223> OTHER INFORMATION: Synthesized molecular recognition unit - heavy
      CDR3

```
<400> SEQUENCE: 459

Cys Asn Lys Val Asn Ala Ile Thr Lys Leu
1               5                   10

<210> SEQ ID NO 460
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 460

Cys Asn Leu Arg Glu Trp Asn Asn Ser Gly Ala Gly Tyr Trp
1               5                   10

<210> SEQ ID NO 461
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 461

Cys Asn Thr Ser Pro Tyr Met His Asp Val Trp
1               5                   10

<210> SEQ ID NO 462
<211> LENGTH: 10
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 462

Cys Asn Thr Val Arg Pro Leu Trp Ala Trp
1               5                   10

<210> SEQ ID NO 463
<211> LENGTH: 16
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 463

Cys Asn Thr Tyr Pro Phe Pro Ile Tyr Lys Lys Gly Tyr Pro Phe Trp
1               5                   10                  15

<210> SEQ ID NO 464
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 464

Cys Asn Val Asp Arg Thr Leu Tyr Gly Lys Tyr Lys Glu Tyr Trp
1               5                   10                  15

<210> SEQ ID NO 465
<211> LENGTH: 16
<212> TYPE: PRT
```

-continued

<213> ORGANISM: Artificial Sequence
<220> FEATURE:
<223> OTHER INFORMATION: Synthesized molecular recognition unit - heavy
      CDR3

<400> SEQUENCE: 465

Cys Ser Lys Gly Gly Val Tyr Gly Gly Thr Tyr Val Pro Asp Ser Trp
1               5                   10                  15

<210> SEQ ID NO 466
<211> LENGTH: 7
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 466

Cys Ser Ser Arg Gly Tyr Trp
1               5

<210> SEQ ID NO 467
<211> LENGTH: 21
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 467

Cys Thr Ala Gly Arg Ser Arg Tyr Leu Tyr Gly Ser Ser Leu Asn Gly
1               5                   10                  15

Pro Tyr Asp Tyr Trp
            20

<210> SEQ ID NO 468
<211> LENGTH: 7
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 468

Cys Thr Lys Gly Gly Ile Gln
1               5

<210> SEQ ID NO 469
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 469

Cys Thr Leu Val Asn Glu Ile Lys Thr Trp Trp
1               5                   10

<210> SEQ ID NO 470
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 470

Cys Thr Arg Glu His Ser Tyr Tyr Tyr Gly Met Asp Val Trp
1               5                   10                  15

<210> SEQ ID NO 471
<211> LENGTH: 11
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 471

Cys Thr Arg Val Ala Trp Gly Leu Asp Tyr Trp
1               5                   10

<210> SEQ ID NO 472
<211> LENGTH: 23
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 472

Cys Thr Thr Ala Gly Tyr Lys Ala Ala Arg Arg Ser Val Tyr Pro Arg
1               5                   10                  15

Ile Phe Asn Phe Asp Tyr Trp
            20

<210> SEQ ID NO 473
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 473

Cys Thr Thr Asp Asp Tyr Gly Asp Leu Thr His Leu Asp Tyr Trp
1               5                   10                  15

<210> SEQ ID NO 474
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 474

Cys Thr Thr Asp Asp Tyr Gly Asp Gln Tyr Gly Met Asp Val Trp
1               5                   10                  15

<210> SEQ ID NO 475
<211> LENGTH: 9
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 475

Cys Thr Thr Asp Leu Trp Asp Tyr Trp
1               5

<210> SEQ ID NO 476

```
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 476

Cys Val Lys Asp Gly Gly Ser Phe Pro Leu Ala Tyr Ala Phe Asp Ile
1               5                   10                  15

Trp

<210> SEQ ID NO 477
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 477

Cys Val Arg Gly Asp Ser Gly Trp Gly Ile Leu Tyr Tyr Val Met Asp
1               5                   10                  15

Val Trp

<210> SEQ ID NO 478
<211> LENGTH: 12
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 478

Cys Val Arg Tyr Ala Trp Pro Glu Phe Asp His Trp
1               5                   10

<210> SEQ ID NO 479
<211> LENGTH: 10
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 479

Cys Val Tyr Gly Arg Asp Phe Asp Tyr Trp
1               5                   10

<210> SEQ ID NO 480
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 480

Cys Tyr Ala Asp Ser Arg Ser Ser Trp Tyr Asp Glu Tyr Leu Glu His
1               5                   10                  15

Trp

<210> SEQ ID NO 481
<211> LENGTH: 16
<212> TYPE: PRT
<213> ORGANISM: Artificial Sequence
```

```
<220> FEATURE:
<223> OTHER INFORMATION: Synthesized molecular recognition unit - heavy
      CDR3

<400> SEQUENCE: 481

Cys Tyr Ala Asn Ile Tyr Tyr Thr Arg Arg Ala Pro Glu Glu Tyr Trp
1               5                   10                  15

<210> SEQ ID NO 482
<211> LENGTH: 15
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 482

Cys Tyr Ala Arg Thr Gln Arg Met Gly Val Val Asn Ser Tyr Trp
1               5                   10                  15

<210> SEQ ID NO 483
<211> LENGTH: 17
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 483

Cys Tyr Ala Arg Thr Val Ile Gly Gly Phe Gly Ala Phe Arg Ala His
1               5                   10                  15

Trp

<210> SEQ ID NO 484
<211> LENGTH: 18
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 484

Cys Tyr Arg Arg Gln Trp Ala Ser Ser Trp Gly Ala Arg Asn Tyr Glu
1               5                   10                  15

Tyr Trp

<210> SEQ ID NO 485
<211> LENGTH: 13
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 485

Cys Tyr Val Lys Leu Arg Asp Asp Asp Tyr Val Tyr Arg
1               5                   10

<210> SEQ ID NO 486
<211> LENGTH: 12
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 486
```

Gly Ala Ser Gln Ser Val Pro Arg Asn Ser Leu Ala
1               5                   10

<210> SEQ ID NO 487
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 487

His Gly Ser Gln Asp Ile Ser Asn Tyr Leu Asn
1               5                   10

<210> SEQ ID NO 488
<211> LENGTH: 17
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 488

Lys Ser Ser His Ser Leu Leu Ser Thr Ser Thr Asn Arg Asn His Leu
1               5                   10                  15

Ala

<210> SEQ ID NO 489
<211> LENGTH: 17
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 489

Lys Ser Ser His Ser Leu Leu Ser Thr Ser Thr Asn Arg Asn Gln Leu
1               5                   10                  15

Ala

<210> SEQ ID NO 490
<211> LENGTH: 17
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 490

Lys Ser Ser His Ser Leu Leu Tyr Ser Ser Asp Asn Lys Asn Tyr Leu
1               5                   10                  15

Ala

<210> SEQ ID NO 491
<211> LENGTH: 17
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 491

Lys Ser Ser Gln Ser Ile Leu Ser Ser Ser Asn Arg Asp Ser Leu
1               5                   10                  15

Ala

<210> SEQ ID NO 492
<211> LENGTH: 17
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 492

Lys Ser Ser Gln Ser Val Leu Tyr Thr Thr Thr Asn Arg Asn His Ile
1               5                   10                  15

Ala

<210> SEQ ID NO 493
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 493

Gln Ala Ser Gln Asp Ile Ala Asn Tyr Leu Asn
1               5                   10

<210> SEQ ID NO 494
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 494

Gln Ala Ser Gln Asp Ile Ser Asn Tyr Leu Ala
1               5                   10

<210> SEQ ID NO 495
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 495

Gln Ala Ser Gln Asp Ile Ser Asn Tyr Leu Asn
1               5                   10

<210> SEQ ID NO 496
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 496

Arg Ala Ser Gln Asp Ile Ser Ser Tyr Leu Ala
1               5                   10

<210> SEQ ID NO 497
<211> LENGTH: 11
<212> TYPE: PRT

```
<213> ORGANISM: Artificial Sequence
<220> FEATURE:
<223> OTHER INFORMATION: Synthesized molecular recognition unit - light
      CDR1

<400> SEQUENCE: 497

Arg Ala Ser Gln Gly Ile Asn Ser Tyr Leu Ala
1               5                   10

<210> SEQ ID NO 498
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 498

Arg Ala Ser Gln Gly Ile Ser Asn Asn Leu Asn
1               5                   10

<210> SEQ ID NO 499
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 499

Arg Ala Ser Gln Gly Ile Ser Asn Tyr Leu Ala
1               5                   10

<210> SEQ ID NO 500
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 500

Arg Ala Ser Gln Gly Ile Ser Asn Tyr Leu Asn
1               5                   10

<210> SEQ ID NO 501
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 501

Arg Ala Ser Gln Gly Ile Ser Arg Asp Leu Ala
1               5                   10

<210> SEQ ID NO 502
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 502

Arg Ala Ser Gln Gly Ile Ser Ser Ala Leu Ala
1               5                   10
```

```
<210> SEQ ID NO 503
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 503

Arg Ala Ser Gln Gly Ile Ser Ser Tyr Leu Ala
1               5                   10

<210> SEQ ID NO 504
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 504

Arg Ala Ser Gln Asn Ile Gly Leu Tyr Leu Asn
1               5                   10

<210> SEQ ID NO 505
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 505

Arg Ala Ser Gln Arg Val Ser Asn Tyr Leu Asn
1               5                   10

<210> SEQ ID NO 506
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 506

Arg Ala Ser Gln Ser Ile Ser Asn Tyr Leu Asn
1               5                   10

<210> SEQ ID NO 507
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 507

Arg Ala Ser Gln Ser Ile Ser Arg Trp Leu Ala
1               5                   10

<210> SEQ ID NO 508
<211> LENGTH: 11
<212> TYPE: PRT
<213> ORGANISM: Artificial Sequence
<220> FEATURE:
<223> OTHER INFORMATION: Synthesized molecular recognition unit - light
      CDR1
```

```
<400> SEQUENCE: 508

Arg Ala Ser Gln Ser Ile Ser Arg Tyr Leu Asn
1               5                   10

<210> SEQ ID NO 509
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 509

Arg Ala Ser Gln Ser Ile Ser Ser Tyr Leu Ala
1               5                   10

<210> SEQ ID NO 510
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 510

Arg Ala Ser Gln Ser Ile Ser Ser Tyr Leu Asn
1               5                   10

<210> SEQ ID NO 511
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 511

Arg Ala Ser Gln Ser Ile Glx Asn Tyr Leu Asn
1               5                   10

<210> SEQ ID NO 512
<211> LENGTH: 12
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 512

Arg Ala Ser Gln Ser Val Arg Ser Ser Asp Leu Ala
1               5                   10

<210> SEQ ID NO 513
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 513

Arg Ala Ser Gln Ser Val Ser Ser Asn Leu Ala
1               5                   10

<210> SEQ ID NO 514
<211> LENGTH: 11
```

```
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 514

Arg Ala Ser Gln Ser Val Tyr Ser Asn Leu Ala
1               5                   10

<210> SEQ ID NO 515
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 515

Arg Ala Ser Gln Tyr Ile Ser Asn Tyr Leu Asn
1               5                   10

<210> SEQ ID NO 516
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 516

Arg Ala Ser Arg Asn Ile Asn Arg Tyr Leu Asn
1               5                   10

<210> SEQ ID NO 517
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 517

Arg Pro Ser Gln Ser Ile Gly Ser Trp Leu Ala
1               5                   10

<210> SEQ ID NO 518
<211> LENGTH: 16
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 518

Arg Ser Ser Gln Ser Leu Leu His Ser Asp Gly Tyr Thr Tyr Leu Tyr
1               5                   10                  15

<210> SEQ ID NO 519
<211> LENGTH: 16
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 519

Arg Ser Ser Gln Ser Leu Leu His Ser Asn Gly Tyr Asn Tyr Leu Asp
```

-continued

```
<210> SEQ ID NO 520
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 520

Arg Val Ser Gln Gly Ile Ser Ser Tyr Leu Asn
1               5                   10

<210> SEQ ID NO 521
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 521

Arg Val Ser Gln Ser Ile Ser Ser Tyr Leu Asn
1               5                   10

<210> SEQ ID NO 522
<211> LENGTH: 11
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 522

Arg Glx Ser Gln Ser Glx Ser Glx Tyr Leu Asn
1               5                   10

<210> SEQ ID NO 523
<211> LENGTH: 13
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 523

Ser Gly Ser Ser Ser Asn Val Gly Asn Asn Tyr Val Ser
1               5                   10

<210> SEQ ID NO 524
<211> LENGTH: 12
<212> TYPE: PRT
<213> ORGANISM: Artificial Sequence
<220> FEATURE:
<223> OTHER INFORMATION: Synthesized molecular recognition unit - light
      CDR1

<400> SEQUENCE: 524

Trp Ala Ser Gln Ser Val Arg Gly Asn Tyr Val Ala
1               5                   10

<210> SEQ ID NO 525
<211> LENGTH: 7
<212> TYPE: PRT
<213> ORGANISM: Artificial Sequence
<220> FEATURE:
<223> OTHER INFORMATION: Synthesized molecular recognition unit - light
```

```
                        CDR2

<400> SEQUENCE: 525

Ala Ala Ser Ile Leu Gln Ser
1               5

<210> SEQ ID NO 526
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 526

Ala Ala Ser Ser Leu His Ser
1               5

<210> SEQ ID NO 527
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 527

Ala Ala Ser Ser Leu Leu Ser
1               5

<210> SEQ ID NO 528
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 528

Ala Ala Ser Ser Leu Gln Gly
1               5

<210> SEQ ID NO 529
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 529

Ala Ala Ser Ser Leu Gln Ser
1               5

<210> SEQ ID NO 530
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 530

Ala Ala Ser Thr Leu Glu Ser
1               5

<210> SEQ ID NO 531
```

```
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 531

Ala Ala Ser Thr Leu Gln Arg
1               5

<210> SEQ ID NO 532
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 532

Ala Ala Ser Thr Leu Gln Ser
1               5

<210> SEQ ID NO 533
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 533

Asp Ala Lys Gly Leu His Pro
1               5

<210> SEQ ID NO 534
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 534

Asp Ala Ser Asn Leu Glu Thr
1               5

<210> SEQ ID NO 535
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 535

Asp Ala Ser Asn Leu Gln Ser
1               5

<210> SEQ ID NO 536
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 536
```

Asp Ala Ser Asn Arg Ala Ala
1               5

<210> SEQ ID NO 537
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 537

Asp Ala Ser Asn Arg Ala Gly
1               5

<210> SEQ ID NO 538
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 538

Asp Ala Ser Asn Arg Gln Ser
1               5

<210> SEQ ID NO 539
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 539

Asp Ala Ser Ser Leu Glu Ser
1               5

<210> SEQ ID NO 540
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 540

Asp Ala Ser Ser Leu Gln Arg
1               5

<210> SEQ ID NO 541
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 541

Asp Asn Asp Lys Arg Pro Ser
1               5

<210> SEQ ID NO 542
<211> LENGTH: 7
<212> TYPE: PRT
<213> ORGANISM: Artificial Sequence
<220> FEATURE:

```
<223> OTHER INFORMATION: Synthesized molecular recognition unit - light
      CDR2

<400> SEQUENCE: 542

Asp Thr Ser Asn Arg Ala Thr
1               5

<210> SEQ ID NO 543
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 543

Gly Ala Ser Gln Arg Ala Thr
1               5

<210> SEQ ID NO 544
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 544

Gly Ala Ser Thr Arg Ala Thr
1               5

<210> SEQ ID NO 545
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 545

Gly Ser Ser Ser Arg Ala Thr
1               5

<210> SEQ ID NO 546
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 546

Gly Ser Ser Thr Leu Gln Ser
1               5

<210> SEQ ID NO 547
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 547

Gly Thr Ser Asn Leu Gln Ser
1               5
```

```
<210> SEQ ID NO 548
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 548

Gly Thr Ser Ser Leu His Thr
1               5

<210> SEQ ID NO 549
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 549

Lys Ala Ser Ser Leu Glu Ser
1               5

<210> SEQ ID NO 550
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 550

Leu Gly Ser Asn Arg Ala Ser
1               5

<210> SEQ ID NO 551
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 551

Ser Ala Ser Ser Leu Gln Ser
1               5

<210> SEQ ID NO 552
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 552

Ser Ala Ser Thr Leu Gln Ser
1               5

<210> SEQ ID NO 553
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 553
```

```
Thr Leu Ser Tyr Arg Ala Ser
1               5

<210> SEQ ID NO 554
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 554

Trp Ala Ser Ser Arg Lys Ser
1               5

<210> SEQ ID NO 555
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 555

Glx Ala Ser Ser Leu Gln Ser
1               5

<210> SEQ ID NO 556
<211> LENGTH: 7
<212> TYPE: PRT
<213> ORGANISM: Artificial Sequence
<220> FEATURE:
<223> OTHER INFORMATION: Synthesized molecular recognition unit - light
      CDR2

<400> SEQUENCE: 556

Glx Ala Ser Thr Leu Glu Ser
1               5

<210> SEQ ID NO 557
<211> LENGTH: 13
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 557

Cys Glu Ser Trp Asp Ser Ser Leu Ser Ser Glu Val Phe
1               5                   10

<210> SEQ ID NO 558
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 558

Cys Leu Gln Asp Phe Ser Phe Pro Trp Thr Phe
1               5                   10

<210> SEQ ID NO 559
<211> LENGTH: 11
<212> TYPE: PRT
<213> ORGANISM: Artificial Sequence
```

```
<220> FEATURE:
<223> OTHER INFORMATION: Synthesized molecular recognition unit - light
      CDR3

<400> SEQUENCE: 559

Cys Leu Gln Asp Tyr Ser Tyr Pro Arg Thr Phe
1               5                   10

<210> SEQ ID NO 560
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 560

Cys Leu Gln Asp Tyr Thr Asp Pro Phe Thr Phe
1               5                   10

<210> SEQ ID NO 561
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 561

Cys Leu Gln His Asn Ser Tyr Pro Phe Thr Phe
1               5                   10

<210> SEQ ID NO 562
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 562

Cys Met Gln Ala Leu Glu Ala Leu Phe Thr Phe
1               5                   10

<210> SEQ ID NO 563
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 563

Cys Met Gln Ala Leu Gln Thr Pro Ile Thr Phe
1               5                   10

<210> SEQ ID NO 564
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 564

Cys Met Gln Ala Thr Gln Phe Pro Leu Thr Phe
1               5                   10
```

<210> SEQ ID NO 565
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 565

Cys Gln His Arg Ser Asn Trp Pro Leu Thr Phe
1               5                   10

<210> SEQ ID NO 566
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 566

Cys Gln Gln Ala Asn Ser Phe Pro Phe Thr Phe
1               5                   10

<210> SEQ ID NO 567
<211> LENGTH: 10
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 567

Cys Gln Gln Ala Asn Ser Leu Phe Thr Phe
1               5                   10

<210> SEQ ID NO 568
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 568

Cys Gln Gln Ala Tyr Ser Phe Pro Trp Thr Phe
1               5                   10

<210> SEQ ID NO 569
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 569

Cys Gln Gln Phe Asp Arg Ser Pro Leu Thr Phe
1               5                   10

<210> SEQ ID NO 570
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

-continued

<400> SEQUENCE: 570

Cys Gln Gln Gly Asn Ser Phe Pro Tyr Thr Phe
1               5                   10

<210> SEQ ID NO 571
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 571

Cys Gln Gln Gly Tyr Gly Thr Pro Pro Met Phe
1               5                   10

<210> SEQ ID NO 572
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 572

Cys Gln Gln Gly Tyr Asn Thr Pro Arg Thr Phe
1               5                   10

<210> SEQ ID NO 573
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 573

Cys Gln Gln Ile His Ser Tyr Pro Leu Thr Phe
1               5                   10

<210> SEQ ID NO 574
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 574

Cys Gln Gln Ser Phe Ser Thr Pro Arg Thr Phe
1               5                   10

<210> SEQ ID NO 575
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 575

Cys Gln Gln Ser Asn Ser Phe Pro Tyr Thr Phe
1               5                   10

<210> SEQ ID NO 576
<211> LENGTH: 11
<212> TYPE: PRT

<213> ORGANISM: Artificial Sequence
<220> FEATURE:
<223> OTHER INFORMATION: Synthesized molecular recognition unit - light
      CDR3

<400> SEQUENCE: 576

Cys Gln Gln Ser Ser Ser Thr Pro Tyr Thr Phe
1               5                   10

<210> SEQ ID NO 577
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 577

Cys Gln Gln Ser Tyr Asp Ser Pro Trp Thr Phe
1               5                   10

<210> SEQ ID NO 578
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 578

Cys Gln Gln Ser Tyr Ile Thr Pro Leu Thr Phe
1               5                   10

<210> SEQ ID NO 579
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 579

Cys Gln Gln Ser Tyr Asn Thr Pro Arg Thr Phe
1               5                   10

<210> SEQ ID NO 580
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 580

Cys Gln Gln Ser Tyr Asn Val Pro Phe Thr Phe
1               5                   10

<210> SEQ ID NO 581
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 581

Cys Gln Gln Ser Tyr Arg Ile His Trp Thr Phe
1               5                   10

```
<210> SEQ ID NO 582
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 582

Cys Gln Gln Ser Tyr Arg Thr Pro Leu Thr Phe
1               5                   10

<210> SEQ ID NO 583
<211> LENGTH: 10
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 583

Cys Gln Gln Ser Tyr Arg Tyr Pro Thr Phe
1               5                   10

<210> SEQ ID NO 584
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 584

Cys Gln Gln Ser Tyr Ser Ala Pro Leu Ser Phe
1               5                   10

<210> SEQ ID NO 585
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 585

Cys Gln Gln Ser Tyr Ser Ala Pro Leu Thr Phe
1               5                   10

<210> SEQ ID NO 586
<211> LENGTH: 12
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 586

Cys Gln Gln Ser Tyr Ser Phe Pro Pro Phe Thr Phe
1               5                   10

<210> SEQ ID NO 587
<211> LENGTH: 11
<212> TYPE: PRT
<213> ORGANISM: Artificial Sequence
<220> FEATURE:
<223> OTHER INFORMATION: Synthesized molecular recognition unit - light
      CDR3
```

<400> SEQUENCE: 587

Cys Gln Gln Ser Tyr Ser Ile Pro Phe Thr Phe
1               5                   10

<210> SEQ ID NO 588
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 588

Cys Gln Gln Ser Tyr Ser Leu Pro Leu Thr Phe
1               5                   10

<210> SEQ ID NO 589
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 589

Cys Gln Gln Ser Tyr Ser Met Pro Leu Thr Phe
1               5                   10

<210> SEQ ID NO 590
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 590

Cys Gln Gln Ser Tyr Ser Pro Pro Phe Thr Phe
1               5                   10

<210> SEQ ID NO 591
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 591

Cys Gln Gln Ser Tyr Ser Ser Pro Pro Thr Phe
1               5                   10

<210> SEQ ID NO 592
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 592

Cys Gln Gln Ser Tyr Ser Thr Pro Leu Thr Phe
1               5                   10

<210> SEQ ID NO 593
<211> LENGTH: 11

```
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 593

Cys Gln Gln Ser Tyr Ser Thr Pro Trp Thr Phe
1               5                   10

<210> SEQ ID NO 594
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 594

Cys Gln Gln Ser Tyr Ser Thr Pro Tyr Thr Phe
1               5                   10

<210> SEQ ID NO 595
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 595

Cys Gln Gln Ser Tyr Ser Thr Ser Ile Thr Phe
1               5                   10

<210> SEQ ID NO 596
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 596

Cys Gln Gln Ser Tyr Ser Val Pro Tyr Thr Phe
1               5                   10

<210> SEQ ID NO 597
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 597

Cys Gln Gln Ser Tyr Thr Ser Arg Leu Thr Phe
1               5                   10

<210> SEQ ID NO 598
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 598

Cys Gln Gln Ser Tyr Thr Thr Pro Phe Thr Phe
```

<210> SEQ ID NO 599
<211> LENGTH: 11
<212> TYPE: PRT
<213> ORGANISM: Artificial Sequence
<220> FEATURE:
<223> OTHER INFORMATION: Synthesized molecular recognition unit - light
    CDR3

<400> SEQUENCE: 599

Cys Gln Gln Thr Tyr Ser Ile Pro Pro Thr Phe
1               5                   10

<210> SEQ ID NO 600
<211> LENGTH: 11
<212> TYPE: PRT
<213> ORGANISM: Artificial Sequence
<220> FEATURE:
<223> OTHER INFORMATION: Synthesized molecular recognition unit - light
    CDR3

<400> SEQUENCE: 600

Cys Gln Gln Thr Tyr Thr Ile Pro Phe Thr Phe
1               5                   10

<210> SEQ ID NO 601
<211> LENGTH: 12
<212> TYPE: PRT
<213> ORGANISM: Artificial Sequence
<220> FEATURE:
<223> OTHER INFORMATION: Synthesized molecular recognition unit - light
    CDR3

<400> SEQUENCE: 601

Cys Gln Gln Tyr Gly Arg Ser Pro Arg Tyr Ser Phe
1               5                   10

<210> SEQ ID NO 602
<211> LENGTH: 13
<212> TYPE: PRT
<213> ORGANISM: Artificial Sequence
<220> FEATURE:
<223> OTHER INFORMATION: Synthesized molecular recognition unit - light
    CDR3

<400> SEQUENCE: 602

Cys Gln Gln Tyr His Asn Trp Pro Pro Glu Tyr Thr Phe
1               5                   10

<210> SEQ ID NO 603
<211> LENGTH: 12
<212> TYPE: PRT
<213> ORGANISM: Artificial Sequence
<220> FEATURE:
<223> OTHER INFORMATION: Synthesized molecular recognition unit - light
    CDR3

<400> SEQUENCE: 603

Cys Gln Gln Tyr Asn Asn Trp Pro Pro Ile Thr Phe
1               5                   10

<210> SEQ ID NO 604
<211> LENGTH: 11
<212> TYPE: PRT
<213> ORGANISM: Artificial Sequence
<220> FEATURE:
<223> OTHER INFORMATION: Synthesized molecular recognition unit - light

CDR3

<400> SEQUENCE: 604

Cys Gln Gln Tyr Asn Asn Trp Pro Tyr Thr Phe
1               5                   10

<210> SEQ ID NO 605
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 605

Cys Gln Gln Tyr Tyr Asn Ile Pro Tyr Ser Phe
1               5                   10

<210> SEQ ID NO 606
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 606

Cys Gln Gln Tyr Tyr Ser Thr Pro Gln Thr Phe
1               5                   10

<210> SEQ ID NO 607
<211> LENGTH: 11
<212> TYPE: PRT
<213> ORGANISM: Artificial Sequence
<220> FEATURE:
<223> OTHER INFORMATION: Synthesized molecular recognition unit - light
      CDR3

<400> SEQUENCE: 607

Cys Gln Gln Tyr Tyr Ser Thr Pro Tyr Thr Phe
1               5                   10

<210> SEQ ID NO 608
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 608

Cys Asn Ala Lys Arg Pro Trp Gly Ser Arg Asp Glu Tyr Trp
1               5                   10

<210> SEQ ID NO 609
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 609

Cys Asn Ala Ala Arg Pro Trp Gly Ser Arg Asp Glu Tyr Trp
1               5                   10

<210> SEQ ID NO 610

-continued

```
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 610

Cys Asn Ala Lys Ala Pro Trp Gly Ser Arg Asp Glu Tyr Trp
1               5                   10

<210> SEQ ID NO 611
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 611

Cys Asn Ala Lys Arg Ala Trp Gly Ser Arg Asp Glu Tyr Trp
1               5                   10

<210> SEQ ID NO 612
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 612

Cys Asn Ala Lys Arg Pro Ala Gly Ser Arg Asp Glu Tyr Trp
1               5                   10

<210> SEQ ID NO 613
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 613

Cys Asn Ala Lys Arg Pro Trp Ala Ser Arg Asp Glu Tyr Trp
1               5                   10

<210> SEQ ID NO 614
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 614

Cys Asn Ala Lys Arg Pro Trp Gly Ala Arg Asp Glu Tyr Trp
1               5                   10

<210> SEQ ID NO 615
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 615
```

Cys Asn Ala Lys Arg Pro Trp Gly Ser Ala Asp Glu Tyr Trp
1               5                   10

<210> SEQ ID NO 616
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 616

Cys Asn Ala Lys Arg Pro Trp Gly Ser Arg Ala Glu Tyr Trp
1               5                   10

<210> SEQ ID NO 617
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 617

Cys Asn Ala Lys Arg Pro Trp Gly Ser Arg Asp Ala Tyr Trp
1               5                   10

<210> SEQ ID NO 618
<211> LENGTH: 14
<212> TYPE: PRT
<213> ORGANISM: Artificial Sequence
<220> FEATURE:
<223> OTHER INFORMATION: Synthesized molecular recognition unit - heavy
      CDR3

<400> SEQUENCE: 618

Cys Asn Ala Lys Arg Pro Trp Gly Ser Arg Asp Glu Ala Trp
1               5                   10

<210> SEQ ID NO 619
<211> LENGTH: 648
<212> TYPE: PRT
<213> ORGANISM: Artificial Sequence
<220> FEATURE:
<223> OTHER INFORMATION: Made in Lab - LRP6E3E4_O75581 construct

<400> SEQUENCE: 619

Glu Ala Phe Leu Leu Phe Ser Arg Arg Ala Asp Ile Arg Arg Ile Ser
1               5                   10                  15

Leu Glu Thr Asn Asn Asn Val Ala Ile Pro Leu Thr Gly Val Lys
            20                  25                  30

Glu Ala Ser Ala Leu Asp Phe Asp Val Thr Asp Asn Arg Ile Tyr Trp
        35                  40                  45

Thr Asp Ile Ser Leu Lys Thr Ile Ser Arg Ala Phe Met Asn Gly Ser
    50                  55                  60

Ala Leu Glu His Val Val Glu Phe Gly Leu Asp Tyr Pro Glu Gly Met
65                  70                  75                  80

Ala Val Asp Trp Leu Gly Lys Asn Leu Tyr Trp Ala Asp Thr Gly Thr
                85                  90                  95

Asn Arg Ile Glu Val Ser Lys Leu Asp Gly Gln His Arg Gln Val Leu
            100                 105                 110

Val Trp Lys Asp Leu Asp Ser Pro Arg Ala Leu Ala Leu Asp Pro Ala
        115                 120                 125

```
Glu Gly Phe Met Tyr Trp Thr Glu Trp Gly Gly Lys Pro Lys Ile Asp
            130                 135                 140
Arg Ala Ala Met Asp Gly Ser Glu Arg Thr Thr Leu Val Pro Asn Val
145                 150                 155                 160
Gly Arg Ala Asn Gly Leu Thr Ile Asp Tyr Ala Lys Arg Arg Leu Tyr
                165                 170                 175
Trp Thr Asp Leu Asp Thr Asn Leu Ile Glu Ser Ser Asn Met Leu Gly
            180                 185                 190
Leu Asn Arg Glu Val Ile Ala Asp Leu Pro His Pro Phe Gly Leu
            195                 200                 205
Thr Gln Tyr Gln Asp Tyr Ile Tyr Trp Thr Asp Trp Ser Arg Arg Ser
    210                 215                 220
Ile Glu Arg Ala Asn Lys Thr Ser Gly Gln Asn Arg Thr Ile Ile Gln
225                 230                 235                 240
Gly His Leu Asp Tyr Val Met Asp Ile Leu Val Phe His Ser Ser Arg
                245                 250                 255
Gln Ser Gly Trp Asn Glu Cys Ala Ser Ser Asn Gly His Cys Ser His
            260                 265                 270
Leu Cys Leu Ala Val Pro Val Gly Gly Phe Val Cys Gly Cys Pro Ala
    275                 280                 285
His Tyr Ser Leu Asn Ala Asp Asn Arg Thr Cys Ser Ala Pro Thr Thr
    290                 295                 300
Phe Leu Leu Phe Ser Gln Lys Ser Ala Ile Asn Arg Met Val Ile Asp
305                 310                 315                 320
Glu Gln Gln Ser Pro Asp Ile Ile Leu Pro Ile His Ser Leu Arg Asn
                325                 330                 335
Val Arg Ala Ile Asp Tyr Asp Pro Leu Asp Lys Gln Leu Tyr Trp Ile
            340                 345                 350
Asp Ser Arg Gln Asn Met Ile Arg Lys Ala Gln Glu Asp Gly Ser Gln
        355                 360                 365
Gly Phe Thr Val Val Ser Ser Val Pro Ser Gln Asn Leu Glu Ile
    370                 375                 380
Gln Pro Tyr Asp Leu Ser Ile Asp Ile Tyr Ser Arg Tyr Ile Tyr Trp
385                 390                 395                 400
Thr Cys Glu Ala Thr Asn Val Ile Asn Val Thr Arg Leu Asp Gly Arg
                405                 410                 415
Ser Val Gly Val Val Leu Lys Gly Glu Gln Asp Arg Pro Arg Ala Val
            420                 425                 430
Val Val Asn Pro Glu Lys Gly Tyr Met Tyr Phe Thr Asn Leu Gln Glu
        435                 440                 445
Arg Ser Pro Lys Ile Glu Arg Ala Ala Leu Asp Gly Thr Glu Arg Glu
450                 455                 460
Val Leu Phe Phe Ser Gly Leu Ser Lys Pro Ile Ala Leu Ala Leu Asp
465                 470                 475                 480
Ser Arg Leu Gly Lys Leu Phe Trp Ala Asp Ser Asp Leu Arg Arg Ile
                485                 490                 495
Glu Ser Ser Asp Leu Ser Gly Ala Asn Arg Ile Val Leu Glu Asp Ser
            500                 505                 510
Asn Ile Leu Gln Pro Val Gly Leu Thr Val Phe Glu Asn Trp Leu Tyr
        515                 520                 525
Trp Ile Asp Lys Gln Gln Gln Met Ile Glu Lys Ile Asp Met Thr Gly
    530                 535                 540
Arg Glu Gly Arg Thr Lys Val Gln Ala Arg Ile Ala Gln Leu Ser Asp
```

```
                545                 550                 555                 560
Ile His Ala Val Lys Glu Leu Asn Leu Gln Glu Tyr Arg Gln His Pro
                    565                 570                 575

Cys Ala Gln Asp Asn Gly Gly Cys Ser His Ile Cys Leu Val Lys Gly
                580                 585                 590

Asp Gly Thr Thr Arg Cys Ser Cys Pro Met His Leu Val Leu Leu Gln
            595                 600                 605

Asp Glu Leu Ser Cys Gly Glu Pro Pro Ser Ser Gly Gly Leu Asn
        610                 615                 620

Asp Ile Phe Glu Ala Gln Lys Ile Glu Trp His Glu Gly Ser Gly Ser
625                 630                 635                 640

His His His His His His His His
                    645

<210> SEQ ID NO 620
<211> LENGTH: 130
<212> TYPE: PRT
<213> ORGANISM: Artificial Sequence
<220> FEATURE:
<223> OTHER INFORMATION: Made in Lab - Lrp6E3E4:VHH26 complex

<400> SEQUENCE: 620

Asp Val Gln Leu Val Glu Ser Gly Gly Gly Leu Val Gln Ala Gly Gly
1               5                   10                  15

Ser Leu Arg Leu Ala Cys Ala Gly Ser Gly Arg Ile Phe Ala Ile Tyr
            20                  25                  30

Asp Ile Ala Trp Tyr Arg His Pro Pro Gly Asn Gln Arg Glu Leu Val
        35                  40                  45

Ala Met Ile Arg Pro Val Val Thr Glu Ile Asp Tyr Ala Asp Ser Val
    50                  55                  60

Lys Gly Arg Phe Thr Ile Ser Arg Asn Asn Ala Met Lys Thr Val Tyr
65                  70                  75                  80

Leu Gln Met Asn Asn Leu Lys Pro Glu Asp Thr Ala Val Tyr Tyr Cys
                85                  90                  95

Asn Ala Lys Arg Pro Trp Gly Ser Arg Asp Glu Tyr Trp Gly Gln Gly
            100                 105                 110

Thr Gln Val Thr Val Ser Ser Gly Ser Gly Ser Gly His His His His
        115                 120                 125

His His
    130

<210> SEQ ID NO 621
<211> LENGTH: 122
<212> TYPE: PRT
<213> ORGANISM: Artificial Sequence
<220> FEATURE:
<223> OTHER INFORMATION: Made in Lab - Lrp6E3E4:VHH36 complex

<400> SEQUENCE: 621

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Ile Phe Ser Ile Tyr
            20                  25                  30

Asp Met Gly Trp Phe Arg Gln Ala Pro Gly Lys Glu Arg Glu Phe Val
        35                  40                  45

Ser Gly Ile Arg Trp Ser Gly Gly Thr Ser Tyr Ala Asp Ser Val Lys
    50                  55                  60
```

-continued

```
Gly Arg Phe Thr Ile Ser Lys Asp Asn Ala Lys Asn Thr Ile Tyr Leu
 65              70                  75                  80

Gln Met Asn Asn Leu Lys Ala Glu Asp Thr Ala Val Tyr Tyr Cys Gly
             85                  90                  95

Ser Arg Gly Tyr Trp Gly Gln Gly Thr Leu Val Thr Val Ser Ser Gly
            100                 105                 110

Ser Gly Ser Gly His His His His His His
        115             120
```

ANTI-LRP5/6 ANTIBODIES AND METHODS OF USE

CROSS REFERENCE TO RELATED APPLICATIONS

This application is a U.S. National Phase Application, filed under 35 U.S.C. § 371, of International Application No. PCT/US2018/066620, filed on Dec. 19, 2018, which claims priority to U.S. Provisional Application No. 62/607,879, filed Dec. 19, 2017, and U.S. Provisional Application No. 62/680,515, filed Jun. 4, 2018, all of which are incorporated by reference herein in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is SRZN_005_02WO_ST25.txt. The text file is 181 KB, was created on Dec. 19, 2018, and is being submitted electronically via EFS-Web.

BACKGROUND

Technical Field

The present invention relates generally to anti-LRP5/6 antibodies, compositions and methods of using same. Such antibodies are useful, for example, in methods of modulating Wnt signaling pathways.

DESCRIPTION OF THE RELATED ART

Wnt ("Wingless-related integration site" or "Wingless and Int-1" or "Wingless-Int") ligands and their signals play key roles in the control of development, homeostasis and regeneration of many essential organs and tissues, including bone, liver, skin, stomach, intestine, kidney, central nervous system, mammary gland, taste bud, ovary, cochlea and many other tissues (reviewed, e.g., by Clevers, Loh, and Nusse, 2014; 346:1table 1B8012). Modulation of Wnt signaling pathways has potential for treatment of degenerative diseases and tissue injuries.

One of the challenges for modulating Wnt signaling as a therapeutic is the existence of multiple Wnt ligands and Wnt receptors, Frizzled 1-10 (Fzd1-10), with many tissues expressing multiple and overlapping Fzds. Canonical Wnt signals also involve Low-density lipoprotein (LDL) receptor-related protein 5 (LRP5) or Low-density lipoprotein (LDL) receptor-related protein 6 (LRP6) as co-receptors, which are broadly expressed in various tissues, in addition to Fzds. Accordingly, there is clearly a need in the art for binding moieties, such as antibodies, that specifically bind to one or more Fzd, LRP5, or LRP6. The present invention addresses this need.

BRIEF SUMMARY

An isolated antibody, or an antigen-binding fragment thereof, that binds to one or more LRP5 or LRP6 receptor, comprising a sequence comprising: CDRH1, CDRH2 and CDRH3 sequences set forth for any of the antibodies of Table 1A; and/or CDRL1, CDRL2 and CDRL3 sequences set forth for any of the antibodies of Table 1A, or a variant of said antibody, or antigen-binding fragment thereof, comprising one or more amino acid modifications, wherein said variant comprises less than 8 amino acid substitutions in said CDR sequences. In particular embodiments, the isolated antibody, or antigen-binding fragment thereof comprises a heavy chain variable region comprising an amino acid sequence having at least 90% identity to the amino acid sequence set forth in any of SEQ ID NOs:1-24 or a heavy chain variable region comprising the amino acid sequence set forth in any of SEQ ID NOs:1-24.

In particular embodiments, any of the antibodies, or antigen-binding fragments thereof, are humanized. In certain embodiments, any of the antibodies, or antigen-binding fragments thereof, are a single chain antibody, a scFv, a univalent antibody lacking a hinge region, a VHH or single domain antibody (sdAb), or a minibody. In particular embodiments, any of the antibodies, or antigen-binding fragments thereof, are a VHH or sdAb. In particular embodiments, any of the antibodies, or antigen-binding fragments thereof, are a Fab or a Fab' fragment.

In certain embodiments, any of the antibodies, or antigen-binding fragments thereof, are a fusion protein. In certain embodiments, the antibody, or antigen-binding fragment thereof, is fused to a polypeptide sequence that binds one or more Fzd receptors. In certain embodiments, the polypeptide sequence that binds one or more Fzd receptors is an antibody, or an antigen-binding fragment thereof, that binds to one or more Fzd receptors.

In certain embodiments, any of the isolated antibodies, or antigen-binding fragments thereof, disclosed herein binds to LRP5, LRP6, or both LRP5 and LRP6.

In a related embodiment, the disclosure provides an isolated antibody, or an antigen-binding fragment thereof, that competes with any of the antibodies disclosed herein for binding to LRP5 or LRP6.

In particular embodiments, any of the antibodies, or antigen-binding fragments thereof, bind to LRP5 or LRP6 with a KD of 50 µM or lower.

In particular embodiments, any of the antibodies, or antigen-binding fragments thereof, modulate a Wnt signaling pathway in a cell, optionally a mammalian cell. In particular embodiments, any of the antibodies, or antigen-binding fragments thereof increase signaling via a Wnt signaling pathway in the cell. In particular embodiments, any of the antibodies, or antigen-binding fragments thereof decrease signaling via a Wnt signaling pathway in the cell. In certain embodiments, the Wnt signaling pathway is a canonical Wnt signaling pathway or a non-canonical Wnt signaling pathway.

In a further related embodiment, the present disclosure provides an isolated polynucleotide encoding an antibody, or antigen-binding fragment thereof, disclosed herein. In certain embodiments, the present disclosure provides an expression vector comprising the isolated polynucleotide and an isolated host cell comprising the expression vector.

In another embodiment, the present disclosure provides a pharmaceutical composition comprising a physiologically acceptable excipient, diluent, or carrier, and a therapeutically effective amount of the isolated antibody, or antigen-binding fragment thereof, disclosed herein.

In a further embodiment, the present disclosure provides a method for agonizing a Wnt signaling pathway in a cell, comprising contacting the cell with an isolated antibody, or antigen-binding fragment thereof, disclosed herein that increases Wnt signaling. In particular embodiments, the antibody, or antigen-binding fragment thereof, is a fusion protein comprising a polypeptide sequence that binds one or more frizzled (Fzd) receptors.

In another embodiment, the present disclosure provides a method for inhibiting a Wnt signaling pathway in a cell, comprising contacting the cell with the isolated antibody, or antigen-binding fragment thereof, disclosed herein the inhibits Wnt signaling.

In another embodiment, the present disclosure includes a method for treating a subject having a disease or disorder associated with reduced Wnt signaling, comprising administering to the subject an effective amount of a pharmaceutical composition comprising an isolated antibody, or antigen-binding fragment thereof, disclosed herein that is an agonist of a Wnt signaling pathway. In particular embodiments, the disease or disorder is selected from the group consisting of: bone fractures, stress fractures, vertebral compression fractures, osteoarthritis, osteoporosis, osteoporotic fractures, non-union fractures, delayed union fractures, spinal fusion, pre-operative optimization for spine surgeries, osteonecrosis, osseointegration of implants or orthopedic devices, osteogenesis imperfecta, bone grafts, tendon repair, tendon-bone integration, tooth growth and regeneration, maxillofacial surgery, dental implantation, periodontal diseases, maxillofacial reconstruction, osteonecrosis of the jaw, hip or femoral head, avascular necrosis, alopecia, hearing loss, vestibular hypofunction, macular degeneration, age-related macular degeneration (AMD), vitreoretinopathy, retinopathy, diabetic retinopathy, diseases of retinal degeneration, Fuchs' dystrophy, cornea diseases, stroke, traumatic brain injury, Alzheimer's disease, multiple sclerosis, muscular dystrophy, muscle atrophy in sarcopenia and cachexia, diseases affecting blood brain barrier (BBB), spinal cord injuries, spinal cord diseases, oral mucositis, short bowel syndrome, inflammatory bowel diseases (IBD), metabolic syndrome, diabetes, dyslipidemia, pancreatitis, exocrine pancreatic insufficiency, wound healing, diabetic foot ulcers, pressure sores, venous leg ulcers, epidermolysis bullosa, dermal hypoplasia, myocardial infarction, coronary artery disease, heart failure, hematopoietic cell disorders, immunodeficiencies, graft versus host diseases, acute kidney injuries, chronic kidney diseases, chronic obstructive pulmonary diseases (COPD), idiopathic pulmonary fibrosis, acute liver failure of all causes, acute liver failure drug-induced, alcoholic liver diseases, chronic liver failure of all causes, cirrhosis, liver fibrosis of all causes, portal hypertension, chronic liver insufficiency of all causes, nonalcoholic steatohepatitis (NASH), nonalcoholic fatty liver disease (NAFLD) (fatty liver), alcoholic hepatitis, hepatitis C virus-induced liver diseases (HCV), hepatitis B virus-induced liver diseases (HBV), other viral hepatitis (e.g., hepatitis A virus-induced liver diseases (HAV) and hepatitis D virus-induced liver diseases (HDV)), primary biliary cirrhosis, autoimmune hepatitis, livery surgery, liver injury, liver transplantation, "small for size" syndrome in liver surgery and transplantation, congenital liver disease and disorders, any other liver disorder or detect resulting from genetic diseases, degeneration, aging, drugs, or injuries.

In a related embodiment, the present disclosure provides a method for treating a subject having a disease or disorder associated with increased or enhanced Wnt signaling, comprising administering to the subject an effective amount of the pharmaceutical composition comprising an isolated antibody, or antigen-binding fragment thereof, disclosed herein that is an inhibitor of a Wnt signaling pathway. In certain embodiments, the disease or disorder is selected from the group consisting of: tumors and cancers, degenerative disorders, fibrosis, heart failure, coronary artery disease, heterotopic ossification, osteopetrosis, and congenital high bone mass disorders.

DETAILED DESCRIPTION

Figure 1:
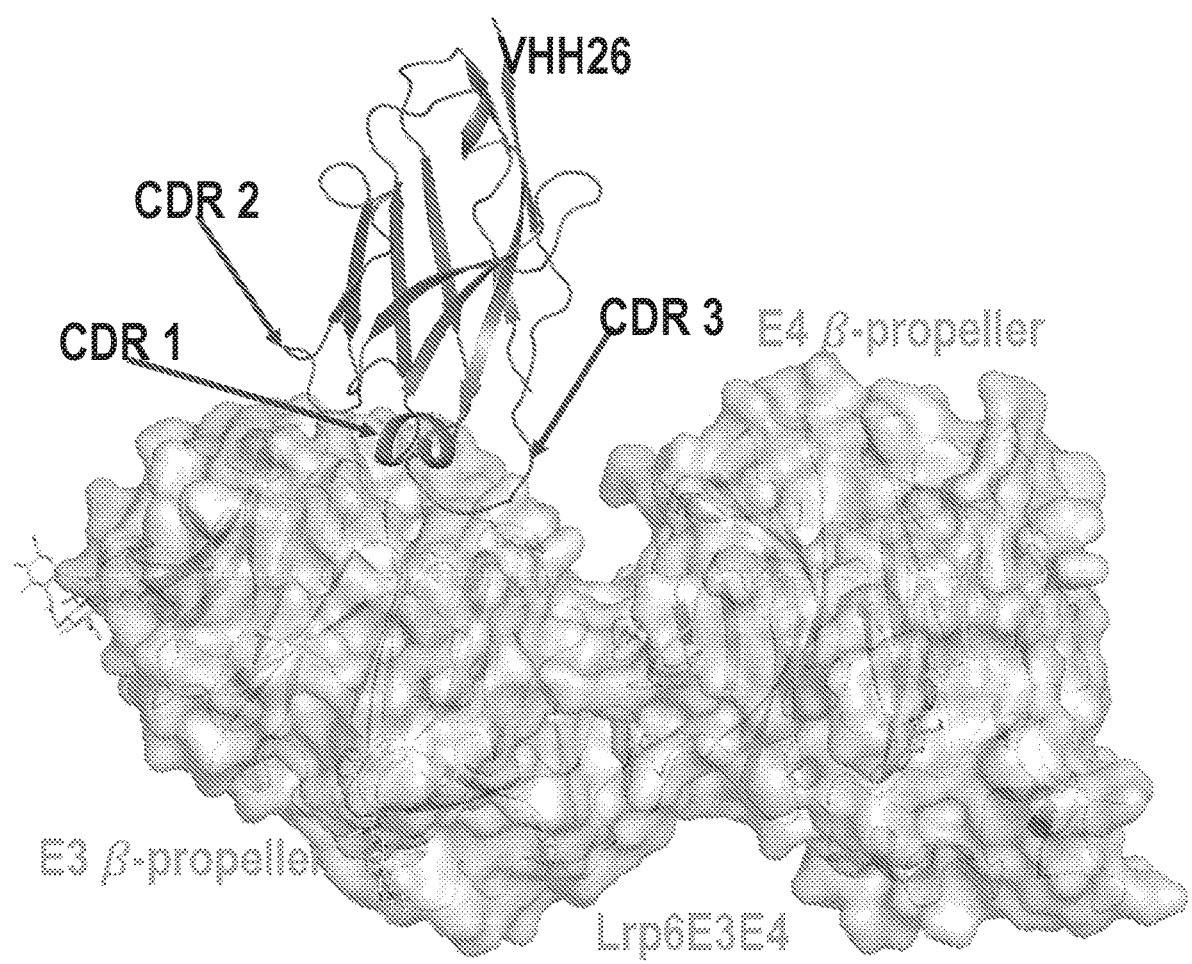
FIG. 1 shows a graphic representation of the crystal structure of LRP6E3E4:VHH26 binding complex. LRP6E3E4 is represented as transparent grey and VHH26 is darker grey. Positions of the CDR loops of VHH26 are marked. Glycans on the surface of LRP6E3E4 are shown as sticks representations.
Figure 2:
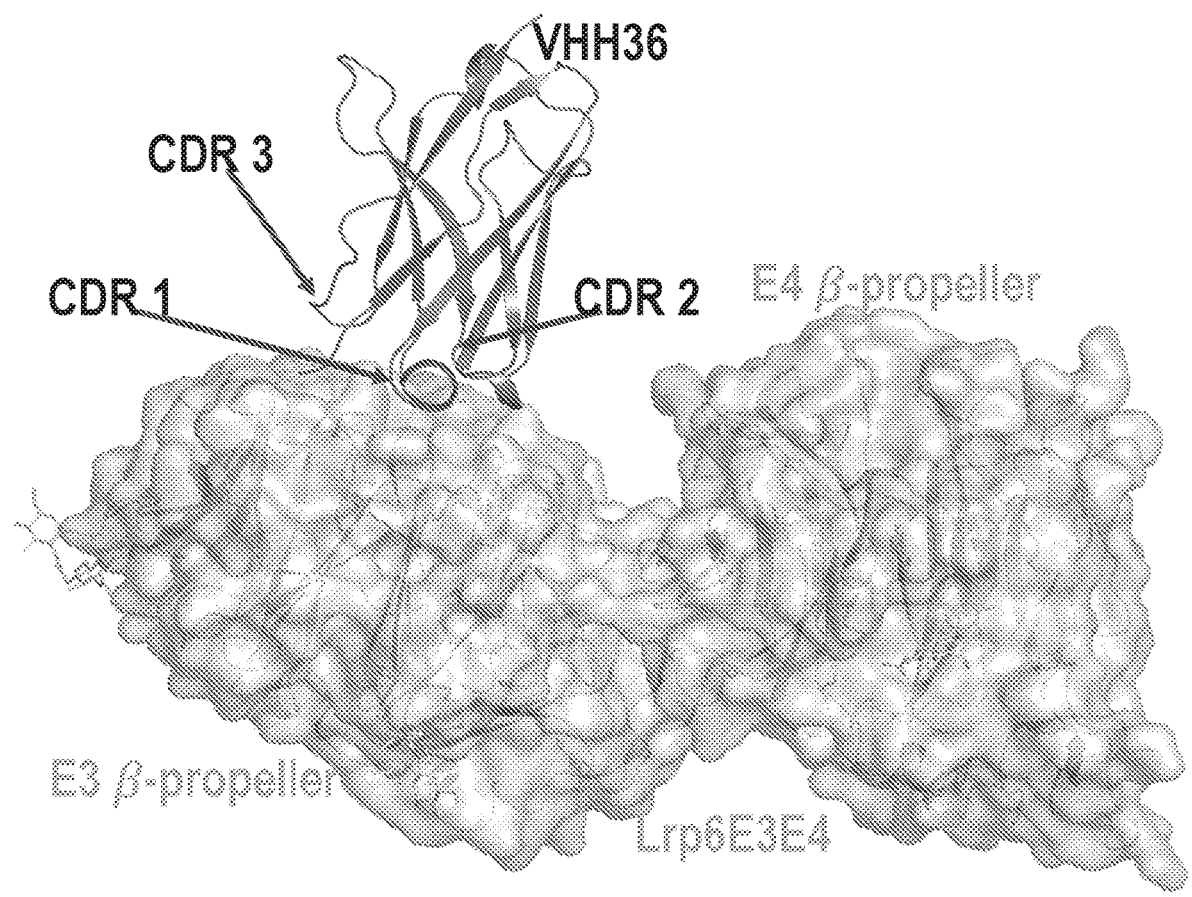
FIG. 2 shows a graphic representation of the crystal structure of LRP6E3E4:VHH36 binding complex. LRP6E3E4 is shown as transparent grey and VHH36 is darker grey. Positions of the CDR loops of VHH36 are marked. Glycans on the surface of LRP6E3E4 are shown as sticks representations.

The present disclosure relates to antibodies and antigen-binding fragments thereof the specifically bind to LRP5 and/or LRP6, in particular antibodies having specific LRP receptor specificity and functional properties. One embodiment of the invention encompasses specific humanized antibodies and fragments thereof capable of binding to LRP5 and/or LRP6 and modulating downstream Wnt pathway signaling and biological effects. For convenience, the term "anti-LRP5/6" is used to refer collectively to antibodies and antigen-binding fragments thereof that bind to either or both of LRP5 and/or LRP6.

Embodiments of the invention pertain to the use of anti-LRP5/6 antibodies or antigen-binding fragments thereof for the diagnosis, assessment and treatment of diseases and disorders associated with Wnt signaling pathways. In certain embodiments, the subject antibodies are used in the treatment or prevention of diseases and disorders associated with aberrant (e.g., increased or decreased) Wnt signaling, or for which either decreased or increased Wnt signaling would provide a therapeutic benefit.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Current Protocols in Molecular Biology or Current Protocols in Immunology, John Wiley & Sons, New York, N.Y. (2009); Ausubel et al., Short Protocols in Molecular Biology, 3$^{rd}$ ed., Wiley & Sons, 1995; Sambrook and Russell, Molecular Cloning: A Laboratory Manual (3rd Edition, 2001); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984) and other like references.

As used in this specification and the appended claims, the singular forms "a," "an" and "the" include plural references unless the content clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients.

Embodiments of the present invention relate to antibodies that bind to LRP5 and/or LRP6. Sequences of illustrative antibodies, or antigen-binding fragments, or complementarity determining regions (CDRs) thereof, are set forth in SEQ ID NOs:1-24.

As is well known in the art, an antibody is an immunoglobulin molecule capable of specific binding to a target, such as a carbohydrate, polynucleotide, lipid, polypeptide, etc., through at least one epitope recognition site, located in the variable region of the immunoglobulin molecule. As used herein, the term encompasses not only intact polyclonal or monoclonal antibodies, but also fragments thereof (such as dAb, Fab, Fab', F(ab')$_2$, Fv), single chain (scFv), VHH or sdAbs (also known as nanobodies), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity. "Diabodies", multivalent or multispecific fragments constructed by gene fusion (WO94/13804; P. Holliger et al., Proc. Natl. Acad. Sci. USA 90 6444-6448, 1993) are also a particular form of antibody contemplated herein. Minibodies comprising a scFv joined to a CH3 domain are also included herein (S. Hu et al., Cancer Res., 56, 3055-3061, 1996). See e.g., Ward, E. S. et al., Nature 341, 544-546 (1989); Bird et al., Science, 242, 423-426, 1988; Huston et al., PNAS USA, 85, 5879-5883,1988); PCT/US92/09965; WO94/13804; P. Holliger et al., Proc. Natl. Acad. Sci. USA 90 6444-6448, 1993; Y. Reiter et al., Nature Biotech, 14, 1239-1245, 1996; S. Hu et al., Cancer Res., 56, 3055-3061, 1996.

The term "antigen-binding fragment" as used herein refers to a polypeptide fragment that contains at least one CDR of an immunoglobulin heavy and/or light chains that binds to the antigen of interest, in particular to LRP5 and/or LRP6. In this regard, an antigen-binding fragment of the herein described antibodies may comprise 1, 2, 3, 4, 5, or all 6 CDRs of a VH and VL sequence set forth herein from antibodies that bind LRP5 and/or LRP6. An antigen-binding fragment of the LRP5/6-specific antibodies described herein is capable of binding to LRP5 and/or LRP6. In certain embodiments, an antigen-binding fragment or an antibody comprising an antigen-binding fragment, increases Wnt signaling events. In certain embodiments, the antibody or antigen-binding fragment binds specifically to and/or modulates the biological activity of the human Wnt signaling pathway. In certain embodiments, the antibody or antigen-binding fragment thereof increases or decreases Wnt signaling.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes. In certain embodiments, an antibody is said to specifically bind an antigen when it preferentially recognizes its target antigen in a complex mixture of proteins and/or macromolecules. In certain embodiments, an antibody is said to specifically bind an antigen when the equilibrium dissociation constant is ≤104 or ≤$10^{-8}$ M. In some embodiments, the equilibrium dissociation constant may be ≤$10^{-9}$ M or ≤$10^{-10}$ M.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. In certain embodiments, an antibody is said to specifically bind an antigen when it preferentially recognizes its target antigen in a complex mixture of proteins and/or macromolecules. An antibody is said to specifically bind an antigen when the equilibrium dissociation constant is ≤$10^{-7}$ or ≤$10^{-8}$ M. In some embodiments, the equilibrium dissociation constant may be ≤$10^{-9}$ M or ≤$10^{-10}$ M.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Wnt hin FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures-regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof, now available on the Internet (immuno.bme.nwu.edu). Alternatively, CDRs may be determined by using "IMGT®, the international ImMunoGeneTics information System® available at http://www.imgt.org (see, e.g., Lefranc, M.-P. et al. (1999) *Nucleic Acids Res.*, 27:209-212; Ruiz, M. et al. (2000) *Nucleic Acids Res.*, 28:219-221; Lefranc, M.-P. (2001) *Nucleic Acids Res.*, 29:207-209; Lefranc, M.-P. (2003) *Nucleic Acids Res.*, 31:307-310; Lefranc, M.-P. et al. (2004) *In Silico* Biol., 5, 0006 [Epub], 5:45-60 (2005)]; Lefranc, M.-P. et al. (2005) *Nucleic Acids Res.*, 33:D593-597; Lefranc, M.-P. et al. (2009) *Nucleic Acids Res.*, 37:D1006-1012; Lefranc, M.-P. et al. (2015) *Nucleic Acids Res.*, 43:D413-422).

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')$_2$, Fv), single chain (scFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody".

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent $V_H::V_L$ heterodimer including an antigen-binding site which retains much of the antigen recognition and binding capabilities of the native antibody molecule. Inbar et al. (1972) *Proc. Nat. Acad. Sci. USA* 69:2659-2662; Hochman et al. (1976) *Biochem* 15:2706-2710; and Ehrlich et al. (1980) *Biochem* 19:4091-4096.

In certain embodiments, single chain Fv or scFV antibodies are contemplated. For example, Kappa bodies (III et al., Prot. Eng. 10: 949-57 (1997); minibodies (Martin et al., EMBO J 13: 5305-9 (1994); diabodies (Holliger et al., PNAS 90: 6444-8 (1993); or Janusins (Traunecker et al., *EMBO J*10: 3655-59 (1991) and Traunecker et al., *Int. J. Cancer Suppl.* 7: 51-52 (1992), may be prepared using standard molecular biology techniques following the teachings of the present application with regard to selecting antibodies having the desired specificity. In still other embodiments, bispecific or chimeric antibodies may be made that encompass the ligands of the present disclosure. For example, a chimeric antibody may comprise CDRs and framework regions from different antibodies, while bispecific antibodies may be generated that bind specifically to LRP5 and/or LRP6 through one binding domain and to a second molecule through a second binding domain. These antibodies may be produced through recombinant molecular biological techniques or may be physically conjugated together.

A single chain Fv (scFv) polypeptide is a covalently linked $V_H::V_L$ heterodimer which is expressed from a gene fusion including $V_H$- and $V_L$-encoding genes linked by a peptide-encoding linker. Huston et al. (1988) *Proc. Nat. Acad. Sci. USA* 85(16):5879-5883. A number of methods have been described to discern chemical structures for converting the naturally aggregated—but chemically separated—light and heavy polypeptide chains from an antibody V region into an scFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, an LRP5/6 binding antibody as described herein is in the form of a diabody. Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

A dAb fragment of an antibody consists of a $V_H$ domain (Ward, E. S. et al., Nature 341, 544-546 (1989)).

Where bispecific antibodies are to be used, these may be conventional bispecific antibodies, which can be manufactured in a variety of ways (Holliger, P. and Winter G. *Current Opinion Biotechnol.* 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (J. B. B. Ridgeway et al., Protein Eng., 9, 616-621, 1996).

In certain embodiments, the antibodies described herein may be provided in the form of a UniBody®. A UniBody® is an IgG4 antibody with the hinge region removed (see GenMab Utrecht, The Netherlands; see also, e.g., US20090226421). This proprietary antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells. For certain cancer cell surface antigens, this univalent binding may not stimulate the cancer cells to grow as may be seen using bivalent antibodies having the same antigen specificity, and hence UniBody® technology may afford treatment options for some types of cancer that may be refractory to treatment with conventional antibodies. The small size of the UniBody@ can be a great benefit when treating some forms of cancer, allowing for better distribution of the molecule over larger solid tumors and potentially increasing efficacy.

In certain embodiments, the antibodies of the present disclosure may take the form of a VHH or sdAb. VHH or sdAb are encoded by single genes and are efficiently produced in almost all prokaryotic and eukaryotic hosts e.g. *E. coli* (see e.g. U.S. Pat. No. 6,765,087), molds (for example *Aspergillus* or *Trichoderma*) and yeast (for example *Saccharomyces, Kluyvermyces, Hansenula* or *Pichia* (see e.g. U.S. Pat. No. 6,838,254). The production process is scalable and multi-kilogram quantities of VHH or sdAb have been produced. VHH or sdAbs may be formulated as a ready-to-use solution having a long shelf life. The Nanoclone® method (see, e.g., WO 06/079372) is a proprietary method for generating VHH or sdAbs against a desired target, based on automated high-throughput selection of B-cells.

In certain embodiments, the anti-LRP5/6 antibodies or antigen-binding fragments thereof as disclosed herein are humanized. This refers to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild type or modified by one or more amino acid substitutions. This eliminates the constant region as an immunogen in human individuals, but the possibility of an immune response to the foreign variable region remains (LoBuglio, A. F. et al., (1989) *Proc Natl Acad Sci USA* 86:4220-4224; Queen et al., PNAS (1988) 86:10029-10033; Riechmann et al., *Nature* (1988) 332:323-327). Illustrative methods for humanization of the anti-LRP5/6 antibodies disclosed herein include the methods described in U.S. Pat. No. 7,462,697.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato, K., et al., (1993) *Cancer Res* 53:851-856. Riechmann, L., et al., (1988) *Nature* 332:323-327; Verhoeyen, M., et al., (1988) *Science* 239:1534-1536; Kettleborough, C. A., et al., (1991) *Protein Engineering* 4:773-3783; Maeda, H., et al., (1991) *Human Antibodies Hybrdoma* 2:124-134; Gorman, S. D., et al., (1991) *Proc Natl Acad Sci USA* 88:4181-4185; Tempest, P. R., et al., (1991) *Bio/Technology* 9:266-271; Co, M. S., et al., (1991) *Proc Natl Acad Sci USA* 88:2869-2873; Carter, P., et al., (1992) *Proc Natl Acad Sci USA* 89:4285-4289; and Co, M. S. et al., (1992) *J Immunol* 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

In certain embodiments, the antibodies of the present disclosure may be chimeric antibodies. In this regard, a chimeric antibody is comprised of an antigen-binding fragment of an anti-LRP5/6 antibody operably linked or otherwise fused to a heterologous Fc portion of a different antibody. In certain embodiments, the heterologous Fc domain is of human origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of CH2 and CH3 domains from one or more of the different Ig classes. As noted above with regard to humanized antibodies, the anti-LRP5/6 antigen-binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, VH or both).

In certain embodiments, the Fc region of an antibody or fragment thereof may be derived from any of a variety of different Fcs, including but not limited to, a wild-type or modified IgG1, IgG2, IgG3, IgG4 or other isotype, e.g., wild-type or modified human IgG1, human IgG2, human IgG3, human IgG4, human IgG4Pro (comprising a mutation in core hinge region that prevents the formation of IgG4 half molecules), human IgA, human IgE, human IgM, or the modified IgG1 referred to as IgG1 LALAPG. The L235A, P329G (LALA-PG) variant has been shown to eliminate complement binding and fixation as well as Fcγdependent antibody-dependent cell-mediated cytotoxity (ADCC) in both murine IgG2a and human IgG1. In particular embodiments of any of the IgG disclosed herein, the IgG comprises one or more of the following amino acid substitutions: N297G, N297A, N297E, L234A, L235A, or P236G.

In certain embodiments, antibodies or antigen-binding fragments thereof disclosed herein include fusion proteins, e.g., Wnt signaling pathway agonist fusion proteins, also referred to herein as "Wnt surrogates." Wnt surrogates of the present invention are usually biologically active in binding to a cognate Frizzled receptor, and in activation of Wnt signaling, i.e., the surrogate is a Wnt agonist. The term "Wnt agonist activity" refers to the ability of an agonist to mimic the effect or activity of a Wnt protein binding to a frizzled protein. The ability of the agonists of the invention to mimic the activity of Wnt can be confirmed by a number of assays. The agonists of the invention typically initiate a reaction or activity that is similar to or the same as that initiated by the receptor's natural ligand. In particular, the agonists of the invention enhance the canonical Wnt/β-catenin signaling pathway. As used herein, the term "enhances" refers to a measurable increase in the level of Wnt/β-catenin signaling compared with the level in the absence of an agonist of the invention.

In particular embodiments, a Wnt signaling pathway agonist fusion protein (or Wnt surrogate) comprises an anti-LRP5/6 antibody, or antigen-binding fragment thereof, disclosed herein fused to a polypeptide that specifically binds to one or more Frizzled (Fzd) receptors. In particular embodiments, the polypeptide that specifically binds to one or more Fzd receptor is an antibody or antigen-binding fragment thereof. If certain embodiments, it is an antibody or antigen-binding fragment thereof disclosed in the U.S. provisional patent application No. 62/607,877, titled, "Anti-Frizzled antibodies and Methods of Use," filed on Dec. 19, 2017, which is incorporated herein by reference in its entirety.

In certain embodiment, the Fzd binding domain may be selected from any domain that binds Fzd at high affinity, e.g., a KD of at least about $1 \times 10^{-7}$ M, at least about $1 \times 10^{-8}$ M, at least about $1 \times 10^{-9}$ M, or at least about $1 \times 10^{-10}$ M. Suitable Fzd binding domains include, without limitation, de novo designed Fzd binding proteins, antibody derived binding proteins, e.g. scFv, Fab, etc. and other portions of antibodies that specifically bind to one or more Fzd proteins; VHH or sdAb derived binding domains; knottin-based engineered scaffolds; norrin and engineered binding fragments derived therefrom, naturally occurring Fzd binding domains, and the like. A Fzd binding domain may be affinity selected to enhance binding to a desired Fzd protein or plurality of Fzd proteins, e.g. to provide tissue selectivity.

In some embodiments the Fzd binding domain binds to one, two, three, four, five or more different frizzled proteins, e.g., one or more of human frizzled proteins Fzd1, Fzd2, Fzd3, Fzd4, Fzd5, Fzd6, Fzd7, Fzd8, Fzd9, Fzd10. In some embodiments, the Fzd binding domain binds to Fzd1, Fzd2, Fzd5, Fzd7 and Fzd8. In other embodiments the Fzd binding domain is selective for one or more frizzled protein of interest, e.g. having a specificity for the one or more desired frizzled protein of at least 10-fold, 25-fold, 50-fold, 100-fold, 200-fold or more relative to other frizzled proteins.

In certain embodiments, the Fzd binding domain comprises the six CDR regions of the pan specific frizzled antibody OMP-18R5 (vantictumab). In certain embodiments, the Fzd binding domain is an scFv comprising the six CDR regions of the pan-specific frizzled antibody OMP-18R5 (vantictumab). See, for example, U.S. Pat. No. 8,507,442, herein specifically incorporated by reference. For example, the CDR sequences of OMP-18R5 include a heavy chain CDR1 comprising GFTFSHYTLS (SEQ ID NO:25), a heavy chain CDR2 comprising VISGDGSYTYY-ADSVKG (SEQ ID NO:26), and a heavy chain CDR3 comprising NFIKYVFAN (SEQ ID NO:27), and (ii) a light chain CDR1 comprising SGDKLGKKYAS (SEQ ID NO:28) or SGDNIGSFYVH (SEQ ID NO:31), a light chain CDR2 comprising EKDNRPSG (SEQ ID NO:29) or DKSNRPSG (SEQ ID NO:32), and a light chain CDR3 comprising SSFAGNSLE (SEQ ID NO:30) or QSY-ANTLSL (SEQ ID NO:33). In particular embodiments, the frizzled binding domain is an antibody or derivative thereof, including without limitation scFv, minibodies, VHH or sdAbs and various antibody mimetics comprising any of these CDR sequences. In certain embodiments, these CDR sequences comprise one or more amino acid modifications.

In other embodiments, the Fzd binding domain comprises a variable region sequence, or the CDRs thereof, from any of a number of frizzled specific antibodies, which are known in the art and are commercially available, or can be generated de novo. Any of the frizzled polypeptides can be used as an immunogen or in screening assays to develop an antibody. Non-limiting examples of frizzled binding domains include antibodies available from Biolegend, e.g. Clone CH3A4A7 specific for human frizzled 4 (CD344); Clone W3C4E11 specific for human Fz9 (CD349); antibodies available from Abcam, e.g. ab64636 specific for Fz7; ab83042 specific for human Fz4; ab77379 specific for human Fz7; ab75235 specific for human Fz8; ab102956 specific for human Fz9; and the like. Other examples of suitable antibodies are described in, inter alia, US Patent application 20140105917; US Patent application 20130230521; US Patent application 20080267955; US Patent application 20080038272; US Patent application 20030044409; etc., each herein specifically incorporated by reference.

The Fzd binding moiety of the surrogate may be an engineered protein that is selected for structural homology to the frizzled binding region of a Wnt protein. Such proteins can be identified by screening a structure database for homologies. The initial protein thus identified, for example the microbial Bh1478 protein. The native protein is then engineered to provide amino acid substitutions that increase affinity, and may further be selected by affinity maturation for increased affinity and selectivity in binding to the desired frizzled protein. Non-limiting examples of frizzled binding moieties include the Fz27 and Fz27-B12 proteins.

The anti-LRP5/6 antibody, or antigen binding fragment thereof, and the Fzd binding domain may be directly joined, or may be separated by a linker, e.g. a polypeptide linker, or a non-peptidic linker, etc. The region of the Wnt surrogate that binds one or more Fzd receptor and the region of the Wnt surrogate that binds LRP5 and/or LRP6 may be contiguous or separated by a linker, e.g. a polypeptide linker, or a non-peptidic linker, etc. The length of the linker, and therefore the spacing between the binding domains can be used to modulate the signal strength, and can be selected depending on the desired use of the Wnt surrogate. The enforced distance between binding domains can vary, but in certain embodiments may be less than about 100 angstroms, less than about 90 angstroms, less than about 80 angstroms, less than about 70 angstroms, less than about 60 angstroms, or less than about 50 angstroms. In some embodiments the linker is a rigid linker, in other embodiments the linker is a flexible linker. Where the linker is a peptide linker, it may be from about 1, 2, 3, 4, 5, 6, 7, 8, 9, 10, 11, 12, 13, 14, 15, 16, 17, 18, 19, 2021, 22, 23, 24, 25, 26, 27, 28, 29, 30 or more amino acids in length, and is of sufficient length and amino acid composition to enforce the distance between binding domains. In some embodiments, the linker comprises or consists of one or more glycine and/or serine residues.

A Wnt surrogate can be multimerized, e.g. through an Fc domain, by concatenation, coiled coils, polypeptide zippers, biotin/avidin or streptavidin multimerization, and the like. The Wnt surrogate can also be joined to a moiety such as PEG, Fc, etc. as known in the art to enhance stability in vivo.

In certain embodiments, a Wnt surrogate direct activates canonical Wnt signaling through binding to one or more Fzd proteins and to LRP5 and or LRP6, particularly by binding to these proteins on a cell surface, e.g. the surface of a human cell. The direct activation of Wnt signaling by a Wnt surrogate is in contrast to potentiation of Wnt signaling, which enhances activity only when native Wnt proteins are present.

Wnt surrogates of the present activate Wnt signaling, e.g., by mimicking the effect or activity of a Wnt protein binding to a frizzled protein. The ability of the Wnt surrogates of the invention to mimic the activity of Wnt can be confirmed by a number of assays. The Wnt surrogates typically initiate a reaction or activity that is similar to or the same as that initiated by the receptor's natural ligand. In particular, the Wnt surrogates of the invention enhance the canonical Wnt/β-catenin signaling pathway. As used herein, the term "enhances" refers to a measurable increase in the level of Wnt/1-catenin signaling compared with the level in the absence of a Wnt surrogate of the invention.

In certain embodiments, an antibody or antigen-binding fragment thereof disclosed herein inhibits Wnt pathway signaling. In particular embodiments, binding of an anti-LRP5/6 antibody or antigen-binding fragment thereof blocks or inhibits the binding of endogenous Wnt to one or more LRP5/6 receptor on a cell surface, thus reducing or inhibiting Wnt signaling.

Various methods are known in the art for measuring the level of canonical Wnt/β-catenin signaling. These include, but are not limited to assays that measure: Wnt/β-catenin target gene expression; TCF reporter gene expression; β-catenin stabilization; LRP phosphorylation; Axin translocation from cytoplasm to cell membrane and binding to LRP. The canonical Wt/β-catenin signaling pathway ultimately leads to changes in gene expression through the transcription factors TCF7, TCF7 L1, TCF7 L2 and LEF. The transcriptional response to Wnt activation has been characterized in a number of cells and tissues. As such, global transcriptional profiling by methods well known in the art can be used to assess Wnt/β-catenin signaling activation or inhibition.

Changes in Wnt-responsive gene expression are generally mediated by TCF and LEF transcription factors. A TCF reporter assay assesses changes in the transcription of TCF/LEF controlled genes to determine the level of Wnt/β-catenin signaling. A TCF reporter assay was first described by Korinek, V. et al., 1997. Also known as TOP/FOP this method involves the use of three copies of the optimal TCF motif CCTTTGATC, or three copies of the mutant motif CCTTTGGCC, upstream of a minimal c-Fos promoter driving luciferase expression (pTOPFI_ASH and pFOPFI_ASH, respectively) to determine the transactivational activity of endogenous β-catenin/TCF4. A higher ratio of these two reporter activities (TOP/FOP) indicates higher β-catenin/TCF4 activity, whereas a lower ratio of these two reporter activities indicates lower β-catenin/TCF4 activity.

Various other reporter transgenes that respond to Wnt signals exist intact in animals and therefore, effectively reflect endogenous Wnt signaling. These reporters are based on a multimerized TCF binding site, which drives expression of LacZ or GFP, which are readily detectable by methods known in the art. These reporter genes include: TOP-GAL, BAT-GAL, ins-TOPEGFP, ins-TOPGAL, LEF-EGFP, Axin2-LacZ, Axin2-d2EGFP, Lgr5tm1 (cre/ERT2), TOPdGFP.

The recruitment of dephosphorylated β-catenin to the membrane, stabilization and phosphorylation status of β-catenin, and translocation of β-catenin to the nucleus (Klapholz-Brown Z et al., PLoS One. 2(9) e945, 2007), in some cases mediated by complex formation with TCF transcription factors and TNIK are key steps in the Wnt signaling pathway. Stabilization is mediated by Disheveled family proteins that inhibit the "destruction" complex so that degradation of intracellular β-catenin is reduced, and translocation of β-catenin to the nucleus follows thereafter. Therefore, measuring the level and location of β-catenin in a cell is a good reflection of the level of Wnt/β-catenin signaling. A non-limiting example of such an assay is the "Biolmage β-Catenin Redistribution Assay" (Thermo Scientific) which provides recombinant U20S cells that stably express human β-catenin fused to the C-terminus of enhanced green fluorescent protein (EGFP). Imaging and analysis is performed with a fluorescence microscope or HCS platform allowing the levels and distribution of EGFP-β-catenin to be visualized.

Another way, in which the destruction complex is inhibited, is by removal of Axin by recruitment of Axin to the cytoplasmic tail of the Wnt co-receptor LRP. Axin has been shown to bind preferentially to a phosphorylated form of the LRP tail. Visualization of Axin translocation, for example with a GFP-Axin fusion protein, is therefore another method for assessing levels of Wnt/D-catenin signaling.

In certain embodiments, a Wnt signaling pathway agonist enhances or increases canonical Wnt pathway signaling, e.g., β-catenin signaling, by at least 30%, 35%, 40%, 45%, 50%, 60%, 70%, 75%, 80%, 85%, 90%, 95%, 100%, 110%, 150%, 200%, 250%. 300%, 400% or 500%, as compared to the β-catenin signaling induced by a neutral substance or negative control as measured in an assay described above, for example as measured in the TOPFlash assay. A negative control may be included in these assays. In particular embodiments, Wnt agonists may enhance β-catenin signaling by a factor of 2×, 5×, 10×, 100×, 1000×, 10000× or more as compared to the activity in the absence of the agonist when measured in an assay described above, for example when measured in the TOPFlash assay, or any of the other assays mentioned herein.

In certain embodiments, a Wnt signaling pathway antagonist or inhibitor inhibits or decreases canonical Wnt pathway signaling, e.g., β-catenin signaling, by at least 10%, 20%, 30%, 40%, 50%, 60%, 70%, 75%, 80%, 90%, 95%, or 100%, as compared to the β-catenin signaling observed in the presence of a neutral substance or negative control as measured in an assay described above, for example as measured in the TOPFlash assay. A positive control may be included in these assays.

"Wnt gene product" or "Wnt polypeptide" when used herein encompass native sequence Wnt polypeptides, Wnt polypeptide variants, Wnt polypeptide fragments and chimeric Wnt polypeptides. In particular embodiments, a Wnt polypeptide is a native human full length mature Wnt protein.

For example, human native sequence Wnt proteins of interest in the present application include the following: Wnt-1 (GenBank Accession No. NM_005430); Wnt-2 (GenBank Accession No. NM_003391); Wnt-2B (Wnt-13) (Gen- Bank Accession No. NM_004185 (isoform 1), NM_024494.2 (isoform 2)), Wnt-3 (RefSeq.: NM_030753), Wnt3a (GenBank Accession No. NM_033131), Wnt-4 (GenBank Accession No. NM_030761), Wnt-5A (GenBank Accession No. NM_003392), Wnt-5B (GenBank Accession No. NM_032642), Wnt-6 (GenBank Accession No. NM_006522), Wnt-7A (GenBank Accession No. NM_004625), Wnt-7B (GenBank Accession No. NM_058238), Wnt-8A (GenBank Accession No. NM_058244), Wnt-8B (GenBank Accession No. NM_003393), Wnt-9A (Wnt-14) (GenBank Accession No. NM_003395), Wnt-9B (Wnt-15) (GenBank Accession No. NM_003396), Wnt-1 OA (GenBank Accession No. NM_025216), Wnt-10B (GenBank Accession No. NM_003394), Wnt-11 (GenBank Accession No. NM_004626), Wnt-16 (GenBank Accession No. NM_016087)). Although each member has varying degrees of sequence identity with the family, all encode small (i.e., 39-46 kD), acylated, palmitoylated, secreted glycoproteins that contain 23-24 conserved cysteine residues whose spacing is highly conserved (McMahon, A P et al., Trends Genet. 1992; 8: 236-242: Miller, J R. Genome Biol. 2002; 3(1): 3001.1-3001.15). Other native sequence Wnt polypeptides of interest include orthologs of the above from any mammal, including domestic and farm animals, and zoo, laboratory or pet animals, such as dogs, cats, cattle, horses, sheep, pigs, goats, rabbits, rats, mice, frogs, zebra fish, fruit fly, worm, etc.

"Wnt pathway signaling" or "Wnt signaling" is used herein to refer to the mechanism by which a biologically active Wnt exerts its effects upon a cell to modulate a cell's activity. Wnt proteins modulate cell activity by binding to Wnt receptors, including proteins from the Frizzled (Fzd) family of proteins, proteins from the ROR family of proteins, the proteins LRP5 and LRP6 from the LRP family of proteins, the protein FRL1/crypto, and the protein Derailed/Ryk. Once activated by Wnt binding, the Wnt receptor(s) will activate one or more intracellular signaling cascades. These include the canonical Wnt signaling pathway; the Wnt/planar cell polarity (Wnt/PCP) pathway; the Wnt-calcium (Wnt/Ca$^{2+}$) pathway (Giles, R H et al, (2003) Biochim Biophys Acta 1653, 1-24; Peifer, M. et al. (1994) Development 120: 369-380; Papkoff, J. et al (1996) Mol. Cell Biol. 16: 2128-2134; Veeman, M. T. et al. (2003) Dev. Cell 5: 367-377); and other Wnt signaling pathways as is well known in the art.

For example, activation of the canonical Wnt signaling pathway results in the inhibition of phosphorylation of the intracellular protein β-catenin, leading to an accumulation of β-catenin in the cytosol and its subsequent translocation to the nucleus where it interacts with transcription factors, e.g. TCF/LEF, to activate target genes. Activation of the Wnt/PCP pathway activates RhoA, c-Jun N-terminal kinase (JNK), and nemo-like kinase (NLK) signaling cascades to control such biological processes as tissue polarity and cell movement. Activation of the Wnt/Ca$^{2+}$ by, for example, binding of Wnt-4, Wnt-5A or Wnt-11, elicits an intracellular release of calcium ions, which activates calcium sensitive enzymes like protein kinase C (PKC), calcium-calmodulin dependent kinase II (CamKII) or calcineurin (CaCN). By assaying for activity of the above signaling pathways, the biological activity of an antibody or antigen-binding fragment thereof, e.g., a Wnt surrogate, can be readily determined.

In certain embodiments, functional properties of anti-LRP5/6 antibodies and antigen-binding fragments thereof may be assessed using a variety of methods known to the skilled person, including e.g., affinity/binding assays (for example, surface plasmon resonance, competitive inhibition assays), cytotoxicity assays, cell viability assays, cell proliferation or differentiation assays in response to a Wnt, cancer cell and/or tumor growth inhibition using in vitro or in vivo models, including but not limited to any described herein. Other assays may test the ability of antibodies described herein to block normal Wnt/LRP5/6-mediated responses. The antibodies and antigen-binding fragments thereof described herein may also be tested for effects on LRP5/6 receptor internalization, in vitro and in vivo efficacy, etc. Such assays may be performed using well-established protocols known to the skilled person (see e.g., Current Protocols in Molecular Biology (Greene Publ. Assoc. Inc. & John Wiley & Sons, Inc., NY, NY); Current Protocols in Immunology (Edited by: John E. Coligan, Ada M. Kruisbeek, David H. Margulies, Ethan M. Shevach, Warren Strober 2001 John Wiley & Sons, NY, NY); or commercially available kits.

In certain embodiments, an LRP5/6-binding antibody comprises one or more of the CDRs of the antibodies described herein. In this regard, it has been shown in some cases that the transfer of only the VHCDR3 of an antibody can be performed while still retaining desired specific binding (Barbas et al., *PNAS* (1995) 92: 2529-2533). See also, McLane et al., *PNAS* (1995) 92:5214-5218, Barbas et al., *J. Am. Chem. Soc.* (1994) 116:2161-2162.

Marks et al. (*Bio/Technology,* 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al further describe how this repertoire may be combined with a CDR3 of a particular antibody. Using analogous techniques, the CDR3-derived sequences of the presently described antibodies may be shuffled with repertoires of VH or VL domains lacking a CDR3, and the shuffled complete VH or VL domains combined with a cognate VL or VH domain to provide an antibody or antigen-binding fragment thereof that binds LRP5 and/or LRP6. The repertoire may then be displayed in a suitable host system such as the phage display system of WO92/01047 so that suitable antibodies or antigen-binding fragments thereof may be selected. A repertoire may consist of at least from about 104 individual members and upwards by several orders of magnitude, for example, to about from $10^6$ to $10^8$ or $10^{10}$ or more members. Analogous shuffling or combinatorial techniques are also disclosed by Stemmer (Nature, 1994, 370:389-391), who describes the technique in relation to a β-lactamase gene but observes that the approach may be used for the generation of antibodies.

A further alternative is to generate novel VH or VL regions carrying one or more CDR-derived sequences of the herein described invention embodiments using random mutagenesis of one or more selected VH and/or VL genes to generate mutations within the entire variable domain. Such a technique is described by Gram et al (1992, Proc. Natl. Acad. Sci., USA, 89:3576-3580), who used error-prone PCR. Another method which may be used is to direct mutagenesis to CDR regions of VH or VL genes. Such techniques are disclosed by Barbas et al., (1994, Proc. Natl. Acad. Sci., USA, 91:3809-3813) and Schier et al (1996, J. Mol. Biol. 263:551-567).

In certain embodiments, a specific VH and/or VL of the antibodies described herein may be used to screen a library of the complementary variable domain to identify antibodies with desirable properties, such as increased affinity for LRP5 and/or LRP6. Such methods are described, for example, in Portolano et al., J. Immunol. (1993) 150:880-887; Clarkson et al., Nature (1991) 352:624-628.

Other methods may also be used to mix and match CDRs to identify antibodies having desired binding activity, such as binding to LRP5 and/or LRP6. For example: Klimka et al., British Journal of Cancer (2000) 83: 252-260, describe a screening process using a mouse VL and a human VH library with CDR3 and FR4 retained from the mouse VH. After obtaining antibodies, the VH was screened against a human VL library to obtain antibodies that bound antigen. Beiboer et al., J. Mol. Biol. (2000) 296:833-849 describe a screening process using an entire mouse heavy chain and a human light chain library. After obtaining antibodies, one VL was combined with a human VH library with the CDR3 of the mouse retained. Antibodies capable of binding antigen were obtained. Rader et al., PNAS (1998) 95:8910-8915 describe a process similar to Beiboer et al above.

These just-described techniques are, in and of themselves, known as such in the art. The skilled person will, however, be able to use such techniques to obtain antibodies or antigen-binding fragments thereof according to several embodiments of the invention described herein, using routine methodology in the art.

Also disclosed herein is a method for obtaining an antibody antigen binding domain specific for LRP5 and/or LRP6 antigen, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VHNL combination or combinations to identify a specific binding member or an antibody antigen binding domain specific for LRP5 and/or LRP6 and optionally with one or more desired properties. The VL domains may have an amino acid sequence which is substantially as set out herein. An analogous method may be employed in which one or more sequence variants of a VL domain disclosed herein are combined with one or more VH domains.

In particular embodiments, anti-LRP5/6 antibodies, and antigen-binding fragments thereof, are water soluble. By "water soluble" it is meant a composition that is soluble in aqueous buffers in the absence of detergent, usually soluble at a concentration that provides a biologically effective dose of the polypeptide. Compositions that are water soluble form a substantially homogenous composition that has a specific activity that is at least about 5% that of the starting material from which it was purified, usually at least about 10%, 20%, or 30% that of the starting material, more usually about 40%, 50%, or 60% that of the starting material, and may be about 50%, about 90% or greater. Anti-LRP5/6 antibodies and antigen-binding fragments thereof, including Wnt surrogates, of the present invention typically form a substantially homogeneous aqueous solution at concentrations of at least 25 µM and higher, e.g. at least 25 µM, 40 µM, or 50 µM, usually at least 60 µM, 70 µM, 80 µM, or 90 µM, sometimes as much as 100 µM, 120 µM, or 150 µM. In other words, compositions of the present invention typically form a substantially homogeneous aqueous solution at concentrations of about 0.1 mg/ml, about 0.5 mg/ml, of about 1 mg/ml or more.

An epitope that "specifically binds" or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to LRP5 is an antibody that binds LRP5 with greater affinity, avidity, more readily, and/or with greater duration than it binds to LRP6 or non-LRP5/6 proteins. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439-473.

In certain embodiment, the anti-LRP5/6 antibodies bind LRP5 and/or LRP6 with a $K_D$ of less than or equal to about $1 \times 10^{-4}$ M, less than or equal to about $1 \times 10^{-5}$ M, less than or equal to about $1 \times 10^{-6}$ M, less than or equal to about $1 \times 10^{-7}$ M, less than or equal to about $1 \times 10^{-8}$ M, less than or equal to about $1 \times 10^{-9}$ M, or at least about $1 \times 10^{-10}$ M. In certain embodiments, the anti-LRP5/6 antibodies described herein bind LRP5 and/or LRP6 with a $K_D$ of less than about 10,000 nM, less than about 1000 nM, less than about 100 nM, less than about 10 nM, less than about 1 nM or less than about 0.1 nM, and in some embodiments, the antibodies may have even higher affinity for one or more Fzd receptor. In certain embodiments, the anti-LRP5/6 antibodies described herein have an affinity $K_D$ of about 100, 150, 155, 160, 170, 175, 180, 185, 190, 191, 192, 193, 194, 195, 196, 197, 198 or 199 picomolar, and in some embodiments, the antibodies may have even higher affinity for LRP5 and/or LRP6.

The term "immunologically active", with reference to an epitope being or "remaining immunologically active", refers to the ability of an antibody (e.g., anti-LRP5/6 antibody) to bind to the epitope under different conditions, for example, after the epitope has been subjected to reducing and denaturing conditions.

An antibody or antigen-binding fragment thereof according to certain preferred embodiments of the present application may be one that competes for binding to LRP5 and/or LRP6 with any antibody described herein which both (i) specifically binds to the antigen and (ii) comprises a VH and/or VL domain disclosed herein, or comprises a VH CDR3 disclosed herein, or a variant of any of these. Competition between antibodies may be assayed easily in vitro, for example using ELISA and/or by tagging a specific reporter molecule to one antibody which can be detected in the presence of other untagged antibodies, to enable identification of specific antibodies which bind the same epitope or an overlapping epitope. Thus, there is provided herein a specific antibody or antigen-binding fragment thereof, comprising a human antibody antigen-binding site which competes with an antibody described herein that binds to LRP5 and/or LRP6.

In this regard, as used herein, the terms "competes with", "inhibits binding" and "blocks binding" (e.g., referring to inhibition/blocking of binding of a Wnt to LRP5 and/or LRP6 or referring to inhibition/blocking of binding of an anti-LRP5/6 antibody to LRP5 and/or LRP6) are used interchangeably and encompass both partial and complete inhibition/blocking. The inhibition/blocking of a Wnt to LRP5 and/or LRP6 preferably reduces or alters the normal level or type of cell signaling that occurs when the Wnt binds to the LRP5 and/or LRP6 without inhibition or blocking. Inhibition and blocking are also intended to include any measurable decrease in the binding of a Wnt to LRP5 and/or LRP6 when in contact with an anti-LRP5/6 antibody as disclosed herein as compared to the ligand not in contact with an anti-LRP5/6 antibody, e.g., the blocking of the Wnt to LRP5 and/or LRP6 by at least about 10%, 20%, 30%, 40%, 50%, 60%, 65%, 70%, 75%, 80%, 85%, 90%, 91%, 92%, 93%, 94%, 95%, 96%, 97%, 98%, 99%, or 100%.

The constant regions of immunoglobulins show less sequence diversity than the variable regions, and are responsible for binding a number of natural proteins to elicit important biochemical events. In humans there are five different classes of antibodies including IgA (which includes subclasses IgA1 and IgA2), IgD, IgE, IgG (which includes subclasses IgG1, IgG2, IgG3, and IgG4), and IgM. The distinguishing features between these antibody classes are their constant regions, although subtler differences may exist in the V region.

The Fc region of an antibody interacts with a number of Fc receptors and ligands, imparting an array of important functional capabilities referred to as effector functions. For IgG the Fc region comprises Ig domains CH2 and CH3 and the N-terminal hinge leading into CH2. An important family of Fc receptors for the IgG class are the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack.

The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP). All FcγRs bind the same region on Fc, at the N-terminal end of the Cγ2 (CH2) domain and the preceding hinge. This interaction is well characterized structurally (Sondermann et al., 2001, J Mol Biol 309:737-749), and several structures of the human Fc bound to the extracellular domain of human FcγRIIIb have been solved (pdb accession code 1E4K) (Sondermann et al., 2000, Nature 406:267-273.) (pdb accession codes 1IIS and 1IIX) (Radaev et al., 2001, J Biol Chem 276:16469-16477.)

The different IgG subclasses have different affinities for the FcγRs, with IgG1 and IgG3 typically binding substantially better to the receptors than IgG2 and IgG4 (Jefferis et al., 2002, Immunol Lett 82:57-65). All FcRs bind the same region on IgG Fc, yet with different affinities: the high affinity binder FcγRI has a $K_d$ for IgG1 of $10^{-8}$ $M^{-1}$, whereas the low affinity receptors FcγRII and FcγRIII generally bind at $10^{-6}$ and $10^{-5}$ respectively. The extracellular domains of FcγRIIIa and FcγRIIIb are 96% identical; however, FcγRIIIb does not have an intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. The receptors also differ in expression pattern and levels on different immune cells. Yet another level of complexity is the existence of a number of FcγR polymorphisms in the human proteome. A particularly relevant polymorphism with clinical significance is V158/F158 FcγRIIa. Human IgG1 binds with greater affinity to the V158 allotype than to the F158 allotype. This difference in affinity, and presumably its effect on ADCC and/or ADCP, has been shown to be a significant determinant of the efficacy of the anti-CD20 antibody rituximab (Rituxan, a registered trademark of IDEC Pharmaceuticals Corporation). Patients with the V158 allotype respond favorably to rituximab treatment; however, patients with the lower affinity F158 allotype respond poorly (Cartron et al., 2002, Blood 99:754-758). Approximately 10-20% of humans are V158N158 homozygous, 45% are V158/F158 heterozygous, and 35-45% of humans are F158/F158 homozygous (Lehmbecher et al., 1999, Blood 94:4220-4232; Cartron et al., 2002, Blood 99:754-758). Thus 80-90% of humans are poor responders, that is, they have at least one allele of the F158 FcγRIIIa.

The Fc region is also involved in activation of the complement cascade. In the classical complement pathway, C1 binds with its C1q subunits to Fc fragments of IgG or IgM, which has formed a complex with antigen(s). In certain embodiments of the invention, modifications to the Fc region comprise modifications that alter (either enhance or decrease) the ability of an ***-specific antibody as described herein to activate the complement system (see e.g., U.S. Pat. No. 7,740,847). To assess complement activation, a complement-dependent cytotoxicity (CDC) assay may be performed (See, e.g., Gazzano-Santoro et al., J. Immunol. Methods, 202:163 (1996)).

Thus in certain embodiments, the present invention provides anti-LRP5/6 antibodies having a modified Fc region with altered functional properties, such as reduced or enhanced CDC, ADCC, or ADCP activity, or enhanced binding affinity for a specific FcγR or increased serum half-life. Other modified Fc regions contemplated herein are described, for example, in issued U.S. Pat. Nos. 7,317,091; 7,657,380; 7,662,925; 6,538,124; 6,528,624; 7,297,775; 7,364,731; Published U.S. Applications US2009092599; US20080131435; US20080138344; and published International Applications WO2006/105338; WO2004/063351; WO2006/088494; WO2007/024249.

Thus, in certain embodiments, antibody variable domains with the desired binding specificities are fused to immunoglobulin constant domain sequences. In certain embodiments, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

Antibodies of the present invention (and antigen-binding fragments and variants thereof) may also be modified to include an epitope tag or label, e.g., for use in purification or diagnostic applications. There are many linking groups known in the art for making antibody conjugates, including, for example, those disclosed in U.S. Pat. No. 5,208,020 or EP Patent 0 425 235 B1, and Char et al., Cancer Research 52: 127-131 (1992). The linking groups include disulfide groups, thioether groups, acid labile groups, photolabile groups, peptidase labile groups, or esterase labile groups, as disclosed in the above-identified patents, disulfide and thioether groups being preferred.

In another contemplated embodiment, a LRP5/6-specific antibody as described herein may be conjugated or operably linked to another therapeutic compound, referred to herein as a conjugate. The conjugate may be a cytotoxic agent, a chemotherapeutic agent, a cytokine, an anti-angiogenic agent, a tyrosine kinase inhibitor, a toxin, a radioisotope, or other therapeutically active agent. Chemotherapeutic agents, cytokines, anti-angiogenic agents, tyrosine kinase inhibitors, and other therapeutic agents have been described above, and all of these aforementioned therapeutic agents may find use as antibody conjugates.

Immunoconjugates may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particular coupling agents include N-succinimidyl-3-(2-pyrdyldithio) propionate (SPDP) (Carlsson et al., Biochem. J. 173:723-737 [1978]) and N-succinimidyl-4-(2-pyridylthio)pentanoate (SPP) to provide for a disulfide linkage. The linker may be a "cleavable linker" facilitating release of one or more cleavable components. For example, an acid-labile linker may be used (Cancer Research 52:127-131 (1992); U.S. Pat. No. 5,208,020).

In certain embodiments, anti-LRP5/6 antibodies and antigen-binding fragments thereof are monoclonal antibodies. In certain embodiments, they are humanized.

The present invention further provides in certain embodiments an isolated nucleic acid encoding an antibody or antigen-binding fragment thereof as described herein, for instance, a nucleic acid which codes for a CDR or VH or VL domain as described herein. Nucleic acids include DNA and RNA. These and related embodiments may include polynucleotides encoding antibodies that bind LRP5 and/or LRP6 as described herein. The term "isolated polynucleotide" as used herein shall mean a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

The term "operably linked" means that the components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated or operably linked. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as referred to herein means single-stranded or double-stranded nucleic acid polymers. In certain embodiments, the nucleotides comprising the polynucleotide can be ribonucleotides or deoxyribonucleotides or a modified form of either type of nucleotide. Said modifications include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "naturally occurring nucleotides" includes deoxyribonucleotides and ribonucleotides. The term "modified nucleotides" includes nucleotides with modified or substituted sugar groups and the like.

The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, Nucl. Acids Res., 14:9081; Stec et al., 1984, J. Am. Chem. Soc., 106:6077; Stein et al., 1988, Nucl. Acids Res., 16:3209; Zon et al., 1991, Anti-Cancer Drug Design, 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990, Chemical Reviews, 90:543, the disclosures of which are hereby incorporated by reference for any purpose. An oligonucleotide can include a detectable label to enable detection of the oligonucleotide or hybridization thereof.

The term "vector" is used to refer to any molecule (e.g., nucleic acid, plasmid, or virus) used to transfer coding information to a host cell. The term "expression vector" refers to a vector that is suitable for transformation of a host cell and contains nucleic acid sequences that direct and/or control expression of inserted heterologous nucleic acid sequences. Expression includes, but is not limited to, processes such as transcription, translation, and RNA splicing, if introns are present.

As will be understood by those skilled in the art, polynucleotides may include genomic sequences, extra-genomic and plasmid-encoded sequences and smaller engineered gene segments that express, or may be adapted to express, proteins, polypeptides, peptides and the like. Such segments may be naturally isolated, or modified synthetically by the skilled person.

As will be also recognized by the skilled artisan, polynucleotides may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide according to the present disclosure, and a polynucleotide may, but need not, be linked to other molecules and/or support materials. Polynucleotides may comprise a native sequence or may comprise a sequence that encodes a variant or derivative of such a sequence.

Therefore, according to these and related embodiments, the present disclosure also provides polynucleotides encoding the anti-LRP5/6 antibodies and antigen-binding fragments thereof described herein. In certain embodiments, polynucleotides are provided that comprise some or all of a polynucleotide sequence encoding an antibody or antigen-binding fragment thereof as described herein and complements of such polynucleotides.

It will be appreciated by those of ordinary skill in the art that, as a result of the degeneracy of the genetic code, there are many nucleotide sequences that encodes an antibody as described herein. Some of these polynucleotides bear minimal sequence identity to the nucleotide sequence of the native or original polynucleotide sequence that encode antibodies that bind to LRP5 and/or LRP6. Nonetheless, polynucleotides that vary due to differences in codon usage are expressly contemplated by the present disclosure. In certain embodiments, sequences that have been codon-optimized for mammalian expression are specifically contemplated.

Therefore, in another embodiment of the invention, a mutagenesis approach, such as site-specific mutagenesis, may be employed for the preparation of variants and/or derivatives of the antibodies described herein. By this approach, specific modifications in a polypeptide sequence can be made through mutagenesis of the underlying polynucleotides that encode them. These techniques provide a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, the inventors contemplate the mutagenesis of the polynucleotide sequences that encode an antibody disclosed herein, or an antigen-binding fragment thereof, to alter one or more properties of the encoded polypeptide, such as the binding affinity of the antibody or the antigen-binding fragment thereof, or the function of a particular Fc region, or the affinity of the Fc region for a particular FcR. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phages are readily commercially available and their use is generally well-known to those skilled in the art. Double-stranded plasmids are also routinely employed in site directed mutagenesis that eliminates the step of transferring the gene of interest from a plasmid to a phage.

In many embodiments, the nucleic acids encoding a subject monoclonal antibody are introduced directly into a host cell, and the cell incubated under conditions sufficient to induce expression of the encoded antibody. The antibodies of this disclosure are prepared using standard techniques well known to those of skill in the art in combination with the polypeptide and nucleic acid sequences provided herein. The polypeptide sequences may be used to determine appropriate nucleic acid sequences encoding the particular antibody disclosed thereby. The nucleic acid sequence may be optimized to reflect particular codon "preferences" for various expression systems according to standard methods well known to those of skill in the art.

According to certain related embodiments there is provided a recombinant host cell which comprises one or more constructs as described herein; a nucleic acid encoding any antibody, CDR, VH or VL domain, or antigen-binding fragment thereof; and a method of production of the encoded product, which method comprises expression from encoding nucleic acid therefor. Expression may conveniently be achieved by culturing under appropriate conditions recombinant host cells containing the nucleic acid. Following production by expression, an antibody or antigen-binding fragment thereof, may be isolated and/or purified using any suitable technique, and then used as desired.

Antibodies or antigen-binding fragments thereof as provided herein, and encoding nucleic acid molecules and vectors, may be isolated and/or purified, e.g. from their natural environment, in substantially pure or homogeneous form, or, in the case of nucleic acid, free or substantially free of nucleic acid or genes of origin other than the sequence encoding a polypeptide with the desired function. Nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli.

The expression of antibodies and antigen-binding fragments in prokaryotic cells such as E. coli is well established in the art. For a review, see for example Pluckthun, A. Bio/Technology 9: 545-551 (1991). Expression in eukaryotic cells in culture is also available to those skilled in the art as an option for production of antibodies or antigen-binding fragments thereof, see recent reviews, for example Ref, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

The term "host cell" is used to refer to a cell into which has been introduced, or which is capable of having introduced into it, a nucleic acid sequence encoding one or more of the herein described antibodies, and which further expresses or is capable of expressing a selected gene of interest, such as a gene encoding any herein described antibody. The term includes the progeny of the parent cell, whether or not the progeny are identical in morphology or in genetic make-up to the original parent, so long as the selected gene is present. Accordingly there is also contemplated a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. In one embodiment, the nucleic acid is integrated into the genome (e.g. chromosome) of the host cell. Integration may be promoted by inclusion of sequences which promote recombination with the genome, in accordance-with standard techniques.

The present invention also provides, in certain embodiments, a method which comprises using a construct as stated above in an expression system in order to express a particular polypeptide such as an LRP5- or LRP6-specific antibody as described herein. The term "transduction" is used to refer to the transfer of genes from one bacterium to another, usually by a phage. "Transduction" also refers to the acquisition and transfer of eukaryotic cellular sequences by retroviruses. The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, MOLECULAR CLONING, A LABORATORY MANUAL, Cold Spring Harbor Laboratories; Davis et al., 1986, BASIC METHODS IN MOLECULAR BIOLOGY, Elsevier; and Chu et al., 1981, Gene 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "naturally occurring" or "native" when used in connection with biological materials such as nucleic acid molecules, polypeptides, host cells, and the like, refers to materials which are found in nature and are not manipulated by a human. Similarly, "non-naturally occurring" or "non-native" as used herein refers to a material that is not found in nature or that has been structurally modified or synthesized by a human.

The terms "polypeptide" "protein" and "peptide" and "glycoprotein" are used interchangeably and mean a polymer of amino acids not limited to any particular length. The term does not exclude modifications such as myristylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the antibodies that bind to LRP and/or LRP6 of the present disclosure, or sequences that have deletions from, additions to, and/or substitutions of one or more amino acid of an anti-LRP5 or anti-LRP6 antibody. Thus, a "polypeptide" or a "protein" can comprise one (termed "a monomer") or a plurality (termed "a multimer") of amino acid chains.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

Amino acid sequence modification(s) of the antibodies described herein are contemplated. For example, it may be desirable to improve the binding affinity and/or other biological properties of the antibody. For example, amino acid sequence variants of an antibody may be prepared by introducing appropriate nucleotide changes into a polynucleotide that encodes the antibody, or a chain thereof, or by peptide synthesis. Such modifications include, for example, deletions from, and/or insertions into and/or substitutions of, residues within the amino acid sequences of the antibody. Any combination of deletion, insertion, and substitution may be made to arrive at the final antibody, provided that the final construct possesses the desired characteristics (e.g., high affinity binding to LRP5 and/or LRP6). The amino acid changes also may alter post-translational processes of the antibody, such as changing the number or position of glycosylation sites. Any of the variations and modifications described above for polypeptides of the present invention may be included in antibodies of the present invention.

The present disclosure provides variants of the antibodies disclosed herein. In certain embodiments, such variant antibodies or antigen-binding fragments, or CDRs thereof, bind to LRP5 and/or LRP6 at least about 50%, at least about 70%, and in certain embodiments, at least about 90% as well as an antibody sequence specifically set forth herein. In further embodiments, such variant antibodies or antigen-binding fragments, or CDRs thereof, bind to LRP5 and/or LRP6 with greater affinity than the antibodies set forth herein, for example, that bind quantitatively at least about 105%, 106%, 107%, 108%, 109%, or 110% as well as an antibody sequence specifically set forth herein.

In particular embodiments, the antibody or antigen-binding fragment thereof, e.g., a Fab, scFv, VHH or sdAb, or Wnt surrogate, may comprise: a) a heavy chain variable region comprising: i. a CDR1 region that is identical in amino acid sequence to the heavy chain CDR1 region of a selected antibody described herein; ii. a CDR2 region that is identical in amino acid sequence to the heavy chain CDR2 region of the selected antibody; and iii. a CDR3 region that is identical in amino acid sequence to the heavy chain CDR3 region of the selected antibody; and/or b) a light chain variable domain comprising: i. a CDR1 region that is identical in amino acid sequence to the light chain CDR1 region of the selected antibody; ii. a CDR2 region that is identical in amino acid sequence to the light chain CDR2 region of the selected antibody; and iii. a CDR3 region that is identical in amino acid sequence to the light chain CDR3 region of the selected antibody; wherein the antibody specifically binds a selected target (e.g., LRP5 and/or LRP6). In a further embodiment, the antibody, or antigen-binding fragment thereof, is a variant antibody wherein the variant comprises a heavy and light chain identical to the selected antibody except for up to 8, 9, 10, 11, 12, 13, 14, 15, or more amino acid substitutions in the CDR regions of the VH and VL regions. In this regard, there may be 1, 2, 3, 4, 5, 6, 7, 8, or in certain embodiments, 9, 10, 11, 12, 13, 14, 15 more amino acid substitutions in the CDR regions of the selected antibody. Substitutions may be in CDRs either in the VH and/or the VL regions. (See e.g., Muller, 1998, Structure 6:1153-1167).

In particular embodiments, the antibody or antigen-binding fragment thereof, e.g., a Fab, scFv, VHH or sdAb, or Wnt surrogate, may comprise one or more, two or more, three or more, four or more, five or more, or six the CDRs identified in Table 1A for any particular antibody. In certain embodiments, the antibody or antigen-binding fragment thereof comprises a CDRH1 comprising or consisting of any of SEQ ID NOs:34-172; a CDRH2 comprising or consisting of any of SEQ ID NOs:173-312; a CDRH3 comprising or consisting of any of SEQ ID NOs: 313-485; a CDRL1 comprising or consisting of any of SEQ ID NOs: 486-524; a CDRL2 comprising or consisting of any of SEQ ID NOs: 525-556; and/or a CDRL3 comprising or consisting of any of SEQ ID NOs: 557-607.

In particular embodiments, a subject antibody, e.g., a Fab, scFv, VHH or sdAb, or Wnt surrogate, may have: a) a heavy chain variable region having an amino acid sequence that is at least 80% identical, at least 95% identical, at least 90%, at least 95% or at least 98% or 99% identical, to the heavy chain variable region of an anti-LRP5/6 antibody described herein; and/or b) a light chain variable region having an amino acid sequence that is at least 80% identical, at least 85%, at least 90%, at least 95% or at least 98% or 99% identical, to the light chain variable region of an anti-LRP5/6 antibody described herein. The amino acid sequence of illustrative heavy and/or light chain regions are set forth in SEQ ID NOs: 1-24.

Determination of the three-dimensional structures of representative polypeptides (e.g., variant LRP %/6-specific antibodies as provided herein, for instance, an antibody protein having an antigen-binding fragment as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. See, for instance, Donate et al., 1994 *Prot. Sci.* 3:2378; Bradley et al., *Science* 309: 1868-1871 (2005); Schueler-Furman et al., Science 310:638 (2005); Dietz et al., *Proc. Nat. Acad. Sci. USA* 103:1244 (2006); Dodson et al., *Nature* 450:176 (2007); Qian et al., *Nature* 450:259 (2007); Raman et al. Science 327:1014-1018 (2010). Some additional non-limiting examples of computer algorithms that may be used for these and related embodiments, such as for rational design of LRP5/6-specific antibodies antigen-binding domains thereof as provided herein, include VMD which is a molecular visualization program for displaying, animating, and analyzing large biomolecular systems using 3-D graphics and built-in scripting (see the website for the Theoretical and Computational Biophysics Group, University of Illinois at Urbana-Champagne, at ks.uiuc.edu/Research/vmd/. Many other computer programs are known in the art and available to the skilled person and which allow for determining atomic dimensions from space-filling models (van der Waals radii) of energy-minimized conformations; GRID, which seeks to determine regions of high affinity for different chemical groups, thereby enhancing binding, Monte Carlo searches, which calculate mathematical alignment, and CHARMM (Brooks et al. (1983) *J. Comput. Chem.* 4:187-217) and AMBER (Weiner et al (1981) *J. Comput. Chem.* 106: 765), which assess force field calculations, and analysis (see also, Eisenfield et al. (1991) *Am. J. Physiol.* 261:C376-386; Lybrand (1991) *J. Pharm. Beg.* 46:49-54; Froimowitz (1990) *Biotechniques* 8:640-644; Burbam et al. (1990) *Proteins* 7:99-111; Pedersen (1985) *Environ. Health Perspect.* 61:185-190; and Kini et al. (1991) *J. Biomol. Struct. Dyn.* 9:475-488). A variety of appropriate computational computer programs are also commercially available, such as from Schrddinger (Munich, Germany).

In particular embodiments, the disclosure provides antibodies or antigen-binding fragments thereof that bind to the E3 E4 region of LRP6. In particular embodiments, they bind to the E3 β-propeller region of LRP6. In certain embodiments, they bind to a region of LRP6 that comprises or consists of amino acid residues 637-878, where the amino acid sequence and numbering is consist with that described in the Examples. In certain embodiments, they bind to an epitope within the region of LRP6 comprising amino acids 637-878. In certain embodiments, the antibody or antigen-binding fragment thereof contacts the LRP6 at any or all of the contact points disclosed in Table 3. In one embodiment, the core interaction-site or epitope on LRP6 (inter-atomic distances between Lrp6E3E4 and VHH26 less than or equal to 5.0 Å) includes: Arg639, Ala640, Lys622, Glu663, Ile681, Ser682, Lys684, Asp705, Tyr706, Glu708, Thr724, Gly725, Arg751, Try767, Gly768, Gly769, Arg792, Leu810, Asp811, His834, Phe836, Trp850, Ser851, Arg853, Asp874, Tyr875, and Met877 of LRP6. In another embodiment, the core interaction-site (inter-atomic distances between Lrp6E3E4 and VHH36 less than or equal to 5.0 Å) includes: Glu663, Ser665, Ile681, Tyr706, Glu708, Thr724, Ser749, Arg751, Trp767, Gly768, Arg792, Leu810, Asn813, Pro833, His834, Phe836, Trp850, Ser851, Arg853, Asp874, Try875, and Met877 of LRP6.

In another embodiment of invention, the anti-LRP5/6 antibodies and humanized versions thereof are derived from rabbit monoclonal antibodies, and in particular are generated using RabMAb® technology. These antibodies are advantageous as they require minimal sequence modifications, thereby facilitating retention of functional properties after humanization using mutational lineage guided (MLG) humanization technology (see e.g., U.S. Pat. No. 7,462,697). Thus, illustrative methods for making the anti-*** antibodies of the present disclosure include the RabMab® rabbit monoclonal antibody technology described, for example, in U.S. Pat. Nos. 5,675,063 and 7,429,487. In this regard, in certain embodiments, the anti-LRP5/6 antibodies of the disclosure are produced in rabbits. In particular embodiments, a rabbit-derived immortal B-lymphocyte capable of fusion with a rabbit splenocyte is used to produce a hybrid cell that produces an antibody. The immortal B-lymphocyte does not detectably express endogenous immunoglobulin heavy chain and may contain, in certain embodiments, an altered immunoglobulin heavy chain-encoding gene.

Compositions

Pharmaceutical compositions comprising an anti-LRP5/6 antibody or antigen-binding fragment thereof, e.g., a Wnt surrogate, described herein and one or more pharmaceutically acceptable diluent, carrier, or excipient are also disclosed. In particular embodiments, the pharmaceutical composition further comprises one or more Wnt polypeptides or Norrin polypeptides.

In further embodiments, pharmaceutical compositions comprising a polynucleotide comprising a nucleic acid sequence encoding an anti-LRP5/6 antibody or antigen-binding fragment thereof, e.g., a Wnt surrogate, described herein and one or more pharmaceutically acceptable diluent, carrier, or excipient are also disclosed. In particular embodiments, the pharmaceutical composition further comprises one or more polynucleotides comprising a nucleic acid sequence encoding a Wnt polypeptide or Norrin polypeptide. In certain embodiments, the polynucleotides are DNA or mRNA, e.g., a modified mRNA. In particular embodiments, the polynucleotides are modified mRNAs further comprising a 5' cap sequence and/or a 3' tailing sequence, e.g., a polyA tail. In other embodiments, the polynucleotides are expression cassettes comprising a promoter operatively linked to the coding sequences. In certain embodiments, the nucleic acid sequence encoding the anti-LRP5/6 antibody or antigen-binding fragment thereof, e.g., a Wnt surrogate, and the nucleic acid sequence encoding the Wnt polypeptide or Norrin polypeptide are present in the same polynucleotide.

In further embodiments, pharmaceutical compositions comprising an expression vector, e.g., a viral vector, comprising a polynucleotide comprising a nucleic acid sequence encoding an anti-LRP5/6 antibody or antigen-binding fragment thereof, e.g., a Wnt surrogate, described herein and one or more pharmaceutically acceptable diluent, carrier, or excipient are also disclosed. In particular embodiments, the pharmaceutical composition further comprises an expression vector, e.g., a viral vector, comprising a polynucleotide comprising a nucleic acid sequence encoding a Wnt polypeptide or Norrin polypeptide. In certain embodiments, the nucleic acid sequence encoding the anti-LRP5/6 antibody or antigen-binding fragment thereof, e.g., a Wnt surrogate, and the nucleic acid sequence encoding the Wnt polypeptide or Norrin polypeptide are present in the same polynucleotide, e.g., expression cassette.

The present invention further contemplates a pharmaceutical composition comprising a cell comprising an expression vector comprising a polynucleotide comprising a promoter operatively linked to a nucleic acid encoding an anti-LRP5/6 antibody or antigen-binding fragment thereof described herein and one or more pharmaceutically acceptable diluent, carrier, or excipient. In particular embodiments, the pharmaceutical composition further comprises a cell comprising an expression vector comprising a polynucleotide comprising a promoter operatively linked to a nucleic acid sequence encoding a Wnt polypeptide or a Norrin polypeptide. In certain embodiments, the nucleic acid sequence encoding the anti-LRP5/6 antibody or antigen-binding fragment thereof, e.g., a Wnt surrogate, and the nucleic acid sequence encoding the Wnt polypeptide or Norrin polypeptide are present in the same polynucleotide, e.g., expression cassette and/or in the same cell. In particular embodiments, the cell is a heterologous cell or an autologous cell obtained from the subject to be treated. In particular embodiments, the cell is a stem cell, e.g., an adipose-derived stem cell or a hematopoietic stem cell.

The present disclosure contemplates pharmaceutical compositions comprising a first molecule for delivery of anti-LRP5/6 antibody or antigen-binding fragment thereof, e.g., a Wnt surrogate, as a first active agent and a second molecule for delivery of a Wnt polypeptide or Norrin polypeptide. The first and second molecule may be the same type of molecule or different types of molecules. For example, in certain embodiments, the first and second molecule may each be independently selected from the following types of molecules: polypeptides, small organic molecules, nucleic acids encoding the first or second active agent (optionally DNA or mRNA, optionally modified RNA), vectors comprising a nucleic acid sequence encoding the first or second active agent (optionally expression vectors or viral vectors), and cells comprising a nucleic acid sequence encoding the first or second active agent (optionally an expression cassette).

The subject molecules, alone or in combination, can be combined with pharmaceutically-acceptable carriers, diluents, excipients and reagents useful in preparing a formulation that is generally safe, non-toxic, and desirable, and includes excipients that are acceptable for mammalian, e.g., human or primate, use. Such excipients can be solid, liquid, semisolid, or, in the case of an aerosol composition, gaseous. Examples of such carriers, diluents and excipients include, but are not limited to, water, saline, Ringer's solutions, dextrose solution, and 5% human serum albumin. Supplementary active compounds can also be incorporated into the formulations. Solutions or suspensions used for the formulations can include a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates; detergents such as Tween 20 to prevent aggregation; and compounds for the adjustment of tonicity such as sodium chloride or dextrose. The pH can be adjusted with acids or bases, such as hydrochloric acid or sodium hydroxide. In particular embodiments, the pharmaceutical compositions are sterile.

Pharmaceutical compositions may further include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In some cases, the composition is sterile and should be fluid to the extent that easy syringability exists. In certain embodiments, it is stable under the conditions of manufacture and storage and is preserved against the contaminating action of microorganisms such as bacteria and fungi. The carrier can be, e.g., a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the internal compositions can be brought about by including in the composition an agent which delays absorption, for example, aluminum monostearate and gelatin.

Sterile solutions can be prepared by incorporating the anti-LRP5/6 antibody or antigen-binding fragment thereof (or encoding polynucleotide or cell comprising the same) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In one embodiment, the pharmaceutical compositions are prepared with carriers that will protect the antibody or antigen-binding fragment thereof against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions can also be used as pharmaceutically acceptable carriers. These can be prepared according to methods known to those skilled in the art.

It may be advantageous to formulate the pharmaceutical compositions in dosage unit form for ease of administration and uniformity of dosage. Dosage unit form as used herein refers to physically discrete units suited as unitary dosages for the subject to be treated; each unit containing a predetermined quantity of active antibody or antigen-binding fragment thereof calculated to produce the desired therapeutic effect in association with the required pharmaceutical carrier. The specification for the dosage unit forms are dictated by and directly dependent on the unique characteristics of the antibody or antigen-binding fragment thereof and the particular therapeutic effect to be achieved, and the limitations inherent in the art of compounding such an active antibody or antigen-binding fragment thereof for the treatment of individuals.

The pharmaceutical compositions can be included in a container, pack, or dispenser, e.g. syringe, e.g. a prefilled syringe, together with instructions for administration.

The pharmaceutical compositions of the invention encompass any pharmaceutically acceptable salts, esters, or salts of such esters, or any other compound which, upon administration to an animal comprising a human, is capable of providing (directly or indirectly) the biologically active antibody or antigen-binding fragment thereof.

The present invention includes pharmaceutically acceptable salts of the anti-LRP5/6 antibodies or antigen-binding fragments thereof, e.g., Wnt surrogates, described herein. The term "pharmaceutically acceptable salt" refers to physiologically and pharmaceutically acceptable salts of the compounds of the invention: i.e., salts that retain the desired biological activity of the parent compound and do not impart undesired toxicological effects thereto. A variety of pharmaceutically acceptable salts are known in the art and described, e.g., in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). Also, for a review on suitable salts, see "Handbook of Pharmaceutical Salts: Properties, Selection, and Use" by Stahl and Wermuth (Wiley-VCH, 2002).

Pharmaceutically acceptable base addition salts are formed with metals or amines, such as alkali and alkaline earth metals or organic amines. Metals used as cations comprise sodium, potassium, magnesium, calcium, and the like. Amines comprise N—N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. Pharma Sci., 1977, 66, 119). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

In some embodiments, the pharmaceutical composition provided herein comprise a therapeutically effective amount of an anti-LRP5/6 antibody or antigen-binding fragment thereof, e.g., a Wnt surrogate, described herein in admixture with a pharmaceutically acceptable carrier, diluent and/or excipient, for example saline, phosphate buffered saline, phosphate and amino acids, polymers, polyols, sugar, buffers, preservatives and other proteins. Exemplary amino acids, polymers and sugars and the like are octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene and glycol. Preferably, this formulation is stable for at least six months at 4° C.

In some embodiments, the pharmaceutical composition provided herein comprises a buffer, such as phosphate buffered saline (PBS) or sodium phosphate/sodium sulfate, tris buffer, glycine buffer, sterile water and other buffers known to the ordinarily skilled artisan such as those described by Good et al. (1966) Biochemistry 5:467. The pH of the buffer may be in the range of 6.5 to 7.75, preferably 7 to 7.5, and most preferably 7.2 to 7.4.

Methods of Use

The present disclosure also provides methods for using the LRP5/6-specific antibodies, antigen-binding fragments thereof, e.g., Wnt surrogates, disclosed herein, e.g., to modulate a Wnt signaling pathway, e.g., to increase or decrease Wnt signaling, and the administration of Fzd-specific antibodies, antigen-binding fragments thereof, and Wnt surrogates disclosed herein in a variety of therapeutic settings. Provided herein are methods of treatment using the antibodies that bind one or more Fzd receptors or antigen-binding fragments thereof. In one embodiment, an antibody, or antigen-binding fragment thereof, of the present invention is provided to a subject having a disease involving inappropriate or deregulated Wnt signaling, e.g., increased or reduced Wnt signaling.

Increasing Wnt Pathway Signaling and Related Therapeutic Methods

In certain embodiments, an anti-LRP5/6 antibody or antigen-binding fragment thereof, e.g., a Wnt surrogate, may be used to increase Wnt signaling in a tissue or cell. Thus, in some aspects, the present invention provides a method for increasing Wnt signaling or enhancing Wnt signaling in a tissue or cell, comprising contacting the tissue or cell with an effective amount of a an anti-LRP5/6 antibody or antigen-binding fragment thereof, e.g., a Wnt surrogate, disclosed herein, wherein the anti-LRP5/6 antibody or antigen-binding fragment thereof is a Wnt signaling pathway agonist. In some embodiments, contacting occurs in vitro, ex vivo, or in vivo. In particular embodiments, the cell is a cultured cell, and the contacting occurs in vitro. In certain embodiments, the method comprises further contacting the tissue or cell with one or more Wnt polypeptides or Norrin polypeptides.

In related aspects, the present invention provides a method for increasing Wnt signaling in a tissue or cell, comprising contacting the tissue or cell with an effective amount of a polynucleotide comprising an anti-LRP5/6 antibody or antigen-binding fragment thereof, e.g., a Wnt surrogate, of the present invention. In certain embodiments, the target tissue or cell is also contacted with a polynucleotide comprising a nucleic acid sequence that encodes a Wnt polypeptide or a Norrin polypeptide. In certain embodiments, the polynucleotides are DNA or mRNA, e.g., a modified mRNA. In particular embodiments, the polynucleotides are modified mRNAs further comprising a 5' cap sequence and/or a 3' tailing sequence, e.g., a polyA tail. In other embodiments, the polynucleotides are expression cassettes comprising a promoter operatively linked to the coding sequences. In certain embodiments, the nucleic acid sequence encoding the anti-LRP5/6 antibody or antigen-binding fragment thereof, e.g., a Wnt surrogate, and the nucleic acid sequence encoding the Wnt polypeptide or Norrin polypeptide are present in the same polynucleotide.

In related aspects, the present invention provides a method for increasing Wnt signaling in a tissue or cell, comprising contacting the tissue or cell with an effective amount of a vector comprising a nucleic acid sequence encoding an anti-LRP5/6 antibody or antigen-binding fragment thereof, e.g., a Wnt surrogate. In certain embodiments, the tissue or cell is also contacted with a vector comprising a nucleic acid sequence that encodes a Wnt polypeptide or a Norrin polypeptide. In certain embodiments, the vector is an expression vector, and may comprise a promoter operatively linked to the nucleic acid sequence. In particular embodiments, the vector is a viral vector. In certain embodiments, the nucleic acid sequence encoding the anti-LRP56 antibody or antigen-binding fragment thereof, e.g., a Wnt surrogate, and the nucleic acid sequence encoding the Wnt polypeptide or Norrin polypeptide are present in the same vector, e.g., in the same expression cassette.

In related aspects, the present invention provides a method for increasing Wnt signaling in a tissue, comprising contacting the tissue with an effective amount of a cell comprising a nucleic acid sequence encoding an anti-LRP5/6 antibody or antigen-binding fragment thereof, e.g., a Wnt surrogate, of the present invention. In certain embodiments, the tissue is also contacted with a cell comprising a nucleic acid sequence that encodes a Wnt polypeptide or Norrin polypeptide. In certain embodiments, the nucleic acid sequence encoding the anti-LRP56 antibody or antigen-binding fragment thereof, e.g., a Wnt surrogate, and the nucleic acid sequence encoding the Wnt polypeptide or Norrin polypeptide are present in the same cell. In particular embodiments, the cell is a heterologous cell or an autologous cell obtained from the subject to be treated. In certain embodiments, the cell was transduced with a vector comprising an expression cassette encoding the anti-LRP5/6 antibody or antigen-binding fragment thereof, e.g., a Wnt surrogate, or the Wnt polypeptide or Norrin polypeptide. In particular embodiments, the cell is a stem cell, e.g., an adipose-derived stem cell or a hematopoietic stem cell.

Anti-LRP5/6 antibodies and antigen-binding fragments thereof, e.g., Wnt surrogates, may be used in to treat a disease, disorder or condition, for example, by increasing Wnt signaling in a targeted cell, tissue or organ. Thus, in some aspects, the present invention provides a method for treating a disease or condition in a subject in need thereof, e.g., a disease or disorder associated with reduced Wnt signaling, or for which increased Wnt signaling would provide a therapeutic benefit, comprising contacting the subject with an effective amount of a composition of the present disclosure. In particular embodiments, the composition is a pharmaceutical composition comprising any of: an anti-LRP5/6 antibody or antigen-binding fragment thereof, e.g., a Wnt surrogate; a polynucleotide comprising a nucleic acid sequence encoding an anti-LRP5/6 antibody or antigen-binding fragment thereof, e.g., a Wnt surrogate, e.g., a DNA or mRNA, optionally a modified mRNA; a vector comprising a nucleic acid sequence encoding an anti-LRP5/6 antibody or antigen-binding fragment thereof, e.g., a Wnt surrogate, e.g., an expression vector or viral vector; or a cell comprising a nucleic acid sequence encoding an anti-LRP5/6 antibody or antigen-binding fragment thereof, e.g., a Wnt surrogate, e.g., a cell transduced with an expression vector or viral vector encoding an anti-LRP5/6 antibody or antigen-binding fragment thereof, e.g., a Wnt surrogate. In particular embodiments, the disease or condition is a pathological disease or disorder, or an injury, e.g., an injury resulting from a wound. In certain embodiments, the wound may be the result of another therapeutic treatment. In certain embodiments, the disease or condition comprises impaired tissue repair, healing or regeneration, or would benefit from increased tissue repair, healing or regeneration. In some embodiments, contacting occurs in vivo, i.e., the subject composition is administered to a subject.

In certain embodiments, the method comprises further contacting the subject with a pharmaceutical composition comprising one or more Wnt polypeptides or Norrin polypeptides. The present disclosure contemplates contacting a subject with a first molecule for delivery of an anti-LRP5/6 antibody or antigen-binding fragment thereof, e.g., a Wnt surrogate, as a first active agent and a second molecule for delivery of a Wnt polypeptide or Norrin polypeptide. The first and second molecule may be the same type of molecule or different types of molecules. For example, in certain embodiments, the first and second molecule may each be independently selected from the following types of molecules: polypeptides, small organic molecules, nucleic acids encoding the first or second active agent (optionally DNA or mRNA, optionally modified RNA), vectors comprising a nucleic acid sequence encoding the first or second active agent (optionally expression vectors or viral vectors), and cells comprising a nucleic acid sequence encoding the first or second active agent (optionally an expression cassette).

In related aspects, the present invention provides a method for treating a disease or condition, e.g., a disease or disorder associated with reduced Wnt signaling, or for which increased Wnt signaling would provide a therapeutic benefit, comprising contacting a subject in need thereof with a pharmaceutical composition comprising an effective amount of a polynucleotide comprising a nucleic acid sequence encoding an anti-LRP56 antibody or antigen-binding fragment thereof, e.g., a Wnt surrogate, disclosed herein. In certain embodiments, the subject is also contacted with a pharmaceutical composition comprising an effective amount of a polynucleotide comprising a nucleic acid sequence that encodes a Wnt polypeptide or a Norrin polypeptide. In certain embodiments, the polynucleotides are DNA or mRNA, e.g., a modified mRNA. In particular embodiments, the polynucleotides are modified mRNAs further comprising a 5' cap sequence and/or a 3' tailing sequence, e.g., a polyA tail. In other embodiments, the polynucleotides are expression cassettes comprising a promoter operatively linked to the coding sequences. In certain embodiments, the nucleic acid sequence encoding the anti-LRP56 antibody or antigen-binding fragment thereof, e.g., a Wnt surrogate, and the nucleic acid sequence encoding the Wnt polypeptide or Norrin polypeptide are present in the same polynucleotide.

In related aspects, the present invention provides a method for treating a disease or condition, e.g., a disease or disorder associated with reduced Wnt signaling, or for which increased Wnt signaling would provide a therapeutic benefit, comprising contacting a subject in need thereof with a pharmaceutical composition comprising an effective amount of a vector comprising a nucleic acid sequence encoding an anti-LRP56 antibody or antigen-binding fragment thereof, e.g., a Wnt surrogate. In certain embodiments, the subject is also contacted with a pharmaceutical composition comprising an effective amount of a vector comprising a nucleic acid sequence that encodes a Wnt polypeptide or a Norrin polypeptide. In certain embodiments, the vector is an expression vector, and may comprise a promoter operatively linked to the nucleic acid sequence. In particular embodiments, the vector is a viral vector. In certain embodiments, the nucleic acid sequence encoding the anti-LRP5/6 antibody or antigen-binding fragment thereof, e.g., a Wnt surrogate, and the nucleic acid sequence encoding the Wnt polypeptide or Norrin polypeptide are present in the same vector, e.g., in the same expression cassette.

In related aspects, the present invention provides a method for treating a disease or condition, e.g., a disease or disorder associated with reduced Wnt signaling, or for which increased Wnt signaling would provide a therapeutic benefit, comprising contacting a subject in need thereof with a pharmaceutical composition comprising an effective amount of a cell comprising a nucleic acid sequence encoding an anti-LRP5/6 antibody or antigen-binding fragment thereof, e.g., a Wnt surrogate. In certain embodiments, the subject is also contacted with a cell comprising a nucleic acid sequence that encodes a Wnt polypeptide or a Norrin polypeptide. In certain embodiments, the nucleic acid sequence encoding the anti-LRP5/6 antibody or antigen-binding fragment thereof, e.g., a Wnt surrogate, and the nucleic acid sequence encoding the Wnt polypeptide or Norrin polypeptide are present in the same cell. In particular embodiments, the cell is a heterologous cell or an autologous cell obtained from the subject to be treated. In certain embodiments, the cell was transduced with a vector comprising an expression cassette encoding the anti-LRP5/6 antibody or antigen-binding fragment thereof, e.g., a Wnt surrogate, or the Wnt polypeptide or Norrin polypeptide. In particular embodiments, the cell is a stem cell, e.g., an adipose-derived stem cell or a hematopoietic stem cell.

Wnt signaling plays key roles in the developmental process and maintenance of stem cells. Reactivation of Wnt signals is associated with regeneration and repair of most tissues after injuries and diseases. Anti-LRP5/6 antibody or antigen-binding fragment thereof, e.g., a Wnt surrogate, molecules are expected to provide benefit of healing and tissue repair in response to injuries and diseases. Causes of tissue damage and loss include but are not limited to aging, degeneration, hereditary conditions, infection and inflammation, traumatic injuries, toxins/metabolic-induced toxicities, or other pathological conditions. Wnt signals and enhancers of Wnt signals have been shown to activate adult, tissue-resident stem cells. In some embodiments, the compounds of the invention are administered for use in treating diseased or damaged tissue, for use in tissue regeneration and for use in cell growth and proliferation, and/or for use in tissue engineering.

For example, compositions of the present invention may be used to promote or increase bone growth or regeneration, bone grafting, healing of bone fractures, treatment of osteoporosis and osteoporotic fractures, spinal fusion, spinal cord injuries, including vertebral compression fractures, pre-operative spinal surgery optimization, osseointegration of orthopedic devices, tendon-bone integration, tooth growth and regeneration, dental implantation, periodontal diseases, maxillofacial reconstruction, and osteonecrosis of the jaw. They may also be used in the treatment of alopecia; enhancing regeneration of sensory organs, e.g. treatment of hearing loss, including regeneration of inner and outer auditory hair cells treatment of vestibular hypofunction, treatment of macular degeneration, treatment of retinopathies, including vitreoretinopathy, diabetic retinopathy, other diseases of retinal degeneration, Fuchs' dystrophy, other cornea disease, etc.; treatment of stroke, traumatic brain injury, Alzheimer's disease, multiple sclerosis, muscular dystrophy, muscle atrophy as a result of sarcopenia or cachexia, and other conditions affecting the degeneration or integrity of the blood brain barrier. The compositions of this invention may also be used in treatment of oral mucositis, treatment of short bowel syndrome, inflammatory bowel diseases (IBD), including Crohn's disease (CD) and ulcerative colitis (UC), in particular CD with fistula formation, other gastrointestinal disorders; treatment of metabolic syndrome, dyslipidemia, treatment of diabetes, treatment of pancreatitis, conditions where exocrine or endocrine pancreas tissues are damaged; conditions where enhanced epidermal regeneration is desired, e.g., epidermal wound healing, treatment of diabetic foot ulcers, syndromes involving tooth, nail, or dermal hypoplasia, etc., conditions where angiogenesis is beneficial; treatment of myocardial infarction, coronary artery disease, heart failure; enhanced growth of hematopoietic cells, e.g. enhancement of hematopoietic stem cell transplants from bone marrow, mobilized peripheral blood, treatment of immunodeficiencies, graft versus host diseases, etc.; treatment of acute kidney injuries, chronic kidney diseases; treatment of lung diseases, chronic obstructive pulmonary diseases (COPD), pulmonary fibrosis, including idiopathic pulmonary fibrosis, enhanced regeneration of lung tissues. The compositions of the present invention may also be used in enhanced regeneration of liver cells, e.g. liver regeneration, treatment of cirrhosis, enhancement of liver transplantations, treatment of acute liver failure, treatment of chronic liver diseases with hepatitis C or B virus infection or post-antiviral drug therapies, alcoholic liver diseases, alcoholic hepatitis, non-alcoholic liver diseases with steatosis or steatohepatitis, and the like. The compositions of this invention may treat diseases and disorders including, without limitation, conditions in which regenerative cell growth is desired.

Human genetics involving loss-of-function or gain-of-function mutations in Wnt signaling components show strong evidence supporting enhancing Wnt signals for bone growth. Conditions in which enhanced bone growth is desired may include, without limitation, fractures, grafts, ingrowth around prosthetic devices, osteoporosis, osteoporotic fractures, spinal fusion, vertebral compression fractures, pre-operative optimization for spinal surgeries, osteonecrosis of the jaw, dental implantation, periodontal diseases, maxillofacial reconstruction, and the like. An anti-LRP5/6 antibody or antigen-binding fragment thereof, e.g., a Wnt surrogate, enhances and promotes Wnt signals which are critical in promoting bone regeneration. Methods for regeneration of bone tissues benefit from administration of the compounds of the invention, which can be systemic or localized. In some embodiments, bone marrow cells are exposed to molecules of the invention, such that stem cells within that marrow become activated.

In some embodiments, bone regeneration is enhanced by contacting a responsive cell population, e.g. bone marrow, bone progenitor cells, bone stem cells, etc. with an effective dose of an anti-LRP5/6 antibody or antigen-binding fragment thereof, e.g., a Wnt surrogate, disclosed herein. Methods for regeneration of bone tissues benefit from administration of the anti-LRP5/6 antibody or antigen-binding fragment thereof, e.g., a Wnt surrogate disclosed herein, which can be systemic or localized. In some such embodiments, the contacting is performed in vivo. In other such embodiments, the contacting is performed ex vivo. The molecule may be localized to the site of action, e.g. by loading onto a matrix, which is optionally biodegradable, and optionally provides for a sustained release of the active agent. Matrix carriers include, without limitation, absorbable collagen sponges, ceramics, hydrogels, polymeric microspheres, nanoparticles, bone cements, and the like.

Compositions comprising one or more anti-LRP5/6 antibody or antigen-binding fragment thereof, e.g., a Wnt surrogate, disclosed herein can be used for the in vivo treatment of skeletal tissue deficiencies. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions. The compositions of the present invention can be used as part of a regimen for restoring cartilage function to a connective tissue, for the repair of defects or lesions in cartilage tissue such as degenerative wear and arthritis, trauma to the tissue, displacement of torn meniscus, meniscectomy, a luxation of a joint by a torn ligament, malalignment of joints, bone fracture, or by hereditary disease.

An anti-LRP5/6 antibody or antigen-binding fragment thereof, e.g., a Wnt surrogate, may also be used for treatment of periodontal diseases. Periodontal diseases are a leading cause of tooth loss and are linked to multiple systemic conditions. In some embodiments, tooth or underlying bone regeneration is enhanced by contacting a responsive cell population. In some such embodiments, the contacting is performed in vivo. In other such embodiments, the contacting is performed ex vivo, with subsequent implantation of the activated stem or progenitor cells. The molecule may be localized to the site of action, e.g. by loading onto a matrix, which is optionally biodegradable, and optionally provides for a sustained release of the active agent. Matrix carriers include, without limitation, absorbable collagen sponges, ceramics, hydrogels, bone cements, polymeric microspheres, nanoparticles, and the like.

Studies have shown that biology of Wnt signaling and R-spondins are capable of promoting sensory hair cell regeneration in the inner ear following injuries, aging, or degeneration. Loss of sensory hair cells in the inner ear involved in hearing loss or vestibular hypofunction may also benefit from the compositions of the invention. In the inner ear, the auditory organ houses mechanosensitive hair cells required for translating sound vibration to electric impulses. The vestibular organs, comprised of the semicircular canals (SSCs), the utricle, and the saccule, also contain sensory hair cells in order to detect head position and motion. Compositions of the present invention can be used, for example, in an infusion; in a matrix or other depot system; or other topical application to the ear for enhancement of auditory regeneration.

An anti-LRP5/6 antibody or antigen-binding fragment thereof, e.g., a Wnt surrogate, may also be used in regeneration of retinal tissue. In the adult mammalian retina, Muller glia cells are capable of regenerating retinal cells, including photoreceptors, for example after neurotoxic injury in vivo. Wnt signaling and enhancers of Wnt signals can promote proliferation of Muller glia-derived retinal progenitors after damage or during degeneration. The compositions of the invention may also be used in the regeneration of tissues and other cell types in the eye. For examples age-related macular degeneration (AMD), other retina degenerative diseases, cornea diseases, Fuchs' dystrophy, vitreoretinopathy, hereditary diseases, etc. can benefit from the compositions of the present inventions. AMD is characterized by progressively decreased central vision and visual acuity. Fuchs' dystrophy is characterized by progressive loss of cornea endothelial cells. Wnt signal and enhancing of Wnt signal can promote regeneration of cornea endothelium, retina epithelium, etc. in the eye tissue. In other embodiments, compositions of the present invention can be used, for example, in an infusion; in a matrix or other depot system; or other topical application to the eye for retinal regeneration and treatment of macular degeneration.

Specific populations of proliferating cells for homeostatic renewal of hepatocytes have been identified through lineage tracing studies, for example Axin2-positive cells in pericentral region. Lineage tracing studies also identified additional potential liver progenitor cells, including but not limited to Lgr-positive cells. The self-renewing liver cells and other populations of potential progenitor cells, including Lgr5-positive and Axin2-positive cells, are identified to be capable of regeneration responding to Wnt signals and/or R-spondins following injuries. Numerous preclinical models of acute liver injury and failure and chronic liver diseases showed recovery and regeneration of hepatocytes benefit from enhancing Wnt signals. The compositions of this invention may be used in treatment of acute liver failure, acute alcoholic liver injuries, treatment of chronic liver diseases with hepatitis C or B virus infection or post-antiviral drug therapies, chronic alcoholic liver diseases, alcoholic hepatitis, non-alcoholic fatty liver diseases and non-alcoholic steatohepatitis (NASH), treatment of cirrhosis and severe chronic liver diseases of all causes, and enhanced regeneration of liver cells. Methods for regeneration of liver tissue benefit from administration of the compounds of the invention, which can be systemic or localized. These include, but are not limited to, methods of systemic administration and methods of localized administration e.g. by injection into the liver tissue, by injection into veins or blood vessels leading into the liver, by implantation of a sustained release formulation, and the like.

Wnt signals play an important role in regeneration of various epithelial tissues. Various epidermal conditions benefit from treatment with the compounds of the present invention. Mucositis occurs when there is a breakdown of the rapidly divided epithelial cells lining the gastro-intestinal tract, leaving the mucosal tissue open to ulceration and infection. The part of the epithelial lining that covers the mouth, called the oral mucosa, is one of the most sensitive parts of the body and is particularly vulnerable to chemotherapy and radiation. Oral mucositis is probably the most common, debilitating complication of cancer treatments, particularly chemotherapy and radiation. In addition, the compositions of the invention may also benefit treatment of short bowel syndrome, inflammatory bowel diseases (IBD), or other gastrointestinal disorders. Other epidermal conditions include epidermal wound healing, diabetic foot ulcers, syndromes involving tooth, nail, or dermal hypoplasia, and the like. Molecules of the present invention may be used in all these conditions, where regenerative cells are contacted with compounds of the invention. Methods for regeneration of epithelial tissues benefit from administration of the compounds of the invention, which can be systemic or localized. Contacting can be, for example, topical, including intradermal, subdermal, in a gel, lotion, cream etc. applied at targeted site, etc.

In addition to skin and gastrointestinal tract, Wnt signals and enhancement and promotion of Wnt signals also play an important role in repair and regeneration of tissues including pancreas, kidney, and lung in preclinical models. An anti-LRP5/6 antibody or antigen-binding fragment thereof, e.g., a Wnt surrogate, may benefit various disease conditions involving exocrine and endocrine pancreas, kidney, or lung. The anti-LRP5/6 antibody or antigen-binding fragment thereof, e.g., a Wnt surrogate, may be used in treatment of metabolic syndrome; treatment of diabetes, treatment of acute or chronic pancreatitis, exocrine pancreatic insufficiency, treatment of acute kidney injuries, chronic kidney diseases, treatment of lung diseases, including but not limited to chronic obstructive pulmonary diseases (COPD), pulmonary fibrosis, in particular idiopathic pulmonary fibrosis (IPF), and other conditions that cause loss of lung epithelial tissues. Methods for regeneration of these tissues benefit from administration of the compounds of the invention, which can be systemic or localized.

Epidermal Wnt signaling, in coordination with signaling via other development factors, is critical for adult hair follicle regeneration. Hair loss is a common problem, and androgenetic alopecia, often called male pattern baldness, is the most common form of hair loss in men. In some embodiments, hair follicle regeneration is enhanced by contacting a responsive cell population with a molecule of the present invention. In some such embodiments, the contacting is performed in vivo. In other such embodiments, the contacting is performed ex vivo. The molecule may be localized to the site of action, e.g. topical lotions, gels, creams and the like.

Stroke, traumatic brain injury, Alzheimer's disease, multiple sclerosis and other conditions affecting the blood brain barrier (BBB) may be treated with an anti-LRP5/6 antibody or antigen-binding fragment thereof, e.g., a Wnt surrogate. Angiogenesis is critical to ensure the supply of oxygen and nutrients to many tissues throughout the body, and is especially important for the CNS as the neural tissue is extremely sensitive to hypoxia and ischemia. CNS endothelial cells which form the BBB differ from endothelial cells in non-neural tissue, in that they are highly polarized cells held together by tight junctions and express specific transporters. Wnt signaling regulates CNS vessel formation and/or function. Conditions in which the BBB is compromised can benefit from administration of the compounds of the invention, which can be systemic or localized e.g. by direct injection, intrathecal administration, implantation of sustained release formulations, and the like. In addition, Wnt signal is actively involved in neurogenesis and plays a role of neuroprotection following injury. The compositions of the present invention may also be used in treatment of spinal cord injuries, other spinal cord diseases, stroke, traumatic brain injuries, etc.

Wnt signals also play a role in angiogenesis. An anti-LRP5/6 antibody or antigen-binding fragment thereof, e.g., a Wnt surrogate, may benefit conditions where angiogenesis is beneficial, treatment of myocardial infarction, coronary artery disease, heart failure, diabetic retinopathy, etc., and conditions from hereditary diseases. Methods for regeneration of these tissues benefit from administration of the compounds of the invention, which can be systemic or localized.

In certain embodiments, methods of the present invention promote tissue regeneration, e.g., in a tissue subjected to damage or tissue or cell reduction or loss. The loss or damage can be anything which causes the cell number to diminish, including diseases or injuries. For example, an accident, an autoimmune disorder, a therapeutic side-effect or a disease state could constitute trauma. Tissue regeneration increases the cell number within the tissue and preferably enables connections between cells of the tissue to be re-established, and more preferably the functionality of the tissue to be regained.

Reducing Wnt Pathway Signaling and Related Therapeutic Methods

In certain embodiments, an anti-LRP5/6 antibody or antigen-binding fragment thereof, may be used to decrease or inhibit Wnt signaling in a tissue or cell. Thus, in some aspects, the present invention provides a method for decreasing Wnt signaling or inhibiting Wnt signaling in a tissue or cell, comprising contacting the tissue or cell with an effective amount of an anti-LRP5/6 antibody, or antigen-binding fragment thereof, disclosed herein, wherein the anti-LRP5/6 antibody or antigen-binding fragment thereof is a Wnt signaling pathway antagonist or inhibitor. In some embodiments, contacting occurs in vitro, ex vivo, or in vivo. In particular embodiments, the cell is a cultured cell, and the contacting occurs in vitro.

In related aspects, the present invention provides a method for decreasing or inhibiting Wnt signaling in a tissue or cell, comprising contacting the tissue or cell with an effective amount of a polynucleotide comprising an anti-LRP5/6 antibody or antigen-binding fragment thereof, of the present invention, wherein the anti-LRP5/6 antibody or antigen-binding fragment thereof is a Wnt signaling pathway antagonist or inhibitor. In certain embodiments, the polynucleotides are DNA or mRNA, e.g., a modified mRNA. In particular embodiments, the polynucleotides are modified mRNAs further comprising a 5' cap sequence and/or a 3' tailing sequence, e.g., a polyA tail. In other embodiments, the polynucleotides are expression cassettes comprising a promoter operatively linked to the coding sequences In related aspects, the present invention provides a method for decreasing or inhibiting Wnt signaling in a tissue or cell, comprising contacting the tissue or cell with an effective amount of a vector comprising a nucleic acid sequence encoding an anti-LRP5/6 antibody or antigen-binding fragment thereof, wherein the anti-LRP5/6 antibody or antigen-binding fragment thereof is a Wnt signaling pathway antagonist or inhibitor. In certain embodiments, the vector is an expression vector, and may comprise a promoter operatively linked to the nucleic acid sequence. In particular embodiments, the vector is a viral vector.

In related aspects, the present invention provides a method for decreasing or inhibiting Wnt signaling in a tissue, comprising contacting the tissue with an effective amount of a cell comprising a nucleic acid sequence encoding an anti-LRP5/6 antibody or antigen-binding fragment thereof, wherein the anti-LRP5/6 antibody or antigen-binding fragment thereof is a Wnt signaling pathway antagonist or inhibitor. In particular embodiments, the cell is a heterologous cell or an autologous cell obtained from the subject to be treated. In certain embodiments, the cell was transduced with a vector comprising an expression cassette encoding the anti-LRP5/6 antibody or antigen-binding fragment thereof, wherein the anti-LRP5/6 antibody or antigen-binding fragment thereof is a Wnt signaling pathway antagonist or inhibitor. In particular embodiments, the cell is a stem cell, e.g., an adipose-derived stem cell or a hematopoietic stem cell.

Anti-LRP5/6 antibodies and antigen-binding fragments thereof, wherein the anti-LRP5/6 antibody or antigen-binding fragment thereof is a Wnt signaling pathway antagonist or inhibitor, may be used in to treat a disease, disorder or condition, for example, by decreasing or inhibiting Wnt signaling in a cell, tissue or organ. Thus, in some aspects, the present invention provides a method for treating a disease or condition in a subject in need thereof, e.g., a disease or disorder associated with increased or deregulated Wnt signaling, or for which decreased Wnt signaling would provide a therapeutic benefit, comprising contacting the subject with an effective amount of a composition comprising an anti-LRP5/6 antibody or antigen-binding fragment thereof, wherein the anti-LRP56 antibody or antigen-binding fragment thereof is a Wnt signaling pathway antagonist or inhibitor. In particular embodiments, the composition is a pharmaceutical composition comprising any of: an anti-LRP56 antibody or antigen-binding fragment thereof; a polynucleotide comprising a nucleic acid sequence encoding an anti-LRP5/6 antibody or antigen-binding fragment thereof, e.g., a DNA or mRNA, optionally a modified mRNA; a vector comprising a nucleic acid sequence encoding an anti-LRP56 antibody or antigen-binding fragment thereof, e.g., an expression vector or viral vector; or a cell comprising a nucleic acid sequence encoding an anti- LRP5/6 antibody or antigen-binding fragment thereof, e.g., a cell transduced with an expression vector or viral vector encoding an anti-LRP5/6 antibody or antigen-binding fragment thereof. In particular embodiments, the disease or condition is a pathological disease or disorder, or an injury. In some embodiments, contacting occurs in vivo, i.e., the subject composition is administered to a subject.

In related aspects, the present invention provides a method for treating a disease or condition, e.g., a disease or disorder associated with increased Wnt signaling, or for which reduced Wnt signaling would provide a therapeutic benefit, comprising contacting a subject in need thereof with a pharmaceutical composition comprising an effective amount of a polynucleotide comprising a nucleic acid sequence encoding an anti-LRP56 antibody or antigen-binding fragment thereof, wherein the antibody or antigen-binding fragment thereof is a Wnt signaling pathway antagonist or inhibitor, disclosed herein. In certain embodiments, the polynucleotides are DNA or mRNA, e.g., a modified mRNA. In particular embodiments, the polynucleotides are modified mRNAs further comprising a 5' cap sequence and/or a 3' tailing sequence, e.g., a polyA tail. In other embodiments, the polynucleotides are expression cassettes comprising a promoter operatively linked to the coding sequences In related aspects, the present invention provides a method for treating a disease or condition, e.g., a disease or disorder associated with increased Wnt signaling, or for which decreased Wnt signaling would provide a therapeutic benefit, comprising contacting a subject in need thereof with a pharmaceutical composition comprising an effective amount of a vector comprising a nucleic acid sequence encoding an anti-LRP56 antibody or antigen-binding fragment thereof, wherein the antibody or antigen-binding fragment thereof is a Wnt signaling pathway antagonist or inhibitor. In certain embodiments, the vector is an expression vector, and may comprise a promoter operatively linked to the nucleic acid sequence. In particular embodiments, the vector is a viral vector.

In related aspects, the present invention provides a method for treating a disease or condition, e.g., a disease or disorder associated with increased Wnt signaling, or for which decreased Wnt signaling would provide a therapeutic benefit, comprising contacting a subject in need thereof with a pharmaceutical composition comprising an effective amount of a cell comprising a nucleic acid sequence encoding an anti-LRP56 antibody or antigen-binding fragment thereof, wherein the antibody or antigen-binding fragment thereof is a Wnt signaling pathway antagonist or inhibitor. In particular embodiments, the cell is a heterologous cell or an autologous cell obtained from the subject to be treated. In certain embodiments, the cell was transduced with a vector comprising an expression cassette encoding the anti-LRP5/6 antibody or antigen-binding fragment thereof. In particular embodiments, the cell is a stem cell, e.g., an adipose-derived stem cell or a hematopoietic stem cell.

In certain embodiments, methods of treating or preventing diseases or disorders in a subject in need thereof, by providing to the subject an effective amount of an anti-LRP5/6 antibody, or an antigen-binding fragment thereof, wherein the antibody or the antigen-binding fragment thereof is an inhibitor of a Wnt signaling pathway, may be used to treat a cancer or tumor, e.g., a solid or liquid tumor. Examples of cancers and tumors that may be treated include, but are not limited to: colon tumors (e.g. colon cancer or adenoma), stomach tumors (e.g., stomach cancer), small intestine tumors (e.g., small intestinal cancer), liver tumors (e.g., liver cancer), pancreas tumors (e.g., pancreatic cancer), lung tumors (e.g., lung cancer), ovary tumors (e.g., ovarian cancer), kidney (e.g., kidney cancer), brain tumors (e.g., brain cancer), spinal cord tumors (e.g., spinal cord cancer), skin tumors (e.g., skin cancer or melanoma), head and neck tumors (e.g., head and neck cancer), gastointestinal tract tumors (e.g., gastrointestinal cancer, esophageal cancer, oral mucosa cancer, tongue cancer, stomach cancer, intestinal cancer, colon cancer), breast tumors (e.g., breast cancer), prostate tumors (e.g., prostate cancer), bone tumors (e.g., bone cancer), vascular tumors, Wilms tumor, leukemina/lymphoma, soft tissue tumors (e.g., soft tissue sarcoma or synovial sarcoma) and metastatic cancers, etc.

In certain embodiments, methods of treating or preventing diseases or disorders in a subject in need thereof, by providing to the subject an effective amount of an anti-LRP5/6 antibody, or an antigen-binding fragment thereof, wherein the antibody or the antigen-binding fragment thereof is an inhibitor of a Wnt signaling pathway, may be used to treat degenerative diseases. Examples of degenerative diseases that may be treated include, but are not limited to osteoarthritis, cartilage degeneration, sports injuries (e.g., cartilage injury), retinopathy, atherosclerosis, neurodegenerative disorders, and vascular disorders e.g. vasculitis, conditions with abnormal angiogenesis.

In certain embodiments, methods of treating or preventing diseases or disorders in a subject in need thereof, by providing to the subject an effective amount of an anti-LRP5/6 antibody, or an antigen-binding fragment thereof, wherein the antibody or the antigen-binding fragment thereof is an inhibitor of a Wnt signaling pathway, may be used to treat fibrosis. Examples of fibrosis that may be treated include, but are not limited to, lung fibrosis (including but not limited to COPD. idiopathic pulmonary fibrosis), kidney fibrosis (e.g. end stage renal failure), liver fibrosis, congenital liver storage diseases, and cardiac fibrosis.

In certain embodiments, methods of treating or preventing diseases or disorders in a subject in need thereof, by providing to the subject an effective amount of an anti-LRP5/6 antibody, or an antigen-binding fragment thereof, wherein the antibody or the antigen-binding fragment thereof is an inhibitor of a Wnt signaling pathway, may be used to treat heart failure, e.g., congestive heart failure, systolic heart failure, heart failure with preserved ejection fraction, or coronary artery disease.

In certain embodiments, methods of treating or preventing diseases or disorders in a subject in need thereof, by providing to the subject an effective amount of an anti-LRP5/6 antibody, or an antigen-binding fragment thereof, wherein the antibody or the antigen-binding fragment thereof is an inhibitor of a Wnt signaling pathway, may be used to treat heterotopic ossification, osteopetrosis, or congenital high bone mass disorders.

The terms "administering" or "introducing" or "providing", as used herein, refer to delivery of a composition to a cell, to cells, tissues and/or organs of a subject, or to a subject. Such administering or introducing may take place in vivo, in vitro or ex vivo.

In particular embodiments, a pharmaceutical composition is administered parenterally, e.g., intravenously, orally, rectally, or by injection. In some embodiments, it is administered locally, e.g., topically or intramuscularly. In some embodiments, a composition is administered to target tissues, e.g., to bone, joints, ear tissue, eye tissue, gastrointestinal tract, skin, a wound site or spinal cord. Methods of the invention may be practiced in vivo or ex vivo. In some embodiments, the contacting of a target cell or tissue with a tissue-specific Wnt signal enhancing molecule is performed ex vivo, with subsequent implantation of the cells or tissues, e.g., activated stem or progenitor cells, into the subject. The skilled artisan can determine an appropriate site of and route of administration based on the disease or disorder being treated.

The dose and dosage regimen may depend upon a variety of factors readily determined by a physician, such as the nature of the disease or disorder, the characteristics of the subject, and the subject's history. In particular embodiments, the amount of anti-LRP5/6 antibody or antigen-binding fragment thereof, e.g., a Wnt surrogate, administered or provided to the subject is in the range of about 0.01 mg/kg to about 50 mg/kg, 0.1 mg/kg to about 500 mg/kg, or about 0.1 mg/kg to about 50 mg/kg of the subject's body weight.

The terms "treatment", "treating" and the like are used herein to generally mean obtaining a desired pharmacologic and/or physiologic effect. The effect may be prophylactic in terms of completely or partially preventing a disease or symptom thereof, e.g. reducing the likelihood that the disease or symptom thereof occurs in the subject, and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent (e.g., anti-LRP5/6 antibody or antigen-binding fragment thereof) may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease. In some embodiments, the subject method results in a therapeutic benefit, e.g., preventing the development of a disorder, halting the progression of a disorder, reversing the progression of a disorder, etc. In some embodiments, the subject method comprises the step of detecting that a therapeutic benefit has been achieved. The ordinarily skilled artisan will appreciate that such measures of therapeutic efficacy will be applicable to the particular disease being modified, and will recognize the appropriate detection methods to use to measure therapeutic efficacy.

Promoting Cell, Tissue and Organoid Growth and Related Methods

Other embodiments relate, in part, to the use of the Wnt surrogate molecules disclosed herein to promote or enhance the growth or proliferation of cells, tissues and organoids, for example, by contacting cells or tissue with one or more Wnt surrogate, optionally in combination with a Norrin or Rspondin polypeptide. In certain embodiments, the cells or tissue are contacted ex vivo, in vitro, or in vivo. Such methods may be used to generate cells, tissue or organoids for therapeutic use, e.g., to be transplanted or grafted into a subject. They may also be used to generate cells, tissue or organoids for research use. The Wrt surrogate molecules have widespread applications in non-therapeutic methods, for example in vitro research methods.

The invention provides a method for tissue regeneration of damaged tissue, such as the tissues discussed above, comprising administering a Wnt surrogate molecule to cells. The Wnt surrogate molecule may be administered directly to the cells in vivo, administered to a subject orally, intravenously, or by other methods known in the art, or administered to ex vivo cells. In some embodiments where the Wnt surrogate molecule is administered to ex vivo cells, these cells may be transplanted into a subject before, after or during administration of the Wnt surrogate molecule.

Wnt signaling is a key component of stem cell culture. For example, the stem cell culture media as described in WO2010/090513, WO2012/014076, Sato et al., 2011 (GASTROENTEROLOGY 201 1; 141: 1762-1772) and Sato et al., 2009 (Nature 459, 262-5). The Wnt surrogate molecules disclosed herein are suitable alternatives to Rspondin for use in these stem cell culture media, or may be combined with Rspondin.

Accordingly, in one embodiment, the disclosure provides a method for enhancing the proliferation of stem cells comprising contacting stem cells with one or more Wnt surrogate molecules disclosed herein. In one embodiment, the disclosure provides a cell culture medium comprising one or more Wnt surrogate molecules disclosed herein. In some embodiments, the cell culture medium may be any cell culture medium already known in the art that normally comprises Wnt or Rspondin, but wherein the Wnt or Rspondin is replaced (wholly or partially) or supplemented by Wnt surrogate molecule(s) disclosed herein. For example, the culture medium may be as described in as described in WO2010/090513, WO2012/014076, Sato et al., 2011 (GASTROENTEROLOGY 201 1; 141: 1762-1772) and Sato et al., 2009 (Nature 459, 262-5), which are hereby incorporated by reference in their entirety.

Stem cell culture media often comprise additional growth factors. This method may thus additionally comprise supplying the stem cells with a growth factor. Growth factors commonly used in cell culture medium include epidermal growth factor (EGF, (Peprotech), Transforming Growth Factor-alpha (TGF-alpha, Peprotech), basic Fibroblast Growth Factor (bFGF, Peprotech), brain-derived neurotrophic factor (BDNF, R&D Systems), Hepatocyte Growth Factor (HGF) and Keratinocyte Growth Factor (KGF, Peprotech, also known as FGF7). EGF is a potent mitogenic factor for a variety of cultured ectodermal and mesodermal cells and has a profound effect on the differentiation of specific cells in vivo and in vitro and of some fibroblasts in cell culture. The EGF precursor exists as a membrane-bound molecule which is proteolytically cleaved to generate the 53-amino acid peptide hormone that stimulates cells. EGF or other mitogenic growth factors may thus be supplied to the stem cells. During culturing of stem cells, the mitogenic growth factor may be added to the culture medium every second day, while the culture medium is refreshed preferably every fourth day. In general, a mitogenic factor is selected from the groups consisting of: i) EGF, TGF-alpha, and KGF, ii) EGF, TGF-alpha, and FGF7; iii) EGF, TGF-alpha, and FGF: iv) EGF and KGF; v) EGF and FGF7; vi) EGF and a FGF; vii) TGF-alpha and KGF; viii) TGF-alpha, and FGF7; ix) or from TGF-alpha and a FGF. In certain embodiments, the disclosure includes a stem cell culture media comprising a Wnt surrogate molecule disclosed herein, e.g., optionally in combination with one or more of the growth factors or combinations thereof described herein.

These methods of enhancing proliferation of stem cells can be used to grow new organoids and tissues from stem cells, as for example described in WO2010/090513 WO2012/014076, Sato et al., 201 1 (GASTROENTEROLOGY 2011; 141: 1762-1772) and Sato et al., 2009 (Nature 459, 262-5).

In some embodiments, the Wnt surrogate molecules are used to enhance stem cell regeneration. Illustrative stem cells of interest include but are not limited to: muscle satellite cells; hematopoietic stem cells and progenitor cells derived therefrom (U.S. Pat. No. 5,061,620); neural stem cells (see Morrison et al. (1999) Cell 96: 737-749); embryonic stem cells: mesenchymal stem cells: mesodermal stem cells; liver stem cells; adipose-tissue derived stem cells, etc.

Diagnostic and Related Methods

Other embodiments of the present invention relate, in part, to diagnostic applications for detecting the presence of cells or tissues expressing LRP5 and/or LRP6. Thus, the present disclosure provides methods of detecting LRP5 and/or LRP6 in a sample, such as detection of cells or tissues expressing LRP5 or LRP6. Such methods can be applied in a variety of known detection formats, including, but not limited to immunohistochemistry (IHC), immunocytochemistry (ICC), in situ hybridization (ISH), whole-mount in situ hybridization (WISH), fluorescent DNA in situ hybridization (FISH), flow cytometry, enzyme immuno-assay (EIA), and enzyme linked immuno-assay (ELISA). In particular embodiments, a method comprises contacting a tissue or cell, e.g., obtained from a subject, with an antibody or antigen-binding fragment thereof disclosed herein, and then determining an amount of binding of the antibody or antigen-binding fragment thereof to the tissue or cell, thus determining the presence of or an amount of the LRP5 and/or LRP6 receptor(s) in the tissue or cell.

ISH is a type of hybridization that uses a labeled complementary DNA or RNA strand (i.e., primary binding agent) to localize a specific DNA or RNA sequence in a portion or section of a cell or tissue (in situ), or if the tissue is small enough, the entire tissue (whole mount ISH). One having ordinary skill in the art would appreciate that this is distinct from immunohistochemistry, which localizes proteins in tissue sections using an antibody as a primary binding agent. DNA ISH can be used on genomic DNA to determine the structure of chromosomes. Fluorescent DNA ISH (FISH) can, for example, be used in medical diagnostics to assess chromosomal integrity. RNA ISH (hybridization histochemistry) is used to measure and localize mRNAs and other transcripts within tissue sections or whole mounts.

In various embodiments, the antibodies and antigen-binding fragments thereof described herein are conjugated to a detectable label that may be detected directly or indirectly. In this regard, an antibody "conjugate" refers to an anti-LRP5/6 antibody or antigen-binding fragment thereof that is covalently linked to a detectable label. In the present invention, DNA probes, RNA probes, monoclonal antibodies, antigen-binding fragments thereof, and antibody derivatives thereof, such as a single-chain-variable-fragment antibody or an epitope tagged antibody, may all be covalently linked to a detectable label. In "direct detection", only one detectable antibody is used, i.e., a primary detectable antibody. Thus, direct detection means that the antibody that is conjugated to a detectable label may be detected, per se, without the need for the addition of a second antibody (secondary antibody).

A "detectable label" is a molecule or material that can produce a detectable (such as visually, electronically or otherwise) signal that indicates the presence and/or concentration of the label in a sample. When conjugated to an antibody, the detectable label can be used to locate and/or quantify the target to which the specific antibody is directed. Thereby, the presence and/or concentration of the target in a sample can be detected by detecting the signal produced by the detectable label. A detectable label can be detected directly or indirectly, and several different detectable labels conjugated to different specific-antibodies can be used in combination to detect one or more targets.

Examples of detectable labels, which may be detected directly, include fluorescent dyes and radioactive substances and metal particles. In contrast, indirect detection requires the application of one or more additional antibodies, i.e., secondary antibodies, after application of the primary antibody. Thus, the detection is performed by the detection of the binding of the secondary antibody or binding agent to the primary detectable antibody. Examples of primary detectable binding agents or antibodies requiring addition of a secondary binding agent or antibody include enzymatic detectable binding agents and hapten detectable binding agents or antibodies.

In some embodiments, the detectable label is conjugated to a nucleic acid polymer which comprises the first binding agent (e.g., in an ISH, WISH, or FISH process). In other embodiments, the detectable label is conjugated to an antibody which comprises the first binding agent (e.g., in an IHC process).

Examples of detectable labels which may be conjugated to antibodies used in the methods of the present disclosure include fluorescent labels, enzyme labels, radioisotopes, chemiluminescent labels, electrochemiluminescent labels, bioluminescent labels, polymers, polymer particles, metal particles, haptens, and dyes.

Examples of fluorescent labels include 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, green fluorescent protein (GFP) and analogues thereof, and conjugates of R-phycoerythrin or allophycoerythrin, inorganic fluorescent labels such as particles based on semiconductor material like coated CdSe nanocrystallites.

Examples of polymer particle labels include micro particles or latex particles of polystyrene, PMMA or silica, which can be embedded with fluorescent dyes, or polymer micelles or capsules which contain dyes, enzymes or substrates.

Examples of metal particle labels include gold particles and coated gold particles, which can be converted by silver stains. Examples of haptens include DNP, fluorescein isothiocyanate (FITC), biotin, and digoxigenin. Examples of enzymatic labels include horseradish peroxidase (HRP), alkaline phosphatase (ALP or AP), β-galactosidase (GAL), glucose-6-phosphate dehydrogenase, β-N-acetylglucosamimidase, β-glucuronidase, invertase, Xanthine Oxidase, firefly luciferase and glucose oxidase (GO). Examples of commonly used substrates for horseradishperoxidase include 3,3'-diaminobenzidine (DAB), diaminobenzidine with nickel enhancement, 3-amino-9-ethylcarbazole (AEC), Benzidine dihydrochloride (BDHC), Hanker-Yates reagent (HYR), Indophane blue (IB), tetramethylbenzidine (TMB), 4-chloro-1-naphtol (CN), .alpha.-naphtol pyronin (.alpha.-NP), o-dianisidine (OD), 5-bromo-4-chloro-3-indolylphosphate (BCIP), Nitro blue tetrazolium (NBT), 2-(p-iodophenyl)-3-p-nitropheny-I-5-phenyl tetrazolium chloride (INT), tetranitro blue tetrazolium (TNBT), 5-bromo-4-chloro-3-indoxyl-beta-D-galactosideferro-ferricyanide (BCIG/FF).

Examples of commonly used substrates for Alkaline Phosphatase include Naphthol-AS-B 1-phosphate/fast red TR (NABP/FR), Naphthol-AS-MX-phosphate/fast red TR (NAMP/FR), Naphthol-AS-B1-phosphate/fast red TR (NABP/FR), Naphthol-AS-MX-phosphatefast red TR (NAMP/FR), Naphthol-AS-B1-phosphate/new fuschin (NABP/NF), bromochloroindolyl phosphate/nitroblue tetrazolium (BCIP/NBT), 5-Bromo-4-chloro-3-indolyl-b-d-galactopyranoside (BCIG).

Examples of luminescent labels include luminol, isoluminol, acridinium esters, 1,2-dioxetanes and pyridopyridazines. Examples of electrochemiluminescent labels include ruthenium derivatives. Examples of radioactive labels include radioactive isotopes of iodide, cobalt, selenium, tritium, carbon, sulfur and phosphorous.

Detectable labels may be linked to the antibodies described herein or to any other molecule that specifically binds to a biological marker of interest, e.g., an antibody, a nucleic acid probe, or a polymer. Furthermore, one of ordinary skill in the art would appreciate that detectable labels can also be conjugated to second, and/or third, and/or fourth, and/or fifth binding agents or antibodies, etc. Moreover, the skilled artisan would appreciate that each additional binding agent or antibody used to characterize a biological marker of interest may serve as a signal amplification step. The biological marker may be detected visually using, e.g., light microscopy, fluorescent microscopy, electron microscopy where the detectable substance is for example a, a colloidal gold particle, a luminescent reagent. Visually detectable substances bound to a biological marker may also be detected using a spectrophotometer. Where the detectable substance is a radioactive isotope detection can be visually by autoradiography, or non-visually using a scintillation counter. See, e.g., Larsson, 1988, Immunocytochemistry: Theory and Practice, (CRC Press, Boca Raton, Fla.); Methods in Molecular Biology, vol. 80 1998, John D. Pound (ed.) (Humana Press, Totowa, N.J.).

The invention further provides kits for detecting one or more LRP receptor or cells or tissues expressing one or more LRP receptors in a sample, wherein the kits contain at least one antibody, polypeptide, polynucleotide, vector or host cell as described herein. In certain embodiments, a kit may comprise buffers, enzymes, labels, substrates, beads or other surfaces to which the antibodies of the invention are attached, and the like, and instructions for use.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

EXAMPLES

Example 1

Characterization of Anti-Lrp5/6 Antibodies

Antibody Fab, scFv and VHH or sdAb fragments disclosed herein were sequenced and sub-cloned into mammalian expression vectors for expression, purification, and characterization of binding affinities to various LRP receptors.

Soluble recombinant proteins were prepared by transfection of respective expression vectors into Expi293F cells (Thermo Fisher Scientific, Waltham, Mass.) according to the manufacturer's instructions. Briefly, four days after the transfection, cell culture medium was collected after spin down the cell pellet. The media were incubated with either Protein A resin (REPLIGEN, Waltham, Mass.) for collecting proteins containing human IgG-Fc portion, or Nickel affinity resin (Roche, Basel, Switzerland) for collecting proteins conjugated with His-tag. Proteins were eluted with 10 mM glycine, pH 3.5 from Protein A resin, or with 150 mM imidazole, pH 7.4 from Nickel affinity resin, respectively.

Subsequently, the protein elutes were fractionated and further purified by size-exclusion chromatography (SEC). SEC was performed by a fast protein liquid chromatography using a Superdex 200 Increase 10/300 GL (GE Healthcare, Pittsburgh, Pa.) in HBS buffer (10 mM HEPES, 150 mM NaCl, pH7.4). Each protein was injected onto the column at a volume of 475 µl or 500 µl. The absorbance at 280 nm was monitored, and the 500 µl fractions of all elutes were collected. Each collected faction near main peak was further analyzed by SDS-Polyacrylamide Gel Electrophoresis (SDS-PAGE) to confirm the content. SDS-PAGE was performed using Tris-HCl 4-15% gel (Bio-Rad, Hercules, Calif.) under both non-reducing and reducing conditions. The samples were prepared in Laemmli sample buffer and heated at 100° C. for 5 min.

Protein concentrations were determined using a NanoDrop Spectrophotometer (Thermo Scientific) by the direct UV A280 method. The relationship of absorbance to protein concentration is linear based on Beer-Lamber equation, $A=\varepsilon l\ c$; A is the absorbance value, $\varepsilon$ is the wavelength-dependent extinction coefficient, l is the path length in centimeters, and c is the protein concentration. The experimental extinction coefficients of all produced proteins were estimated by their amino acid sequences.

Binding kinetics of antibody fragments to LRP5 extracellular domain (LRP5 ECD) and/or LRP6 extracellular domain (LRP6 ECD) protein targets was determined by bio-layer interferometry (BLI) using Octet Red 96 (PALL ForteBio, Fremont, Calif.) instruments at 30° C., 1000 rpm with streptavidin (SA) biosensors. C-terminal biotinylated LRP ECD recombinant protein was diluted to 20 nM in the running buffer (PBS, 0.05% Tween-20, 0.5% BSA, pH 7.2) and captured to the SA biosensor until coupling length reached 0.2 nm. Following capture of the LRP5 or LRP6, the SA biosensor with captured biotinylated-LRP5 or biotinylated LRP6 was dipped into wells containing the relevant antibody fragment at 7 different concentrations (0, 1.37, 4.12, 12.4, 37, 111.1, 333.3, 1000 nM) in running buffer, plus a well with only running buffer as a reference channel. $K_D$ was determined by global fitting, 1:1 binding model according to manufacturer recommended settings.

Binding measurements were also performed by surface plasmon resonance on a BIAcore T100 (GE Healthcare, Pittsburgh, Pa.) and all proteins purified on SEC prior to experiments. Biotinylated Lrp6 E3E4 was coupled at a low density to streptavidin on a SA sensor chip (GE Healthcare, Pittsburgh, Pa.). An unrelated biotinylated protein was captured at equivalent coupling density to the control flow cells. Increasing concentrations of scFv-Nab fusion molecules (e.g., 18R5 scFv-LRP6 binding Nabs) were flown over the chip in 1×HBS-P (GE Healthcare, Pittsburgh, Pa.) containing 0.5% BSA at 40 µl/ml. The chip surface was regenerated after each injection with 2 M MgCl2 in HBS-P for 60 seconds. Curves were reference-subtracted and all data were analyzed using the Biacore T100 evaluation software version 2.0 with a 1:1 Langmuir binding model to determine the KD values.

Table 1A provides the heavy chain CDRs (CDRH1, CDRH2, and CDRH3) and light chain CDRs (CDRL1, CDRL2, and CDRL3) for the indicated antibody clones, and indicates the initial LRP5 or LRP6 that the antibody fragment was shown to bind. The Abgenesis software from Distributed Bio was used to map the specificity determining regions (SDRs) shown below, which include the Kabat definition of CDRs (Padlan et al. *FASEB J.* 9, 133-139 (1995).

Where light chain CDRs are not provided, the antibody fragment did not comprise a light chain.

TABLE 1A

Clone IDs and CDR sequences

| Clone ID | Confirmed Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 001S-C08 | LRP6e1e2 | YTISNYYIH | 171 | GMINPSGGST TYA | 249 | CAIVRGKKWYFD LW | 330 | RASQYISNYL N | 515 | AASSLQ S | 529 | CQQSYITPLT F | 578 |
| 001S-C10 | LRP6e1e2 | RTFGTYPN G | 121 | AAISWGGRT AYA | 188 | CYARTVIGGFGAF RAHW | 483 | | | | | | |
| 001S-D10 | LRP6e1e2 | RTFSRYAM A | 131 | AAIRWSGGG TYYA | 177 | CAASMEAMNSL RVNKERYYQSW | 324 | | | | | | |
| 001S-E10 | LRP6e1e2 | LTFSNAAM A | 102 | AAISRSGANT AYS | 184 | CTLVNEIKTWW | 469 | | | | | | |
| 001S-F10 | LRP6e1e2 | RTFSSYAM A | 134 | AAIKWSGTNT YYA | 173 | CAASMEAMNSL RVNKERYYQSW | 324 | | | | | | |
| 001S-G10 | LRP6e1e2 | RTFSRYVM G | 133 | AAITWRGGST YYA | 194 | CATGPNSIY | 433 | | | | | | |
| 001S-A11 | LRP6e1e2 | RTFGNYD MG | 119 | AGIRWSGSTL YA | 197 | CYARTVIGGFGAF RAHW | 483 | | | | | | |
| 001S-B11 | LRP6e1e2 | RRFTTYGM G | 112 | AAVTWRSGS TYYA | 196 | CAAGSTVVAEFN YW | 320 | | | | | | |
| 001S-C11 | LRP6e1e2 | SISSFNTM G | 148 | AVITTGGDTS YS | 228 | CNKVNAITKL | 459 | | | | | | |
| 001S-E11 | LRP6e1e2 | RTLSRYSM G | 140 | AAISRSGDRIY YS | 185 | CTLVNEIKTWW | 469 | | | | | | |
| 001S-F11 | LRP6e1e2 | RTFSSYAM S | 135 | AVIGRSGGIKY YA | 224 | CATRRPPNSYNTE QSYDSW | 434 | | | | | | |
| 001S-G11 | LRP6e1e2 | SIFRLGTMY | 144 | ASIGKSGSTN YA | 207 | CKQHPNGYR | 446 | | | | | | |
| 001S-H11 | LRP6e1e2 | RTLSSFAM G | 141 | ATISRSGGNT YYA | 220 | CNLREWNNSGA GYW | 460 | | | | | | |
| 001S-A12 | LRP6e1e2 | IAFRYYDM G | 96 | AAITWNGRSS DYA | 192 | CAAVFTGRFYGR PPREKYDYW | 326 | | | | | | |
| 001S-B12 | LRP6e1e2 | RLLSYYALA | 111 | AAISRNGDKS HYS | 182 | CTLVNEIKTWW | 469 | | | | | | |

TABLE 1A-continued

Clone IDs and CDR sequences

| Clone ID | Confirmed Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 001S-C12 | LRP6e1e2 | RTFSNYAVG | 130 | AAISRFGGSTYYV | 181 | CAADRIENYLGRYYDPSEYEYW | 317 | | | | | | |
| 001S-D12 | LRP6e1e2 | RTFSRYAMG | 132 | GAISRSGNNTYYA | 231 | CTLVNEIKTWW | 469 | | | | | | |
| 001S-F12 | LRP6e1e2 | RTFRSYTMG | 126 | AAISGSGGSTTYA | 178 | CNADIKTTTYSPLRNYW | 449 | | | | | | |
| 008S-B01 | LRP5 | TIFSINTMG | 153 | ATMTSGGNTNYA | 222 | CYRRQWASSWGARNYEYW | 484 | | | | | | |
| 008S-C01 | LRP5 | NINSIETLG | 106 | ANMRGGGYMKYA | 204 | CHGRDYGSNAPQYW | 442 | | | | | | |
| 008S-D01 | LRP5 | NINSIETLG | 106 | ANMRGGGYMKYA | 204 | CYVKLRDDDIVYR | 485 | | | | | | |
| 008S-E01 | LRP5 | NINSIETLG | 106 | ANMRGGGYMKYA | 204 | CNAVTYNGYTIR | 457 | | | | | | |
| 008S-G01 | LRP5 | NINSIETLG | 106 | ANMRGGGYMKYA | 204 | CYARTQRMGVVNSYW | 482 | | | | | | |
| 008S-A02 | LRP5 | NINSIETLG | 106 | ANMRGGGYMKYA | 204 | CNAVTFGGNTIR | 455 | | | | | | |
| 008S-C02 | LRP5 | NINSIETLG | 106 | ANMRGGGYMKYA | 204 | CNAVTYDGY | 456 | | | | | | |
| 008S-D02 | LRP5 | NINSIETLG | 106 | ANMRGGGYMKYA | 204 | CAAQFRNDYGLRYQSTNNYW | 322 | | | | | | |
| 008S-E02 | LRP5 | NINSIETLG | 106 | ANMRGGGYMKYA | 204 | CNANYRGNRYW | 453 | | | | | | |
| 009S-C01 | LRP6e3e4 | GSFSGYYT | 82 | GEINHSGATNYN | 232 | CVRYAWPEFDHW | 478 | RASQRVSNYLN | 505 | AASSLQG | 528 | CQQSYSVPYIF | 596 |
| 009S-B02 | LRP6e3e4 | GSLSGYYS | 83 | GEINHSGSTNYN | 233 | CVRYAWPEFDHW | 478 | RASQSISNYLN | 506 | AASSLQS | 529 | CQQSYSLPLTF | 588 |
| 009S-C02 | LRP6e3e4 | GSFSDYYS | 81 | GEINHSGSTNYN | 233 | CVRYAWPEFDHW | 478 | RASQSISNYLN | 506 | AASSLQS | 529 | CQQSYSMPLIF | 589 |
| 009S-D02 | LRP6e3e4 | GTFSSYAIS | 90 | GGIPIFGTANYA | 236 | CVYGRDFDYW | 479 | SGSSSNVGNNYVS | 523 | DNDKRPS | 541 | CESWDSSLSSEVF | 557 |

TABLE 1A-continued

Clone IDs and CDR sequences

| Clone ID | Confirmed Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 010S-A02 | LRP6e1e2 | HTFSSYAMG | 95 | AAISQSGYVRYYA | 179 | CKIYGLNGQPLGSW | 444 | | | | | | |
| 010S-B02 | LRP6e1e2 | RTFNSGTMG | 123 | AAITWRGGITYYA | 193 | CNADGYSWDGRSGRRLELW | 448 | | | | | | |
| 010S-D02 | LRP6e1e2 | RTFSSYAVG | 136 | AAISYSGGSTKYA | 190 | CAASVVISRRDSDYGYW | 325 | | | | | | |
| 010S-E02 | LRP6e1e2 | LSSGRPFSSYVMG | 100 | AAISWSGGSTKYA | 189 | CKLQVRPIGYSSAYSRNYW | 445 | | | | | | |
| 010S-F02 | LRP6e1e2 | RSFNSYVIG | 114 | AAIRWSGDNTYYA | 176 | CAASMEAMNSLRVNKERYYQSW | 324 | | | | | | |
| 009S-F02 | LRP6e1e2 | RRFTTYGMG | 112 | AAVTWRSGSTYYA | 196 | CAAGSTVAEFNVW | 320 | | | | | | |
| 009S-F02 | LRP6e1e2 | RTFSYYAMG | 138 | AAISRSGGIYYA | 186 | CNTVRPLWAW | 462 | | | | | | |
| 009S-G02 | LRP6e1e2 | SIFSIYAMG | 147 | AVITSGGKTVYA | 227 | CYADSRSSWYDEYLEHW | 480 | | | | | | |
| 009S-H02 | LRP6e1e2 | SIVRSLPMA | 149 | ATINDAQRYYA | 215 | CNTSPYMHDVW | 461 | | | | | | |
| 009S-A03 | LRP6e1e2 | RTFSVYGVG | 137 | AAVSASGGYTWYA | 195 | CKAAPRWGGATAYW | 443 | | | | | | |
| 010S-G02 | LRP6e1e2 | SIVRSLPMA | 149 | ATINDAQRYYA | 215 | CNTSPYMHDVW | 461 | | | | | | |
| 010S-A03 | LRP6e1e2 | RTFRRYAMG | 125 | ATISASGGNTAYA | 219 | CNAPAWLYDDDVW | 454 | | | | | | |
| 009S-B03 | LRP6e1e2 | RTFSNYAVG | 130 | AAISRFGGSTYYV | 181 | CAADRIENYLGRYYDPSEYEYW | 317 | | | | | | |
| 010S-B03 | LRP6e1e2 | RTFSNYAVG | 130 | AAISRFGGSTYYA | 180 | CHAKQLRNGQMYTYW | 440 | | | | | | |
| 009S-D03 | LRP6e1e2 | ISSVYGMG | 97 | AAIQWSADNTFYA | 175 | CAARTSGGLFHYRRSDHWDTW | 323 | | | | | | |
| 009S-C03 | LRP6e1e2 | LPFSRYAMA | 98 | AGMSGEGRNTKYR | 201 | CSSRGYW | 466 | | | | | | |

TABLE 1A-continued

Clone IDs and CDR sequences

| Clone ID | Confirmed Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 009S-D03 | LRP6e1e2 | SIFSDGAMG | 145 | AVISGGRTGYA | 225 | CNTYPPPIYKKGYPEW | 463 | | | | | | |
| 009S-E03 | LRP6e1e2 | RRFTTYGMG | 112 | AAVTWRSGSTYYA | 196 | CAAGSTVVAEFNYW | 320 | | | | | | |
| 009S-F03 | LRP6e1e2 | RTFSSYAMS | 135 | AVIGRSGGIKYYA | 224 | CATRRPFNSYNTEQSYDSW | 434 | | | | | | |
| 010S-E03 | LRP6e1e2 | RSVSIYPMG | 117 | AAINWSGDSTKYA | 174 | CNAVVVGLSRRIDNIW | 458 | | | | | | |
| 010S-F03 | LRP6e1e2 | RTFSRYVMG | 133 | AAITWRGGSTYYA | 194 | CATGPNSIY | 433 | | | | | | |
| 009S-G03 | LRP6e1e2 | RSVSSYNMG | 118 | AAISRRGGIIEYG | 183 | CHAVENILGRFVDYW | 441 | | | | | | |
| 009S-H03 | LRP6e1e2 | SIFSINTMG | 146 | AVITSGGKTVYA | 227 | CYADSRSSWYDEYLEHW | 480 | | | | | | |
| 009S-A04 | LRP6e1e2 | RTLSAYDMG | 139 | GGIRWSGGTTLYP | 240 | CYARTVIGGFGAFRAHW | 483 | | | | | | |
| 009S-B04 | LRP6e3e4 | SIFMINTMA | 143 | ATIRPVVSETTYA | 216 | CNAKRPWGTRDEYW | 452 | | | | | | |
| 010S-G03 | LRP6e3e4 | RSFNSYTTT | 113 | AAIRGSSGSTFYA | 175 | CNAASTVTAWPYYGPDYW | 447 | | | | | | |
| 009S-C04 | LRP6e3e4 | FRFSISTMG | 40 | AYITGGGRTMDG | 230 | CNAFVRSDFDRYYDYW | 451 | | | | | | |
| 009S-D04 | LRP6e3e4 | TIVSIYRIN | 154 | AGITSSGRTIYA | 200 | CNAASTVTAWPYYGPDYW | 447 | | | | | | |
| 010S-H03 | LRP6e3e4 | RIFSIYDMG | 110 | SGIRWSGGTSYA | 283 | CSSRGYW | 466 | | | | | | |
| 009S-E04 | LRP6e3e4 | RIFAIYDIA | 107 | AMIRPVVTEIDYA | 203 | CNAKRPWGSRDEYW | 452 | | | | | | |
| 010S-A04 | LRP6e3e4 | SLFSFNAVG | 151 | ASISSGGRTNYA | 210 | CSKGGVYGGTVPDSW | 465 | | | | | | |
| 009S-F04 | LRP6e3e4 | RSLSSFAMG | 116 | ARISRGDGYTDEA | 206 | CAAVQAVIGGTLTTAYDYW | 327 | | | | | | |

TABLE 1A-continued

Clone IDs and CDR sequences

| Clone ID | Confirmed Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 010S-B04 | LRP6e3e4 | RVLSYYAMA | 142 | AGITRGGATTYYS | 199 | CAAGPNWSTRNREYDYW | 319 | | | | | | |
| 009S-G04 | LRP6e3e4 | GTFSRYHMG | 88 | SAITWSGGRTYYA | 282 | CALTWAPTPTNRRSDYAYW | 349 | | | | | | |
| 009S-H04 | LRP6e3e4 | RIFAIYDMA | 108 | ATIRPVVSETTYA | 216 | CNAKRPWGTRDEYW | 452 | | | | | | |
| 010S-C04 | LRP6e3e4 | SLFSFNAMG | 150 | ASISSGSRTNYA | 211 | CSKGGVYGGTYVPDSW | 465 | | | | | | |
| 010S-D04 | LRP6e3e4 | RIFAIYDIA | 107 | ATIRPVVTQIDYA | 218 | CNAKRPWGSRDEYW | 452 | | | | | | |
| 010S-E04 | LRP6e3e4 | RTFGSDVMG | 120 | ALTGWGDGSTTYYE | 202 | CAAARSGTYDIGQYLRESAYVFW | 313 | | | | | | |
| 010S-F04 | LRP6e3e4 | RTFSRYAMG | 132 | AAITRSGSNTYYA | 191 | CAADPRGVTLPRATAYEYW | 316 | | | | | | |
| 009S-A05 | LRP6e3e4 | RTFSDYSMG | 128 | AGISWIADNRYYA | 198 | CTAGRSRYLYGSSLNGPYDYW | 467 | | | | | | |
| 010S-G04 | LRP6e3e4 | VIFALYDIA | 155 | ATIRPVVTETDYA | 217 | CNAKRPWGSRDEYW | 452 | | | | | | |
| 010S-H04 | LRP6e3e4 | RSFSDFFMG | 115 | ATISWSGSSANYE | 221 | CAAAYSYSQYGSSYSYW | 314 | | | | | | |
| 010S-A05 | LRP6e3e4 | LSFSSYAMG | 99 | AAISRSGVSTYYA | 187 | CAAKFGVLATTESRHDYW | 321 | | | | | | |
| 010S-C05 | LRP6e3e4 | RTFNIDDMG | 122 | ASIRWSGQSPYYA | 208 | CNAETYSGNTIW | 450 | | | | | | |
| 010S-D05 | LRP6e3e4 | RTFSDYSMA | 127 | AGISWIADNRYYA | 198 | CAGDRSRYLYGDSLRGPYGYW | 329 | | | | | | |
| 010S-E05 | LRP6e3e4 | SVFTTFAKG | 152 | ASITASSDRTFYA | 213 | CAAYSTFNTDVASMKPDYW | 328 | | | | | | |
| 010S-F05 | LRP6e3e4 | RIFSIYDIA | 109 | ATIRPVVTETDYA | 217 | CNAKRPWGSRDEYW | 452 | | | | | | |
| 013S-G04 | LRP6e3e4 | RIFAIYDIA | 107 | ATIRPVVSETTYA | 216 | CNAKRPWGTRDEYW | 452 | | | | | | |

TABLE 1A-continued

Clone IDs and CDR sequences

| Clone ID | Confirmed Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 013S-H04 | LRP6e3e4 | RTFSMYDMG | 129 | ASIRWSSGNTWYA | 209 | CYANIYYTRRAPEEYW | 481 | | | | | | |
| 013S-A05 | LRP6e3e4 | RTFNTYAMG | 124 | ASVSWRYDRTYYT | 214 | CAADTNWRAGPRVGIDEYAYW | 318 | | | | | | |
| 013S-B05 | LRP6e3e4 | FAFSTTAMS | 36 | STINPGGLSKSYA | 298 | CTKGGIQ | 468 | | | | | | |
| 013S-C05 | LRP6e3e4 | NIFPIDDMS | 105 | ATVTSGGRINYA | 223 | CNVDRTLYGKYKEVW | 464 | | | | | | |
| 013S-D05 | LRP6e3e4 | RIFSIYDMG | 110 | SGIRWSGGTSYA | 283 | CGSRGYW | 439 | | | | | | |
| 013S-E05 | LRP6e3e4 | YTFTYRYLH | 170 | GGIPIPIFGTADYA | 235 | CARDWELYGMDVW | 376 | RASQSISSYLN | 510 | AASSLQS | 529 | CQQSYSTPLIF | 592 |
| 013S-F05 | LRP6e3e4 | GTFSSYAIS | 90 | GIINPSGGSTSYA | 248 | CARAGYYDSSGYYAFDIW | 358 | RASQSISSYLN | 510 | AASSLQS | 529 | CQQSYSTPLIF | 592 |
| 013S-G05 | LRP6e3e4 | YTFTYRYLH | 170 | GGVIPIFGTADYA | 242 | CASDIVVDDAFDTW | 422 | RASQDISNYLN | 495 | AASTLQS | 532 | CQQGNSFPYIF | 570 |
| 010S-G06 | LRP6e3e4 | FSFETYGMS | 42 | SGISGSGGRTHYA | 285 | CARDLDYW | 369 | QASQDISNYLN | 495 | AASSLQS | 529 | CQQSYRIHWIF | 581 |
| 009S-B05 | LRP6e3e4 | FTFDAYAMH | 47 | STLSGDANNAYYA | 304 | CARGGSGWSNYYGMDVW | 395 | RASQSISSYLN | 510 | AASSLQS | 529 | CQQSYSTPLIF | 592 |
| 009S-C05 | LRP6e3e4 | YTFTYRYLH | 170 | GRIIPVLKITNYA | 255 | CAVVDDAFDIW | 438 | | | | | | |
| 009S-D05 | LRP6e3e4 | FTLRNHWLS | 78 | SAISGSGGSTYYA | 280 | CATRTGSYSGFNFWAFDIW | 435 | RASQSISSYLN | 510 | AASSLQS | 529 | CQQSYSTPLIF | 592 |
| 009S-E05 | LRP6e3e4 | YTFTNNFMH | 165 | GHVDPDGDETIYA | 243 | CARDWGIAAAGDYYYYGMDVW | 377 | RASQGINSYA | 497 | DAKGLHP | 533 | CQQSYSAPLSF | 584 |
| 009S-F05 | LRP6e3e4 | FTFDDYGMS | 48 | SAIGTGGGTYYA | 277 | CARLGSYGSPYYYYGMDVW | 415 | RASQSISSYLN | 510 | AASSLQS | 529 | CQQSYSTPLIF | 592 |
| 009S-G05 | LRP6e3e4 | FTFSDYYMS | 55 | SGVSWNGSRTHYA | 292 | CAKDSGLV | 337 | QASQDISNYLN | 495 | AASTLQR | 531 | CQQSYSAPLIF | 585 |
| 009S-C06 | LRP6e3e4 | YTFASYDIH | 160 | GWMNPNSGNTGYA | 272 | CARATGSGWYTDLGYW | 359 | RASRNINRYLN | 516 | AASSLLS | 527 | CQQSYNVPFIF | 580 |

TABLE 1A-continued

Clone IDs and CDR sequences

| Clone ID | Confirmed Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 009S-D06 | LRP6e3e4 | FTFSSHSTH | 60 | STISDTNSGTYYA | 299 | CAKAQATGWSGYYTFDYW | 331 | RASQSISSYLN | 510 | AASSLQS | 529 | CQQSYSTPLIF | 592 |
| 009S-E06 | LRP6e3e4 | FTFTDYGLH | 74 | AVISYGGSNKYYA | 226 | CASGYSYGLYYYGMDVW | 425 | RASQSISSYLN | 510 | AASSLQS | 529 | CQQSYSTPLIF | 592 |
| 009S-F06 | LRP6e3e4 | YTFTYRYLH | 170 | GGIPIFGTANYA | 236 | CATEAALDAFDIW | 432 | RASQSISSYLN | 510 | AASSLQS | 529 | CQQSYSTPLIF | 592 |
| 009S-G06 | LRP6e3e4 | YIFTDYYMH | 158 | GWINPNSGGTNYA | 270 | CARDFLGSTGDYW | 365 | RASQNIGLYLN | 504 | DASLQR | 540 | CQQSYSTPYIF | 594 |
| 009S-H06 | LRP6e3e4 | FTFSSSAMH | 61 | SAIGTGGSTYYA | 277 | CAKGGDYFYYYYGMDVW | 340 | RASQSISSYLN | 510 | AASSLQS | 529 | CQQSYSTPLIF | 592 |
| 009S-A07 | LRP6e3e4 | YTFTYRYLH | 170 | GGIPIFGTANYA | 236 | CATAYGSSSLNIDVW | 429 | RASQSISSYLN | 510 | AASSLQS | 529 | CQQSYSTPLIF | 592 |
| 009S-B07 | LRP6e3e4 | YTFTGYYMH | 164 | GWINPNSGGTNYA | 270 | CVKDGGSFPLAYAFDIW | 476 | RASQSISSYLN | 510 | AASSLQS | 529 | CQQSYSTPLIF | 592 |
| 009S-D07 | LRP6e3e4 | FPFRYYGMS | 38 | ARIGWNGGSIYYA | 205 | CARDYSDRSGIDYW | 378 | RSSQSLLHSNGYNYLD | 519 | LGSNRAS | 550 | CMQATQFPLIF | 564 |
| 009S-F07 | LRP6e3e4 | GTFSSYAIS | 90 | GIINPSGGSTSYA | 248 | CARAAGNFWSGYYTFDYW | 353 | RASQSISSYLN | 510 | AASSLQS | 529 | CQQSYSTPLIF | 592 |
| 009S-G07 | LRP6e3e4 | YTFTYRYLH | 170 | GGIPIFGTANYA | 236 | CARGSYGMDVW | 407 | RASQGISNYLA | 499 | DASNLET | 534 | CLQDFSFPWIF | 558 |
| 009S-H07 | LRP6e3e4 | YTFTGYYMH | 164 | GWMNPNSGNTGYA | 272 | CASSVVPAGPAGVYAFDIW | 426 | RASQSISSYLN | 510 | AASSLQS | 529 | CQQSYSTPLIF | 592 |
| 009S-A08 | LRP6e3e4 | GTFSSHAIN | 89 | GWISANNGNTDYA | 271 | CARDQDYGDYGWYYYGMDVW | 372 | RASQGISNYLA | 499 | GSSTLQS | 546 | CQQTYSIPPTF | 599 |
| 011S-C01 | LRP6e3e4 | LTFTSHGMS | 103 | SYVSDSGSSVYYA | 311 | CARHPGSFGGYSYAWYYYGMDVW | 413 | RASQSISSYLN | 510 | AASSLQS | 529 | CQQSYSTPLIF | 592 |
| 009S-C08 | LRP6e3e4 | FSENTFGIH | 43 | AVISYDGSNKYYA | 226 | CAKSIAAAGTGYYGMDVW | 346 | RASQSISSYLN | 510 | AASSLQS | 529 | CQQSYSTPLIF | 592 |
| 009S-D08 | LRP6e3e4 | YTFTSYDIN | 168 | GGIPIFGTANYA | 236 | CARGPYFFDYW | 401 | RASQGISNNLN | 498 | DASSLES | 539 | CLQHNSYPFIF | 561 |
| 011S-F01 | LRP6e3e4 | FSFSDYYMS | 45 | SGIESSGGRTYYA | 284 | CASAADFDYW | 420 | RASQDISNYLN | 495 | AASSLQS | 529 | CLQDYSYPRIF | 559 |

TABLE 1A-continued

Clone IDs and CDR sequences

| Clone ID | Confirmed Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 009S-E08 | LRP6e3e4 | YGFTGYYIH | 157 | GWMNPNSGNTGYA | 272 | CARGYGDYDLW | 410 | QASQDISNYLN | 495 | DASSLES | 539 | CQQSYRYPTF | 583 |
| 009S-F08 | LRP6e3e4 | DTFANYGFS | 34 | GXVNAGNGNTTYA | 273 | CAKGWLDFDYW | 345 | QASQDISNYLN | 495 | DASSLES | 539 | CQQSYSTSITF | 595 |
| 009S-G08 | LRP6e3e4 | FTFSDFAMT | 53 | SYISGDSGYTNYA | 306 | CARLGSYPGPYYYYMDVW | 416 | RASQSISSYLN | 510 | AASSLQS | 529 | CQQSYSTPLIF | 592 |
| 009S-H08 | LRP6e3e4 | YTFTDYFMN | 162 | GIINPSGDSTRFA | 245 | CARDDGLGGMDVW | 362 | RASQSISSYLA | 494 | AASSLQS | 529 | CQQSYSTPLIF | 592 |
| 009S-A09 | LRP6e3e4 | YTFTYRYLH | 170 | GRIPILGSTNYA | 254 | CTTDLMDYW | 475 | QASQGITNYLN | 495 | AASSLQS | 529 | CLQDYTDPFIF | 560 |
| 011S-F02 | LRP6e3e4 | FTFSTYGMH | 71 | SSISVSSGTTHYA | 297 | CARGGSGSYYYAFDIW | 394 | RASQSISSYLN | 510 | AASSLQS | 529 | CQQSYSTPLIF | 592 |
| 011S-G02 | LRP6e3e4 | YTFTSYAMN | 167 | GGIPIFGTANYA | 236 | CARDASGGSTGWYYFDSW | 361 | RASQGISSYLA | 503 | AASSLQS | 529 | CQQAYSFPWTF | 568 |
| 011S-A03 | LRP6e3e4 | FTFSSYWMH | 67 | STISGSGGRTYYA | 300 | CATSPYGVFTLDYW | 436 | RASQSISSYLN | 510 | AASSLQS | 529 | CQQSYSTPLIF | 592 |
| 011S-C03 | LRP6e3e4 | YTFSYRYLH | 161 | GGIPIPFGTANYA | 236 | CASTVTTDAFDIW | 427 | QASQDISNYLN | 495 | DASSLES | 539 | CQQSYSFPPFTF | 586 |
| 011S-D03 | LRP6e3e4 | FSFPDDYGMS | 41 | SVISSGGTIYYA | 305 | CARHLSSGYLSYYGMDVW | 412 | RASQSISSYLA | 509 | AASTLQS | 532 | CQQSYSTPLIF | 592 |
| 011S-F03 | LRP6e3e4 | FTFSSYAMS | 64 | SAISGSGGSTYA | 280 | CAKGGRDGYKGYFDYW | 342 | KSSQSVLYTTTNRNHIA | 492 | WASSRKS | 554 | CQQYYSTPYIF | 607 |
| 011S-C04 | LRP6e1e2 | GTFNSNAIS | 85 | GWMNPNSGNTGYA | 272 | CARDYYGSGSYNYGMDVW | 379 | GASQSVPRNSLA | 486 | GASQRAT | 543 | CQQHNWPPEYTF | 602 |
| 011S-D04 | LRP6e1e2 | YTFTSYDIN | 168 | GIINPSGGSTSYA | 248 | CAREAYYYYYGMDVW | 381 | RASQSISSYLN | 510 | AASSLQS | 529 | CQQSYSTPLIF | 592 |
| 011S-H04 | LRP6e1e2 | YIFTDYYMH | 158 | GRIPILGRANYA | 252 | CARGGYSTLDYW | 396 | QASQDISNYLN | 495 | AASTLQS | 532 | CQQSFSTPRIF | 574 |
| 008S-F02 | LRP5 | YTFTNYCMH | 166 | GIINPSDGSTSHA | 244 | CAKDMVHLIVALAIDYW | 336 | RSSQLLHSDGYTYLY | 518 | TLSYRAS | 553 | CMQALEALFIF | 562 |
| 010S-C06 | LRP6e1e2 | FTFNSYSMD | 50 | SSISPRGGSTYYA | 295 | CAPYYYDKSAKPLRSYFDHW | 352 | RASQSISSYLN | 510 | AASSLQS | 529 | CQQSYSTPLIF | 592 |

TABLE 1A-continued

Clone IDs and CDR sequences

| Clone ID | Confirmed Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 010S-E06 | LRP6e3e4 | LTVSNYMS | 104 | SGISWNSGSIGYA | 289 | CARGSDCSGGSCYYSFDYW | 404 | RASQSISSYLN | 510 | AASSLQS | 529 | CQQSYSTPLIF | 592 |
| 010S-F06 | LRP6e3e4 | FTFSSSWMH | 62 | SAIGTGGGTYYA | 277 | CAREVAVKDYYYYYMDVW | 386 | RASQSISSYLN | 510 | AASSLQS | 529 | CQQSYSTPLIF | 592 |
| 010S-H06 | LRP6e3e4 | YTFTSYDIN | 168 | GRIIPILGRTNYA | 253 | CARERGATGRAFDIW | 383 | RASQSISSYLN | 510 | AASSLQS | 529 | CQQSYSTPLIF | 592 |
| 010S-A07 | LRP6e3e4 | FTFSSYAMH | 63 | ASISSTSGSKYYA | 212 | CAKTYIDFWSGYYTFDYW | 347 | RASQSISSYLN | 510 | AASSLQS | 529 | CQQSYSTPLIF | 592 |
| 010S-B07 | LRP6e3e4 | FTFSDYYMS | 55 | SMISYNGGRAEYA | 293 | CARGNPYYFDYW | 399 | RASQSISSYLN | 510 | AASSLQS | 529 | CQQSYSTPLIF | 592 |
| 010S-C07 | LRP6e3e4 | FTFSKTDMH | 56 | STITTDSRGTYYA | 303 | CAKGGDYYYYYGMDVW | 341 | RASQSISSYLN | 510 | AASSLQS | 529 | CQQSYSTPLIF | 592 |
| 010S-D07 | LRP6e3e4 | YTFTYRYLH | 170 | GGIIPIFGTANYA | 236 | CANGLEDAYAFDIW | 350 | RASQSISSYLN | 510 | AASSLQS | 529 | CQQSYSTPLIF | 592 |
| 009S-D05 | LRP6e3e4 | FTLRNHWLS | 78 | SAISGSGGSTYYA | 280 | CATRTGYSYGFNFWAFDIW | 435 | RASQSISSYLN | 510 | AASSLQS | 529 | CQQSYSTPLIF | 592 |
| 009S-E05 | LRP6e3e4 | YTFTNNFMH | 165 | GHVDPGDGETIYA | 243 | CARDWGIAAAGDYYYYGMDVW | 377 | RASQGINSSYLA | 497 | DAKGLHP | 533 | CQQSYSAPLSF | 584 |
| 010S-E07 | LRP6e3e4 | YTFTYRYLH | 170 | GGIIPIFGTANYA | 236 | CAKDDFSLYGMDVW | 332 | RASQSISSYLN | 510 | AASSLQS | 529 | CQQSYSTPLIF | 592 |
| 009S-F05 | LRP6e3e4 | FTFPDDYGMS | 48 | SAIGTGGGTYYA | 277 | CARLGSYGSPYYYYGMDVW | 415 | RASQSISSYLN | 510 | AASSLQS | 529 | CQQSYSTPLIF | 592 |
| 010S-F07 | LRP6e3e4 | YTFTYRYLH | 170 | GGIIPIFGTANYA | 236 | CARLDYGETEGNGDW | 414 | RASQSISSYLN | 510 | AASSLQS | 529 | CQQSYSTPLIF | 592 |
| 010S-G07 | LRP6e3e4 | FTFSSYAMH | 63 | STISGSGGSTYYA | 301 | CARAGYGRYYYGMDVW | 356 | RVSQGISYLN | 520 | DTSNRAT | 542 | CQQYNNWPPITF | 603 |
| 009S-G05 | LRP6e3e4 | FTFSDYYMS | 55 | SGVSWNGSRTHYA | 292 | CAKDSGLV | 337 | QASQDISNYLN | 495 | AASTLQR | 531 | CQQTYIPFTF | 600 |
| 010S-H07 | LRP6e3e4 | YTFTYRYLH | 170 | GGIIPIFGTANYA | 236 | CARDDSMGAFDIW | 363 | QASQDISNYLN | 495 | GTSNLQS | 547 | CQQSYSTPYIF | 585 |
| 010S-A08 | LRP6e3e4 | HTFLTYDIN | 94 | GRITPRLGIANYA | 257 | CASYFGVMDVW | 428 | RASQSISSYLN | 510 | AASSLQS | 529 | CQQSYSTPLIF | 592 |

TABLE 1A-continued

Clone IDs and CDR sequences

| Clone ID | Confirmed Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 009S-A07 | LRP6e3e4 | YTFTYRYLH | 170 | GGIIPIFGTANYA | 236 | CATAYGSSSLNIDVW | 429 | RASQSISSYLN | 510 | AASSLQS | 529 | CQQSYSTPLIF | 592 |
| 009S-B07 | LRP6e3e4 | YTFTGYYMH | 164 | GWINPNSGGTNYA | 270 | CVKDGGSFPLAYAFDIW | 476 | RASQSISSYLN | 510 | AASSLQS | 529 | CQQSYSTPLIF | 592 |
| 009S-B06 | LRP6e3e4 | YTFTYRYLH | 170 | GGIIPIFGTANYA | 236 | CAPALTDAGSFDVW | 351 | RVSQSISSYLN | 521 | AASSLQS | 529 | CQQSYSTPLIF | 592 |
| 009S-B08 | LRP6e3e4 | YTFTYRYLH | 170 | GGIIPVFGTADYA | 238 | CARDREQQILDYW | 373 | RASQGISNNLN | 498 | DASNLET | 534 | CQQSYTSRLIF | 597 |
| 010S-C08 | LRP6e3e4 | FTFSTFGMH | 69 | STITSSGGSTYYA | 302 | CARAGIAAAPGSRNYYGMDVW | 354 | RASQSISSYLN | 510 | AASSLQS | 529 | CQQSYSTPLIF | 592 |
| 009S-C06 | LRP6e3e4 | YTFASYDIH | 160 | GWMNPNSGNTGYA | 272 | CARATGSGWYTDLGYW | 359 | RASRNINRYL | 516 | AASSLLS | 527 | CQQSYNVPFIF | 580 |
| 009S-D06 | LRP6e3e4 | FTFSSHSTH | 60 | STISDTNSGTYYA | 299 | CAKAQATGWSGYYTFDYW | 331 | RASQSISSYLN | 510 | AASSLQS | 529 | CQQSYSTPLIF | 592 |
| 010S-D08 | LRP6e3e4 | FTFSSSWMH | 62 | SAIGTGGGTYYA | 277 | CAKEDYDSSGYYYYYFQHW | 339 | RASQSISSYLN | 510 | AASSLQS | 529 | CQQSYSTPLIF | 592 |
| 009S-E06 | LRP6e3e4 | FTFTDYGLH | 74 | AVISYGGSNKYYA | 226 | CASGYSYGLYYYGMDVW | 425 | RASQSISSYLN | 510 | AASSLQS | 529 | CQQSYSTPLIF | 592 |
| 010S-E08 | LRP6e3e4 | YSFTRTDM | 159 | GYISAYTGHTSYA | 274 | CARDLGGTADYW | 370 | RASQSISSYLN | 510 | ZASSLQS | 555 | CQQSYSTPLIF | 592 |
| 010S-F08 | LRP6e3e4 | LTFPDDHAMH | 101 | SYISSSGRTIFYA | 308 | CVRGDSGWGILYYVMDVW | 477 | RASQSISSYLN | 510 | AASSLQS | 529 | CQQSYSTPLIF | 592 |
| 009S-F08 | LRP6e3e4 | YTFTYRYLH | 170 | GGIIPIFGTANYA | 236 | CATEAALDAFDIW | 432 | RASQSISSYLN | 510 | AASSLQS | 529 | CQQSYSTPLIF | 592 |
| 010S-G08 | LRP6e3e4 | YIFTDYYMH | 158 | GGFDPEDGETIYA | 234 | CARGGGPNEHDYYFDYW | 392 | RASQSVRSSDLA | 512 | GSSSRAT | 545 | CQQYGRSPRYSF | 601 |
| 010S-H08 | LRP6e3e4 | FTFZNAWMS | 77 | SGISGSGGSTYYA | 286 | CARGRGKKNYYYGMDVW | 402 | RASQSISSYLN | 510 | AASSLQS | 529 | CQQSYSTPLIF | 592 |
| 010S-A09 | LRP6e3e4 | FTFSTYYMS | 73 | SGISWNGGKTHYV | 287 | CARGDFDYW | 390 | QASQDIANYLN | 493 | AASSLQS | 529 | CQQSYSTPYIF | 594 |
| 010S-B09 | LRP6e3e4 | GTFSSYAIS | 90 | GWINPNSGDTNYA | 260 | CARGEQMLVWGFDPW | 389 | RASQSISRYLN | 508 | KASSLES | 549 | CQQSYDSPWTF | 577 |

TABLE 1A-continued

Clone IDs and CDR sequences

| Clone ID | Confirmed Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 009S-G06 | LRP6e3e4 | YIFTDYYMH | 158 | GWINPNSGGTNYA | 270 | CARDFLGSTGDYW | 365 | RASQNIGLYLN | 504 | DASSLQR | 540 | CQQSYSTPYIF | 594 |
| 010S-C09 | LRP6e3e4 | YTFTYRYLH | 170 | GGIIPIFGTANYA | 236 | CARDEVEGGMDVW | 364 | RASQSISSYLN | 510 | AASSLQS | 529 | CQQSYSTPLIF | 592 |
| 009S-H06 | LRP6e3e4 | FTFSSSAMH | 61 | SAIGTGGSTYYA | 277 | CAKGDYFYYYYGMDVW | 340 | RASQSISSYLN | 510 | AASSLQS | 529 | CQQSYSTPLIF | 592 |
| 010S-D09 | LRP6e3e4 | GTFSSYTIS | 91 | GGIVPAYRRANYA | 241 | CAKGGYELDYW | 344 | QASQDISNYLN | 495 | AASSLQS | 529 | CQQIHSYPLTF | 573 |
| 010S-E09 | LRP6e3e4 | GDLSIYTIN | 80 | GWINAGNGNMA | 259 | CARGDSSGYYYYAFDIW | 391 | RASQSISSYLN | 510 | AASSLQS | 529 | CQQSYSTPLIF | 592 |
| 010S-H09 | LRP6e3e4 | YTFTYRYLH | 170 | GGIIPIFGTANYA | 236 | CATAYGSSSLNIDVW | 429 | RASQSISSYLN | 510 | AASSLQS | 529 | CQQSYSTPLIF | 592 |
| 009S-A07 | LRP6e3e4 | YTFTGYYMH | 164 | GWINPNSGGTNYA | 270 | CVKDGGSFPLAYAFDIW | 476 | RASQSISSYLN | 510 | AASSLQS | 529 | CQQSYSTPLIF | 592 |
| 009S-B07 | LRP6e3e4 | YTFTSYDIN | 168 | GGIIPIFGTANYA | 236 | CARGPYYFDYW | 401 | RASQSISNNLN | 498 | DASSLES | 539 | CLQHNSYPFIF | 561 |
| 009S-D08 | LRP6e3e4 | FTFDEYAMH | 49 | STISGSGGSTYYA | 301 | CASAKNDFWSGYFAFDYW | 421 | RASQSISSYLN | 510 | AASSLQS | 529 | CQQSYSTPLIF | 592 |
| 010S-F09 | LRP6e3e4 | GTFNTHTIT | 86 | GWMNPNSGNTGYA | 272 | CARGNLDFDYW | 398 | QASQDISNYLN | 495 | DASNLET | 534 | CQQSYSTPLIF | 592 |
| 009S-G09 | LRP6e3e4 | FTFSDHYMS | 54 | SAISSGSDRTYYA | 281 | CARYSGYDFDYW | 419 | RASQSISNYLN | 500 | AASTLQS | 532 | CQQGYGTPPMF | 571 |
| 010S-H09 | LRP6e3e4 | FSFSSYSMN | 46 | SYISSSSSTIYYA | 309 | CARGGYGPGYYGMDVW | 406 | RASQSISSYLN | 510 | AASSLQS | 529 | CQQSYSTPLTF | 592 |
| 010S-A10 | LRP6e3e4 | FPFRYYGMS | 38 | ARIGWNGGSIYYA | 205 | CARDYSDRSGIDYW | 378 | RSSQSLLHSNGYNYLD | 519 | LGSNRAS | 550 | CMQATQFPLIE | 564 |
| 009S-D07 | LRP6e3e4 | FAFKDYYMT | 35 | SAIGAGGGTYYA | 275 | CARESALYSSSWYYYYYGMDVW | 385 | RASQSISSYLN | 510 | GTSSLHT | 548 | CQQANSFPFIF | 566 |
| 010S-B10 | LRP6e3e4 | FTFSSYAMS | 64 | SAISGSGGSTYYA | 280 | CAKGGRDGYKGYFDYW | 342 | KSSQSILSSSSNRDSLA | 491 | WASSRKS | 554 | CQQYYNIPYSF | 605 |
| 010S-C10 | LRP6e3e4 | YTFTGYYIH | 163 | ZHVDPEDGETIYA | 312 | CARGPAAIGILGWFDPW | 400 | RASQSISSYLN | 510 | AASSLQS | 529 | CQQSYSTPLTF | 592 |

TABLE 1A-continued

Clone IDs and CDR sequences

| Clone ID | Confirmed Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 010S-D10 | LRP6e3e4 | YIFTDYYMH | 158 | GWMNPNSGNTGYA | 272 | CARTLSGYSSSWYVFDYW | 418 | RASQSISSYLN | 510 | AASSLQS | 529 | CQQSYSTPLIF | 592 |
| 010S-E10 | LRP6e3e4 | FTFSSYSMN | 66 | SGISWNSGTTGYS | 290 | CARDHSSGWRHYFDYW | 367 | RASQSISSYLN | 510 | AASSLQS | 529 | CQQSYSTPLIF | 592 |
| 010S-F10 | LRP6e3e4 | FTFSNSDMN | 57 | SYISGNSGYTNYA | 307 | CASGSYYSDFDYW | 424 | RASQSNYLN | 506 | AASTLES | 530 | CQQANSFPPIF | 566 |
| 010S-G10 | LRP6e3e4 | GTFSSYAIS | 90 | GRINPNGGGTIYA | 256 | CAREGGYYFDYW | 384 | RASQSNYLA | 499 | AASSLQS | 529 | CQQSYSTPWTF | 593 |
| 009S-F07 | LRP6e3e4 | GTFSSYAIS | 90 | GIINPSGGSTSYA | 248 | CARAAGNFWSGYYTFDYW | 353 | RASQSISSYLN | 510 | AASSLQS | 529 | CQQSYSTPLIF | 592 |
| 009S-G07 | LRP6e3e4 | YTFTYRYLH | 170 | GGIIPIFGTANYA | 236 | CARGSYGMDVW | 407 | RASQGISNYLA | 499 | DASNLET | 534 | CLQDFSFPWIF | 558 |
| 010S-H10 | LRP6e3e4 | YTFTGYYMH | 169 | GWINPNSGGTNYA | 270 | CAREAAEIPVGAFDIW | 380 | KSSHSLLYSSDNKNYLA | 490 | WSSTRES | 554 | CQQSYSTPLIF | 606 |
| 010S-A11 | LRP6e3e4 | FTFSNSDMN | 57 | SYISGNSGYTNYA | 307 | CASGSYYSDFDYW | 424 | RASQSIZNYLN | 511 | ZASTLES | 556 | CQQANSFPPIF | 566 |
| 010S-B11 | LRP6e3e4 | FTFRNYAIH | 51 | SAIGTGGDTYYA | 276 | CARDGIRDFDYW | 366 | QASQDISNYLN | 495 | AASTLQS | 532 | CQQSYSTPLIF | 592 |
| 010S-C11 | LRP6e3e4 | YTFTYRYLH | 170 | GGIIPIFGTANYA | 236 | CAADDLGLEHYW | 315 | RASQSISSYLN | 510 | AASSLQS | 529 | CQQSYSTPLIF | 592 |
| 009S-H07 | LRP6e3e4 | YTFTGYYMH | 164 | GWMNPNSGNTGYA | 272 | CASSVVPAGPAGVYAFDIW | 426 | RASQSISSYLN | 510 | AASSLQS | 529 | CQQSYSTPLIF | 592 |
| 009S-A08 | LRP6e3e4 | GTFSSHAIN | 89 | GWISANNGNTDYA | 271 | CARDQDYGDYGWYYYGMDVW | 372 | RASQGISNYLA | 499 | GSSTLQS | 546 | CQQTYSIPPTF | 599 |
| 010S-D11 | LRP6e3e4 | YTFTYRYLH | 170 | GGIIPVFGTANYA | 239 | CATDEYSSSYAFDIW | 430 | RASQSVSSNLA | 513 | GASTRAT | 544 | CQQFDRSPLIF | 569 |
| 010S-E11 | LRP6e3e4 | FTFSAHGMH | 52 | SGISESGGSTYYA | 284 | CARGRGYSYGYYAFDIW | 403 | RASQSISSYLN | 510 | AASSLQS | 529 | CQQSYSTPLIF | 592 |
| 010S-F11 | LRP6e3e4 | YTFTYRYLH | 170 | GGIIPIFGTANYA | 236 | CARDSDMGVVDPW | 374 | RASQSISSYLN | 510 | AASSLQS | 529 | CQQSYSTPLIF | 592 |
| 010S-G11 | LRP6e3e4 | YTFTYRYLH | 170 | GRIIPVLKITNYA | 255 | CAVVDDAFDIW | 438 | RASQSISSYLN | 510 | AASSLQS | 529 | CQQSYSTPLIF | 592 |

TABLE 1A-continued

Clone IDs and CDR sequences

| Clone ID | Confirmed Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 010S-H11 | LRP6e3e4 | YTFTYRYLH | 170 | GGIIPIFGTANYA | 236 | CAKDGTDGRFDPW | 333 | RASQDISSYLA | 496 | SASTLQS | 552 | CQQSNSFPYIF | 575 |
| 009S-B08 | LRP6e3e4 | FTFTSSAVQ | 76 | GWINAGNGNMA | 259 | CARRGGDVTVPAAYYAMDVW | 417 | RASQSISSYLN | 510 | ZASSLQS | 555 | CQQSYSTPLIF | 592 |
| 010S-A12 | LRP6e3e4 | VTFSRYPIS | 156 | GGIIPIFGTANYA | 236 | CAKDSGNYGYYGMDVW | 338 | RASQSISSYLN | 510 | AASSLQS | 529 | CQQSYSTPLIF | 592 |
| 010S-B12 | LRP6e3e4 | FTFSSYDMH | 65 | SGITSNGGATYYA | 291 | CARGTTCKGYYYYGMDVW | 408 | RASQSISSYLN | 510 | AASSLQS | 529 | CQQSYSTPLIF | 592 |
| 010S-C12 | LRP6e3e4 | FTFSNYWIH | 58 | SAIGTGGGTYYA | 277 | CTTAGYKAARSVYPRIFNFDYW | 472 | RASQSISSYLN | 510 | AASSLQS | 529 | CQQSYSTPLIF | 592 |
| 010S-D12 | LRP6e3e4 | YTFTYRYLH | 170 | GRIPIPFGTANYA | 250 | CAREEGVGGMDVW | 382 | RPSQSIGSWLA | 517 | DASNLQS | 535 | CQQSSSTPYIF | 576 |
| 010S-E12 | LRP6e3e4 | FTFSSYAMH | 63 | SAIGAGGGTYYA | 275 | CARGVSSGYYYYYGMDVW | 409 | RASQSISSYLN | 510 | AASSLQS | 529 | CQQSYSTPLIF | 592 |
| 010S-F12 | LRP6e3e4 | FTVSNYMS | 79 | SAIGTGGGTYYA | 277 | CARAGTNWGGWYFDLW | 355 | RASQGISRDLA | 501 | AASSLQS | 532 | CQQSYSPPFIF | 590 |
| 010S-G12 | LRP6e3e4 | FALSGYYMS | 37 | SSISSSSTYIRYA | 296 | CATVTGYSSAGAFDIW | 437 | RASQSISSYLN | 510 | AASSLQS | 529 | CQQSYSTPLIF | 592 |
| 011S-A01 | LRP6e3e4 | FTFSTHAFH | 70 | SAIRGSGERTYYA | 278 | CARDLRNWGSPYWYFDLW | 371 | RASQSISSYLN | 510 | AASSLQS | 529 | CQQSYSTPLIF | 592 |
| 011S-B01 | LRP6e3e4 | GTFSHYTIS | 87 | GWINAGNGNTKYS | 258 | CAKGGSLDMDVW | 343 | RASQGISNYLA | 499 | AASSLHS | 526 | CQQSYRTPLIF | 582 |
| 011S-C01 | LRP6e3e4 | LTFFTSHGMS | 103 | SYVSDSGSSV | 311 | CARHPGSFGGYSYAWYYYYGMDVW | 413 | RASQSISSYLN | 510 | AASSLQS | 529 | CQQSYSTPLIF | 592 |
| 011S-D01 | LRP6e3e4 | GTISDYTVS | 93 | GIINPSGGSTSYA | 248 | CARGYYDFDYW | 411 | RASQGISNYLA | 499 | AASSLQS | 529 | CQQSYSTPLIF | 592 |
| 009S-C08 | LRP6e3e4 | FSENTFGIH | 43 | AVISYDGSNKYYA | 226 | CAKSIAAAGTGYYGMDVW | 346 | RASQSISSYLN | 510 | AASSLQS | 529 | CQQSYSTPLIF | 592 |
| 011S-E01 | LRP6e3e4 | FPFZYYSMN | 39 | SAISGRDGRTYYA | 279 | CAKDLGIQLPDYYFDYW | 334 | RASQGISSALA | 502 | AASTLQS | 532 | CQQSYSSPPIF | 591 |

TABLE 1A-continued

Clone IDs and CDR sequences

| Clone ID | Confirmed Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 009S-D08 | LRP6e3e4 | YTFTSYDIN | 168 | GGIIPIFGTANYA | 236 | CARGPYFDYW | 401 | RASQGISNNLN | 498 | DASSLES | 539 | CLQHNSYPFIF | 561 |
| 011S-F01 | LRP6e3e4 | FSFSDYYMS | 45 | SGISBSGGRTYYA | 284 | CASAADFDYW | 420 | RASQDISNYLN | 495 | AASSLQS | 529 | CLQDYSYPRIF | 559 |
| 009S-E08 | LRP6e3e4 | YGFTGYYIH | 157 | GWMNPNSGNTGYA | 272 | CARGYGYDLW | 410 | QASQDISNYLN | 495 | DASSLES | 539 | CQQSYRYPTF | 583 |
| 009S-F08 | LRP6e3e4 | DTFANYGFS | 34 | GXVNAGNGNTTYA | 273 | CAKGWLDFDYW | 345 | QASQDISNYLN | 495 | DASSLES | 539 | CQQSYSTSITF | 595 |
| 011S-G01 | LRP6e3e4 | YTFTYRYLH | 170 | GGIIPLFGTANYA | 237 | CTTDDYGDQYGMDVW | 474 | RASQSISSYLN | 510 | AASSLQS | 529 | CQQSYSTPLIF | 592 |
| 011S-H01 | LRP6e3e4 | YTFTYRYLH | 170 | GGIIPIFGTANYA | 236 | CTTDDYGDLITHLDYW | 473 | RASQSISSYLN | 510 | AASSLQS | 529 | CQQSYSTPLIF | 592 |
| 011S-A02 | LRP6e3e4 | GTFSSYAIS | 90 | GWMNPNSGNTGYA | 272 | CARDKGYAFDIW | 368 | RSSQSLLHSNGYNYLD | 519 | AASSLQS | 529 | CMQALQTPIIF | 563 |
| 011S-B02 | LRP6e3e4 | YSFTRTDMH | 159 | GYISAYTGHTSYA | 274 | CARDLGGTADYW | 370 | RZSQSZSZYLN | 522 | AASSLQS | 529 | CQQSYSTPLIF | 592 |
| 011S-C02 | LRP6e3e4 | FTFSDYYMN | 72 | SGISWNSGRIGYA | 288 | CARDVGAFDIW | 375 | QASQDISNYLN | 495 | AASSLQS | 529 | CQQSYSIPFTF | 587 |
| 011S-D02 | LRP6e3e4 | FTFSDFAMT | 53 | SYISGDSGYTNYA | 306 | CARLGSYPGPYYYYMDVW | 416 | RASQSISSYLN | 510 | AASSLQS | 529 | CQQSYSTPLIF | 592 |
| 009S-G08 | LRP6e3e4 | FTFSSYAMS | 64 | SSISGSGGVTYYA | 294 | CARGGNTYYYYYGMDVW | 393 | RASQSISSYLN | 510 | AASSLQS | 529 | CQQSYSTPLIF | 592 |
| 011S-E02 | LRP6e3e4 | YTFTDYFMN | 162 | GIINPSGDSTRFA | 245 | CARDDLGLGMDVW | 362 | QASQDISNYLA | 494 | AASSLQS | 529 | CQQSYSTPLIF | 592 |
| 009S-H08 | LRP6e3e4 | YTFTYRYLH | 170 | GGIIPIFGTANVA | 236 | CATDYGDYYYGMDVW | 431 | RASQSISSYLN | 510 | AASSLQS | 529 | CQQSYSTPLIF | 592 |
| 009S-A09 | LRP6e3e4 | YTFTYRYLH | 170 | GRIIPILGSTNYA | 254 | CTTDLMDYW | 475 | QASQGITNYLN | 495 | AASSLQS | 529 | CLQDYTDPFIF | 560 |
| 011S-F02 | LRP6e3e4 | FTFSTYGMH | 71 | SSISVSSGTTHVA | 297 | CARGSGSYYYAFDIW | 394 | RASQSISSYLN | 510 | AASSLQS | 529 | CQQSYSTPLIF | 592 |
| 011S-G02 | LRP6e3e4 | YTFTSYAMN | 167 | GGIPIFGTANVA | 236 | CARDASGGGSTGWYYFDSW | 361 | RASQGISSYLA | 503 | AASSLQS | 529 | CQQAYSFPWTF | 568 |

TABLE 1A-continued

Clone IDs and CDR sequences

| Clone ID | Confirmed Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 011S-H02 | LRP6e3e4 | YTFTNNFMH | 165 | GIINPSGGSTSVA | 248 | CARGLYKRYSYGYGMDVW | 397 | RASQSISSYLN | 510 | AASSLQS | 529 | CQQSYSTPLIF | 592 |
| 009S-B09 | LRP6e3e4 | FSFNTYAMN | 44 | AVTSYDGGKKNYA | 229 | CARDAGGDYDY | 360 | QASQDISNYLN | 495 | AASSLQS | 529 | CQQSYNTPRIF | 579 |
| 009S-C09 | LRP6e3e4 | GTFHTYGLS | 84 | GGIPIFGTANVA | 236 | CARGSGWSGLDYW | 405 | QASQDISNYLN | 495 | DASNLET | 534 | CQQSYTTPFIF | 598 |
| 011S-A03 | LRP6e3e4 | FTFSSYWMH | 67 | STIGSGGRTYVA | 300 | CATSPYGVFTLDYW | 436 | RASQSISSYLN | 510 | AASSLQS | 529 | CQQSYSTPLIF | 592 |
| 011S-B03 | LRP6e3e4 | GTFSZYAIS | 92 | GIINPSGGSTNYA | 247 | CARAGYWSGYGYYGMDVW | 357 | RASQSISSYLN | 510 | AASSLQS | 529 | CQQSYSTPLIF | 592 |
| 011S-C03 | LRP6e3e4 | YTFSYRYLH | 161 | GGIPIFGTANVA | 236 | CASTVTTDAPDIW | 427 | QASQDISNYLN | 495 | DASSLES | 539 | CQQSYSFPPFTF | 586 |
| 011S-D03 | LRP6e3e4 | FSFDDYGMS | 41 | SVISSGGTIYYA | 305 | CARHLSSGYLSYYGMDVW | 412 | RASQSISSYLA | 509 | AASTLQS | 532 | CQQSYSTPLIF | 592 |
| 009S-F09 | LRP6e3e4 | YSFTRTDMH | 159 | GYISAYTGHTSVA | 274 | CARDLGGTADYW | 370 | RASQSISSYLN | 510 | AASSLQS | 529 | CQQSYSTPLIF | 592 |
| 011S-E03 | LRP6e3e4 | FTFSSYAMS | 64 | SAIGSGGSTYVA | 280 | CAKGGRDGYKGYFDYW | 342 | KSSHSLLSTSTNRNQLA | 489 | WASSRKS | 554 | CQQGYNNWPYTF | 604 |
| 009S-G09 | LRP6e3e4 | FTFSRHSMN | 59 | SYSSGNSGYT | 310 | CARGDLEFDYW | 388 | RASQGISNYLA | 499 | SASSLQS | 551 | CQQGYNTPRTF | 572 |
| 011S-F03 | LRP6e3e4 | FTFSSYAMS | 64 | SAIGSGGSTYVA | 280 | CAKGGRDGYKGYFDYW | 342 | KSSQVLYTTTNRNHIA | 492 | WASSRKS | 554 | CQQSYSTPYIF | 607 |
| 009S-H09 | LRP6e3e4 | FTFSSYAMS | 64 | SAIGSGGSTYVA | 280 | CAKGGRDGYKGYFDYW | 342 | KSSHSLLSTSTNRNHLA | 488 | WASSRKS | 554 | CQQYYNIPYSF | 605 |
| 011S-G03 | LRP6e3e4 | YTFTYRYLH | 170 | GRIPIHGTANVA | 251 | CAREYSYGYFRYW | 387 | RASQGISNYLA | 503 | DASNLET | 534 | CQQANSLFTF | 567 |
| 009S-A10 | LRP6e3e4 | FTFTSSAMQ | 75 | GIINPSGGSTIVA | 246 | CASGDTYDLYSLDVW | 423 | RASQSISRWLA | 507 | AASSLQS | 529 | CQQAYSFPWTF | 568 |
| 009S-B10 | LRP6e3e4 | YIFTDYYMH | 158 | GWINAGNGNTTYA | 259 | CAKVASGWSWPFDIW | 348 | RASQSISSYLN | 510 | AASSLQS | 529 | CQQSYSTPLIF | 592 |
| 011S-B04 | LRP6e1e2 | YTFTSYDIN | 168 | GIINPSGGSTSVA | 248 | CTREHSYYYYGMDVW | 470 | RASQSISSYLN | 510 | AASSLQS | 529 | CQQSYSTPLIF | 592 |

TABLE 1A-continued

Clone IDs and CDR sequences

| Clone ID | Confirmed Binding | CDRH1 | CDRH1 SEQ ID | CDRH2 | CDRH2 SEQ ID | CDRH3 | CDRH3 SEQ ID | CDRL1 | CDRL1 SEQ ID | CDRL2 | CDRL2 SEQ ID | CDRL3 | CDRL3 SEQ ID |
|---|---|---|---|---|---|---|---|---|---|---|---|---|---|
| 011S-C04 | LRP6e1e2 | GTFNSNAIS | 85 | GWMNPNSGNTGYA | 272 | CARDYGSGSYNYGMDVW | 379 | GASQSVPRNSLA | 486 | GASQRAT | 543 | CQQYHNWPPEYTF | 602 |
| 011S-D04 | LRP6e1e2 | YTFTSYDIN | 168 | GIINPSGGSTSVA | 248 | CAREAYYYYGMDVW | 381 | RASQSISSYLN | 510 | AASSLQS | 529 | CQQSYSTPLIF | 592 |
| 011S-E04 | LRP6e1e2 | FTFSSZZMH | 68 | SAIGTGGGTZVA | 277 | CAKDLGRAAAGSMDVW | 335 | WASQSVRGNYVA | 524 | DASNRAA | 536 | CQHRSNWPLIE | 565 |
| 011S-E04 | LRP6e1e2 | YIFTDYYMH | 158 | GRIIPILGRANVA | 252 | CARGGYSTLDYW | 396 | HGSQDISNYLN | 487 | DASNRQS | 538 | CQQSFSTPRTF | 574 |
| 011S-H04 | LRP6e1e2 | YIFTDYYMH | 158 | GRIIPILGRANVA | 252 | CARGGYSTLDYW | 396 | QASQDISNYLN | 495 | AASTLQS | 532 | CQQSFSTPRTF | 574 |
| 011S-A05 | LRP6e1e2 | FTFSSYAMH | 63 | SAIGTGGGTYVA | 277 | CAKDLGRAAAGSMDVW | 335 | WASQSVRGNYVA | 524 | DASNRAG | 537 | CQHRSNWPLIE | 565 |
| 011S-B05 | LRP6e1e2 | YZFTDYYMH | 172 | GWMNPNSGNTGYA | 272 | CTRVAWGLDYW | 471 | RASQSISSYLN | 510 | AASSLQS | 529 | CQQSYSTPLTF | 592 |
| 011S-C05 | LRP6e1e2 | FTFSSYAMH | 63 | SAIGTGGGTYVA | 277 | CAKDLGRAAAGSMDVW | 335 | WASQSVRGNYVA | 524 | DASNRAA | 536 | CQHRSNWPLIE | 565 |

Table 1B provides the sequence identifier number of the antibody heavy chain fragment (HC) for illustrative clones having only a heavy chain region, and their binding characteristics. In certain embodiments, the LRP5/6 binding domain is an Fab or was derived from an Fab, so Table 1B includes VH and CH1 sequence, but not CH2 or CH3 sequences. In certain embodiments, the LRP5/6 binding domain is a VHH or sdAb or was derived from a VHH or sdAb, so Table 2B includes the VHH domain. $K_D$ data as determined by Octet BLI is shown for various Fzd receptors. The "Confirmed Binding" column indicates binding results from Octet BLI binding or BIAcore SPR. Blank entries denote that the binding to the specific Fzd receptor has not yet been determined. As shown in Table 1B, Octet BLI or BIAcore SPR sensorgrams for anti-LRP5/6 antibody fragments demonstrated a range of affinities for LRP5 and/or LRP6.

TABLE 1B

Clone IDs, Heavy Chain (HC) Seq ID Nos, and Binding Characteristics

| Clone ID | HC Seq ID NO | BLI or SPR Confirmed Binding | Kd (nM) |
|---|---|---|---|
| 001S-F11 | 1 | LRP6e1e2 | * |
| 009S-G02 | 2 | LRP6e1e2 | * |
| 009S-A03 | 3 | LRP6e1e2 | * |
| 009S-D03 | 4 | LRP6e1e2 | * |
| 009S-F03 | 5 | LRP6e1e2 | * |
| 009S-H03 | 6 | LRP6e1e2 | * |
| 009S-A04 | 7 | LRP6e1e2 | * |
| 009S-B04 | 8 | LRP6e3e4 | * |
| 009S-D04 | 9 | LRP6e3e4 | ** |
| 009S-E04 | 10 | LRP6e3e4 | * |
| 009S-F04 | 11 | LRP6e3e4 | ** |
| 009S-G04 | 12 | LRP6e3e4 | * |
| 009S-H04 | 13 | LRP6e3e4 | * |
| 009S-A05 | 14 | LRP6e3e4 | ** |
| 013S-G04 | 15 | LRP6e3e4 | * |
| 013S-H04 | 16 | LRP6e3e4 | * |
| 013S-C05 | 17 | LRP6e3e4 | * |
| 013S-D05 | 18 | LRP6e3e4 | * |
| 013S-G04 | 19 | LRP6e3e4 | * |
| 013S-H04 | 20 | LRP6e3e4 | * |
| 013S-A05 | 21 | LRP6e3e4 | ** |
| 013S-C05 | 22 | LRP6e3e4 | * |
| 013S-D05 | 23 | LRP6e3e4 | * |
| 008S-D01 | 24 | LRP5 | |

* Indicates <500 nM;
** indicates >500 nM

Table 1C provides additional binding characteristics for certain clones, including relative binding affinities to LRP6E E2 and LRP6E3E4 domains. The entry of "n.b." indicates no binding.

TABLE 1C

LRP6 Binding Characteristics of sub-set of clones

| Antigen | Clone ID | Octet confirmed binding | LRP6e1e2 | LRP6e3e4 |
|---|---|---|---|---|
| LRP6e1e2 | 010S-E02 | LRP6e1e2 | * | |
| LRP6e1e2 | 009S-G02 | LRP6e1e2 | * | n.b. |
| LRP6e1e2 | 009S-A03 | LRP6e1e2 | * | ** |
| LRP6e1e2 | 010S-B03 | LRP6e1e2 | ** | |
| LRP6e1e2 | 009S-D03 | LRP6e1e2 | * | n.b. |
| LRP6e1e2 | 009S-F03 | LRP6e1e2 | * | n.b. |
| LRP6e1e2 | 009S-H03 | LRP6e1e2, e3e4 | * | * |
| LRP6e1e2 | 009S-A04 | LRP6e1e2 | * | n.b. |
| LRP6e3e4 | 009S-B04 | LRP6e3e4 | n.b. | * |
| LRP6e3e4 | 009S-D04 | LRP6e1e2, e3e4 | * | * |
| LRP6e3e4 | 009S-E04 | LRP6e3e4 | | * |

TABLE 1C-continued

LRP6 Binding Characteristics of sub-set of clones

| Antigen | Clone ID | Octet confirmed binding | LRP6e1e2 | LRP6e3e4 |
|---|---|---|---|---|
| LRP6e3e4 | 009S-F04 | LRP6e3e4 | | ** |
| LRP6e3e4 | 009S-G04 | LRP6e3e4 | n.b. | * |
| LRP6e3e4 | 009S-H04 | LRP6e3e4 | n.b. | * |
| LRP6e3e4 | 009S-A05 | LRP6e3e4 | | ** |
| LRP6e3e4 | 010S-G04 | Lrp6e3e4 | | * |
| LRP6e3e4 | 010S-E05 | LRP6e3e4 | | * |
| LRP6e3e4 | 013S-G04 | LRP6e3e4 | n.b. | * |
| LRP6e3e4 | 013S-H04 | LRP6e3e4 | n.b. | * |
| LRP6e3e4 | 013S-C05 | LRP6e3e4 | n.b. | * |
| LRP6e3e4 | 013S-D05 | LRP6e3e4 | n.b. | * |
| LRP6e3e4 | 009S-B05 | LRP6e3e4 | | * |
| LRP6e3e4 | 010S-A07 | LRP6e3e4 | | * |
| LRP6e3e4 | 009S-D05 | LRP6e3e4 | | |
| LRP6e3e4 | 010S-E07 | LRP6e3e4 | | * |
| LRP6e3e4 | 009S-F05 | LRP6e3e4 | | * |
| LRP6e3e4 | 010S-G07 | LRP6e3e4 | | * |
| LRP6e3e4 | 009S-G05 | LRP6e3e4 | | |
| LRP6e3e4 | 010S-A08 | LRP6e3e4 | | * |
| LRP6e3e4 | 009S-D06 | LRP6e3e4 | | * |
| LRP6e3e4 | 010S-F08 | Lrp6e3e4 | | * |
| LRP6e3e4 | 010S-A09 | LRP6e3e4 | | ** |
| LRP6e3e4 | 010S-D09 | LRP6e3e4 | | ** |
| LRP6e3e4 | 009S-D08 | LRP6e3e4 | | ** |
| LRP6e3e4 | 010S-D10 | LRP6e3e4 | | ** |
| LRP6e3e4 | 010S-D11 | LRP6e3e4 | | * |
| LRP6e3e4 | 010S-F11 | LRP6e3e4 | | * |
| LRP6e3e4 | 010S-G11 | LRP6e3e4 | | * |
| LRP6e3e4 | 010S-B12 | LRP6e3e4 | | ** |
| LRP6e3e4 | 010S-D12 | LRP6e3e4 | n.b. | ** |
| LRP6e3e4 | 010S-F12 | LRP6e3e4 | | * |
| LRP6e3e4 | 011S-B01 | LRP6e3e4 | | * |
| LRP6e3e4 | 011S-D01 | LRP6e3e4 | | ** |
| LRP6e3e4 | 011S-H01 | LRP6e3e4 | | * |
| LRP6e3e4 | 011S-B02 | LRP6e3e4 | | * |
| LRP6e3e4 | 011S-G02 | LRP6e3e4 | | * |
| LRP6e3e4 | 011S-B03 | LRP6e3e4 | | * |
| LRP6e3e4 | 011S-C03 | LRP6e3e4 | | ** |
| LRP6e3e4 | 009S-F09 | LRP6e3e4 | n.b. | * |
| LRP6e3e4 | 009S-G09 | LRP6e3e4 | | * |
| LRP6e1e2 | 011S-B05 | LRP6e1e2 | * | |
| LRP6e1e2 | 011S-C05 | LRP6e1e2 | * | |

* Indicates <500 nM;
** indicates >500 nM

Example 2

Alanine-Scanning Mutation of Anti-Lrp6 Antibody Fragment

One antibody fragment, 009S-E04, was selected for alanine-scanning mutagenesis of CDRs, and the respective LRP6 binding affinities of the various mutants were determined by Octet BLI as described in Example 1. As shown in Table 2, large number of mutants bound LRP6 with A similar affinity as the wild type antibody fragment, demonstrating that the LRP6 antibodies and antigen-binding fragments thereof can tolerate amino acid modifications within the CDRs.

TABLE 2

009S-E04 alanine-scanning mutant CDR sequences and $K_D$ (nM) to biotinylated-LRP6 CRD as determined by Octet BLI.

| Clone ID | Kd (nM) | CDRH1 | SEQ ID No. | CDRH2 | SEQ ID No. | CDRH3 | SEQ ID No. |
|---|---|---|---|---|---|---|---|
| WT | * | RIFAIYDIA | 107 | AMIRPVVTEIDYA | 203 | CNAKRPWGSRDEYW | 608 |
| K1A | * | RIFAIYDIA | 107 | AMIRPVVTEIDYA | 203 | CNAARPWGSRDEYW | 609 |
| R2A | * | RIFAIYDIA | 107 | AMIRPVVTEIDYA | 203 | CNAKAPWGSRDEYW | 610 |
| P3A | * | RIFAIYDIA | 107 | AMIRPVVTEIDYA | 203 | CNAKRAWGSRDEYW | 611 |
| W4A | * | RIFAIYDIA | 107 | AMIRPVVTEIDYA | 203 | CNAKRPAGSRDEYW | 612 |
| G5A | * | RIFAIYDIA | 107 | AMIRPVVTEIDYA | 203 | CNAKRPWASRDEYW | 613 |
| S6A | * | RIFAIYDIA | 107 | AMIRPVVTEIDYA | 203 | CNAKRPWGARDEYW | 614 |
| R7A | * | RIFAIYDIA | 107 | AMIRPVVTEIDYA | 203 | CNAKRPWGSADEYW | 615 |
| D8A | * | RIFAIYDIA | 107 | AMIRPVVTEIDYA | 203 | CNAKRPWGSRAEYW | 616 |
| E9A | * | RIFAIYDIA | 107 | AMIRPVVTEIDYA | 203 | CNAKRPWGSRDAYW | 617 |
| Y10A | * | RIFAIYDIA | 107 | AMIRPVVTEIDYA | 203 | CNAKRPWGSRDEAW | 618 |

*Indicates <100 nM

Example 3

Characterization of a 18R5Scfv-Lrp VHH Vwt Surrogate Fusion Protein in 293 and A375 Wnt Dependent Reporter Assays The ability of Wnt surrogate fusion proteins comprising an scFv region that binds to one or more Fzd and a VHH or sdAb (or single domain antibody, Nab) region that binds to LRP5 and/or LRP6 was demonstrated. The Fzd binder, 18R5, in scFv format, was fused to various Lrp5 and Lrp6 binders disclosed herein. The LRP binders were Nab and were fused to the C-terminus of 18R5 scFv with a 6-amino acid linker. The fusion proteins containing a C-terminal poly-His-tag were expressed in expi293 cells according to the manufacturer's protocol, and purified from the conditioned media using complete His-tag purification resin, and Superdex 200 10/300 GL equilibrated in HBS (10 mM HEPES, pH 7.3, 150 mM NaCl). Fractions containing monomeric fusions were pooled and concentrated.

The fusion proteins were tested for their ability to induce Wnt pathway signaling using Wnt dependent reporter assays in 293 and A375 cell lines under the following conditions. 10,000 Å375 and HEK293 Wnt reporter cells, stably transfected with the STF Wnt reporter plasmid or a variant thereof, were seeded in triplicate for each condition in 96-well plates, and stimulated with the fusion proteins for 16-20 h in the presence or absence of 25 nM Fc-Rspo2. The conditions tested including various concentrations of each fusion protein ranging from $10^{-2}$ nM to $10^{-3}$ nM. After washing cells with PBS, cells in each well were lysed in 30 µl passive lysis buffer (Promega). 10 µl per well of lysate was assayed using the Firefly Luciferase Assay kit (Promega).

The results demonstrated that a number of the Wnt surrogates tested activated the Wnt signaling pathway in a concentration dependent manner, and this was further enhanced by treatment with Fc-Rspo2 (data not shown).

Example 4

Crystal Structures of Lrp6E3E4:Binder Complexes

Lrp6, Low-density lipoprotein receptor-related protein 6, is a 1613 amino acid containing, single-pass membrane protein that plays a critical role in Wnt-mediated activation of ß-catenin signaling. Lrp6 and related Lrp5 shares 70% sequence identity between them. Extracellular regions of Lrp6 and Lrp5 contains four ß-propeller domains referred to here as E1, E2, E3, and E4 domains. In this session, we describe structures of Lrp6E3E4 domains (residues 631 to 1246 of uniprot entry O75581 (https://www.uniprot.org/uniprot/O75581). Sequence Lrp6E3E4 construct, used for structural studies, containing biotin acceptor peptide (BAP) and an eight-Histidine motif at their C-terminus is as follows:

```
LRP6E3E4_O75581_631-1246:
                                    (SEQ ID NO: 619)
EAFLLFSRRADIRRISLETNNNNVAIPLTGVKEASALDFDVTDNRIYWT

DISLKTISRAFMNGSALEHVVEFGLDYPEGMAVDWLGKNLYWADTGTNR

IEVSKLDGQHRQVLVWKDLDSPRALALDPAEGFMYWTEWGGKPKIDRAA

MDGSERTTLVPNVGRANGLTIDYAKRRLYWTDLDTNLIESSNMLGLNRE

VIADDLPHPFGLTQYQDYIYVVTDWSRRSIERANKTSGQNRTIIQGHLD

YVMDILVFHSSRQSGWNECASSNGHCSHLCLAVPVGGFVCGCPAHYSLN

ADNRTCSAPTTFLLFSQKSAINRMVIDEQQSPDIILPIHSLRNVRAIDY

DPLDKQLYWIDSRQNMIRKAQEDGSQGFTVVVSSVPSQNLEIQPYDLSI

DIYSRYIYWTCEATNVINVTRLDGRSVGVVLKGEQDRPRAVVVNPEKGY

MYFTNLQERSPKIERAALDGTEREVLFFSGLSKPIALALDSRLGKLFWA

DSDLRRIESSDLSGANRIVLEDSNILQPVGLTVFENWLYWIDKQQQMIE
```

-continued

KIDMTGREGRTKVQARIAQLSDIHAVKELNLQEYRQHPCAQDNGGCSHI

CLVKGDGTTRCSCPMHLVLLQDELSCGEPPSGSGGLNDIFEAQKIEWHE

GSGSHHHHHHHH

Example 5

Expression and Purification of Lrp6E3E4 for Structural Studies

A stable-cell line expressing Lrp6E3E4 domain was generated in Expi293 cells with G418 selection. For large-scale expression, a frozen vial Expi293 Cells expressing Lrp6E3E4 was thawed into 20 mL of Expi293 media (Thermofisher). Cells were monitored for viability and expended on alternative days until density of ~3.0 to $4.0 \times 10^8$ cell/mL was reached at desired volumes, typically 6 to 10 L. At this stage, cells treated with 2 mM valparoic acid, allowed to grow continuously to higher density, and media was harvested by centrifugation after ~48 hours. Fzd CRD_Xtal proteins were purified from media by incubation with His-Complete resin (1 mL per L of culture; Roche) pre-equilibrated in PBS (50 mM sodium di-hydrogen phosphate pH 8.0, 300 mM NaCl), and eluted with 250 mM imidazole. Elutions were concentrated to 5 mL, and further polished on a HiLoad 16f00 Superdex 200 pg column (GE Life Sciences) pre-equilibrated with HBS (20 mM HEPES pH 7.4, and 150 mM sodium chloride). Fractions near main peak was further analyzed by SDS-Polyacrylamide Gel Electrophoresis (SDS-PAGE) to confirm the content. SDS-PAGE was performed using Tris-HCl 4-15% gel (Bio-Rad, Hercules, Calif.) under both non-reducing conditions. The samples were prepared in Laemmli sample buffer and heated at 100□C for 5 min. Fractions containing LRP6E3E4 were concentrated to ~2 mg/mL and frozen in the presence of 10% glycerol for storage at −80 C until further use. Protein concentrations were determined using a NanoDrop Spectrophotometer (Thermo Scientific) by the direct UV A280 method. The relationship of absorbance to protein concentration is linear based on Beer-Lamber equation, $A=\varepsilon l\ c$; A is the absorbance value, $\varepsilon$ is the wavelength-dependent extinction coefficient, l is the path length in centimeters, and c is the protein concentration. The extinction coefficients of all produced proteins were estimated by their amino acid sequences.

Example 6

Expression and Purification of Vhh or Sdab or Fab Binders

Plasmids expressing light-chain and heavy chain (with hexa-histidine tag at its C-terminus) in the case of Fab or that expressing VHH binders were transfected for expression in Expi293 cells, typically at 1000 mL scale, following the standard protocols from the manufacturer (Thermofisher). After 4 days of continuous cell growth, media were harvested by centrifugation, and bound to Complete-His resin (2.5 mL per 1 L culture; Roche) pre-equilibrated in PBS, and eluted under gravity-flow using 250 mM imidazole in PBS. Elutions containing Fab binders were concentrated to ~5 mL, and further polished on a HiLoad 16/600 Superdex 200 pg column (GE Life Sciences) column pre-equilibrated with HBS. Fractions near the main peak were further analyzed by SDS-Polyacrylamide Gel Electrophoresis (SDS-PAGE) to confirm the content. SDS-PAGE was performed using Tris-HCl 4-15% gel (Bio-Rad, Hercules, Calif.) under both non-reducing conditions. The samples were prepared in Laemmli sample buffer and heated at 100□C for 5 min. Fractions containing Fab or VHH binders were concentrated to ~3 mg/mL and frozen in the presence of 10% glycerol for storage at −80 C until further use. Protein concentrations were determined using a NanoDrop Spectrophotometer (Thermo Scientific) by the direct UV A280 method. The relationship of absorbance to protein concentration is linear based on Beer-Lamber equation, $A=\varepsilon l\ c$; A is the absorbance value, $\varepsilon$ is the wavelength-dependent extinction coefficient, l is the path length in centimeters, and c is the protein concentration. The extinction coefficients of all produced proteins were estimated by their amino acid sequences.

Example 7

Lrp6E3E4:VHH/Fab Complex Formation, Crystallization, and Structure Determination Purified Lrp6E3E4 and VHH/Fab binders were mixed at 1.1:1 molar ratio (little excess of the smaller molecular weight protein), and incubated with carboxy-peptidase A and B at a w/w ratio of 100:1 for over-night at 4° C. Complex formation was confirmed by observation of a single-major peak on SuperdexS200 Increase (10/300 GL) column pre-equilibrated in HBS. Fractions containing complexes were further checked by SDS-PAGE, and concentrated to 10 to 25 mg/mL for crystallization screens. Initial crystallization screen, using commercially available MCSG1, MCSG2, MCSG3, MCSG4, PACT (Molecular Dimensions), PEGs I, and PEGs II (Qiagen) screen, and optimization by grid-screens or microseed matrix screen [MMS; Microseed matrix screening for optimization in protein crystallization: what have we learned? D'Arcy, A., Bergfors, T., Cowan-Jacob S. W., and Marshd, M. Acta Cryst. F70, 1117-1126 (2014)]. were performed using Mosquito (TTP LabTech) liquid handler, and equilibrated at 18° C. inside an EchoTherm incubator (Torrey Pines Scientific). 96-well plate crystal screening experiments were periodically monitored manually via a DiscoveryV20 stereomicroscope (Zeiss), and crystals were frozen for data collection by plunging into liquid nitrogen in the presence of various cryo-protectants (typically 15 to 30% v/v of glycerol or ethyleneglycol or 1.1 to 2.5 M sodium malanote pH 7.0). X-ray diffraction datasets were collected at the Berkeley Center for Structural Biology at the Advanced Light Source (ALS), Berkeley Calif., and processed with XDS [Kabsch, W. XDS. Acta Cryst. D66, 125-132 (2010)], and xdsme [Legrand, P. XDSME: XDS Made Easier (2017) GitHub repository, https://github.com/legrandp/xdsme DOI 10.5281/zenodo.837885] programs. Structure of Lrp6E3E4: VHH/Fab complexes were determined by molecular replacement method using Phaser [Phaser crystallographic software. A. J. McCoy, R. W. Grosse-Kunstleve, P. D. Adams, M. D. Winn, L. C. Storoni, and R. J. Read. J Appl Crystallogr 40, 658-674 (2007)] with published structures Lrp6E3E4 [PDB code: 4AOP; Chen S, Bubeck D, MacDonald B T, Liang W X, Mao J H, Malinauskas T, Llorca O, Aricescu A R, Siebold C, He X, Jones E Y. Dev. Cell 21 848-61 (2011)] and a VHH or sdAb [PDB code: 6B20, chain E; Gulati S, Jin H, Masuho I, Orban T, Cai Y, Pardon E, Martemyanov K A, Kiser P D, Stewart P L, Ford C P, Steyaert J, Palczewski K. Nat Commun 91996 (2018)], followed by refinement and validation by MolProbity as implemented in Phenix [PHENIX: a comprehensive Pythonbased system for macromolecular structure solution. P. D. Adams, P. V. Afonine, G. Bunkoczi, V. B. Chen, I. W. Davis, N. Echols, J. J. Headd, L. W. Hung, G. J. Kapral, R. W. Grosse-Kunstleve, A. J. McCoy, N. W. Moriarty, R. Oeffner, R. J. Read, D. C. Richardson, J. S. Richardson, T. C. Terwilliger, and P. H. Zwart. Acta Cryst. D66, 213-221 (2010); MolProbity: all-atom structure validation for macromolecular crystallography. V. B. Chen, W. B. Arendall, J. J. Headd, D. A. Keedy, R. M. Immormino, G. J. Kapral, L. W. Murray, J. S. Richardson, and D. C. Richardson. Acta Cryst. D66, 12-21 (2010)]. Crystallography models were manually inspected and built using COOT [Features and development of Coot. P. Emsley, B. Lohkamp, W. G. Scott, and K. Cowtan. Acta Cryst. D66, 486-501 (2010)]. Analyses of refined crystal structures, and image creations were performed using MOE (CCG) and PyMol (Schrodinger).

Example 8

Structure of Lrp6E3E4:VHH26 Complex

```
Sequence of the VHH26 (0095-E04):
                                            (SEQ ID NO: 620)
DVQLVESGGGLVQAGGSLRLACAGSGRIFAIYDIAVVYRHPPGNQREL
VAMIRPVVTEIDYADSVKGRFTISRNNAMKTVYLQMNNLKPEDTAVYY
CNAKRPWGSRDEYWGQGTQVTVSSGSGSGHHHHHH
```

Diffraction quality crystals of Lrp6E3E4:VHH26 (concentration=12.4 mg/mL) were obtained by MMS in the PACT screen, G8 condition containing 0.2 M sodium sufate, 0.1 M bis-Tris-propane pH 7.5, and 20% (v/v) PEG3350. Crystal was cryo-protected using 27% glycerol in well-solution. Lrp6E3E4:VHH26 complex crystallized in the P3121 space group (a=b=136.64 Å and c=104.70 Å) with one complex molecule per asymmetric unit. Structure of Lrp6E3E4:VHH26 complex was determined at a resolution of 2.40 Å, and refined to $R_{cryst}$ and $R_{free}$ factors of 18.5% and 23.0%, respectively.

Figures 3A, 3B:
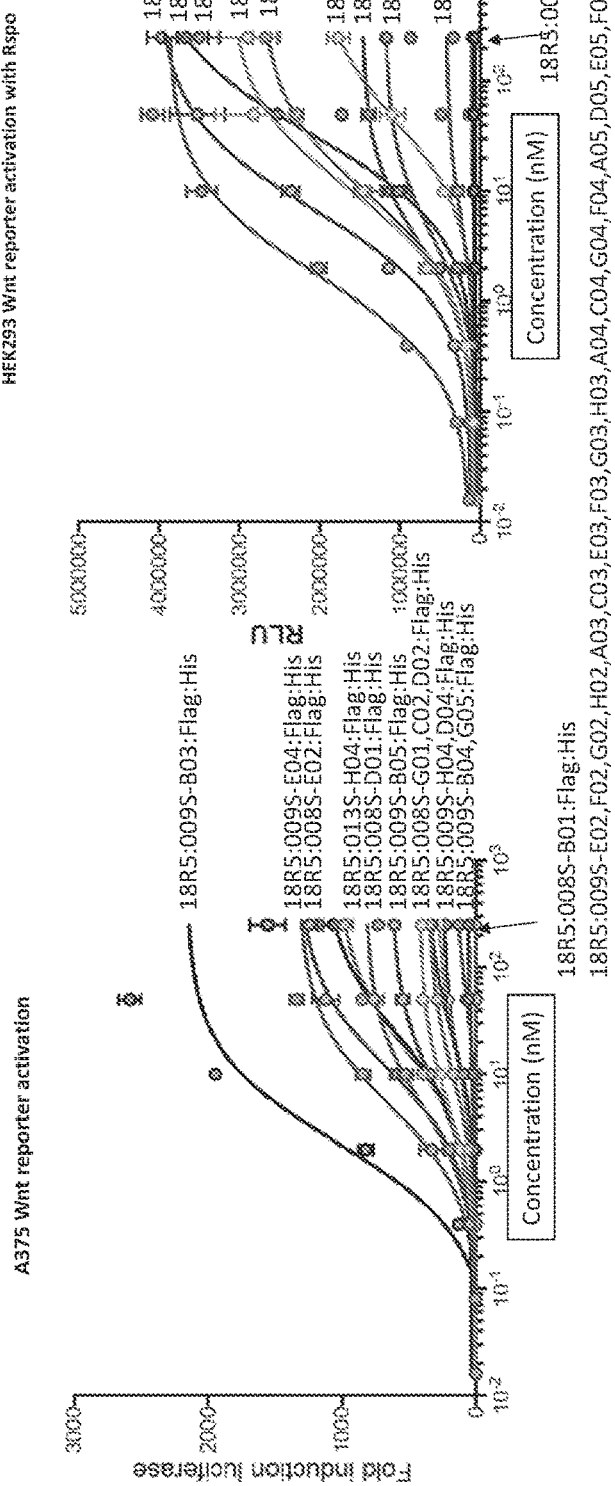
FIG. 3A shows Wnt activation using the A375 Wnt reporter assay.
FIG. 3B shows Wnt report activation in HEK293 cells with added Rspo. Clones tested in both assays are Wnt surrogate molecule comprising the Fzd binder 18R5 scFv combined with LRP VHH or sdAb binders. FLAG and His tags were attached to the 18R5:LRP surrogate molecule.

Overall structure of Lrp6E3E4:VHH26 complex shown in FIG. 3.1(A), which reveals that the epitope on Lrp6E3E4 for VHH26 (FIG. 4.1(B)) localized within the E3 ß-propeller of Lrp6. Structure of the complex allow us to identify epitope of Lrp6E3E4 for VHH26 with the following residues of Lrp6E3E4 defining the core interaction-site (inter-atomic distances between Lrp6E3E4 and VHH26 less than or equal to 5.0 Å):

Arg639, Ala640, Lys622, Glu663, Ile681, Ser682, Lys684, Asp705, Tyr706, Glu708, Thr724, Gly725, Arg751, Trp767, Gly768, Gly769, Arg792, Leu810, Asp811, His834, Phe836, Trp850, Ser851, Arg853, Asp874, Tyr875, and Met877.

In addition, following residues on Lrp6E3E4 could be identified as immediate-interaction site (inter-atomic distances between Lrp6E3E4 and VHH26 greater than 5.0 Å and less than or equal to 8.0 Å):

Arg638, Asp641, Va661, Ala664, Ser665, Asp680, Leu683, Thr685, Leu704, Pro707, Asp723, Thr726, Asn727, Asp748, Ser749, Pro750, Lys770, Pro771, Gly791, Asn794, Asp809, Thr812, Asn813, Pro833, Pro835, Asp849, and Arg852.

Structure of Lrp6E3E4:VHH26 complex also allow us to identify following residues on VHH26 as core-interaction site (inter-atomic distances between Lrp6E3E4 and VHH26 less than or equal to 5.0 Å):

Gly26, Arg27, Phe29, Ala30, Ile31, Tyr32, Arg52, Pro53, Val54, Val55, Glu57, Asn74, Ala75, Lys77, Arg100, Pro101, Trp102, Gly103, Ser104, Arg105 Asp106, and Tyr108.

Structure of Lrp6E3E4:VHH26 complex also allow us to identify following residues on VHH26 as core-interaction site (inter-atomic distances between Lrp6E3E4 and VHH26 greater than 5.0 Å and less than or equal to 8.0 Å):

Gly24, Ser25, Ile28, Asp33, Met50, Ile51, Thr56, Arg72, Asn73, Met76, Lys99, and Glu107.

Example 9

Structure of Lrp6E3E4:VHH36 Complex

```
Sequence of the VHH36 (0135-D05):
                                            (SEQ ID NO: 621)
QVKLEESGGGLVQAGGSLRLSCAASGRIFSIYDMGWFRQAPGKERE
FVSGIRWSGGTSYADSVKGRFTISKDNAKNTIYLQMNNLKAEDTAVY
YCGSRGYWGQGTLVTVSSGSGSGHHHHHH
```

Diffraction quality crystals of Lrp6E3E4:VHH36 (concentration=14.0 mg/mL) were obtained by grid-screen optimization in a condition containing 1.6 M ammonium sulfate and 0.1 M Tris pH 8.2. Crystal was cryo-protected using 1.1 M sodium malonate pH 7.0 in 1.6M ammonium sulfate and Tris pH 9.0. Lrp6E3E4:VHH36 complex crystallized in the P6$_5$ space group (a=b=180.61 Å and c=98.63 Å) with one complex molecule per asymmetric unit. Structure of Lrp6E3E4:VHH36 complex was determined at a resolution of 2.70 Å, and refined to $R_{cryst}$ and $R_{free}$ factors of 18.6% and 22.8%, respectively.

Overall structure of Lrp6E3E4:VHH36 complex shown in FIG. 3.1(A), which reveals that the epitope on Lrp6E3E4 for VHH36 (FIG. 4.1(B) localized within the E3 ß-propeller of Lrp6. Structure of the complex allow us to identify epitope of Lrp6E3E4 for VHH36 with the following residues of Lrp6E3E4 defining the core interaction-site (inter-atomic distances between Lrp6E3E4 and VHH36 less than or equal to 5.0 Å):

Glu663, Ser665, Ile681, Tyr706, Glu708, Thr724, Ser749, Arg751, Trp767, Gly768, Arg792, Leu810, Asn813, Pro833, His834, Phe836, Trp850, Ser851, Arg853, Asp874, Tyr875, and Met877.

In addition, following residues on Lrp6E3E4 could be identified as immediate-interaction site (inter-atomic distances between Lrp6E3E4 and VHH36 greater than 5.0 Å and less than or equal to 8.0 Å):

Ser637, Arg638, Arg639, Lys662, Ala664, Ala666, Thr679, Asp680, Ser682, Lys684, Pro707, Gly725, Asn727, Asp748, Pro750, Glu766, Gly769, Pro771, Asn794, Thr808, Asp809, Asp811, Thr812, Leu814, Leu832, Pro835, Asp849, Arg852, His872, Leu873, Val876, and Asp878.

Structure of Lrp6E3E4:VHH36 complex also allow us to identify following residues on VHH36 as core-interaction site (inter-atomic distances between Lrp6E3E4 and VHH36 less than or equal to 5.0 Å):

Gln1 (modified as pyroglutamate), Val2, Lys3, Ala24, Ser25, Gly26, Arg27, Ile28, Ser30, Ile31, Tyr32, Trp53, Asn73, Asn76, Arg98, and Tyr100.

Structure of Lrp6E3E4:VHH36 complex also allow us to identify following residues on VHH36 as core-interaction site (inter-atomic distances between Lrp6E3E4 and VHH36 greater than 5.0 Å and less than or equal to 8.0 Å):

Leu4, Ala23, Phe29, Asp33, Arg52, Ser54, Lys71, Asp72, Ala74, Lys75, Ser97, and Gly99.

TABLE 3

Summary of Binding Characteristics of Antigen Binding proteins of LRP as determined by co-crystal structures. In the cases of multi-specific binders, corresponding residues of related LRP5 are listed, using amino-acid single-letter codes, in addition to the structurally determined epitope information on LRP for which crystal structures were determined.

| Antigen Binding Protein | Antigen | Interaction site on LRP6 (<5 angstroms) | Interaction site on LRP6 (5-8 angstroms) |
|---|---|---|---|
| VHH26 (009S-E04) | LRP6E3E4 | Arg639, Ala640, Lys662, Glu663, Ile681, Ser682, Lys684, Asp705, Tyr706, Glu708, Thr724, Gly725, Arg751, Trp767, Gly768, Gly769, Arg792, Leu810, Asp811, His834, Phe836, Trp850, Ser851, Arg853, Asp874, Tyr875, Met877. | Arg638, Asp641, Val661, Ala664, Ser665, Asp680, Leu683, Thr685, Leu704, Pro707, Asp723, Thr726, Asn727, Asp748, Ser749, Pro750, Lys770, Pro771, Gly791, Asn794, Asp809, Thr812, Asn813, Pro833, Pro835, Asp849, Arg852. |
| | Corresponding residues on LPR5 | Arg652, Ala653, Lys675, Glu676, Val694, Ser695, Lys697, Asp718, Tyr719, Glu721, Thr737, Gly738, R764, Trp780, Gly781, Gly782, Arg805, Leu823, Asp824, His847, Phe849, Trp863, Asn864, His866, Asp887, Phe888, M890. | Ser651, Ala654, Val674, Ala677, Ser678, Asp693, Leu696, Thr698, Leu717, Pro720, Asp736, Thr739, Asn740, Asp761, Asn762, Pro763, Lys783, Pro784, Gly804, Asn807, Asp822, Thr825, Asn826, Pro846, Pro848, Asp862, Leu865. |
| VHH36 (013S-D05) | LRP6E3E4 | Glu663, Ser665, Ile681, Tyr706, Glu708, Thr724, Ser749, Arg751, Trp767, Gly768, Arg792, Leu810, Asn813, Pro833, His834, Phe836, Trp850, Ser851, Arg853, Asp874, Try875, Met877. | Ser637, Arg638, Arg639, Lys662, Ala664, Ala666, Thr679, Asp680, Ser682, Lys684, Pro707, Gly725, Asn727, Asp748, Pro750, Glu766, Gly769, Pro771, Asn794, Trp808, Asp809, Asp811, Thr812, Leu814, Leu832, Pro835, Asp849, Arg852, His872, Leu873, Val876, Asp878. |
| | Corresponding residues on LPR5 | Glu676, Ser678, Val694, Tyr719, Glu721, Thr737, Asn762, Arg764, Trp780, Gly781, Arg805, Leu823, Asn826, Pro846, His847, Phe849, Trp863, Asn864, His866, Asp887, Phe888, M890. | Thr650, Ser651, Arg652, Lys675, Ala677, Ala679, Thr692, Asp693, Ser695, Lys697, Pro720, Gly738, Asn740, Asp761, Pro763, Glu779, Gly782, Pro784, Asn807, Thr821, Asp822, Asp824, Thr825, Met827, Leu845, Pro848, Asp862, Leu865, His885, Leu885, Val889, Asp891. |

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An isolated antibody, or an antigen-binding fragment thereof, that binds to one or more LRP5 or LRP6 receptor, comprising a sequence comprising:
  a CDRH1 sequence of SEQ ID NO:107, a CDRH2 sequence of SEQ ID NO:203 and a CDRH3 sequence of SEQ ID NO:452 or any one of SEQ ID NOs: 609-618.

2. The isolated antibody, or antigen-binding fragment thereof, of claim 1, comprising a heavy chain variable region comprising an amino acid sequence having at least 90% identity to the amino acid sequence set forth in SEQ ID NO:10.

3. The isolated antibody, or antigen-binding fragment thereof, of claim 1, wherein the antibody, or antigen-binding fragment thereof, is humanized.

4. The isolated antibody, or antigen-binding fragment thereof, of claim 1, wherein the antibody, or antigen-binding fragment thereof, is a single chain antibody, a scFv, a univalent antibody lacking a hinge region, a VHH, an sdAb, a Fab, a Fab' fragment, or a minibody.

5. The isolated antibody, or antigen-binding fragment thereof, of claim 1, wherein the antibody, or antigen-binding fragment thereof, comprises a fusion protein.

6. The isolated antibody, or antigen-binding fragment thereof, of claim 5, wherein the antibody, or antigen-binding fragment thereof, is fused to a polypeptide sequence that binds one or more Frizzled (Fzd) receptors.

7. The isolated antibody, or antigen-binding fragment thereof, of claim 1, which modulates a Wnt signaling pathway in a cell.

8. A method for agonizing a Wnt signaling pathway in a cell, comprising contacting the cell with the isolated antibody, or antigen-binding fragment thereof, according to claim 7, wherein the antibody, or antigen-binding fragment thereof, increases signaling via the Wnt signaling pathway in the cell.

9. An isolated polynucleotide encoding the isolated antibody, or an antigen-binding fragment thereof, according to claim 1.

10. A pharmaceutical composition comprising a physiologically acceptable excipient, diluent, or carrier, and a therapeutically effective amount of the isolated antibody, or antigen-binding fragment thereof, according to claim 1.

* * * * *